United States Patent
Lin et al.

(10) Patent No.: US 11,732,005 B2
(45) Date of Patent: Aug. 22, 2023

(54) PEPTIDOMIMETIC PROTEASOME INHIBITORS

(71) Applicants: CORNELL UNIVERSITY, Ithaca, NY (US); TRI-INSTITUTIONAL THERAPEUTICS DISCOVERY INSTITUTE, New York, NY (US)

(72) Inventors: Gang Lin, Forest Hills, NY (US); Carl Nathan, Larchmont, NY (US); Wenhu Zhan, Elmhurst, NY (US); Trevor Morgan, Royston (GB); Ryoma Hara, Tokyo (JP); Toshihiro Imaeda, Kanagawa (JP); Rei Okamoto, Kanagawa (JP); Kenjiro Sato, Kanagawa (JP); Kazuyoshi Aso, Kanagawa (JP); Tzu-Tshin Wong, Acton, MA (US); Michael A. Foley, New York, NY (US)

(73) Assignees: CORNELL UNIVERSITY, Ithaca, NY (US); TRI-INSTITUTIONAL THERAPEUTICS DISCOVERY INSTITUTE, New York, NY (US)

( * ) Notice: Subject to any disclaimer, the term of this patent is extended or adjusted under 35 U.S.C. 154(b) by 0 days.

(21) Appl. No.: 17/521,328

(22) Filed: Nov. 8, 2021

(65) Prior Publication Data
US 2022/0056073 A1    Feb. 24, 2022

Related U.S. Application Data

(62) Division of application No. 16/755,427, filed as application No. PCT/US2018/055482 on Oct. 11, 2018, now Pat. No. 11,203,613.

(60) Provisional application No. 62/571,146, filed on Oct. 11, 2017.

(51) Int. Cl.
| C07K 5/062 | (2006.01) |
| C07K 5/02 | (2006.01) |
| C07D 235/14 | (2006.01) |
| C07D 235/10 | (2006.01) |
| A61K 38/00 | (2006.01) |

(52) U.S. Cl.
CPC ........ *C07K 5/06026* (2013.01); *C07D 235/10* (2013.01); *C07D 235/14* (2013.01); *C07K 5/02* (2013.01); *A61K 38/00* (2013.01)

(58) Field of Classification Search
CPC .............................. C07D 235/10; A61K 38/00
See application file for complete search history.

(56) References Cited

U.S. PATENT DOCUMENTS 5,763,604 A    6/1998  Ackermann et al.
7,001,921 B1   2/2006  Adams et al.
8,048,911 B2   11/2011 Ogata
8,367,668 B2   2/2013  Stieber et al.
9,988,421 B2   6/2018  Lin et al.
11,066,397 B2  7/2021  Lin et al.
11,202,817 B2  12/2021 Lin et al.
11,203,613 B2  12/2021 Lin et al.
2005/0171146 A1  8/2005 Weber et al.
2006/0241056 A1 10/2006 Orlowski et al.
2007/0010515 A1  1/2007 Masuda et al.
2007/0244153 A1 10/2007 Kakimoto et al.
2009/0227601 A1  9/2009 Zhu et al.

(Continued)

FOREIGN PATENT DOCUMENTS

CN      1984880 A     6/2007
CN    101506224 A     8/2009

(Continued)

OTHER PUBLICATIONS

Office Action for EP Application Serial No. 15834073.7 (dated Mar. 4, 2022).

(Continued)

*Primary Examiner* — Golam M Shameem
(74) *Attorney, Agent, or Firm* — Troutman Pepper Hamilton Sanders LLP (Rochester)

(57) ABSTRACT

The compounds of the present invention are represented by the following compounds having Formula (I) and Formula (I'):

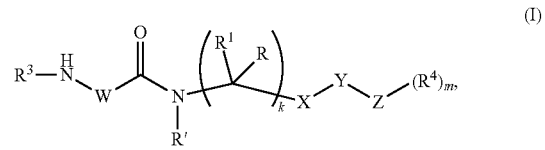

where the substituents R, $R^1$, $R^3$, $R^4$, R, W, X, Y, Z, k, and m are as defined herein and

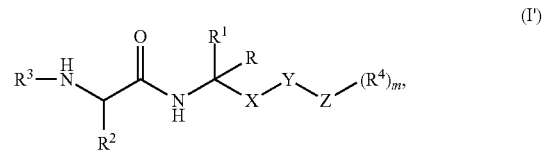

where the substituents R, $R^1$, $R^2$, $R^3$, $R^4$, X, Y, Z, and m are as defined herein. These compounds are used in the treatment of bacterial infections, parasite infections, fungal infections, cancer, immunologic disorders, autoimmune disorders, neurodegenerative diseases and disorders, inflammatory disorders, or muscular dystrophy or for providing immunosuppression for transplanted organs or tissues.

15 Claims, No Drawings

(56) References Cited

U.S. PATENT DOCUMENTS

| | | |
|---|---|---|
| 2010/0249197 A1 | 9/2010 | Watkins et al. |
| 2010/0249400 A1 | 9/2010 | Shiina |
| 2013/0053303 A1 | 2/2013 | Shenk et al. |
| 2013/0072422 A1 | 3/2013 | Shenk et al. |
| 2014/0315786 A1 | 10/2014 | Jirousek et al. |
| 2018/0221431 A1 | 8/2018 | Lin et al. |
| 2018/0282317 A1 | 10/2018 | Lin et al. |
| 2021/0171514 A1 | 6/2021 | Lin et al. |
| 2022/0080022 A1 | 3/2022 | Lin et al. |

FOREIGN PATENT DOCUMENTS

| | | |
|---|---|---|
| CN | 102807601 A | 12/2012 |
| JP | 2006-298785 A | 11/2006 |
| JP | 2008-512476 A | 4/2008 |
| JP | 2014-91731 A | 5/2014 |
| JP | 2014-167005 A | 9/2014 |
| WO | WO 98/29387 A1 | 7/1998 |
| WO | WO 2006/009134 A1 | 1/2006 |
| WO | WO 2006/029210 A2 | 3/2006 |
| WO | WO 2006/065826 A2 | 6/2006 |
| WO | WO 2006/099261 A2 | 9/2006 |
| WO | WO 2007/083394 A1 | 7/2007 |
| WO | WO 2007/149512 A2 | 12/2007 |
| WO | WO 2009/051581 A1 | 4/2009 |
| WO | WO 2010/036357 A1 | 4/2010 |
| WO | WO 2010/038200 A1 | 4/2010 |
| WO | WO 2011/123502 A1 | 10/2011 |
| WO | WO 2012/065891 A1 | 5/2012 |
| WO | WO 2012/116440 A1 | 9/2012 |
| WO | WO 2013/005045 A1 | 1/2013 |
| WO | WO 2013/092979 A1 | 6/2013 |
| WO | WO 2014/095773 A1 | 6/2014 |
| WO | WO 2015/076359 A1 | 5/2015 |
| WO | WO 2015/106200 A2 | 7/2015 |
| WO | WO 2016/028571 A2 | 2/2016 |
| WO | WO 2017/066763 A1 | 4/2017 |

OTHER PUBLICATIONS

Extended European Search Report for EP Application Serial No. 21216660.7 (dated Mar. 29, 2022).

Supplementary European Search Report for EP Application Serial No. 18867283.6 (dated Oct. 14, 2021).

International Search Report and Written Opinion for corresponding Application No. PCT/US2015/044876 (dated Nov. 13, 2015).

Pubchem. SID 132358420.24 Jan. 2012, pp. 1-6 [online], [retrieved on Oct. 1, 2015] Retrieved from the Internet <URL: http://pubchem.ncbi.nih.gov/substance/132358420>; p. 3, formula.

Pubchem. SID 132071324.24 Jan. 2012, pp. 1-6 [online], [retrieved on Oct. 1, 2015]. Retrieved from the Internet <URL: http://pubchem.ncbi.nih.gov/substance/132071324>;p. 3, formula.

Pubchem. SID 146191084. Oct. 10, 2012, pp. 1-6 [online]. [retrieved on Oct. 1, 2015]. Retrieved from the Internet <URL: http://pubchem.ncbi.nih.gov/substance/146191084>;p. 3, formula.

Pubchem. SID 144773390. Oct. 18, 2012, pp. 1-6 [online], [retrieved on Oct. 1, 2015]. Retrieved from the Internet <URL: http://pubchem.ncbi.nih.gov/substance/144773390>; p. 3, formula.

Allen et al., "Analysis of the Cytosolic Proteome in a Cell Culture Model of Familial Amyotrophic Lateral Sclerosis Reveals Alterations to the Proteasome, Antioxidant Defenses, and Nitric Oxide Synthetic Pathways," J. Biol. Chem. 278:6371-6383 (2003).

Basler et al., "Prevention of Experimental Colitis by a Selective Inhibitor of the Immunoproteasome," J. Immunol. 185:634-641 (2010).

Basler et al., "Inhibition of the Immunoproteasome Ameliorates Experimental Autoimmune Encephalomyelitis," EMBO Mol. Med. 6:226-238 (2014).

Baumeister et al., "The Proteasome: Paradigm of a Self-Compartmentalizing Protease," Cell 92:367-380 (1998).

Bedford et al., "Ubiquitin-Like Protein Conjugation and the Ubiquitin-Proteasome System as Drug Targets," Nat. Rev. Drug Discov. 10:29-46 (2011).

Bontscho et al., "Myeloperoxidase-Specific Plasma Cell Depletion by Bortezomib Protects From Anti-Neutrophil Cytoplasmic Autoantibodies-Induced Glomerulonephritis," J. Am. Soc. Nephrol. 22:336-348 (2011).

Brun, "Proteasome Inhibition as a Novel Therapy in Treating Rheumatoid Arthritis," Med. Hypotheses 71:65-72 (2008).

Egerer et al., "Tissue-Specific Up-Regulation of the Proteasome Subunit beta5i (LMP7) in Sjogren's Syndrome," Arthritis Rheum. 54:1501-1508 (2006).

El-Hashim et al., "Effect of Inhibition of the Ubiquitin-Proteasome-System and IkappaB Kinase on Airway Inflammation and Hyper-responsiveness in a Murine Model of Asthma," Int. J. Immunopathol. Pharmacol. 24:33-42 (2011).

Elliott et al., "Proteasome Inhibition: A Novel Mechanism to Combat Asthma," J. Allergy Clin. Immunol. 104:294-300 (1999).

Goldberg, "Functions of the Proteasome: From Protein Degradation and Immune Surveillance to Cancer Therapy," Biochem. Soc. Trans. 35:12-17 (2007).

Guillaume et al., "Two Abundant Proteasome Subtypes That Uniquely Process Some Antigens Presented by HLA Class 1 Molecules," Proc. Natl. Acad. Sci. U.S.A. 107:18599-18604 (2010).

Henry et al., "Proteolytic Activity and Expression of the 20S Proteasome are Increased in Psoriasis Lesional Skin," Br. J. Dermatol. 165:311-320 (2011).

Hirai, et al., "Bortezomib Suppresses Function and Survival of Plasmacytoid Dendritic Cells by Targeting Intracellular Trafficking of Toll-Like Receptors and Endoplasmic Reticulum Homeostasis," Blood 117:500-509 (2011).

Huber et al., "Immuno- and Constitutive Proteasome Crystal Structures Reveal Differences in Substrate and Inhibitor Specificity," Cell 148:727-738 (2012).

Huber et al., "Inhibitors for the Immuno- and Constitutive Proteasome: Current and Future Trends in Drug Development," Angew Chem. Int. Ed Engl. 51:8708-8720 (2012).

Ichikawa et al., "Novel Proteasome Inhibitors Have a Beneficial Effect in Murine Lupus via the Dual Inhibition of Type I Interferon and Autoantibody-Secreting Cells," HHS Public Access Author Manuscript, Available in PMC Sep. 28, 2015, 19 pages, Published in final edited form as: Arthritis Rheum. 64(2):493-503 (2012).

Inoue et al., "The Effect of Proteasome Inhibitor MG132 on Experimental Inflammatory Bowel Disease," Clin. Exp. Immunol. 156:172-82 (2009).

Kincaid et al., "Mice Completely Lacking Immunoproteasomes Display Major Alternatives in Antigen Presentation," HHS Public Access Author Manuscript, Available in PMC Aug. 1, 2012, 18 pages, Published in final edited form as: Nat. Immunol. 13(2):129-135 (2012).

Lang et al., "The Early Marginal Zone B Cell-Initiated T-Independent Type 2 Response Resists the Proteasome Inhibitor Bortezomib," J. Immunol. 185:5637-5647 (2010).

Liang et al., "Proteasome Inhibition in Transplantation-Focusing on the Experience with Bortezomib," Curr. Pharm. Design 19:3299-3304 (2013).

Meng et al., "Epoxomicin, a Potent and Selective Proteasome Inhibitor, Exhibits in Vivo Antiinflammatory Activity ," P. Natl. Acad. Sci. U.S.A. 96:10403-10408 (1999).

Minagar et al., "Plasma Ubiquitin-Proteasome System Profile in Patients With Multiple Sclerosis: Correlation With Clinical Features, Neuroimaging, and Treatment With Interferon-Beta-1 b," Neurol. Res. 34:611-618 (2012).

Muchamuel et al., "A Selective Inhibitor of the Immunoproteasome Subunit LMP7 Blocks Cytokine Production and Attenuates Progression of Experimental Arthritis," Nat. Med. 15:781-787 (2009).

Neubert et al., "The Proteasome Inhibitor Bortezomib Depletes Plasma Cells and Protects Mice With Lupus-Like Disease From Nephritis," Nat. Med. 14:748-755 (2008).

Niewerth et al., "Anti-Leukemic Activity and Mechanisms Underlying Resistance to the Novel Immunoproteasome Inhibitor PR-924," Biochem. Pharmacol. 89:43-51 (2014).

(56) References Cited

OTHER PUBLICATIONS

Padrissa-Altes et al., "The use of a Reversible Proteasome Inhibitor in a Model of Reduced-Size Orthotopic Liver Transplantation in Rats," Exp. Mol. Pathol. 93:99-110 (2012).
Perkins, "Integrating Cell-Signalling Pathways With NF-[kappa]B and IKK Function," Nat. Rev. Mol. Cell. Biol. 8:49-62(2007).
Roccaro et al., "Selective Inhibition of Chymotrypsin-Like Activity of the Immunoproteasome and Constitutive Proteasome in Waldenstrom Macroglobulinemia," Blood 115:4051-4060 (2010).
Rock et al., "Proteases in MHC Class I Presentation and Cross-Presentation," NIH Public Access Author Manuscript, Available in PMC May 13, 2011, 16 pages, Published in final edited form as: J. Immunol. 184 (1):9-15 (2010).
Rock et al., "Inhibitors of the Proteasome Block the Degradation of Most Cell Proteins and the Generation of Peptides Presented on MHC Class I Molecules," Cell 78:761-771 (1994).
Rock et al., "Protein Degradation and the Generation of MHC Class I-Presented Peptides," Adv. Immunol 80:1-70 (2002).
Schmidt et al., "Targeting the Proteasome: Partial Inhibition of the Proteasome by Bortezomib or Deletion of the Immunosubunit LMP7 Attenuates Experimental Colitis," Gut 59:896-906 (2010).
Singh et al., "PR-924, a Selective Inhibitor of the Immunoproteasome Subunit LMP-7, Blocks Multiple Myeloma Cell Growth Both in Vitro and in Vivo," NIH Public Access Author Manuscript, Available in PMC Jan. 1, 2012, 15 pages, Published in final edited form as: Br. J. Haematol. 152:155-163 (2011).
Sureshkumar et al., "Proteasome Inhibition With Bortezomib: an Effective Therapy for Severe Antibody Mediated Rejection After Renal Transplantation," Clin. Nephrol. 77: 246-253 (2012).
Van der Heijden et al., "The Proteasome Inhibitor Bortezomib Inhibits the Release of NFkappaB-Inducible Cytokines and Induces Apoptosis of Activated T Cells From Rheumatoid Arthritis Patients," Clin. Exp. Rheumatol. 27:92-98 (2009).
Verbrugge et al., "Inactivating PSMB5 Mutations and P-glycoprotein (Multidrug Resistance-Associated Protein/ATP-Binding Cassette B1) Mediate Resistance to Proteasome Inhibitors: ex Vivo Efficacy of (Immuno)Proteasome Inhibitors in Mononuclear Blood Cells From Patients With Rheumatoid Arthritis," J. Pharmacol. Exp. Ther. 341:174-182 (2012).
Zhang et al., "In Vitro and in Vivo Therapeutic Efficacy of Carfilzomib in Mantle Cell Lymphoma: Targeting the Immunoproteasome," Mol. Cancer Ther. 12:2494-2504 (2013).
Zollner et al., "Proteasome Inhibition Reduces Superantigen-Mediated T Cell Activation and the Severity of Psoriasis in a SCID-hu Model," J. Clin. Invest. 109:671-679 (2002).
DFHBI IT Datasheet (Lucerna).
International Preliminary Report on Patentability for Application No. PCT/US2015/044876 (dated Feb. 21, 2017).
Supplementary European Search Report dated Mar. 27, 2018 for EP Application Serial No. 15834073.7.
Fuchise et al., "Atlantic Cod Trypsin-Catalyzed Peptide Synthesis with Inverse Substrates as Acyl Donor Components," Chem. Pharm. Bull. 58(4):484-487 (2010).
Notice of Reasons for Rejection for Japanese Patent Application No. 2017-509632 (dated Jun. 5, 2019).
Coumar et al., "3-[2-((2S)-2-Cyano-pyrrolidin-1-yl)-2-oxo-ethylamino]-3-methyl-butyramide Analogues as Selective DPP-IV Inhibitors for the Treatment of Type-II Diabetes," Bioorg. Med. Chem. Lett. 17(5):1274-1279 (2007).
Drey et al., "Synthesis of β-Amino-Acid Peptides by Aminolysis of Substituted Di-hydro-1,3-oxazinones and Amino-Protected β-Lactams," Perkin Transactions 1, J. Chem. Soc. 17:2001-2006 (1973).
Liotta et al., "Antibody-Catalyzed Rearrangement of a Peptide Bond: Mechanistic and Kinetic Investigations," J. Am. Chem. Soc. 117(17):4729-4741 (1995).
Examination Report for Indian Patent Application No. 201747005687 (dated Aug. 29, 2019).
Singh et al., "Immunoproteasome βi-Selective Dipeptidomimetic Inhibitors," ChemMedChem 11:1-6 (2016).
Lin et al., "N,C-Capped Dipeptides with Selectivity for Mycobacterial Proteasome Over Human Proteasomes: Role of S3 and S1 Binding Pockets," J. Am. Chem. Soc. 135(27):9968-9971 (2013).
El-Naggar et al., "Synthesis and Biological Activity of Some New 4-(Aminoacyl)Aminopyridines and 2-(Aminoacyl)Aminopyrimidine Derivatives," Polish Journal of Chemistiy, 56:1279-1285 (1982).
Yamazaki et al., "Two New Tryptamine Derivatives, Leptoclinidamide and (-)-Leptoclinidamine B, from an Indonesian Ascidian Leptoclinides dubius," Marine Drugs, 10(12):349-357 (2012).
Examination report for Europe Patent Application No. 15834073.7 (dated Mar. 25, 2020).
Database Registry Database accession No. 1299989-71-1.
Database Registry Database accession No. 1276335-00-2.
Database Registry Database accession No. 1060993-03-4.
El-Naggar et al., "Database CA [Online]: 'Synthesis and Biological Activity of Some New 4-(Aminoacyl)Aminopyridines and 2-(Aminoacyl)Aminopyrimidine Derivatives,'" Polish Journal of Chemistry, 56:1279-1285 (1982).
Translation of the Office Action for Chinese Patent Application No. 201580056519.4 (dated Jun. 29, 2020).
CAS Registry No. 3641-55-2, Entered STN: Nov. 16, 1984.
CAS Registry No. 294889-15-9, Entered STN: Oct. 12, 2000.
CAS Registry No. 51219-75-1, Entered STN: Nov. 16, 1984.
CAS Registry No. 51219-69-3, Entered STN: Nov. 16, 1984.
CAS Registry No. 59973-55-6, Entered STN: Nov. 16, 1984.
Duke et al., "Synthesis and Biological Evaluation of Sparsomycin Analogues," J. Med. Chem. 26:1556-1561 (1983).
Baud et al., "Defining the Mechanism of Action and Enzymatic Selectivity of Psammaplin A against Its Epigenetic Targets," J. Med. Chem. 55:1731-1750 (2012).
CAS Registry No. 839730-13-1, Entered STN: Mar. 1, 2005.
CAS Registry No. 839730-22-2, Entered STN: Mar. 1, 2005.
CAS Registry No. 839730-21-1, Entered STN: Mar. 1, 2005.
CAS Registry No. 866779-17-1, Entered STN: Nov. 4, 2005.
CAS Registry No. 1461869-28-2, Entered STN: Oct. 21, 2013.
CAS Registry No. 50633-04-0, Entered STN: Nov. 16, 1984.
CAS Registry No. 87639-77-8, Entered STN: Nov. 16, 1984.
CAS Registry No. 120655-16-5, Entered STN: May 12, 1989.
Supplementary European Search Report for European Patent Application No. 15735399.6 (dated Jun. 29, 2017).
Lei et al., "Structural Features and Binding Free Energies for Non-Covalent Inhibitors Interacting with Immunoproteasome by Molecular Modeling and Dynamics Simulations," Theor. Chem. Acc. 131:1-11 (2012).
Blackburn et al., "Characterization of a new Series of Non-Covalent Proteasome Inhibitors with Exquisite Potency and Selectivity for the 20S Beta5-Subunit," Biochem. J. 430:461-476 (2010).
Siebler et al., "Molecular Mutil-Wavelength Optical Anion Sensors," Eur. J. Inorg. Chem. 523-527 (2010).
Ahlford et al., "Fine-Tuning Catalytic Activity and Selectivity-[Rh(Amino Acid Thioamide)] Complexes for Efficient Ketone Reduction," Tetrahedron Lett. 50:6321-6324 (2009).
Blackburn et al. "Optimization of a Series of Dipeptides with a P3 Beta-Neopentyl Asparagine Residue as Non-Covalent Inhibitors of the Chymotrypsin-Like Activity of the Human 20S Proteasome," Med. Chem. Commun. 3:710-719 (2012).
International Preliminary Report on Patentability and Written Opinion for PCT/US2015/011022 (dated Jul. 21, 2016).
International Search Report and Written Opinion for Application No. PCT/US2015/011022 (dated Jun. 24, 2015).
Pubchem: Compound Summary for CID 269632 (Mar. 26, 2005).
Office Action for European Patent Application No. 15735399.6 (dated Jun. 11, 2018).
Pubchem. CID 17857389.04 Dec. 2007, pp. 1-13[online], [retrieved on Feb. 27, 2017] Retrieved from the Internet <URL: https://pubchem.ncbi.nlm.nih.gov/compound/17857389; p. 4, formula.
PCT International Search Report and Written Opinion corresponding to PCT/US2016/057346, dated Mar. 23, 2017.
International Preliminary Report on Patentability for Application No. PCT/US2016/057346 (dated Apr. 17, 2018).
Extended European Search Report and Opinion for European Application No. 16856412.8 dated Mar. 22, 2019.

(56) References Cited

OTHER PUBLICATIONS

Solomon et al., "Synthesis and Antimalarial Activity of Novel Side Chain Modified Antimalarial Agents Derived From 4-Aminoquinoline," Medicinal Chemistry, 4:446-456 (2008).
Office Action in Chinese Patent Application No. 201680065296.2 (dated Dec. 4, 2019).
Pubchem CID 91250924, https://pubchem.ncbi.nlm.nih.gov/compound/91250924, Retrieved Nov. 24, 2019.
International Search Report and Written Opinion for corresponding Application No. PCT/2018/055482 (dated Feb. 8, 2019).
Pubchem CID 64894495, Oct. 23, 2012 (Accession date Nov. 29, 2018).
Pubchem CID 129847054, Sep. 13, 2017 (Accession date Jan. 18, 2019).
Restriction Requirement for U.S. Appl. No. 15/504,951 (dated Jun. 8, 2018).
Office Action for U.S. Appl. No. 15/504,951 (dated Jun. 11, 2019).
Office Action for U.S. Appl. No. 15/504,951 (dated Oct. 12, 2018).
Office Action for U.S. Appl. No. 15/504,951 (dated Sep. 10, 2020).
Ettmayer et al., "Lessons Learned from Marketed and Investigational Prodrugs," J. Med. Chem. 47:2393-2404 (2004).
Han, Hyo-Kyung "Targeted Prodrug Design to Optimize Drug Delivery," AAPS Pharmsci 2:1-11 (2000).
Muller, Christa "Prodrug Approaches for Enhancing the Bioavailability of Drugs with Low Solubility," Chemistry & Biodiversity 6:2071-2083 (2009).
Singh et al., "Recent Trends in Targeted Anticancer Prodrug and Conjugate Design," NIH Public Access Author Manuscript, Available in PMC Jan. 5, 2010, 53 pages, Published in final edited form as: Curr. Med. Chem. 15(18):1802-1826 (2008).
Testa, Bernard "Prodrug Research: Futile or Failure?" Biochemical Pharmacology 68:2097-2106 (2004).
Office Action for U.S. Appl. No. 15/768,628 (dated May 1, 2020).
Office Action for U.S. Appl. No. 15/768,628 (dated Oct. 11, 2019).
Restriction Requirement for U.S. Appl. No. 15/110,000 (dated Mar. 6, 2017).
Office Action for U.S. Appl. No. 15/110,000 (dated Jun. 5, 2017).
Beaumont et al. "Design of Ester Prodrugs to Enhance Oral Absorption of Poorly Permeable Compounds: Challenges to the Discovery Scientist," Curr. Drug Metab. 4:461-485 (2003).
Vippagunta et al. "Crystalline Solids," Advanced Drug Delivery Reviews 48:3-26 (2001).
Hook et al. "The Proteolytic Stability of 'Designed' [beta]-Peptides Containing [alpha]-Peptide-Bond Mimics and of Mixed [alpha,beta]-Peptides: Application to Construction of MHC-Binding Peptides," Chemistry & Biodiversity 2:591-632 (2005).
U.S. Appl. No. 16/893,086, first named inventor Gang Lin, filed Jun. 4, 2020.
Office Action in Chinese Patent Application No. 201680065296.2 (dated Sep. 28, 2020).
Office Action in European Application No. 16856412.8 (dated Sep. 16, 2020).
Notice of Reasons for Rejection for Japanese Patent Application No. 2018-519271 (dated Oct. 22, 2020).
Korshin et al., "Aminoamidines. 7.* 2-(Arylaminomethyl)imidazolines and Their Acylated Derivatives," Izvestiya Akademii Nauk, Seriya Khimicheskaya 3:472-479 (1994) with English translation as Korshin et al., "Aminoamidines. 7 .* 2-(Arylaminomethyl)imidazolines and Their Acylated Derivatives," Russ. Chem. Bull. 43(3):431-438 (1994).
Grudzinski et al., "Studia nad Procesami Uwodomienia Aminonitryli. IX. Otrzymywanie N,N'-Dwuacylo-Trojmetylenodwuamin o Niejednakowych Resztach Kwasowych w Czateczce [Studies on the Hydrogenation of Aminonitriles. IX. Synthesis of N,N'-Diacyltrimethylenediamines Containing Different Acyl Residues]," Acta Poloniae Pharmaceutica 22(6):485-490 (1965) (Article in Polish, English Title and Summary at pp. 489-490).
Muchamuel et al., "A Selective Inhibitor of the Immunoproteasome Subunit LMP7 Blocks Cytokine Production and Attenuates Progression of Experimental Arthritis," Nature Medicine 15(7):781-787 (2009).
Ichikawa et al., "Beneficial Effect of Novel Proteasome Inhibitors in Murine Lupus via Dual Inhibition of Type I Interferon and Autoantibody-Secreting Cells," Arthritis & Rheumatism 64(2):493-503 (2012).
Mutlu et al., "Proteasomal Inhibition After Injury Prevents Fibrosis by Modulating TGF-b1 Signalling," Thorax 67:139-146 (2012).
Mitsiades et al., "Proteasome Inhibition as a New Therapeutic Principle in Hematological Malignancies," Current Drug Targets 7:1341-1347 (2006).
Orlowski "The Ubiquitin Proteasome Pathway from Bench to Bedside," Hematology 220-225 (2005).
Fisher et al., "Multicenter Phase II Study of Bortezomib in Patients With Relapsed or Refractory Mantle Cell Lymphoma," J. Clin. Oncol. 24(30):4867-4874 (2006).
Walsh et al., "Proteasome Inhibitor-Based Primary Therapy for Antibody-Mediated Renal Allograft Rejection," Transplantation 89(3):277-284 (2010).
Mateos-Mazon et al., "Use of Bortezomib in the Management of Chronic Graft-Versus-Host Disease Among Multiple Myeloma Patients Relapsing After Allogeneic Transplantation," Haematologica 92(9):1295-1296 (2007).
Kloda, "Systemic sclerosis—bortezomib—is it wonder drug?," MEDtube.net (2011) https://medtube.net/tribune/systemic-sclerosis-bortezomib-is-it-wonder-drug/.
Office Action for U.S. Appl. No. 15/504,951 (dated Mar. 26, 2021).
International Preliminary Report on Patentability for corresponding Application No. PCT/2018/055482 (dated Apr. 14, 2020).
Office Action in Chinese Patent Application No. 201680065296.2 (dated Apr. 30, 2021).
Office Action for Chinese Patent Application No. 201580056519.4 (dated May 7, 2021).
Examination Report for Indian Patent Application No. 202048025018 (dated Jun. 3, 2021).
Partial Supplementary European Search Report for EP Application Serial No. 18867283.6 (dated Jun. 23, 2021).
O'Mahony et al., "A Practical Synthesis of 2'-Aminoacylamino-2'-Deoxyadenosines," Tetrahedron 63(29):6901-6908 (2007).
Kataoka et al., "Formation of Heterocyclic Amine-Amino Acid Adducts by Heating in a Model System," Food Chemistry 130(3):725-729 (2012).
Extended European Search Report for EP Application Serial No. 18867283.6 (dated Sep. 27, 2021).
Office Action for U.S. Appl. No. 16/893,086 (dated Oct. 5, 2022).
Rowe et al., Handbook of Pharmaceutical Excipients, Sixth Edition, Pharmaceutical Press (2009).
Office Action for U.S. Appl. No. 17/177,729 (dated Mar. 21, 2022).
Notice of Reasons for Rejection for Japanese Patent Application No. 2021-176164 (dated Dec. 8, 2022).

PEPTIDOMIMETIC PROTEASOME INHIBITORS

This application is a divisional of U.S. patent application Ser. No. 16/755,427, filed Apr. 10, 2020, which is a national stage application under 35 U.S.C. § 371 of International Patent Application No. PCT/US2018/055482, filed Oct. 11, 2018, which claims the priority benefit of U.S. Provisional Patent Application Ser. No. 62/571,146, filed Oct. 11, 2017, which are hereby incorporated by reference in their entirety.

FIELD OF THE INVENTION

The present invention relates to peptidomimetic proteasome inhibitors.

BACKGROUND OF THE INVENTION

Proteasomes are highly conserved self-compartmentalizing proteases found in three kingdoms of life. A proteasome is a large, ATP-dependent, multi-subunit, barrel-shaped N-terminal nucleophile hydrolase present in the cytosol and nucleus of eukaryotic cells and is responsible for the degradation of the majority of cellular proteins (Baumeister et al., "The Proteasome: Paradigm of a Self-Compartmentalizing Protease," Cell 92(3):367-380 (1998); Goldberg A L., "Functions of the Proteasome: from Protein Degradation and Immune Surveillance to Cancer Therapy," Biochem. Soc. Trans. 35(Pt 1):12-17 (2007)). Through regulated degradation, a proteasome regulates protein homeostasis, the cell cycle, signal transduction, protein trafficking, immune responses, etc, which are important cellular functions. Degradation product oligopeptides are reservoirs of antigenic peptides for MHC class I antigen presentation.

The 20S core that is constitutively expressed in most cells (c-20S) is a stack of 4 rings of 14 $\alpha$ and $\beta$ subunits organized in a $\alpha_{1-7}\beta_{1-7}\beta_{1-7}\alpha_{1-7}$ fashion, where 2 copies of each caspase-like $\beta$1, trypsin-like $\beta$2, and chymotrypsin-like $\beta$5 active subunits are located in the inner $\beta$ rings (Baumeister, et al., "The Proteasome: Paradigm of a Self-Compartmentalizing Protease," Cell 92:367-380 (1998)). The chymotrypsin-like 05 active subunits of the 20S have been clinically validated as a target for the treatment of multiple myeloma and certain lymphomas. Presently, there are three proteasome inhibitors that were approved by FDA: bortezomib, carfilzomib, and ixazomib: bortezomib and ixazomib are reversible peptide boronates and carfilzomib an irreversible peptide epoxyketone (Borissenko et al., "20S Proteasome and its Inhibitors: Crystallographic Knowledge for Drug Development," Chem. Rev. 107:687-717 (2007); Parlati et al., Haematol-Hematol. J. 94:148-149 (2009); Huber et al., "Inhibitors for the Immuno- and Constitutive Proteasome: Current and Future Trends in Drug Development," Angew. Chem. Int. Ed. Engl. 51(35):8708-8720 (2012)).

Proteasome inhibition interrupts many cellular pathways, particularly, the NF-kB activation pathway, the induction of unfolded protein response, and ER stress, while strongly inducing apoptosis. For this reason, highly specific proteasome inhibitors have been approved for the treatment of hematological cancer. Proteasome inhibitors can also markedly limit the overall supply of peptides for MHC class I molecules and, thus, block antigen presentation (Rock et al., "Protein Degradation and the Generation of MHC Class I-Presented Peptides," Adv. Immunol. 80:1-70 (2002)). As a result, proteasome inhibitors reduce immune response via multiple routes. Antibody-secreting plasma cells are highly sensitive to proteasome inhibition and BTZ, which inhibits both c-20S and i-20S, has been used in renal transplant recipients to prevent antibody-mediated graft rejection (Aull et al., Clin Transpl 495-498 (2009); Raghavan et al., "Bortezomib in Kidney Transplantation," J. Transplant. 2010: 698594 (2010); Al-Homsi et al., "Effect of Novel Proteasome and Immunoproteasome Inhibitors on Dendritic Cell Maturation, Function, and Expression of Iκb and Nfκb," Transpl. Immunol. 29:1-6 (2013); Pai et al., "Treatment of Chronic Graft-Versus-Host Disease with Bortezomib," Blood 124:1677-1688 (2014)). BTZ was also reported to be efficacious in patients with refractory systemic lupus erythematosus (Alexander et al., "The Proteasome Inhibitor Bortezomib Depletes Plasma Cells and Ameliorates Clinical Manifestations of Refractory Systemic Lupus Erythematosus," Ann. Rheum. Dis. 74:1474-1478 (2015).

Plasmodium falciparum (P. falciparum), the most deadly of the human malarias, accounts for nearly 0.5 million deaths a year, primarily in children. The most important current therapies are combinations of artemisinins (ART). The emergence of ART resistant parasites (Ariey et al., "A Molecular Marker of Artemisinin-Resistant Plasmodium Falciparum Malaria," Nature 505(7481):50-55 (2014); Straimer et al., "K13-Propeller Mutations Confer Artemisinin Resistance in Plasmodium Falciparum Clinical Isolates," Science 347(6220):428-431 (2015); Dogovski et al., "Targeting the Cell Stress Response of Plasmodium Falciparum to Overcome Artemisinin Resistance," PLoS Biol. 13(4):e1002132 (2015); Mbengue et al., "A Molecular Mechanism of Artemisinin Resistance in Plasmodium Falciparum Malaria," Nature 520(7549):683-687 (2015)) highlights the need for new antimalarials with novel targets (Wells T N et al., "Malaria Medicines: a Glass Half Full?" Nat. Rev. Drug Discov. 14(6):424-442 (2015)). Upregulation of the ubiquitin proteasome system (UPS) is important for survival of artemisinin-resistant parasites and emphasizes the importance of the UPS in parasite survival and its importance as a drug target moving forward (Dogovski et al., "Targeting the Cell Stress Response of Plasmodium Falciparum to Overcome Artemisinin Resistance," PLoS Biol. 13(4):e1002132 (2015); Mok et al., "Drug Resistance. Population Transcriptomics of Human Malaria Parasites Reveals the Mechanism of Artemisinin Resistance," Science 347(6220):431-435(2015)).

Proteasome inhibitors are known to kill malaria parasites in vitro and are efficacious against multiple parasite stages; peptide epoxyketone inhibitors, a peptide vinyl sulfone inhibitor, and a cyclic peptide inhibitor, have potent antimalarial activities (Dogovski et al., "Targeting the Cell Stress Response of Plasmodium Falciparum to Overcome Artemisinin Resistance," PLoS Biol. 13(4):e1002132 (2015); Featherstone C. "Proteasome Inhibitors in Development for Malaria," Mol. Med. Today 3(9):367 (1997); Gantt et al., "Proteasome Inhibitors Block Development of Plasmodium Spp," Antimicrob. Agents Chemother. 42(10):2731-2738 (1948); Aminake et al., "The Proteasome of Malaria Parasites: A Multi-Stage Drug Target for Chemotherapeutic Intervention?" Int. J. Parasitol. Drugs Drug Resist. 2:1-10 (2012); Li et al., "Validation of the Proteasome as a Therapeutic Target in Plasmodium Using an Epoxyketone Inhibitor with Parasite-Specific Toxicity," Chem. Biol. 19(12): 1535-1545 (2012); Tschan et al., "Broad-Spectrum Antimalarial Activity of Peptido Sulfonyl Fluorides, a New Class of Proteasome Inhibitors," Antimicrob. Agents Chemother. 57(8):3576-8354 (2013); Li et al., "Assessing Subunit Dependency of the Plasmodium Proteasome Using Small Molecule Inhibitors and Active Site Probes," ACS Chem. Biol. 9(8):1869-1876 (2014); Li et al., "Structure- and Function-Based Design of *Plasmodium*-Selective Proteasome Inhibitors," Nature 530(7589):233-236 (2016)). Bortezomib (BTZ) and MLN-273 were effective against *plasmodium* in blood and liver stages (Lindenthal et al., "The Proteasome Inhibitor MLN-273 Blocks Exoerythrocytic and Erythrocytic Development of *Plasmodium* Parasites," Parasitology 131(Pt 1):37-44 (2005); Reynolds et al., "Antimalarial Activity of the Anticancer and Proteasome Inhibitor Bortezomib and its Analog ZL3B," BMC. Clin. Pharmacol. 7:13 (2007)); MG-132 against blood stage and gametocytes (Lindenthal et al., "The Proteasome Inhibitor MLN-273 Blocks Exoerythrocytic and Erythrocytic Development of *Plasmodium* Parasites," Parasitology 131(Pt 1):37-44 (2005); Prudhomme et al., "Marine Actinomycetes: a New Source of Compounds Against the Human Malaria Parasite," PLoS One 3(6):e2335 (2008)); epoxomicin against blood and liver stages and gametocytes (Aminake et al., "Thiostrepton and Derivatives Exhibit Antimalarial And Gametocytocidal Activity by Dually Targeting Parasite Proteasome and Apicoplast," Antimicrob. Agents Chemother. 55(4):1338-1348 (2011); Czesny et al., "The Proteasome Inhibitor Epoxomicin Has Potent *Plasmodium Falciparum* Gametocytocidal Activity," Antimicrob. Agents Chemother. 53(10):4080-4085 (2009); Kreidenweiss et al., "Comprehensive Study of Proteasome Inhibitors Against *Plasmodium Falciparum* Laboratory Strains and Field Isolates From Gabon," Malar. J. 7:187 (2008); Li et al., "Validation of the Proteasome as a Therapeutic Target in *Plasmodium* Using an Epoxyketone Inhibitor With Parasite-Specific Toxicity," Chem. Biol. 19(12):1535-1545 (2012)). These inhibitors are in general not species selective. They are cytotoxic to host cells and unsuitable for treating malaria. There is an urgent need to develop *Plasmodium* spp. proteasome (Pf20S) selective inhibitors that target parasite proteasomes over human host proteasomes.

Species selective proteasome inhibitors have been reported (Hu et al., "Structure of the *Mycobacterium Tuberculosis* Proteasome and Mechanism of Inhibition by a Peptidyl Boronate," Mol. Microbiol. 59:1417-1428 (2006); Li et al., "Structural Basis for the Assembly and Gate Closure Mechanisms of the *Mycobacterium Tuberculosis* 20S Proteasome," Embo. J. 29:2037-2047 (2010); Lin et al., "N,C-Capped Dipeptides With Selectivity for Mycobacterial Proteasome Over Human Proteasomes: Role of S3 and 51 Binding Pockets," J. Am. Chem. Soc. 135:9968-9971 (2013); Lin et al., "*Mycobacterium Tuberculosis* prcBA Genes Encode a Gated Proteasome With Broad Oligopeptide Specificity,"Mol. Microbiol. 59:1405-1416 (2006); Lin et al., "Fellutamide B is a Potent Inhibitor of the *Mycobacterium Tuberculosis* Proteasome,"Arch. Biochem. Biophys. 501:214-220 (2010); Lin et al., "Inhibitors Selective for Mycobacterial Versus Human Proteasomes," Nature 461 (7264):621-626 (2009); Lin et al., "Distinct Specificities of *Mycobacterium Tuberculosis* and Mammalian Proteasomes for N-Acetyl Tripeptide Substrates," J. Biol. Chem. 283: 34423-31 (2008)).

As shown by the above references, the proteasome represents an important target for therapeutic intervention of various disorders. Thus, there is an ongoing need for new and/or improved proteasome inhibitors.

The present invention is directed to overcoming these and other deficiencies in the art.

SUMMARY OF THE INVENTION

A first aspect of the present invention relates to a compound of Formula (I):

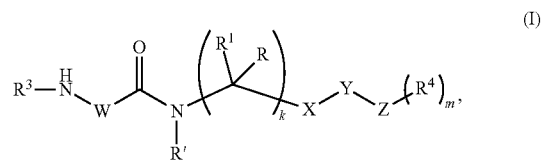

wherein
R is H or $C_{1-6}$ alkyl;
R' is H or $C_{1-6}$ alkyl;
$R^1$ is H or $C_{1-6}$ alkyl;
or R and $R^1$ are taken together with the carbon to which they are attached to form a $C_{3-8}$ cycloalkyl ring;
$R^2$ is independently selected at each occurrence thereof from

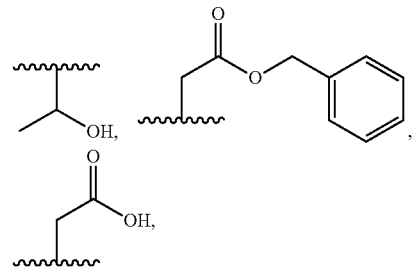

or $-(CH_2)_nC(O)NR^6R^7$;
$R^3$ is independently selected at each occurrence thereof from the group consisting of H, $C_{1-12}$ alkyl, -Boc, $-C(O)(CH_2)_nR^5$, $-(CH_2)C(O)R^5$, $-C(O)OR^5$, $-C(O)(CH_2)NR^6R^7$, $-S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $R^8$;
$R^4$ is H, halogen, $NH_2$, $NHCOOC_{1-12}$ alkyl, or $C_{1-12}$ alkyl;
$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;
$R^6$, $R^7$ are each independently selected from the group consisting of H, $C_{1-6}$ alkyl, and arylalkyl;
or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;
$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

W is $CHR^2$, $NR^2$, or

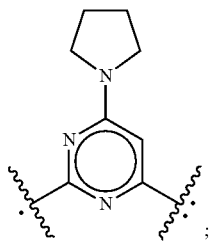

X is selected from the group consisting of —C(O)—NH—, monocyclic and bicyclic heteroaryl, monocyclic and bicyclic heterocyclyl, and monocyclic and bicyclic non-aromatic heterocycle;

Y is optional and, if present, is —$(CH_2)_m$—;

Z is optional and, if present, is aryl or bicyclic heteroaryl;

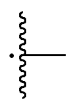

is the point of attachment to $NHR^3$ moiety;

is the point of attachment to C(O) moiety;

k is 1 or 2;

m is 0, 1, or 2; and n is 0, 1, 2, 3, or 4, with the proviso that $R^2$ is not —$CH_2C(O)NH_2$, —$CH_2C(O)NHCH_2C(CH_3)_3$, or —$(CH_2)_2C(O)NH_2$, or an oxide thereof, a pharmaceutically acceptable salt thereof, a solvate thereof, or a prodrug thereof.

A second aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound according to any aspect of the present invention.

A third aspect of the present invention relates to a method of inhibiting proteasome activity. This method includes contacting a proteasome with a compound according to any aspect of the present invention under conditions effective to inhibit proteasome activity.

DETAILED DESCRIPTION OF THE INVENTION

A first aspect of the present invention relates to a compound of Formula (I):

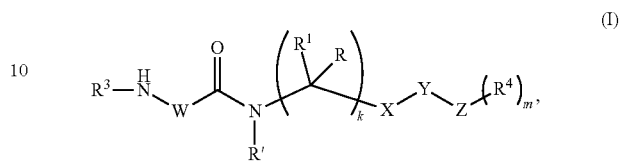

wherein

R is H or $C_{1-6}$ alkyl;

R' is H or $C_{1-6}$ alkyl;

$R^1$ is H or $C_{1-6}$ alkyl;

or R and $R^1$ are taken together with the carbon to which they are attached to form a $C_{3-8}$ cycloalkyl ring;

$R^2$ is independently selected at each occurrence thereof from

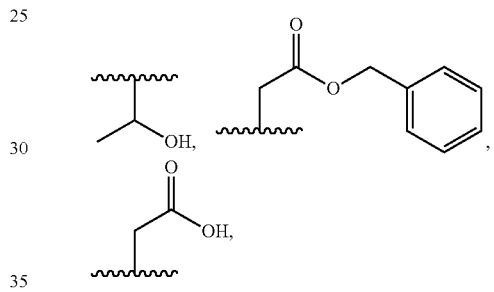

or —$(CH_2)C(O)NR^6R^7$;

$R^3$ is independently selected at each occurrence thereof from the group consisting of H, $C_{1-12}$ alkyl, -Boc, —C(O)$(CH_2)_nR^5$, —$(CH_2)C(O)R^5$, —C(O)OR$^5$, —C(O)$(CH_2)NR^6R^7$, —S(O)$_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $R^8$;

$R^4$ is H, halogen, $NH_2$, $NHCOOC_{1-12}$ alkyl, or $C_{1-12}$ alkyl;

$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;

$R^6$, $R^7$ are each independently selected from the group consisting of H, $C_{1-6}$ alkyl, and arylalkyl;

or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;

$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

W is $CHR^2$, $NR^2$, or

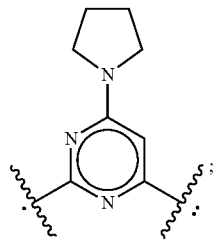

X is selected from the group consisting of —C(O)—NH—, monocyclic and bicyclic heteroaryl, monocyclic and bicyclic heterocyclyl, and monocyclic and bicyclic non-aromatic heterocycle;

Y is optional and, if present, is —$(CH_2)_m$—;

Z is optional and, if present, is aryl or bicyclic heteroaryl;

is the point of attachment to $NHR^3$ moiety;

is the point of attachment to C(O) moiety;

k is 1 or 2;

m is 0, 1, or 2; and n is 0, 1, 2, 3, or 4, with the proviso that $R^2$ is not —$CH_2C(O)NH_2$, —$CH_2C(O)NHCH_2C(CH_3)_3$, or —$(CH_2)_2C(O)NH_2$, or an oxide thereof, a pharmaceutically acceptable salt thereof, a solvate thereof, or a prodrug thereof.

As used above, and throughout the description herein, the following terms, unless otherwise indicated, shall be understood to have the following meanings. If not defined otherwise herein, all technical and scientific terms used herein have the same meaning as is commonly understood by one of ordinary skill in the art to which this technology belongs. In the event that there is a plurality of definitions for a term herein, those in this section prevail unless stated otherwise.

The term "alkyl" means an aliphatic hydrocarbon group which may be straight or branched having about 1 to about 12 carbon atoms in the chain. Branched means that one or more lower alkyl groups such as methyl, ethyl or propyl are attached to a linear alkyl chain. Exemplary alkyl groups include methyl, ethyl, n-propyl, i-propyl, n-butyl, t-butyl, n-pentyl, and 3-pentyl.

The term "cycloalkyl" means a non-aromatic mono- or multicyclic ring system of about 3 to about 12 carbon atoms, preferably of about 3 to about 8 carbon atoms. Exemplary monocyclic cycloalkyls include cyclopentyl, cyclohexyl, cycloheptyl, bicyclo[1.1.1]pentyl, and the like.

The term "cycloalkylalkyl" means a cycloalkyl-alkyl-group in which the cycloalkyl and alkyl are as defined herein. Exemplary cycloalkylalkyl groups include cyclopropylmethyl, cyclobutylmethyl, cyclopentylmethyl, cyclopropylethyl, cyclobutylethyl, and cyclopentylethyl. The alkyl radical and the cycloalkyl radical may be optionally substituted as defined herein.

The term "aryl" means an aromatic monocyclic or multicyclic ring system of 6 to about 14 carbon atoms, preferably of 6 to about 10 carbon atoms. Representative aryl groups include phenyl and naphthyl.

The term "arylalkyl" means an alkyl substituted with one or more aryl groups, wherein the alkyl and aryl groups are as herein described. One particular example is an arylmethyl or arylethyl group, in which a single or a double carbon spacer unit is attached to an aryl group, where the carbon spacer and the aryl group can be optionally substituted as described herein. Representative arylalkyl groups include

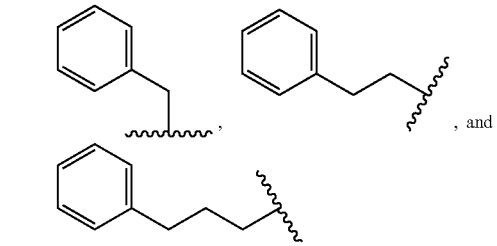

, and

The term "heteroaryl" means an aromatic monocyclic or multicyclic ring system of about 5 to about 14 ring atoms, preferably about 5 to about 10 ring atoms, in which one or more of the atoms in the ring system is/are element(s) other than carbon, for example, nitrogen, oxygen, or sulfur. In the case of multicyclic ring system, only one of the rings needs to be aromatic for the ring system to be defined as "Heteroaryl". Preferred heteroaryls contain about 5 to 6 ring atoms. The prefix aza, oxa, thia, or thio before heteroaryl means that at least a nitrogen, oxygen, or sulfur atom, respectively, is present as a ring atom. A nitrogen atom of a heteroaryl is optionally oxidized to the corresponding N-oxide. Representative heteroaryls include pyridyl, 2-oxo-pyridinyl, pyrimidinyl, pyridazinyl, pyrazinyl, triazinyl, furanyl, pyrrolyl, thiophenyl, pyrazolyl, imidazolyl, oxazolyl, isoxazolyl, thiazolyl, isothiazolyl, triazolyl, oxadiazolyl, thiadiazolyl, tetrazolyl, indolyl, isoindolyl, benzofuranyl, benzothiophenyl, indolinyl, 2-oxoindolinyl, dihydrobenzofuranyl, dihydrobenzothiophenyl, indazolyl, benzimidazolyl, benzooxazolyl, benzothiazolyl, benzoisoxazolyl, benzoisothiazolyl, benzotriazolyl, benzo[1,3]dioxolyl, quinolinyl, isoquinolinyl, quinazolinyl, cinnolinyl, pthalazinyl, quinoxalinyl, 2,3-dihydro-benzo[1,4]dioxinyl, benzo[1,2,3]triazinyl, benzo[1,2,4]triazinyl, 4H-chromenyl, indolizinyl, quinolizinyl, 6aH-thieno[2,3-d]imidazolyl, 1H-pyrrolo[2,3-b]pyridinyl, imidazo[1,2-a]pyridinyl, pyrazolo[1,5-a]pyridinyl, [1,2,4]triazolo[4,3-a]pyridinyl, [1,2,4]triazolo[1,5-a]pyridinyl, thieno[2,3-b]furanyl, thieno[2,3-b]pyridinyl, thieno[3,2-b]pyridinyl, furo[2,3-b]pyridinyl, furo[3,2-b]pyridinyl, thieno[3,2-d]pyrimidinyl, furo[3,2-d]pyrimidinyl, thieno[2,3-b]pyrazinyl, imidazo[1,2-a]pyrazinyl, 5,6,7,8-tetrahydroimidazo[1,2-a]pyrazinyl, 6,7-dihydro-4H-pyrazolo[5,1-c][1,4]oxazinyl, 2-oxo-2,3- dihydrobenzo[d]oxazolyl, 3,3-dimethyl-2-oxoindolinyl, 2-oxo-2,3-dihydro-1H-pyrrolo[2,3-b]pyridinyl, benzo[c][1,2,5]oxadiazolyl, benzo[c][1,2,5]thiadiazolyl, 3,4-dihydro-2H-benzo[b][1,4]oxazinyl, 5,6,7,8-tetrahydro-[1,2,4]triazolo[4,3-a]pyrazinyl, [1,2,4]triazolo[4,3-a]pyrazinyl, 3-oxo-[1,2,4]triazolo[4,3-a]pyridin-2(3H)-yl, and the like.

As used herein, "heterocyclyl" refers to a stable 3- to 18-membered ring (radical) which consists of carbon atoms and from one to five heteroatoms selected from the group consisting of nitrogen, oxygen and sulfur. For purposes of this application, the heterocycle may be a monocyclic, or a polycyclic ring system, which may include fused, bridged, or spiro ring systems; and the nitrogen, carbon, or sulfur atoms in the heterocycle may be optionally oxidized; the nitrogen atom may be optionally quaternized; and the ring may be partially or fully saturated. Examples of such heterocycles include, without limitation, azepinyl, azocanyl, pyranyl dioxanyl, dithianyl, 1,3-dioxolanyl, tetrahydrofuryl, dihydropyrrolidinyl, decahydroisoquinolyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, 2-oxoazepinyl, oxazolidinyl, oxiranyl, piperidinyl, piperazinyl, 4-piperidonyl, pyrrolidinyl, pyrazolidinyl, thiazolidinyl, tetrahydropyranyl, thiamorpholinyl, thiamorpholinyl sulfoxide, and thiamorpholinyl sulfone. Further heterocycles and heteroaryls are described in Katritzky et al., eds., *Comprehensive Heterocyclic Chemistry: The Structure, Reactions, Synthesis and Use of Heterocyclic Compounds*, Vol. 1-8, Pergamon Press, N.Y. (1984), which is hereby incorporated by reference in its entirety.

The term "non-aromatic heterocycle" means a non-aromatic monocyclic or multicyclic system containing 3 to 10 atoms, preferably 4 to about 7 carbon atoms, in which one or more of the atoms in the ring system is/are element(s) other than carbon, for example, nitrogen, oxygen, or sulfur. Representative non-aromatic heterocycle groups include pyrrolidinyl, 2-oxopyrrolidinyl, piperidinyl, 2-oxopiperidinyl, azepanyl, 2-oxoazepanyl, 2-oxooxazolidinyl, morpholino, 3-oxomorpholino, thiomorpholino, 1,1-dioxothiomorpholino, piperazinyl, tetrahydro-2H-oxazinyl, and the like.

The term "monocyclic" used herein indicates a molecular structure having one ring.

The term "polycyclic" or "multi-cyclic" used herein indicates a molecular structure having two or more rings, including, but not limited to, fused, bridged, or spiro rings.

Terminology related to "protecting", "deprotecting," and "protected" functionalities occurs throughout this application. Such terminology is well understood by persons of skill in the art and is used in the context of processes which involve sequential treatment with a series of reagents. In that context, a protecting group refers to a group which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes described herein, the person of ordinary skill can readily envision those groups that would be suitable as "protecting groups." Suitable groups for that purpose are discussed in standard textbooks in the field of chemistry, such as Greene, *Protective Groups in Organic Synthesis*, John Wiley & Sons, New York (1991), which is hereby incorporated by reference in its entirety.

The term "alkoxy" means groups of from 1 to 12 carbon atoms of a straight, branched, or cyclic configuration and combinations thereof attached to the parent structure through an oxygen. Examples include methoxy, ethoxy, propoxy, isopropoxy, cyclopropyloxy, cyclohexyloxy, and the like. Lower-alkoxy refers to groups containing one to four carbons. For the purposes of the present patent application, alkoxy also includes methylenedioxy and ethylenedioxy in which each oxygen atom is bonded to the atom, chain, or ring from which the methylenedioxy or ethylenedioxy group is pendant so as to form a ring. Thus, for example, phenyl substituted by alkoxy may be, for example, or

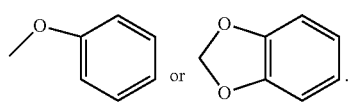

A compound with a hydroxy group drawn next to a nitrogen on a heterocycle can exist as the "keto" form. For example, 3-(2-hydroxy-[1,2,4]triazolo[1,5-a]pyridin yl)propanoic acid can exist as 3-(2-oxo-2,3-dihydro-[1,2,4]triazolo[1,5-a]pyridin-6-yl)propanoic acid.

The term "halogen" means fluoro, chloro, bromo, or iodo.

The term "substituted" or "substitution" of an atom means that one or more hydrogen on the designated atom is replaced with a selection from the indicated group, provided that the designated atom's normal valency is not exceeded.

"Unsubstituted" atoms bear all of the hydrogen atoms dictated by their valency. When a substituent is keto (i.e., =O), then two hydrogens on the atom are replaced. Combinations of substituents and/or variables are permissible only if such combinations result in stable compounds; by "stable compound" or "stable structure" is meant a compound that is sufficiently robust to survive isolation to a useful degree of purity from a reaction mixture, and formulation into an efficacious therapeutic agent.

The term "optionally substituted" is used to indicate that a group may have a substituent at each substitutable atom of the group (including more than one substituent on a single atom), provided that the designated atom's normal valency is not exceeded and the identity of each substituent is independent of the others. Up to three H atoms in each residue are replaced with alkyl, halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "method of treating" means amelioration or relief from the symptoms and/or effects associated with the disorders described herein. As used herein, reference to "treatment" of a patient is intended to include prophylaxis.

The term "compounds of the invention", and equivalent expressions, are meant to embrace compounds of general Formula (I), Formula (IA), Formula (IB), Formula (IC), Formula (I'), Formula (I'A), Formula (I'B), Formula (I'C), Formula (I'D), Formula (I'E), Formula (I'F), Formula (I'G), Formula (I'C'), Formula (I'D'), Formula (I'E'), Formula (I'F'), Formula (I'G'), and Formula (II) as hereinbefore described, which expression includes the prodrugs, the pharmaceutically acceptable salts, and the solvates, e.g. hydrates, where the context so permits. Similarly, reference to intermediates, whether or not they themselves are claimed, is meant to embrace their salts, and solvates, where the context so permits. For the sake of clarity, particular instances when the context so permits are sometimes indicated in the text, but these instances are purely illustrative and it is not intended to exclude other instances when the context so permits.

The term "pharmaceutically acceptable salts" means the relatively non-toxic, inorganic, and organic acid addition salts, and base addition salts, of compounds of the present invention. These salts can be prepared in situ during the final isolation and purification of the compounds. In particular, acid addition salts can be prepared by separately reacting the purified compound in its free base form with a suitable organic or inorganic acid and isolating the salt thus formed. Exemplary acid addition salts include the hydrobromide, hydrochloride, sulfate, bisulfate, phosphate, nitrate, acetate, oxalate, valerate, oleate, palmitate, stearate, laurate, borate, benzoate, lactate, phosphate, tosylate, citrate, maleate, fumarate, succinate, tartrate, naphthylate, mesylate, glucoheptonate, lactiobionate, sulphamates, malonates, salicylates, propionates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates and quinateslaurylsulphonate salts, and the like (see, for example, Berge et al., "Pharmaceutical Salts," *J. Pharm. Sci.*, 66:1-9 (1977) and Remington's Pharmaceutical Sciences, 17th ed., Mack Publishing Company, Easton, Pa., 1985, p. 1418, which are hereby incorporated by reference in their entirety). Base addition salts can also be prepared by separately reacting the purified compound in its acid form with a suitable organic or inorganic base and isolating the salt thus formed. Base addition salts include pharmaceutically acceptable metal and amine salts. Suitable metal salts include the sodium, potassium, calcium, barium, zinc, magnesium, and aluminum salts. The sodium and potassium salts are preferred. Suitable inorganic base addition salts are prepared from metal bases which include, for example, sodium hydride, sodium hydroxide, potassium hydroxide, calcium hydroxide, aluminium hydroxide, lithium hydroxide, magnesium hydroxide, and zinc hydroxide. Suitable amine base addition salts are prepared from amines which have sufficient basicity to form a stable salt, and preferably include those amines which are frequently used in medicinal chemistry because of their low toxicity and acceptability for medical use, such as ammonia, ethylenediamine, N-methyl-glucamine, lysine, arginine, ornithine, choline, N,N'-dibenzylethylenediamine, chloroprocaine, diethanolamine, procaine, N-benzylphenethylamine, diethylamine, piperazine, tris(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e.g., lysine and arginine, dicyclohexylamine, and the like.

The term "pharmaceutically acceptable prodrugs" as used herein means those prodrugs of the compounds useful according to the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" means compounds that are rapidly transformed in vivo to yield the parent compound of the above formula, for example by hydrolysis in blood. Functional groups which may be rapidly transformed, by metabolic cleavage, in vivo form a class of groups reactive with the carboxyl group of the compounds of this invention. They include, but are not limited to, such groups as alkanoyl (such as acetyl, propionyl, butyryl, and the like), unsubstituted and substituted aroyl (such as benzoyl and substituted benzoyl), alkoxycarbonyl (such as ethoxycarbonyl), trialkylsilyl (such as trimethyl- and triethysilyl), monoesters formed with dicarboxylic acids (such as succinyl), and the like. Because of the ease with which the metabolically cleavable groups of the compounds useful according to this invention are cleaved in vivo, the compounds bearing such groups act as pro-drugs. The compounds bearing the metabolically cleavable groups have the advantage that they may exhibit improved bioavailability as a result of enhanced solubility and/or rate of absorption conferred upon the parent compound by virtue of the presence of the metabolically cleavable group. A thorough discussion of prodrugs is provided in the following: Design of Prodrugs, H. Bundgaard, ed., Elsevier (1985); *Methods in Enzymology*, K. Widder et al, Ed., Academic Press, 42, p. 309-396 (1985); *A Textbook of Drug Design and Development*, Krogsgaard-Larsen and H. Bundgaard, ed., Chapter 5; "Design and Applications of Prodrugs" p. 113-191 (1991); *Advanced Drug Delivery Reviews*, H. Bundgard, 8, p. 1-38 (1992); *J. Pharm. Sci.*, 77:285 (1988); Nakeya et al, *Chem. Pharm. Bull.*, 32:692 (1984); Higuchi et al., "Pro-drugs as Novel Delivery Systems," Vol. 14 of the *A.C.S. Symposium Series, and Bioreversible Carriers in Drug Design*, Edward B. Roche, ed., American Pharmaceutical Association and Pergamon Press (1987), which are incorporated herein by reference in their entirety. Examples of prodrugs include, but are not limited to, acetate, formate, and benzoate derivatives of alcohol and amine functional groups in the compounds of the invention.

The term "solvate" refers to a compound of Formula (I), Formula (IA), Formula (IB), Formula (IC), Formula (I'), Formula (I'A), Formula (PB), Formula (I'C), Formula (I'D), Formula (I'E), Formula (I'F), Formula (I'G), Formula (I'C'), Formula (I'D'), Formula (I'E'), Formula (I'F'), Formula (I'G'), and Formula (II) in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions.

The term "therapeutically effective amounts" is meant to describe an amount of compound of the present invention effective to produce the desired therapeutic effect. Such amounts generally vary according to a number of factors well within the purview of ordinarily skilled artisans given the description provided herein to determine and account for. These include, without limitation: the particular subject, as well as its age, weight, height, general physical condition, and medical history; the particular compound used, as well as the carrier in which it is formulated and the route of administration selected for it; and, the nature and severity of the condition being treated.

The term "pharmaceutical composition" means a composition comprising a compound of Formula (I), Formula (IA), Formula (IB), Formula (IC), Formula (I'), Formula (I'A), Formula (I'B), Formula (I'C), Formula (I'D), Formula (I'E), Formula (I'F), Formula (I'G), Formula (I'C'), Formula (I'D'), Formula (I'E'), Formula (I'F'), Formula (I'G'), and Formula (II) and at least one component comprising pharmaceutically acceptable carriers, diluents, adjuvants, excipients, or vehicles, such as preserving agents, fillers, disintegrating agents, wetting agents, emulsifying agents, suspending agents, sweetening agents, flavoring agents, perfuming agents, antibacterial agents, antifungal agents, lubricating agents and dispensing agents, depending on the nature of the mode of administration and dosage forms. Examples of suspending agents include ethoxylated isostearyl alcohols, polyoxyethylene sorbitol and sorbitan esters, microcrystalline cellulose, aluminum metahydroxide, bentonite, agar-agar and tragacanth, or mixtures of these substances. Prevention of the action of microorganisms can be ensured by various antibacterial and antifungal agents, for example, parabens, chlorobutanol, phenol, sorbic acid, and the like. It may also be desirable to include isotonic agents, for example sugars, sodium chloride, and the like. Prolonged absorption of the injectable pharmaceutical form can be brought about by the use of agents delaying absorption, for example, aluminum monosterate and gelatin. Examples of suitable carriers, diluents, solvents, or vehicles include water, ethanol, polyols, suitable mixtures thereof, vegetable oils (such as olive oil), and injectable organic esters such as ethyl oleate. Examples of excipients include lactose, milk sugar, sodium citrate, calcium carbonate, and dicalcium phosphate. Examples of disintegrating agents include starch, alginic acids, and certain complex silicates. Examples of lubricants include magnesium stearate, sodium lauryl sulphate, talc, as well as high molecular weight polyethylene glycols.

The term "pharmaceutically acceptable" means it is, within the scope of sound medical judgement, suitable for use in contact with the cells of humans and lower animals without undue toxicity, irritation, allergic response and the like, and are commensurate with a reasonable benefit/risk ratio.

The term "pharmaceutically acceptable dosage forms" means dosage forms of the compound of the invention, and includes, for example, tablets, dragees, powders, elixirs, syrups, liquid preparations, including suspensions, sprays, inhalants tablets, lozenges, emulsions, solutions, granules, capsules, and suppositories, as well as liquid preparations for injections, including liposome preparations. Techniques and formulations generally may be found in Remington's Pharmaceutical Sciences, Mack Publishing Co., Easton, Pa., latest edition.

Compounds described herein may contain one or more asymmetric centers and may thus give rise to enantiomers, diastereomers, and other stereoisomeric forms. Each chiral center may be defined, in terms of absolute stereochemistry, as (R)- or (S)-. This technology is meant to include all such possible isomers, as well as mixtures thereof, including racemic and optically pure forms. Optically active (R)- and (S)-, (−)- and (+)-, or (D)- and (L)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

This technology also envisions the "quaternization" of any basic nitrogen-containing groups of the compounds disclosed herein. The basic nitrogen can be quaternized with any agents known to those of ordinary skill in the art including, for example, lower alkyl halides, such as methyl, ethyl, propyl and butyl chloride, bromides and iodides; dialkyl sulfates including dimethyl, diethyl, dibutyl and diamyl sulfates; long chain halides such as decyl, lauryl, myristyl and stearyl chlorides, bromides and iodides; and aralkyl halides including benzyl and phenethyl bromides. Water or oil-soluble or dispersible products may be obtained by such quaternization.

In the characterization of some of the substituents, it is recited that certain substituents may combine to form rings. Unless stated otherwise, it is intended that such rings may exhibit various degrees of unsaturation (from fully saturated to fully unsaturated), may include heteroatoms and may be substituted with lower alkyl or alkoxy.

Compounds of the present invention can be produced according to the general schemes outlined below (Scheme 1, Scheme 1a, Scheme 2, and Scheme 2a).

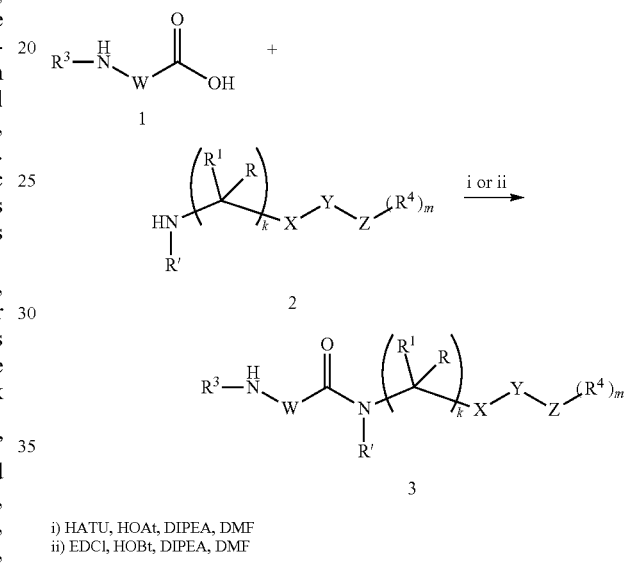

i) HATU, HOAt, DIPEA, DMF
ii) EDCl, HOBt, DIPEA, DMF

Reaction of the carboxylic acid derivative (1) with amine (2) leads to formation of the final product (3). The reaction can be carried out in a variety of solvents, for example in methylene chloride ($CH_2Cl_2$); tetrahydrofuran (THF), dimethylformamide (DMF), or other such solvents or in the mixture of such solvents.

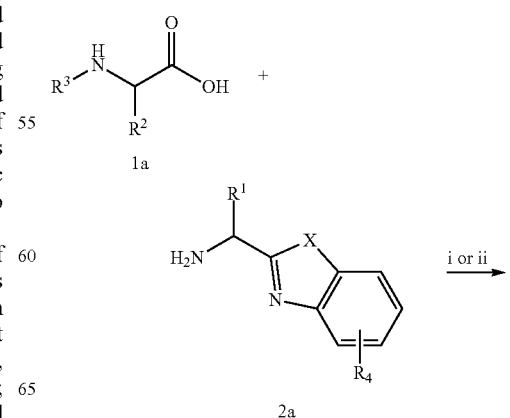

-continued

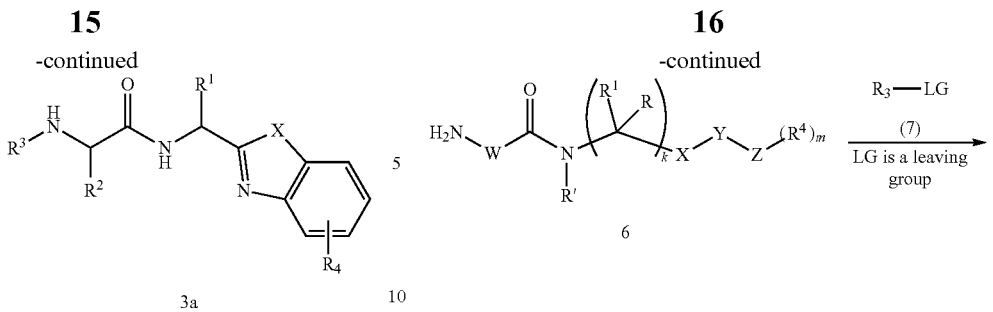

i) HATU, HOAt, DIPEA, DMF
ii) EDCl, HOBt, DIPEA, DMF

Compounds of Formula (I) wherein W is $CHR^2$, k is 1, X is bicyclic heteroaryl, and Y and Z are absent can be prepared according to Scheme 1a. Reaction of the carboxylic acid derivative (1a) with amine (2a) leads to formation of the final product (3a). The reaction can be carried out in a variety of solvents, for example in methylene chloride ($CH_2Cl_2$), tetrahydrofuran (TEE), dimethylformamide (DMF), or other such solvents or in the mixture of such solvents.

Scheme 2

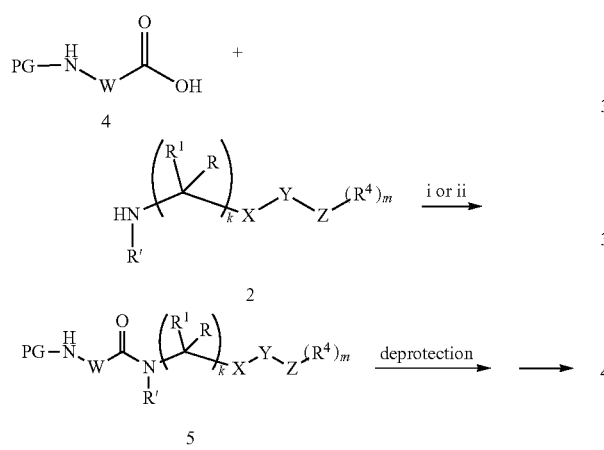

i) HATU, HOAt, DIPEA, DMF
ii) EDCl, HOBt, DIPEA, DMF
PG is a protecting group

Reaction of the carboxylic acid derivative (4) with amine (2) leads to formation of the compound (5). The reaction can be carried out in a variety of solvents, for example in methylene chloride ($CH_2Cl_2$); tetrahydrofuran (THF), dimethylformamide (DMF), or other such solvents or in the mixture of such solvents. During the reaction process, the non-participating carboxylic acids or amines on the reacting set of amino acids or peptide fragments can be protected by a suitable protecting group (PG) which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Following the deprotection, amine (6) is reacted with $R_3$-LG (7) (wherein LG is a suitable leaving group) to form final product (8).

Scheme 2a

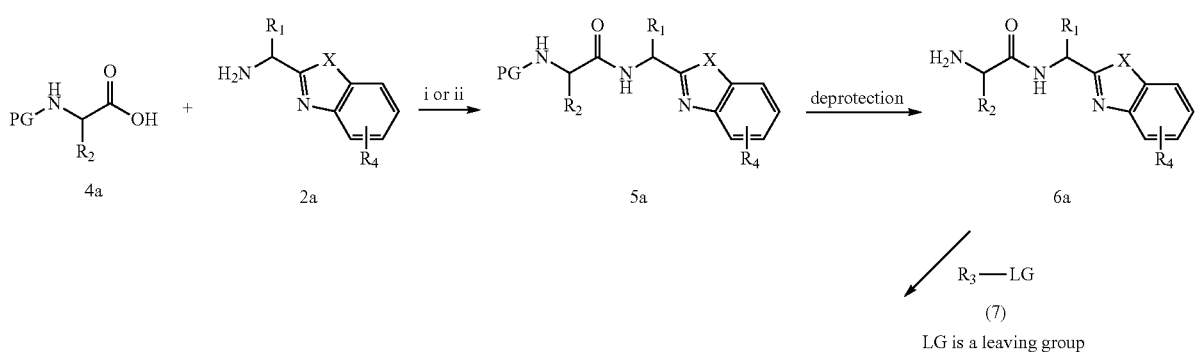

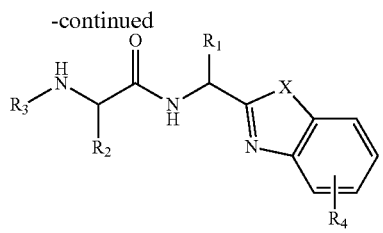

i) HATU, HOAt, DIPEA, DMF
ii) EDCl, HOBt, DIPEA, DMF
  PG is a protecting group

Compounds of Formula (I) wherein W is CHR², k is 1, X is bicyclic heteroaryl, and Y and Z are absent can be prepared according to Scheme 2a. Reaction of the carboxylic acid derivative (4a) with amine (2a) leads to formation of the compound (5a). The reaction can be carried out in a variety of solvents, for example in methylene chloride (CH$_2$Cl$_2$), tetrahydrofuran (THF), dimethylformamide (DMF), or other such solvents or in the mixture of such solvents. During the reaction process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Following the deprotection, amine (6a) is reacted with R$_3$-LG (7) (wherein LG is a suitable leaving group) to form final product (8a).

Compounds of the present invention can also be prepared according to the general schemes outlined below (Scheme 3 and Scheme 4).

Scheme 3

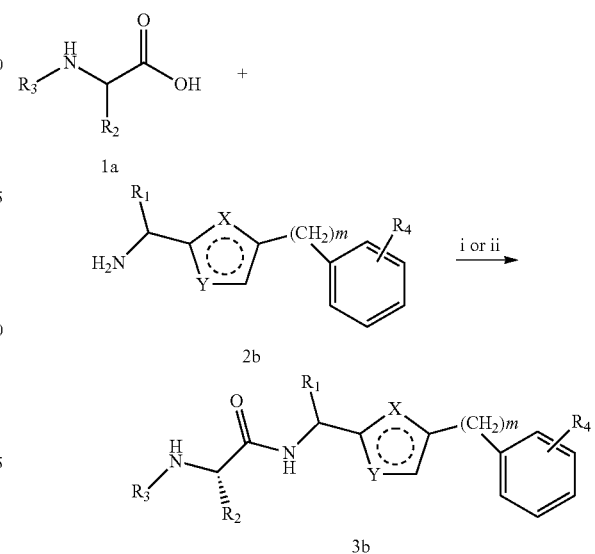

i) HATU, HOAt, DIPEA, DMF
ii) EDCl, HOBt, DIPEA, DMF

Compounds of Formula (I) wherein W is CHR², k is 1, X is monocyclic heteroaryl, Y is —(CH$_2$)$_m$—, and Z is aryl can be prepared according to Scheme 3. Reaction of the carboxylic acid derivative (1a) with amine (2b) leads to formation of the final product (3b). The reaction can be carried out in a variety of solvents, for example in methylene chloride (CH$_2$Cl$_2$), tetrahydrofuran (THF), dimethylformamide (DMF), or other such solvents or in the mixture of such solvents.

Scheme 4

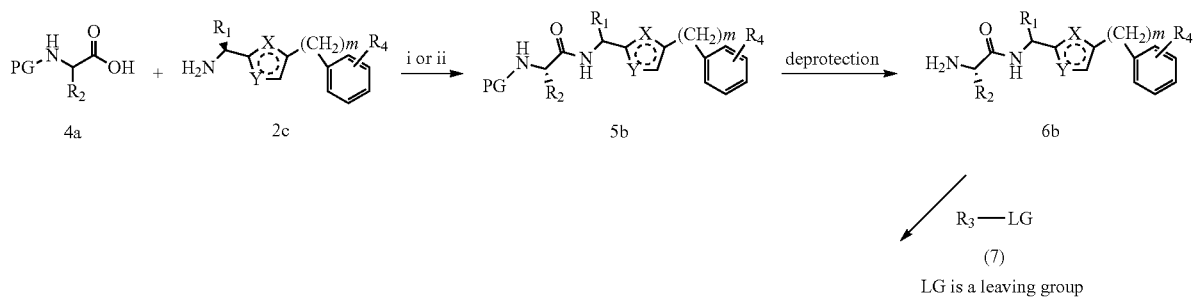

LG is a leaving group

-continued

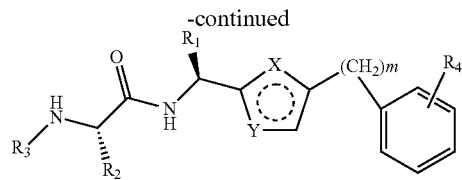

8b i) HATU, HOAt, DIPEA, DMF
ii) EDCl, HOBt, DIPEA, DMF
  PG is a protecting group Compounds of Formula (I) wherein W is $CHR^2$, k is 1, X is monocyclic heteroaryl, Y is $—(CH_2)_m—$, and Z is aryl can also be prepared according to Scheme 4. Reaction of the carboxylic acid derivative (4a) with amine (2c) leads to formation of the compound (5b). The reaction can be carried out in a variety of solvents, for example in methylene chloride ($CH_2Cl_2$), tetrahydrofuran (THF), dimethylformamide (DMF), or other such solvents or in the mixture of such solvents. During the reaction process, the non-participating carboxylic acids or amines on the reacting set of amino acids or peptide fragments can be protected by a suitable protecting group which can be selectively removed at a later time if desired. A detailed description of these groups and their selection and chemistry is contained in "The Peptides, Vol. 3", Gross and Meinenhofer, Eds., Academic Press, New York, 1981, which is hereby incorporated by reference in its entirety. Thus, useful protective groups for the amino group are benzyloxycarbonyl (Cbz), t-butyloxycarbonyl (t-BOC), 2,2,2-trichloroethoxycarbonyl (Troc), t-amyloxycarbonyl, 4-methoxybenzyloxycarbonyl, 2-(trichlorosilyl)ethoxycarbonyl, 9-fluorenylmethoxycarbonyl (Fmoc), phthaloyl, acetyl (Ac), formyl, trifluoroacetyl, and the like. Following the deprotection, amine (6b) is reacted with $R^3$-LG (7) (wherein is a suitable leaving group) to form final product (8b).

In one embodiment, compound has the Formula (IA):

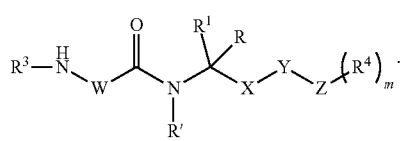

(IA)

In another embodiment, compound has the Formula (IB):

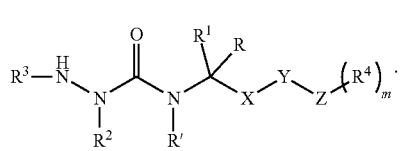

(IB)

In another embodiment, compound has the Formula (IC):

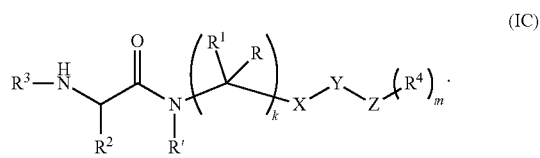

(IC)

One embodiment relates to the compound of Formulae (I) where $R^1$ is H or Me.

Another embodiment relates to the compound of Formulae (I) where R and $R^1$ are taken together with the carbon to which they are attached to form

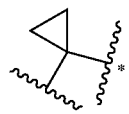

group, and wherein

is the point of attachment to NH; and

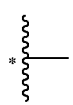

is the point of attachment to X.

Another embodiment relates to the compound of Formulae (I) where R and $R^1$ are taken together with the carbon to which they are attached to form

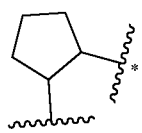 [SMILES: *C1CCCC1*]

group, and wherein
is the point of attachment to NH; and
is the point of attachment to X.
A further embodiment relates to the compound of Formulae (I) where R² is selected from the group consisting of
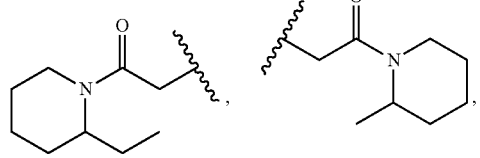
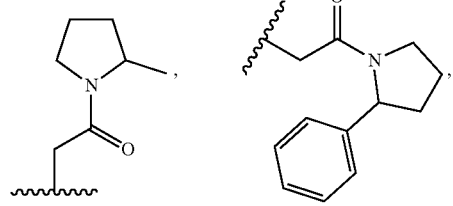
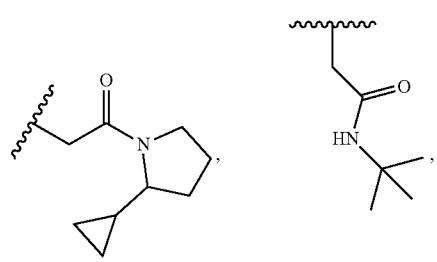
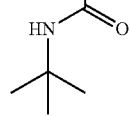
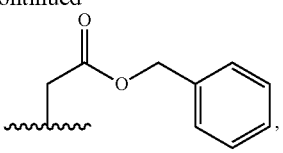
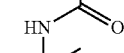
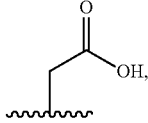
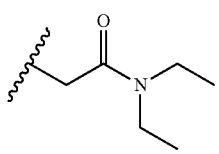
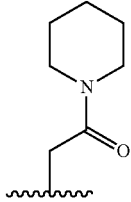
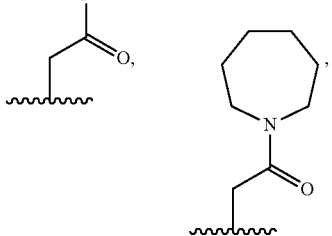
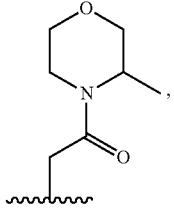
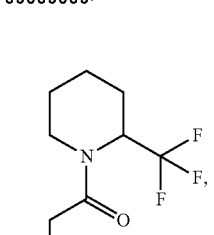
wherein
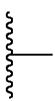
is the point of attachment to the corresponding carbon atom of the structure of Formula (I).

Yet another embodiment relates to the compound of Formulae (I) where $R^3$ is selected from the group consisting of H, Boc,
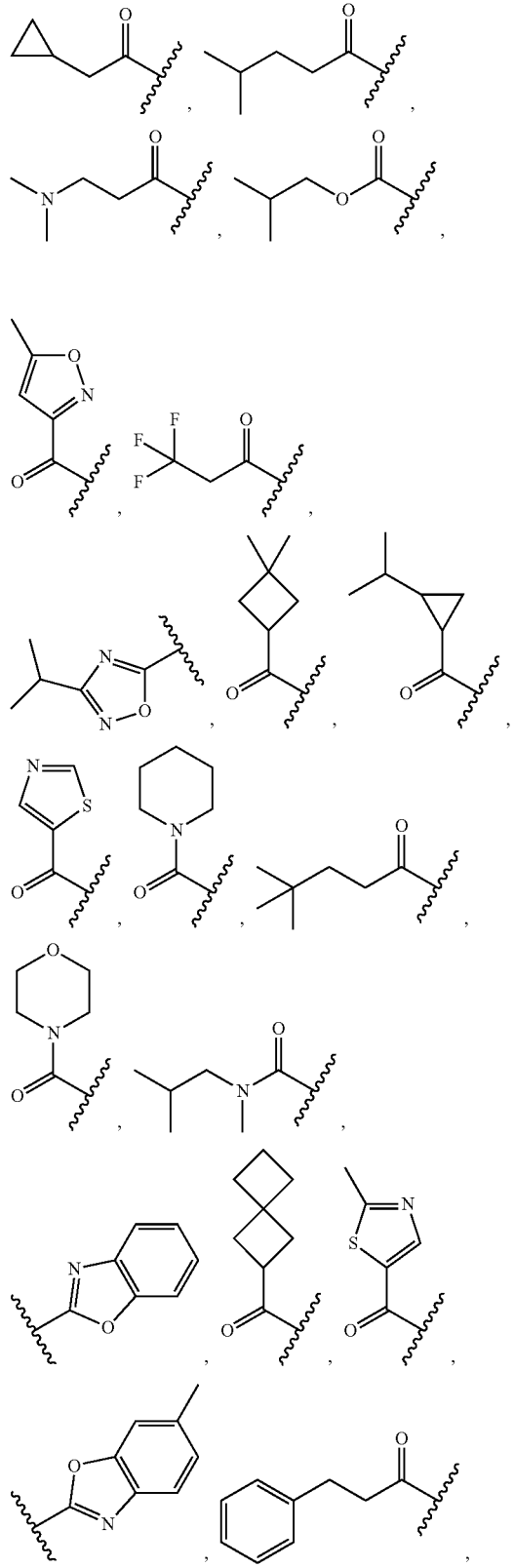
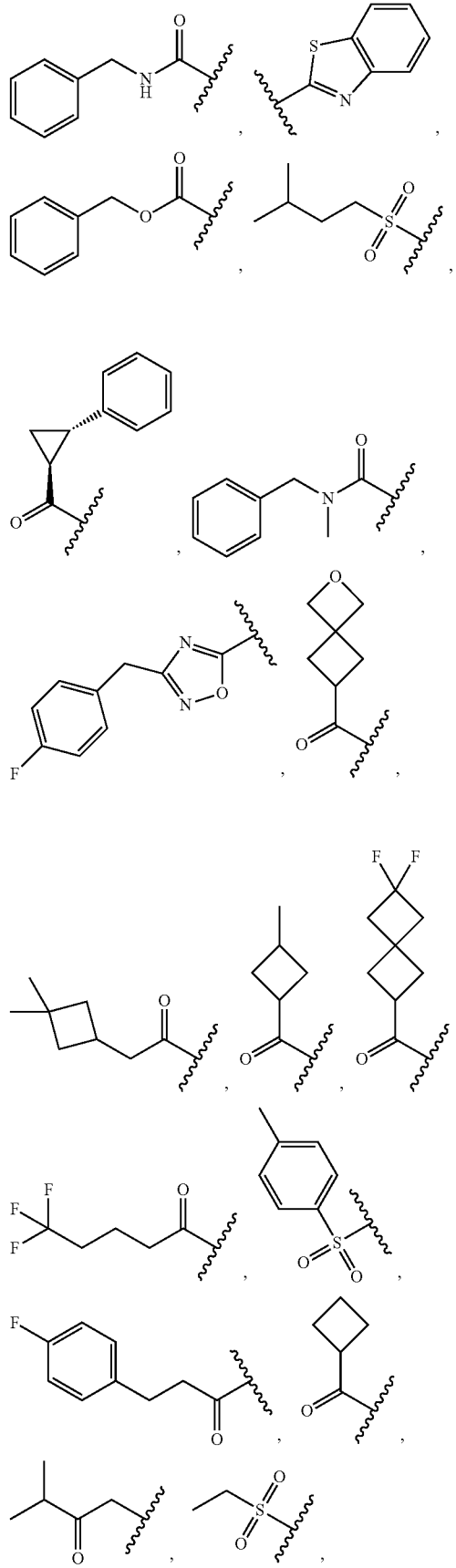

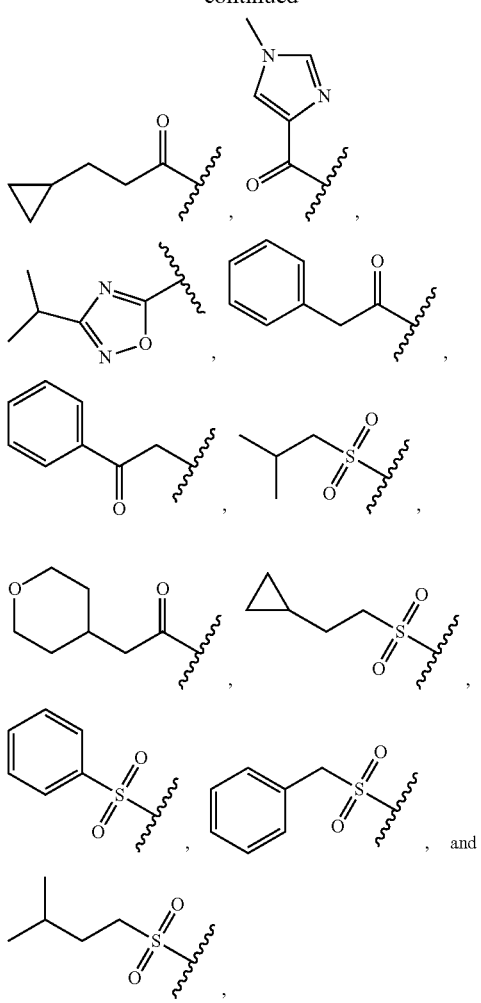

wherein

is the point of attachment to the corresponding carbon atom of the structure of Formula (I).

Another embodiment relates to the compound of Formulae (I) where $R^4$ is H, Me, F, $NH_2$, or NHBoc.

Yet another embodiment relates to the compound of Formulae (I) where X is selected from the group consisting of

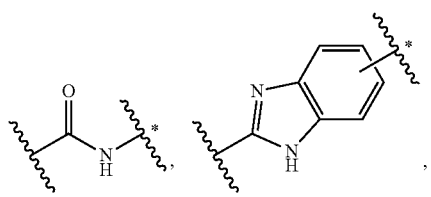

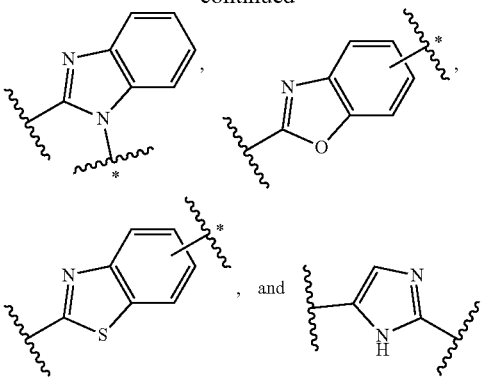

wherein

is the point of attachment to $C(R^1)(R^2)$ moiety;

is the point of attachment to Y, Z, or $R^4$.

Yet another embodiment relates to the compound of Formulae (I) where Y is $—CH_2—$.

A further embodiment relates to the compound of Formulae (I) where Z is

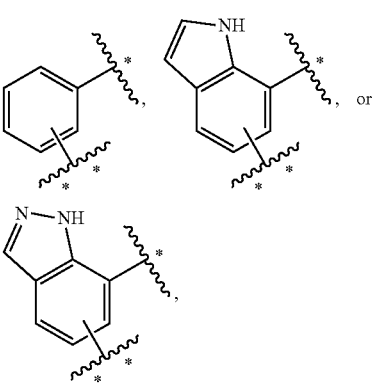

and
wherein

is the point of attachment to Y or X;
is the point of attachment to R⁴.
Another embodiment relates to the compound of Formulae (I) where the compound has a structure selected from the group consisting of:
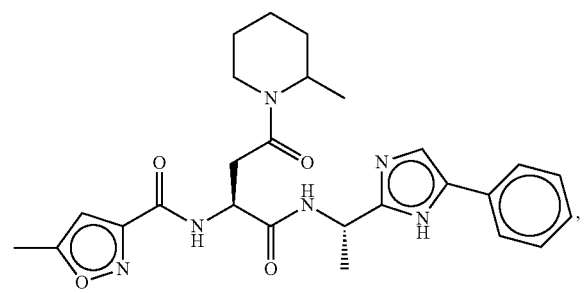,
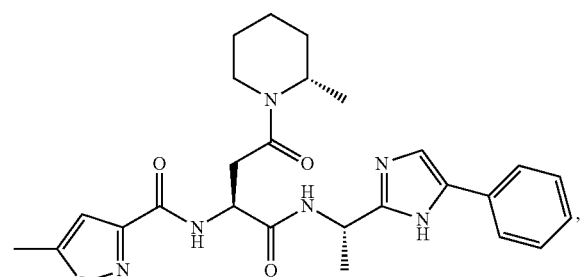,
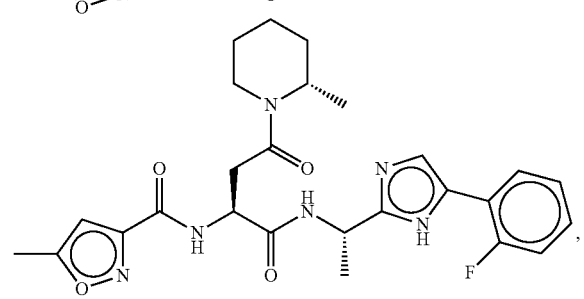,
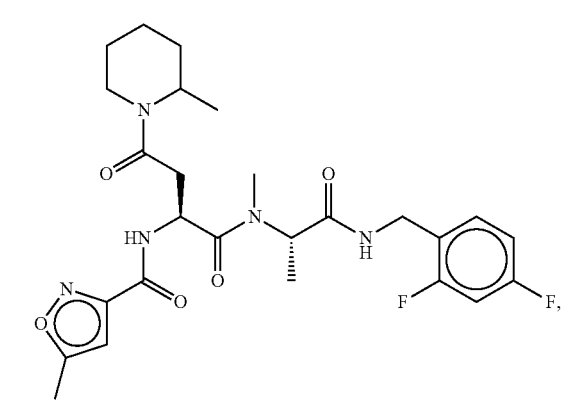,
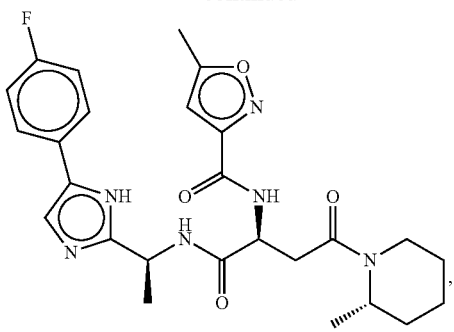,
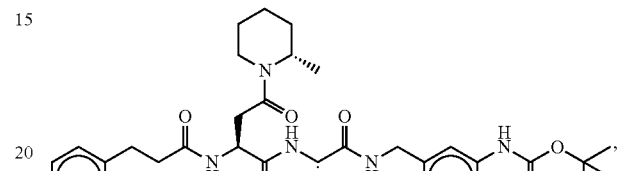,
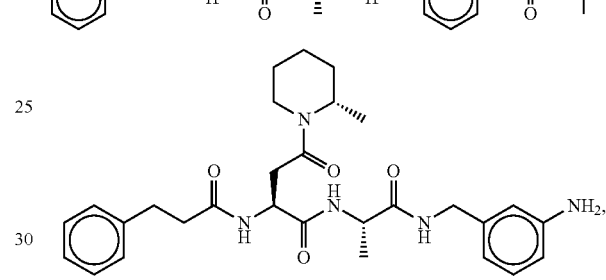,
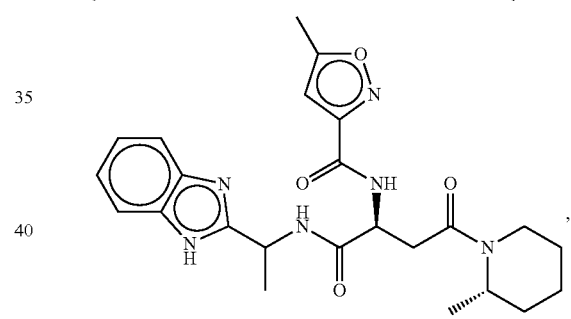,
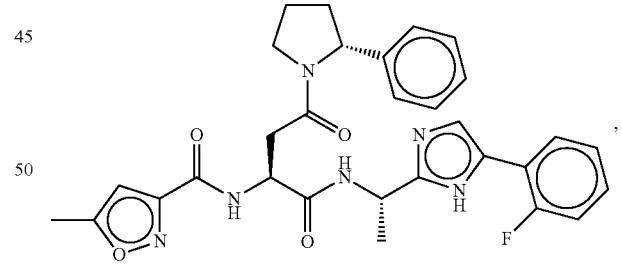,
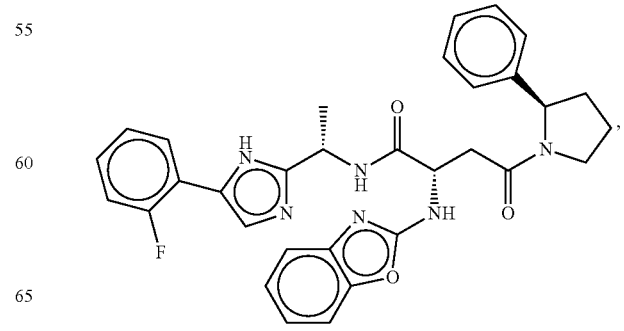,

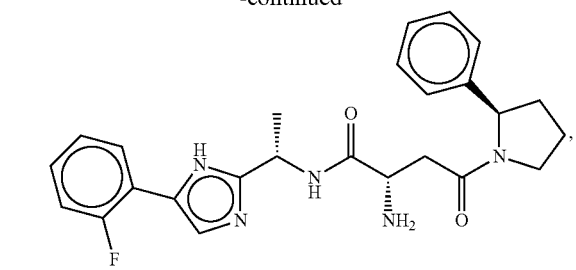
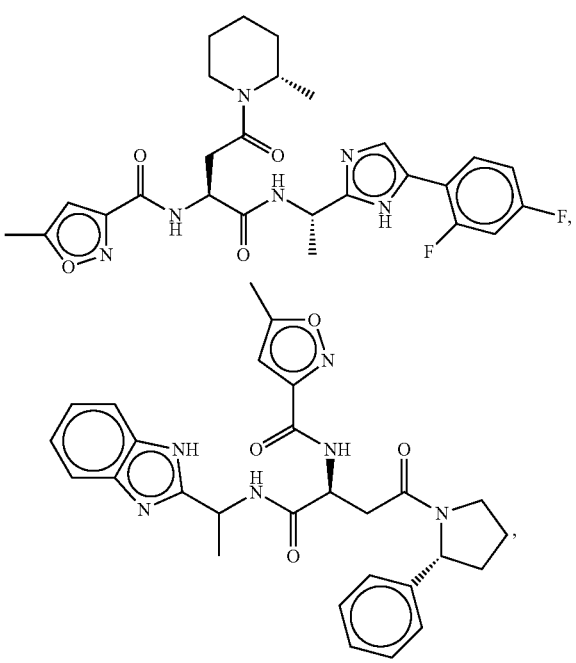
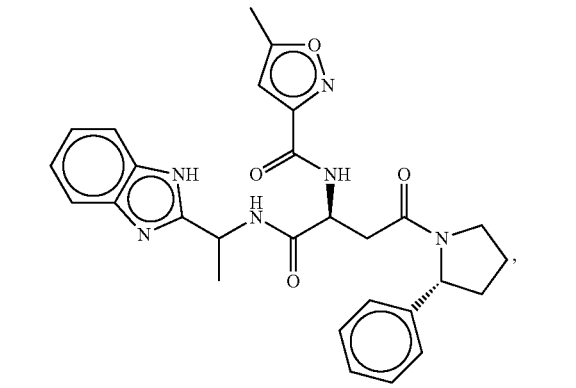
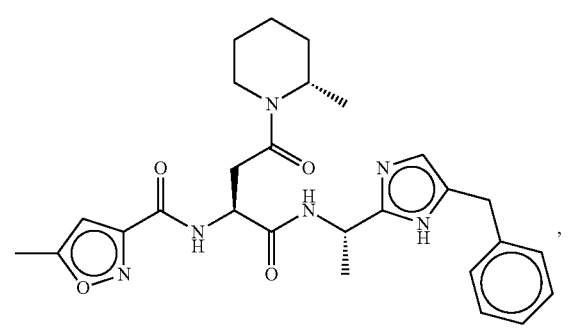
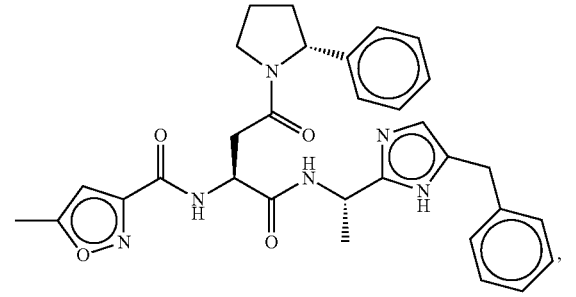
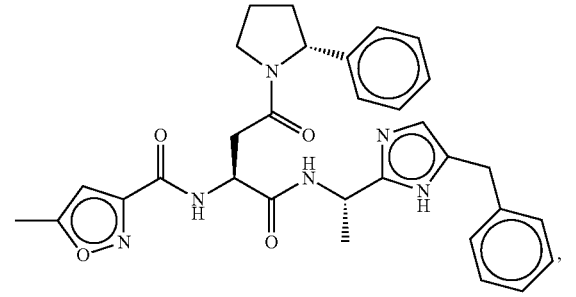
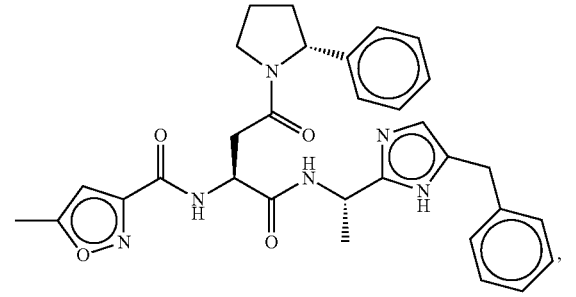
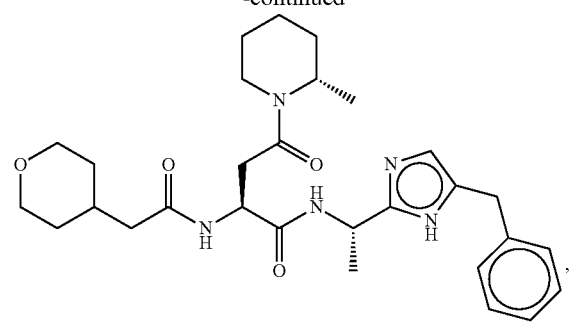
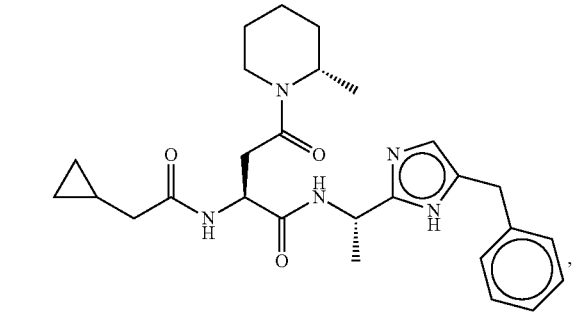
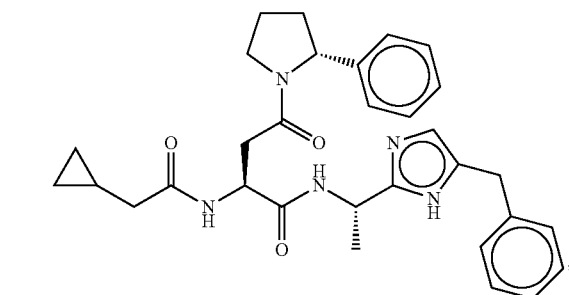
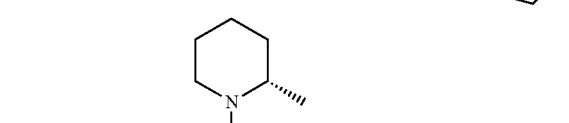
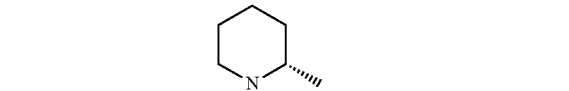
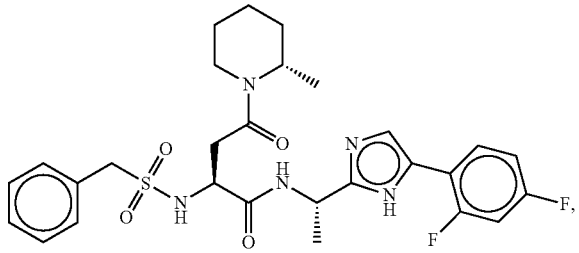

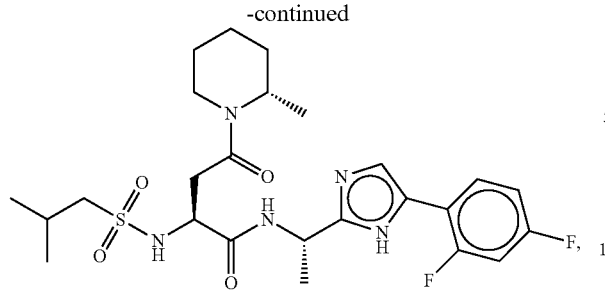

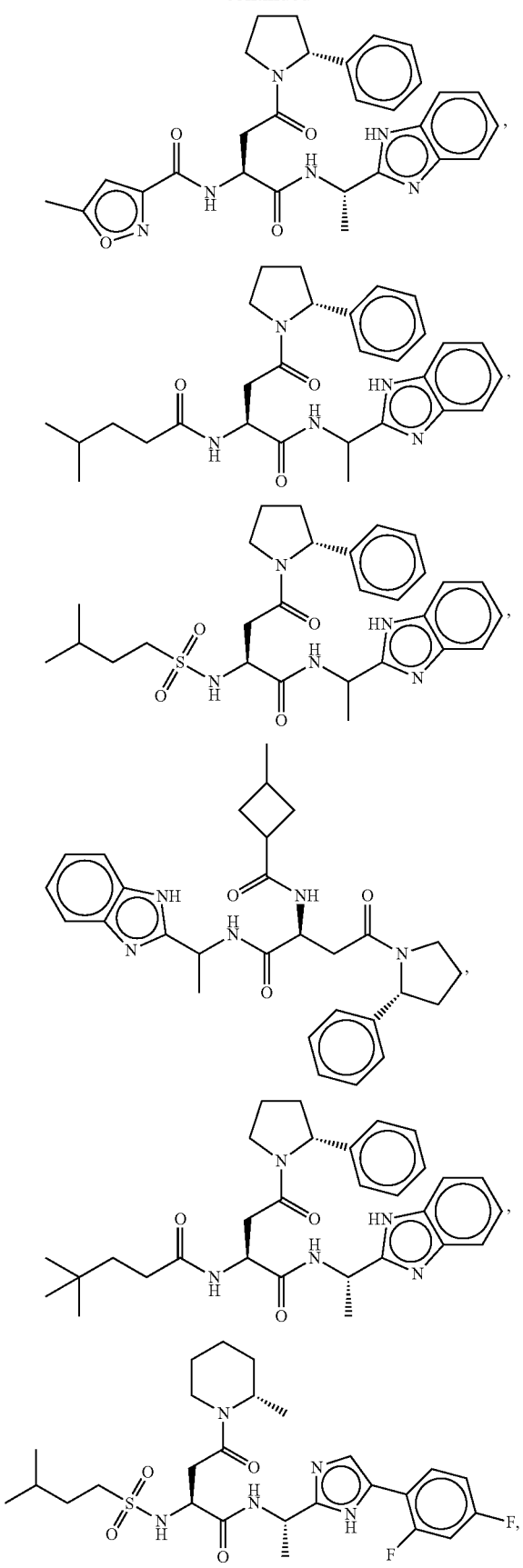
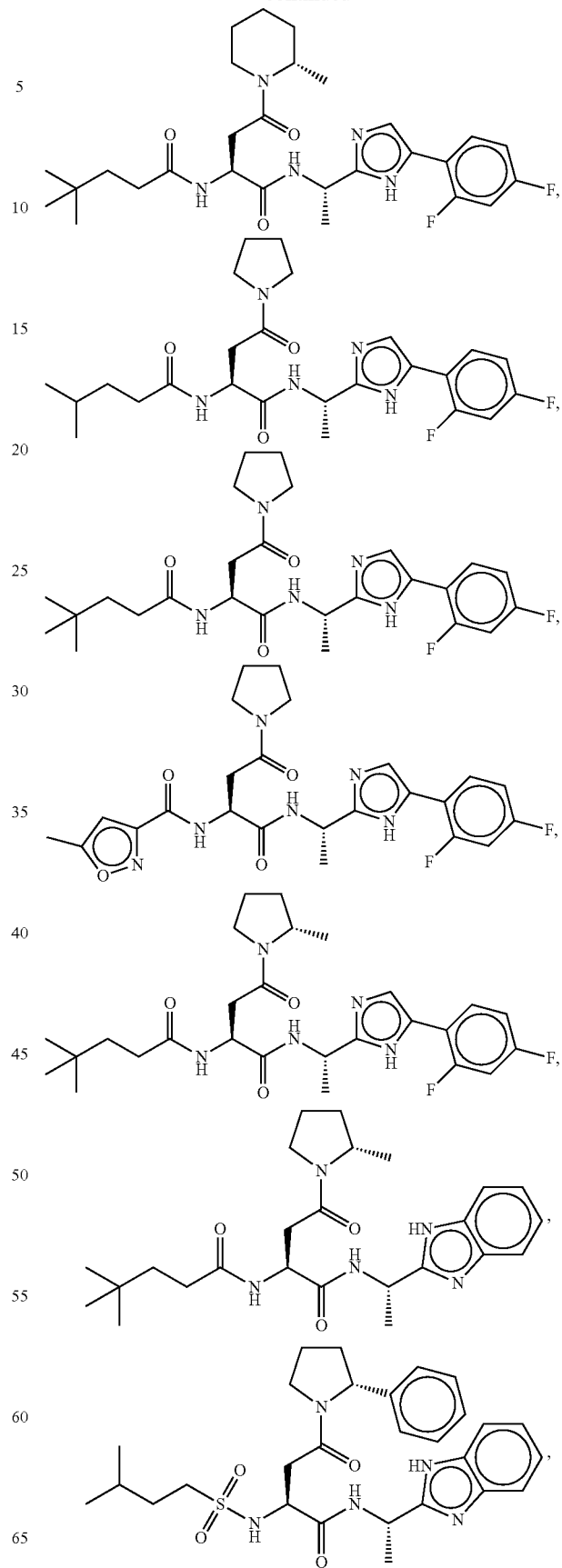

35
-continued
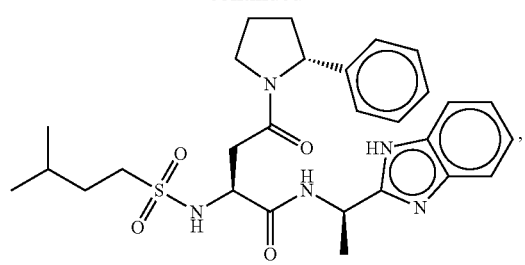
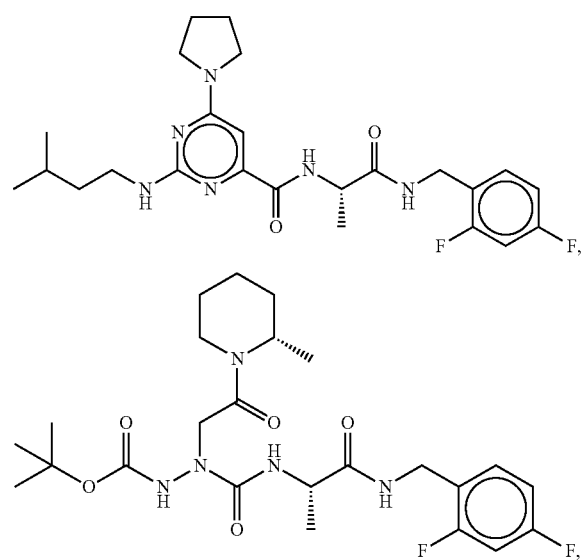
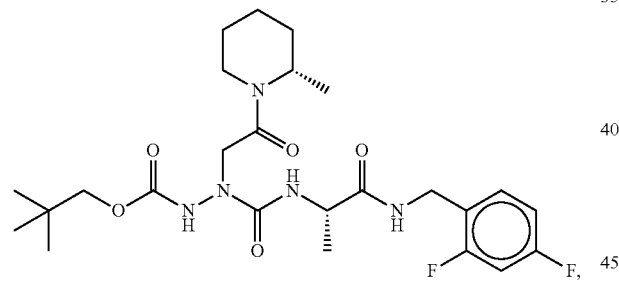
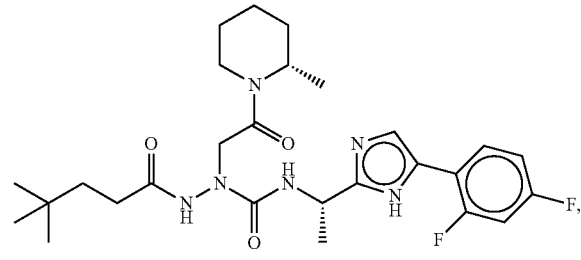
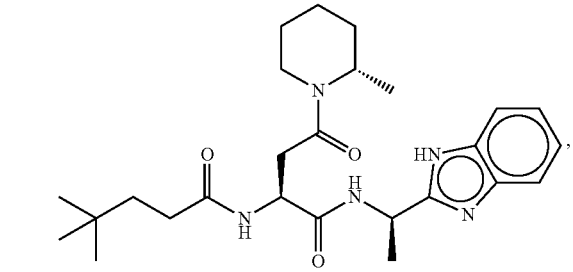
36
-continued
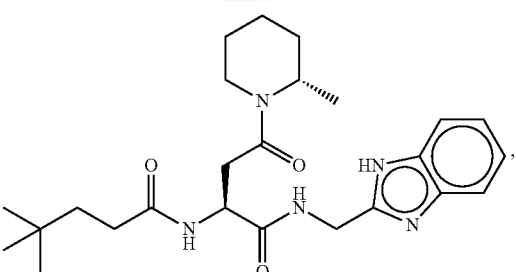
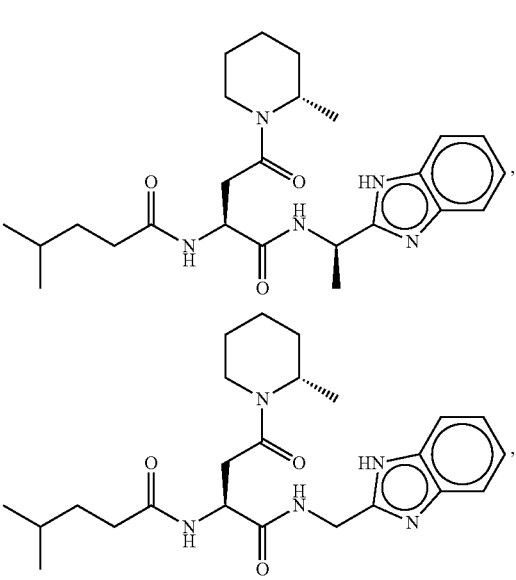
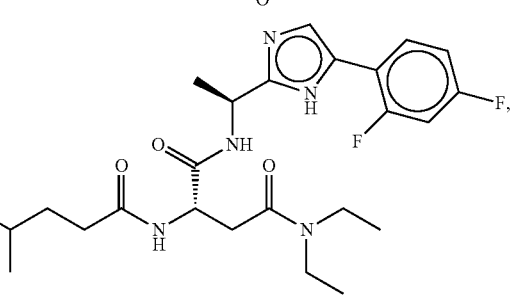
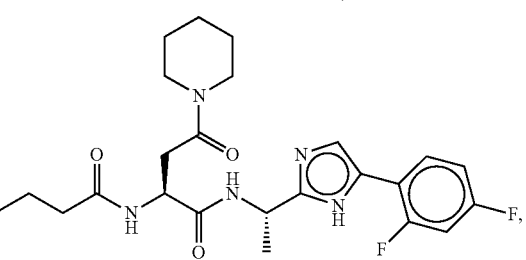
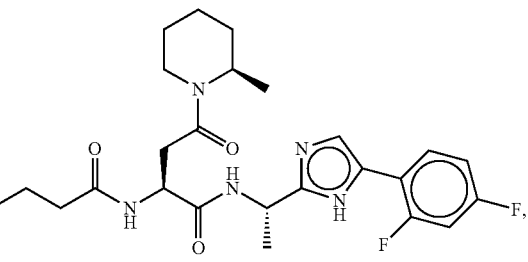

37
-continued
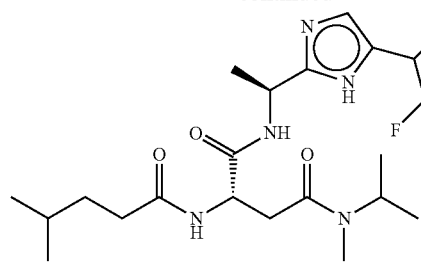
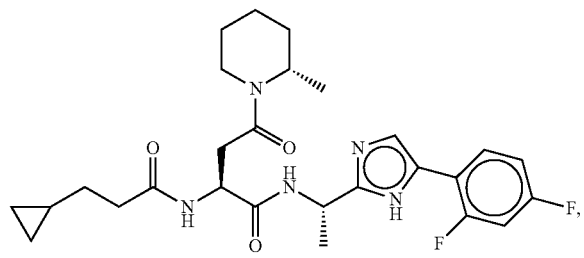
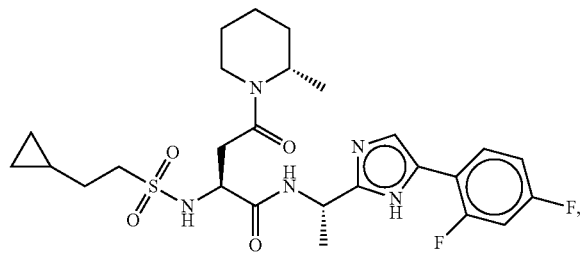
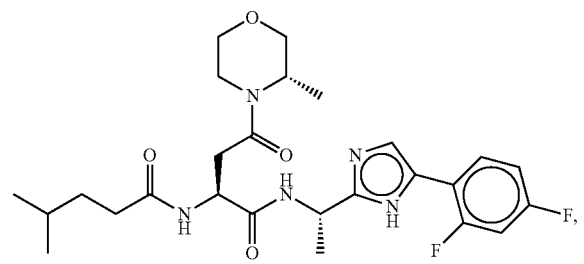
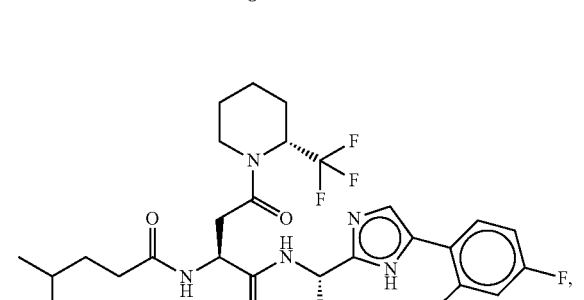
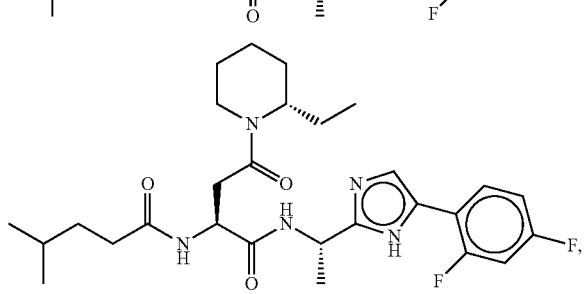
38
-continued
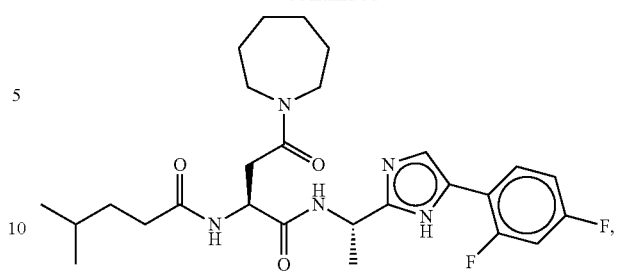
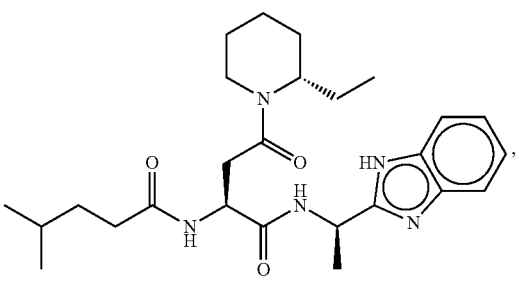
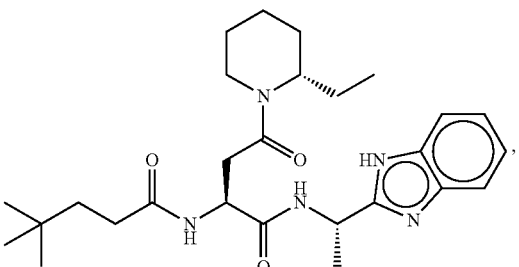
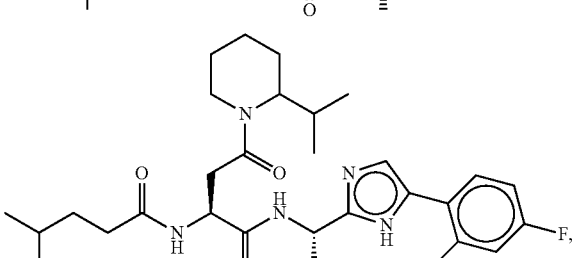
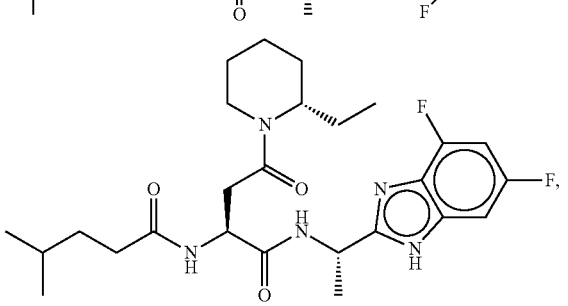
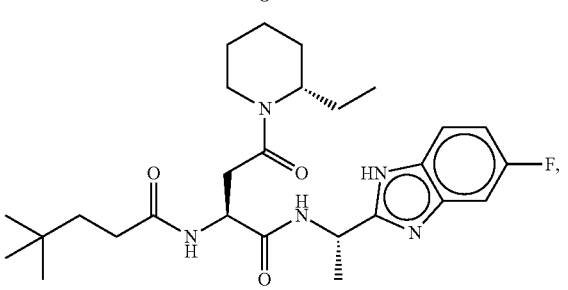

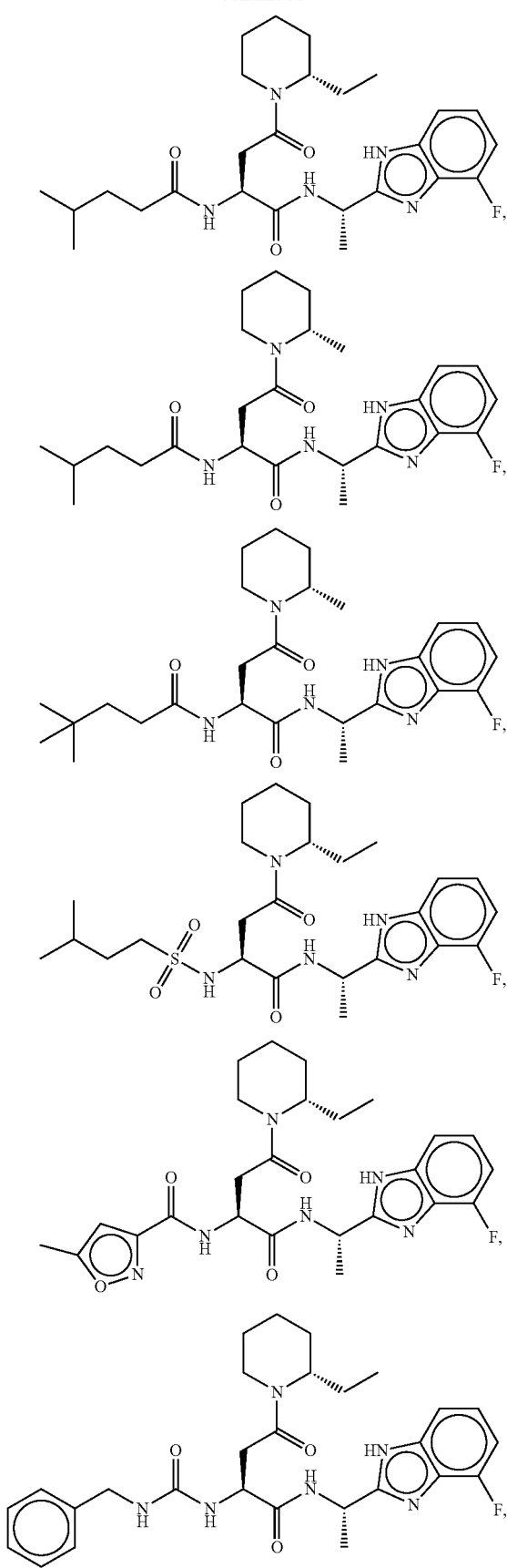
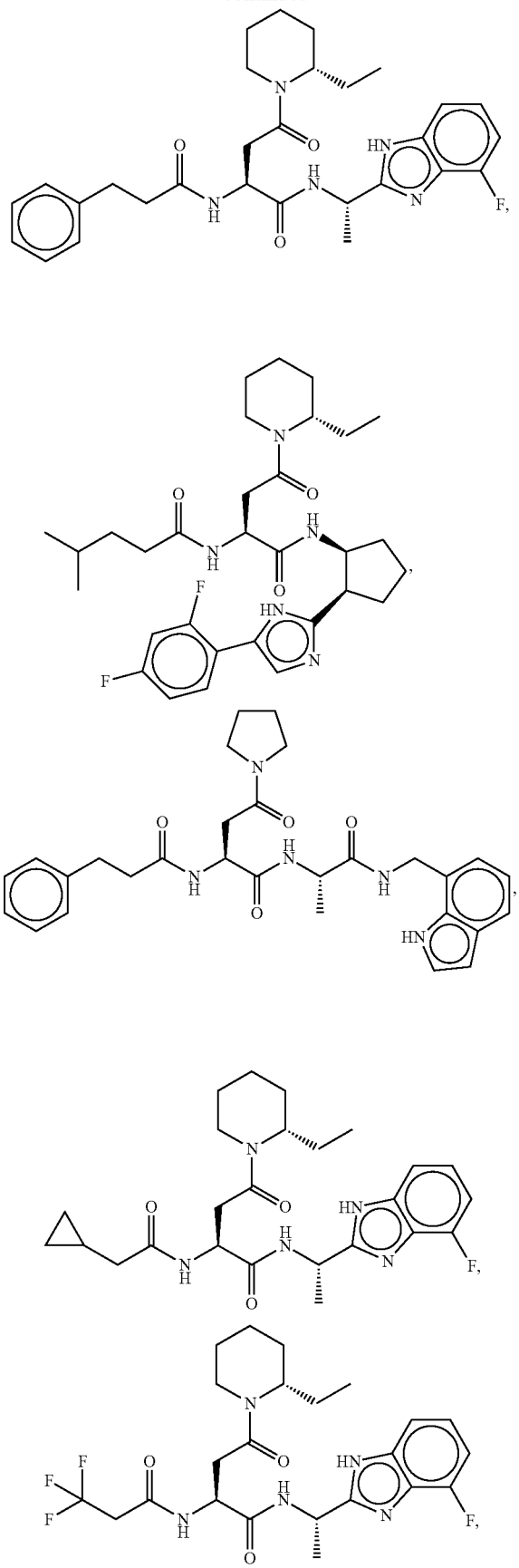

-continued
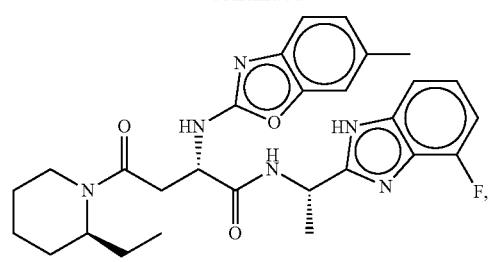
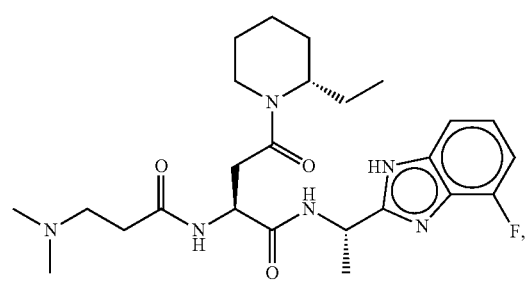
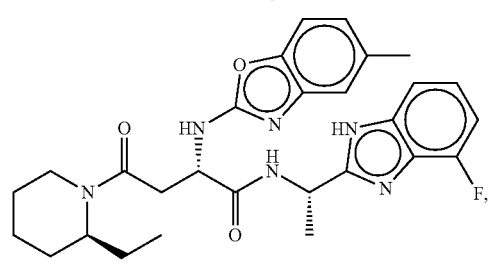
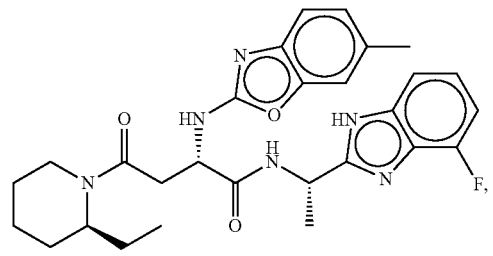
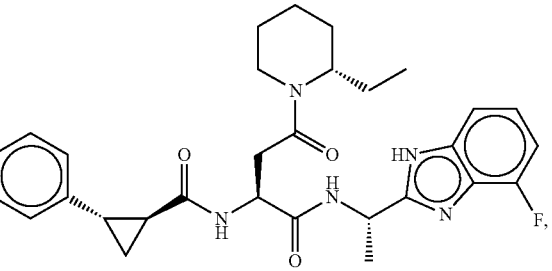
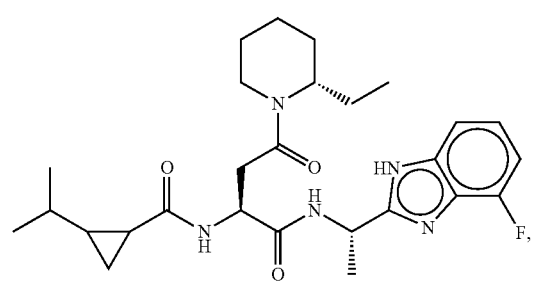
-continued
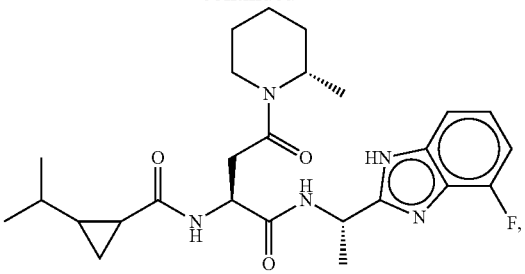
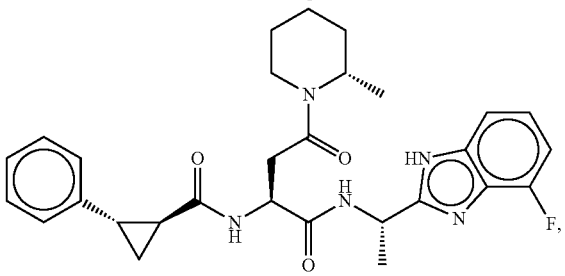
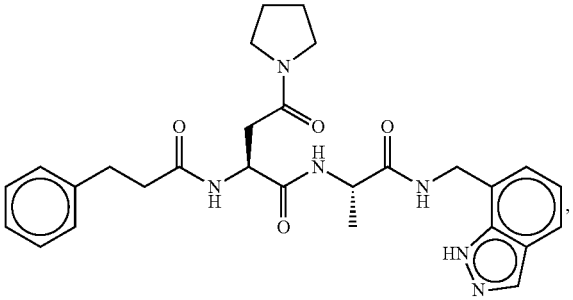
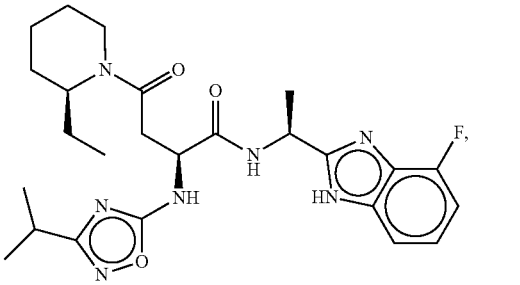
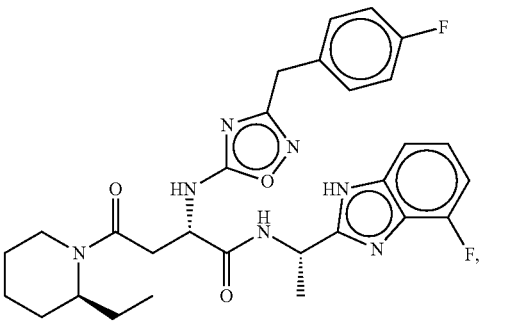
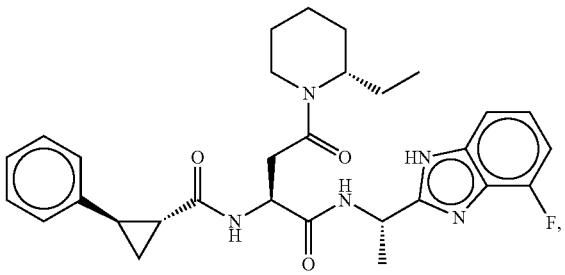

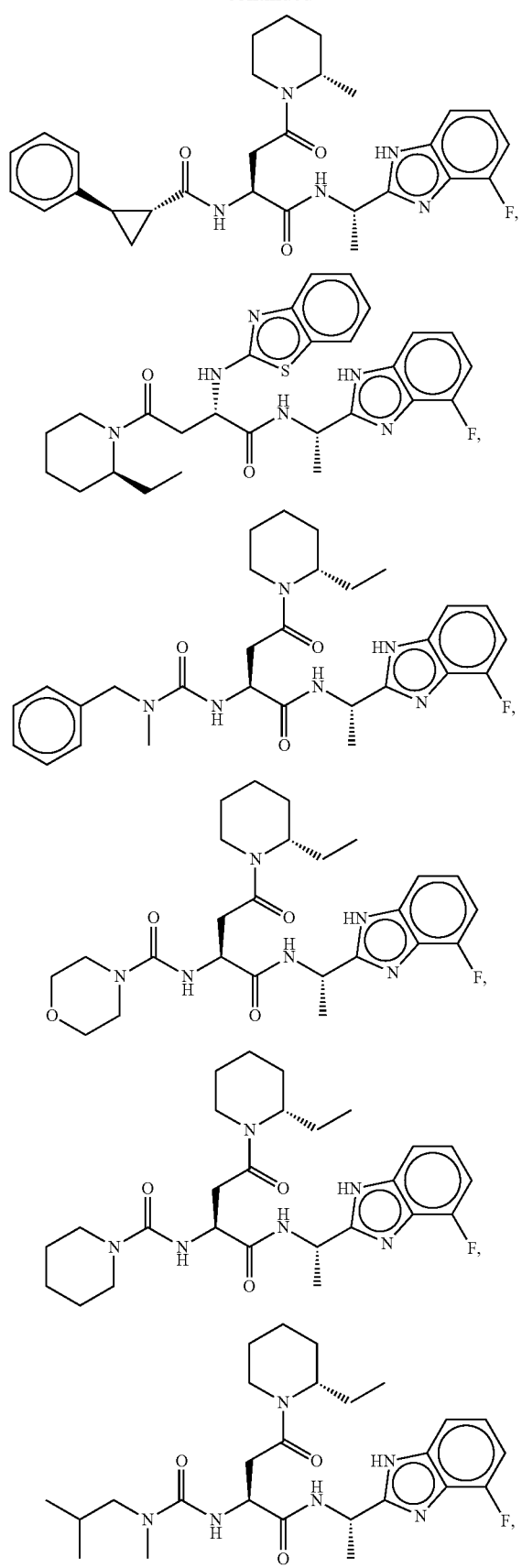
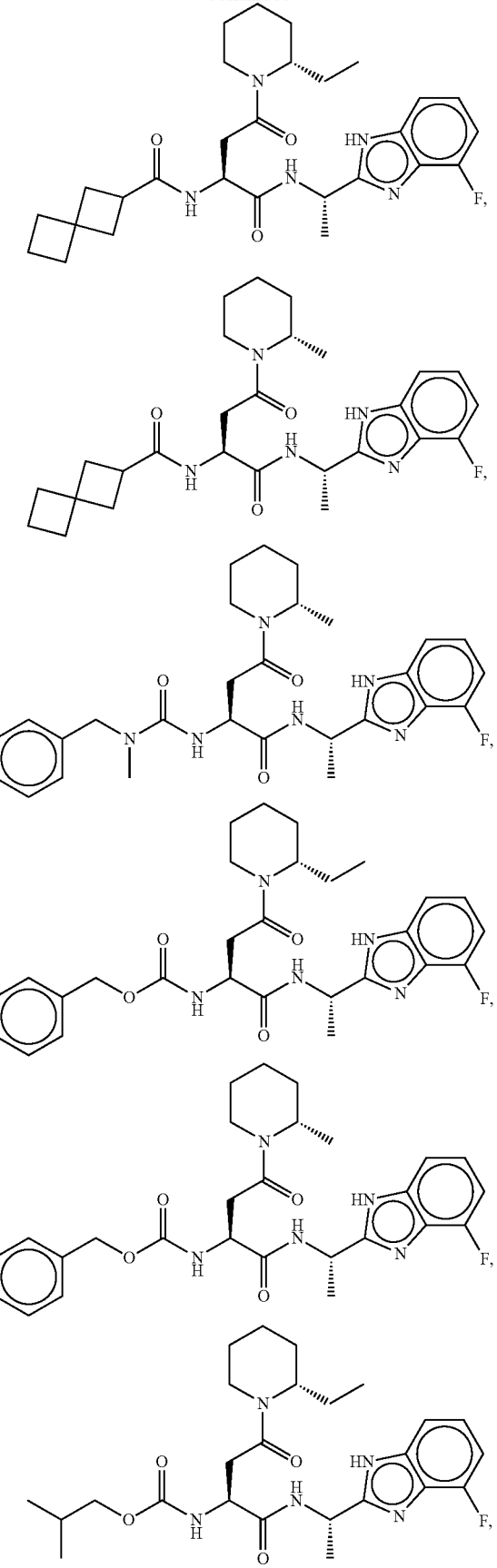

45
-continued
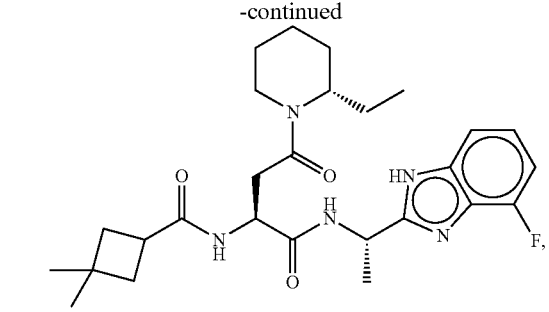
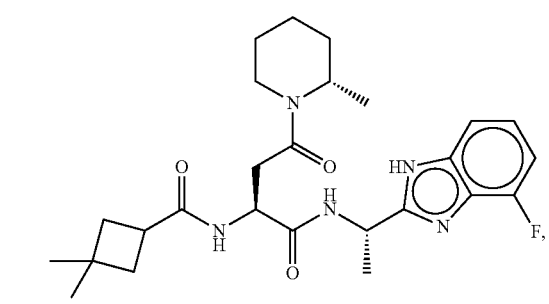
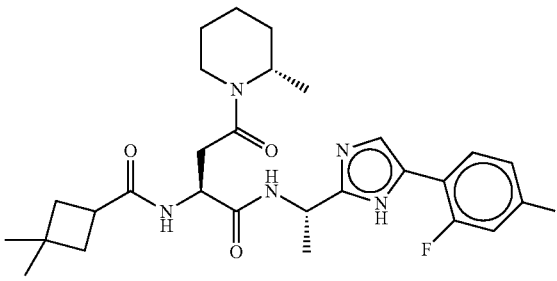
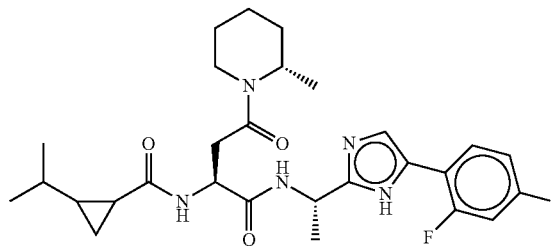
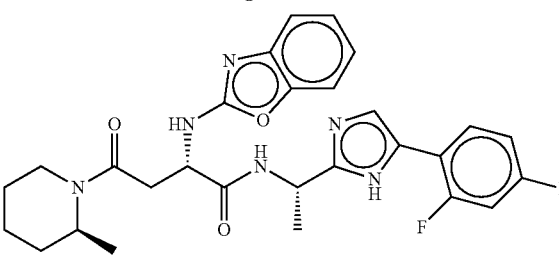
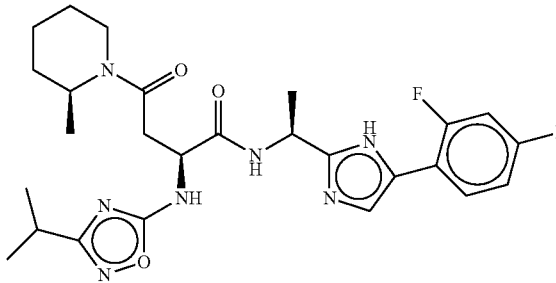
46
-continued
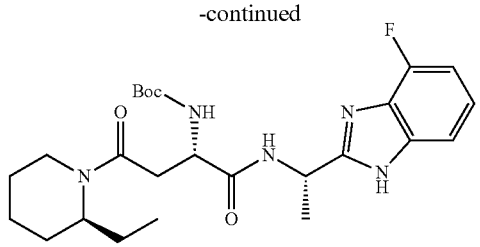
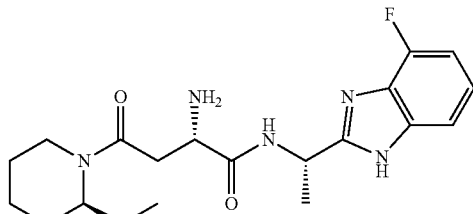
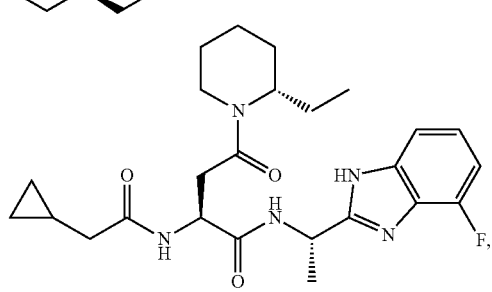
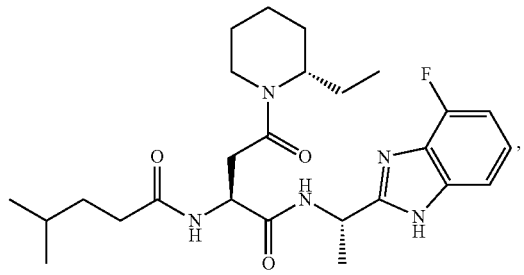
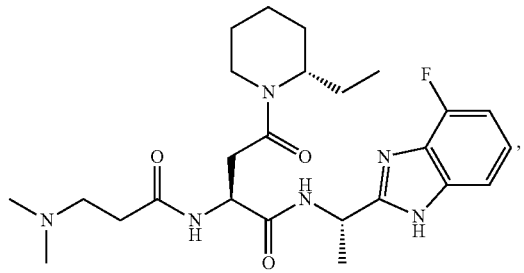
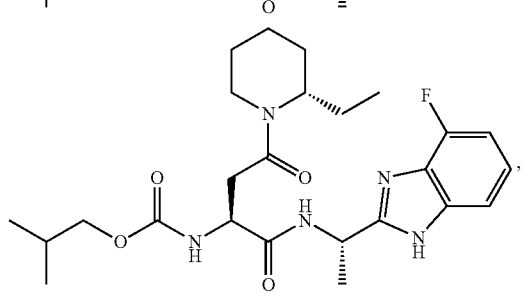

-continued
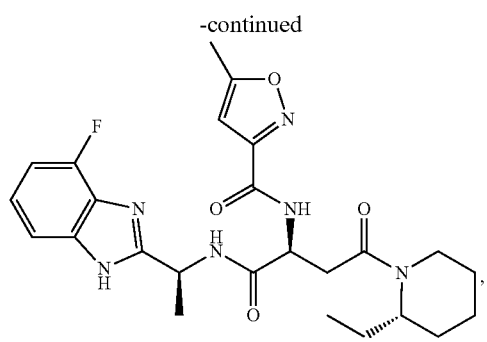
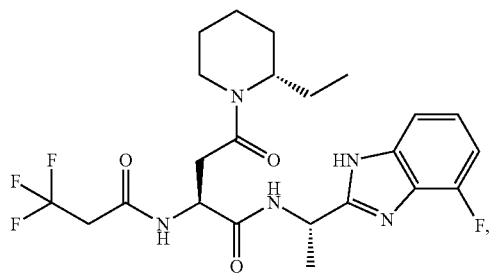
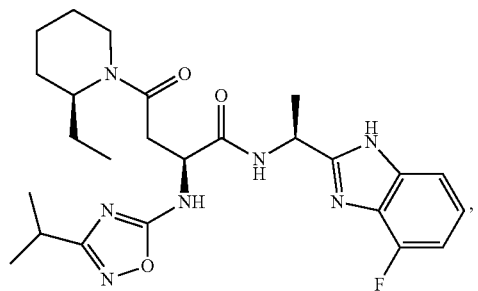
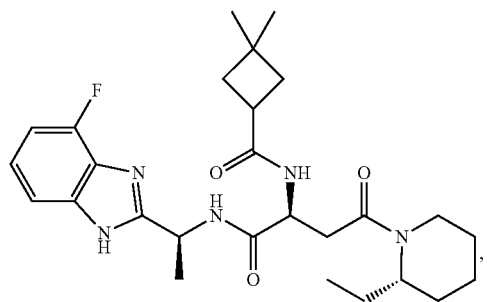
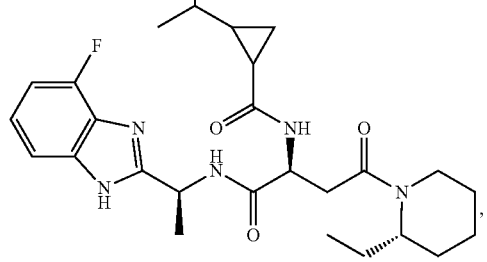
-continued
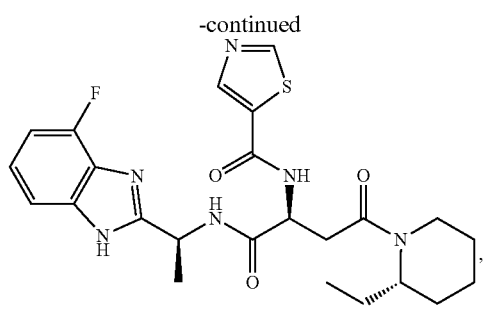
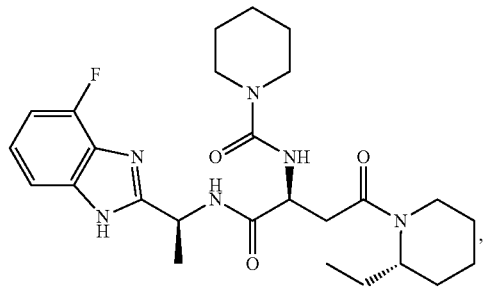
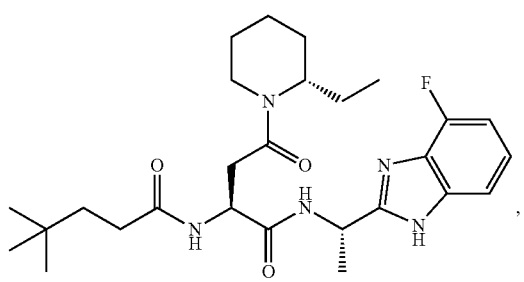
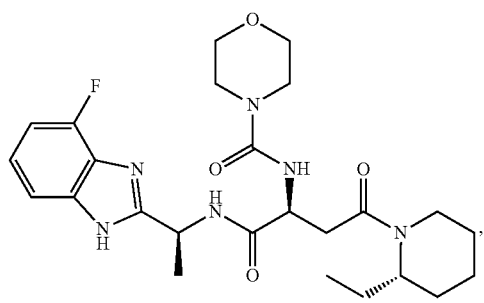
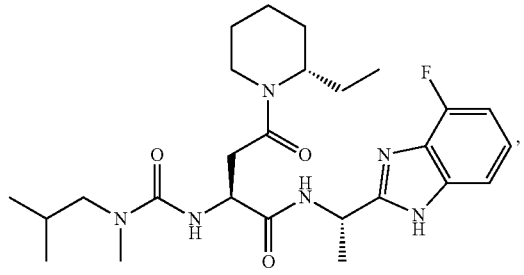
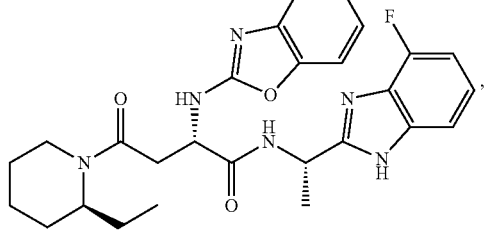

49
-continued
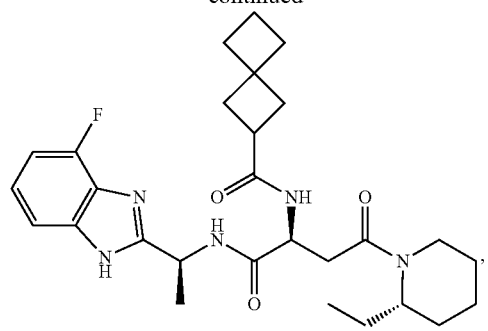
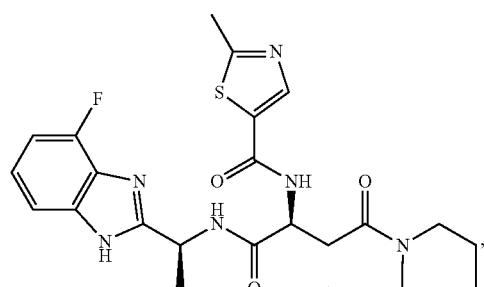
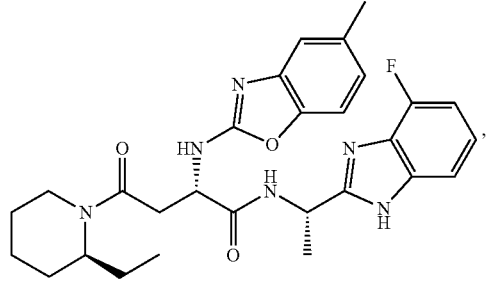
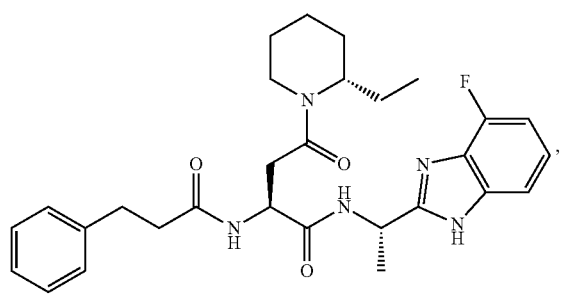
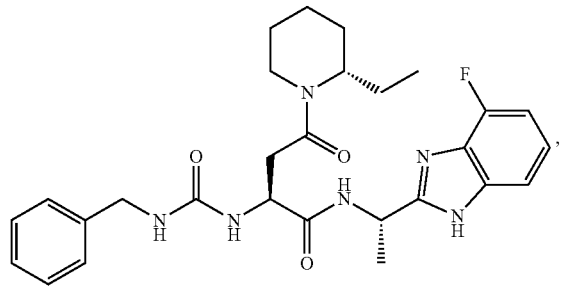
50
-continued
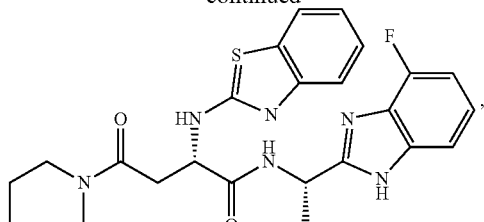
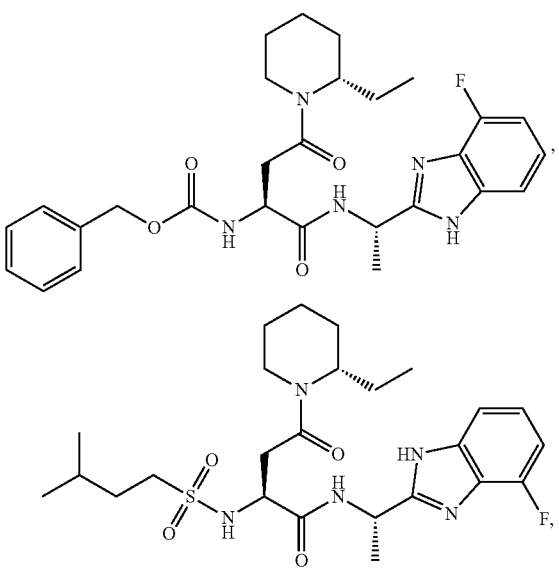
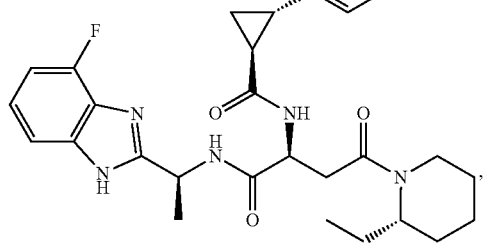
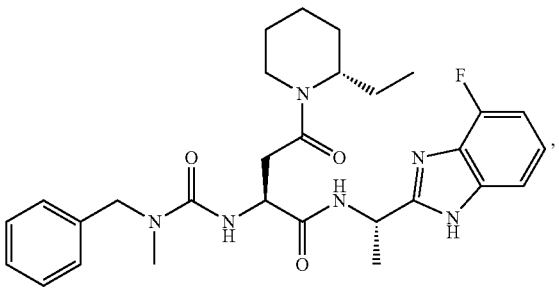

51
-continued
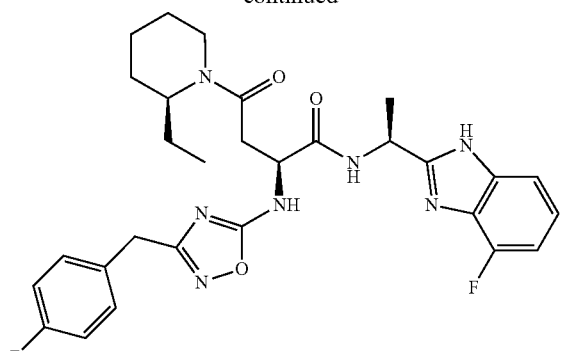
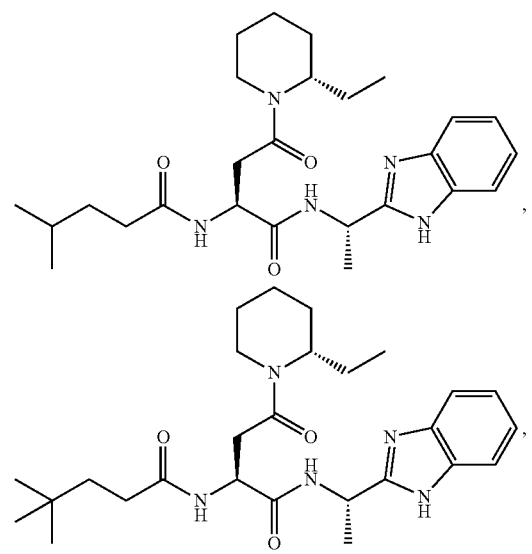
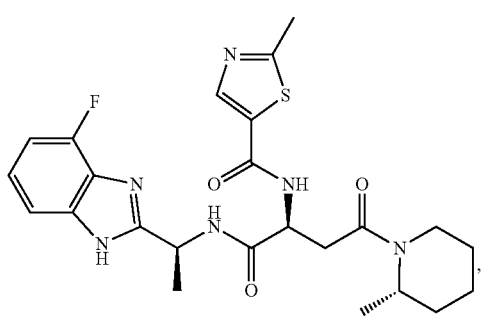
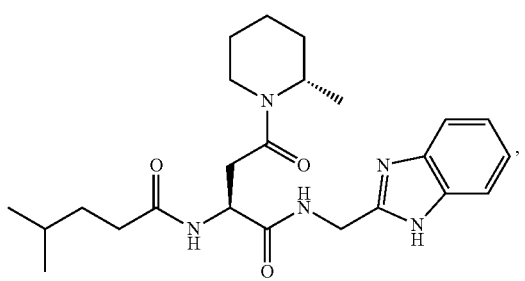
52
-continued
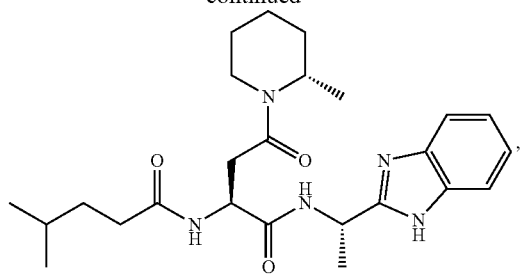
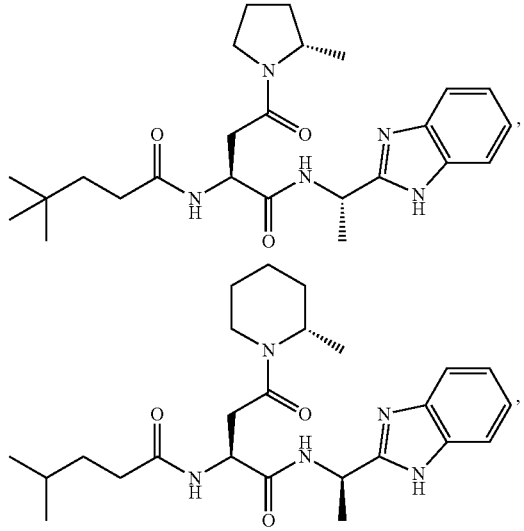

53
-continued
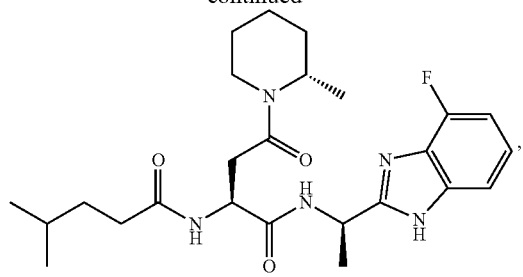
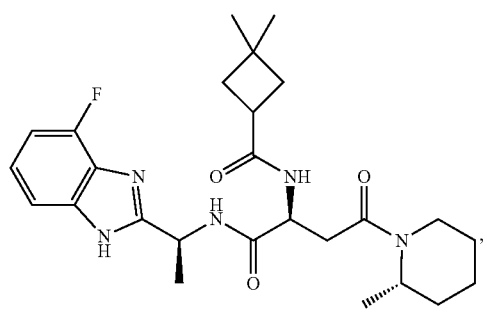
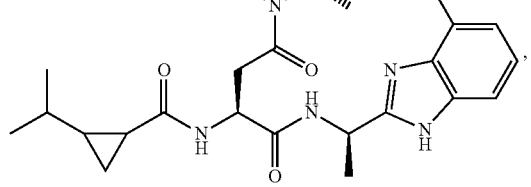
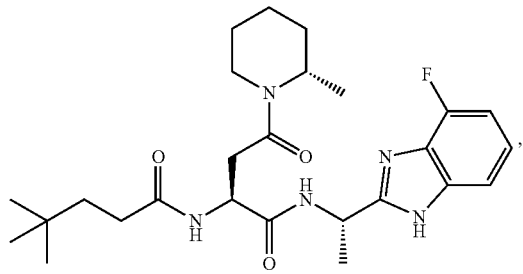
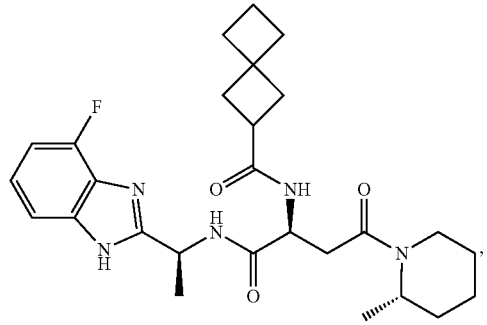
54
-continued
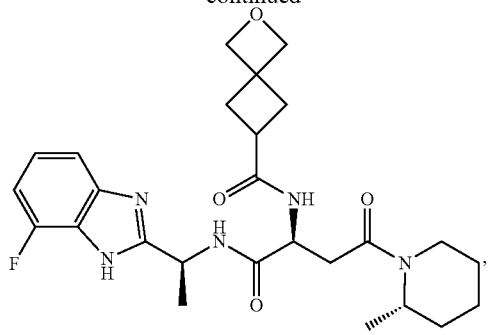
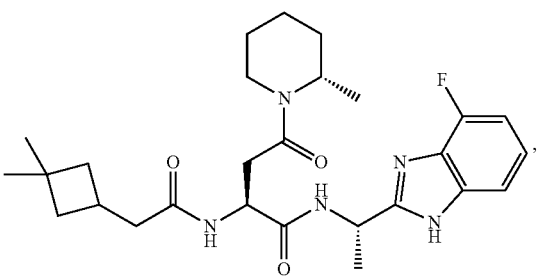
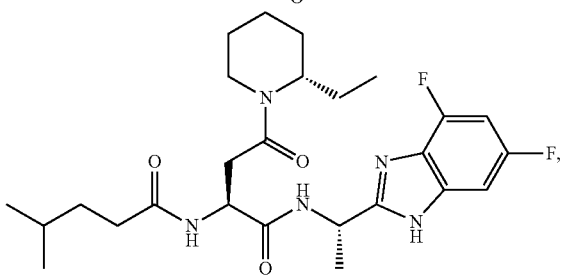
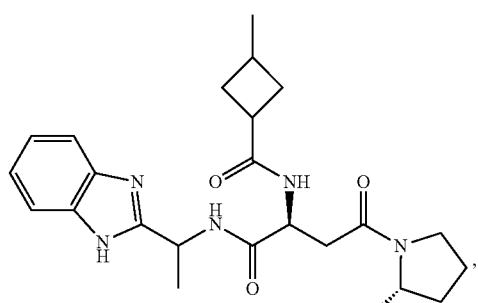

55
-continued
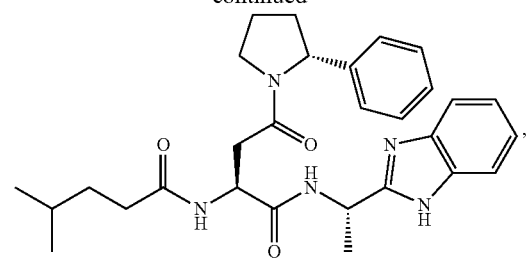
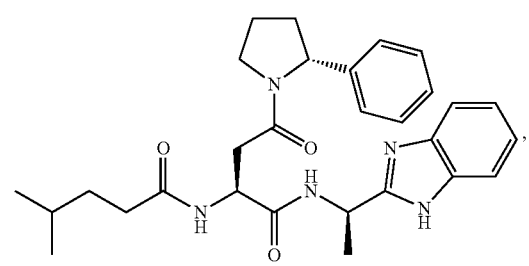
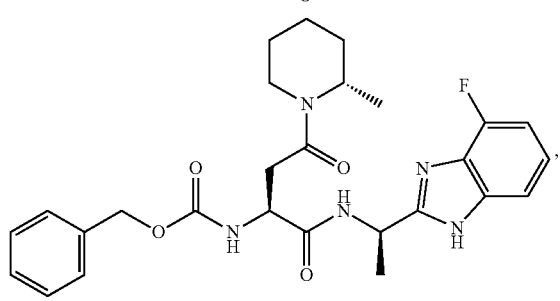
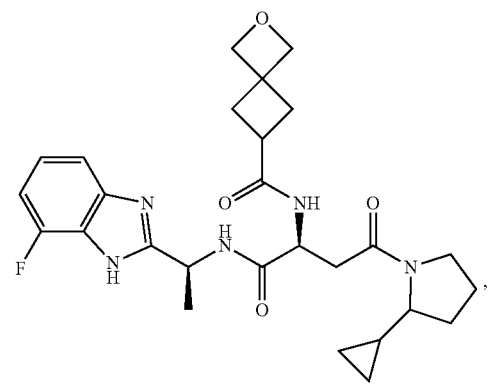
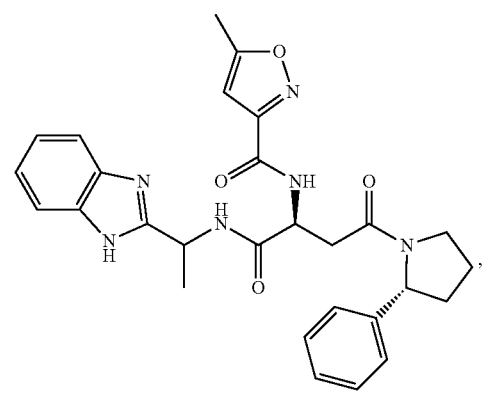
56
-continued
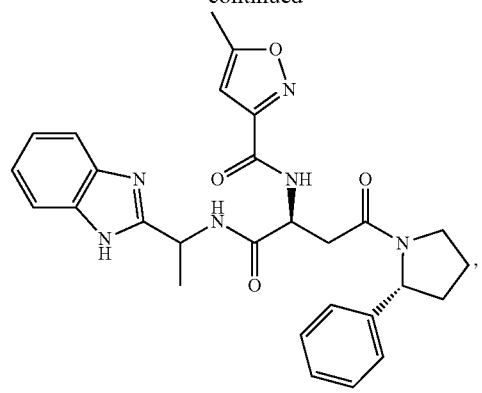
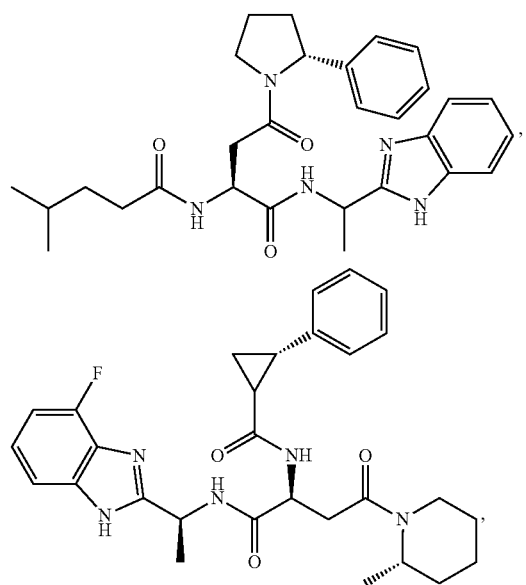
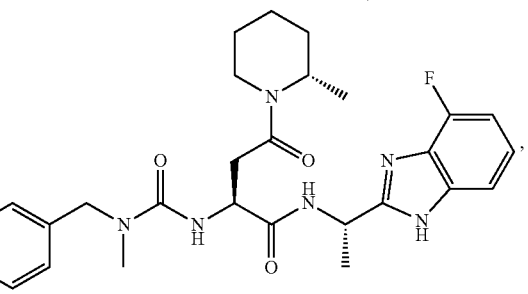
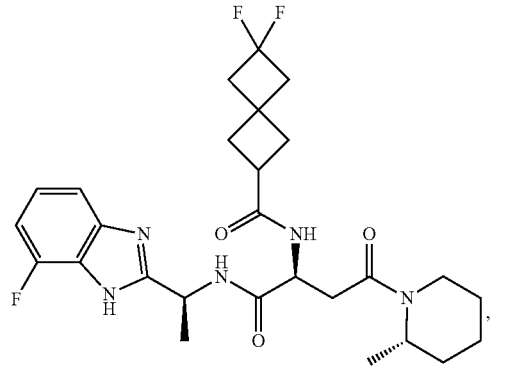

57
-continued
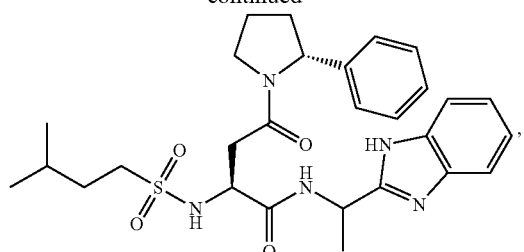
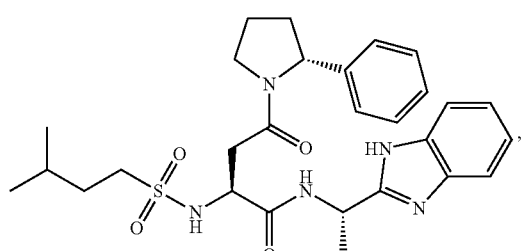
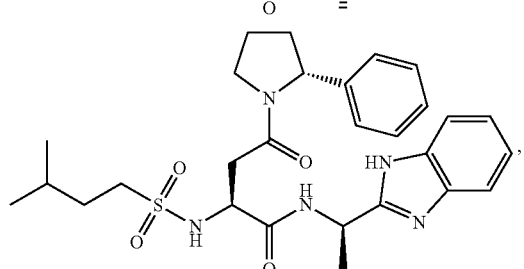
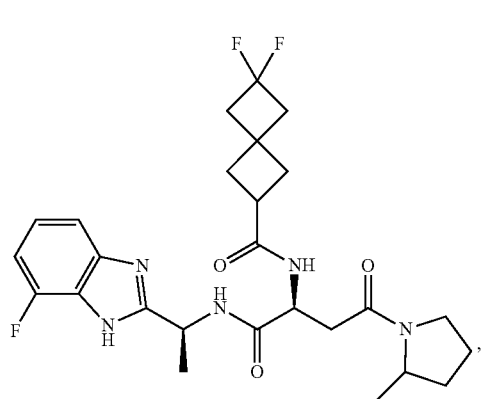
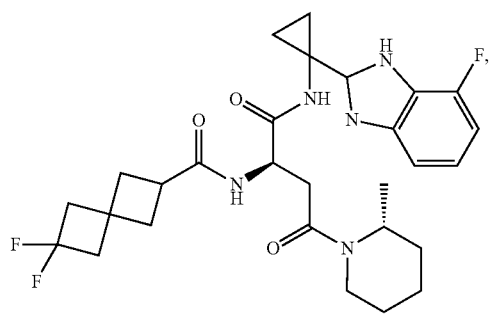
58
-continued
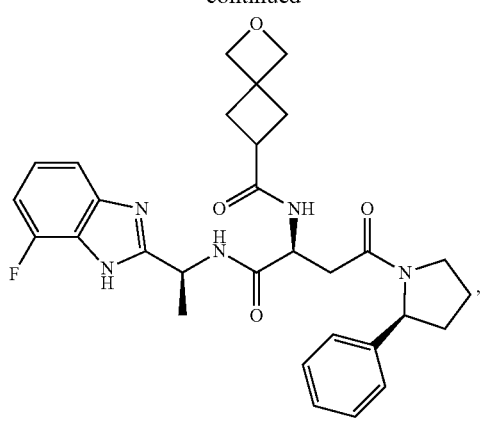
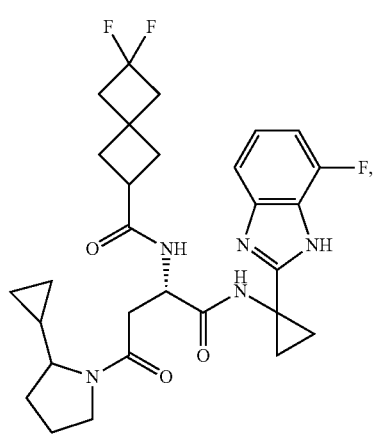
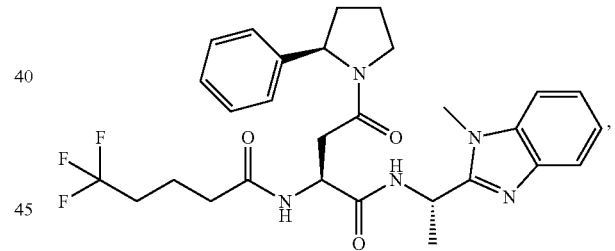
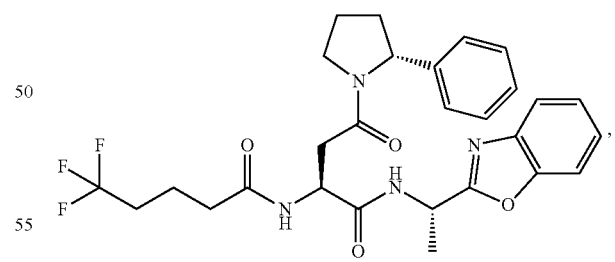
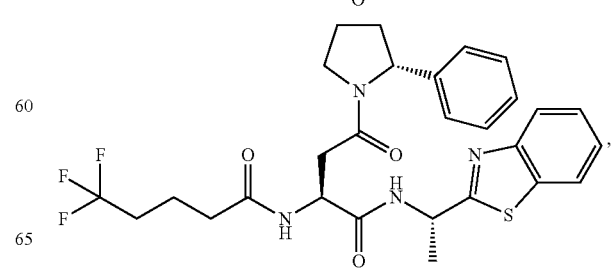

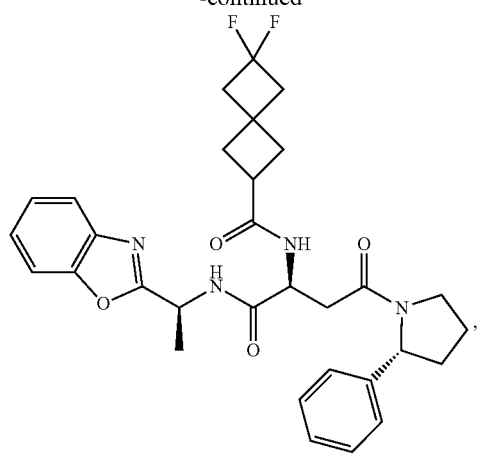
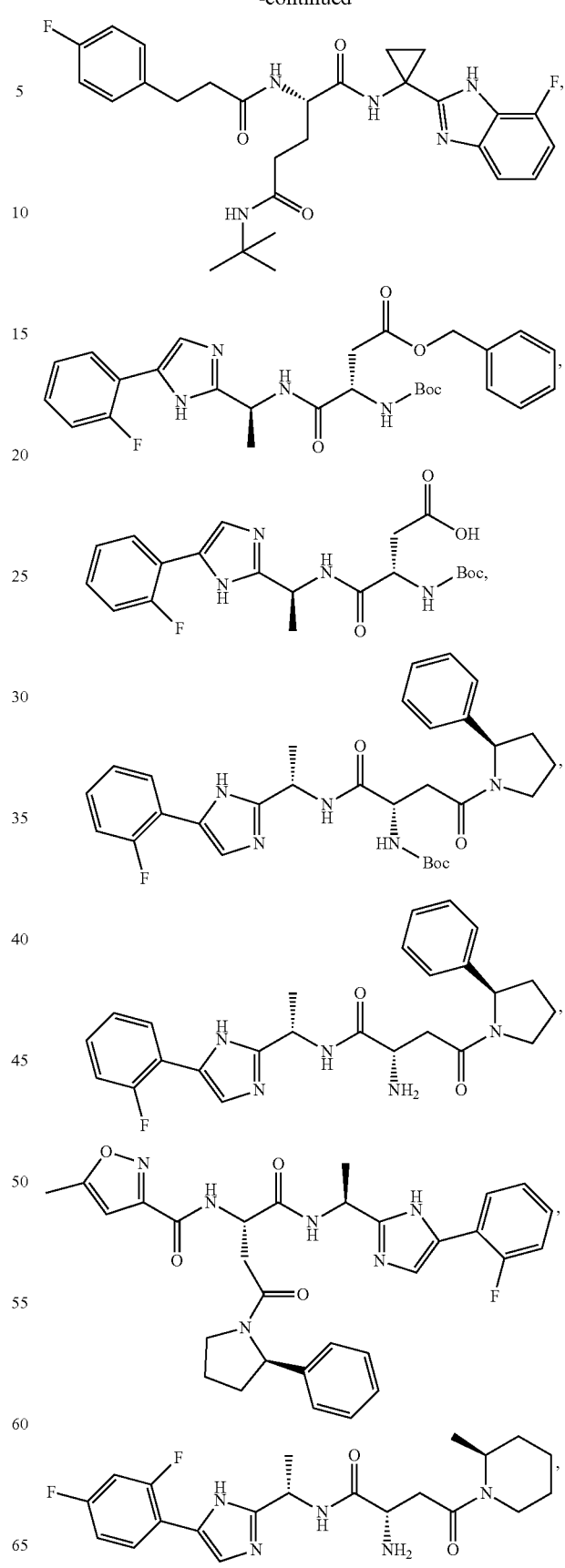

61
-continued
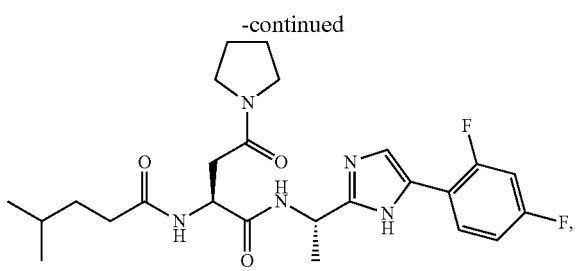
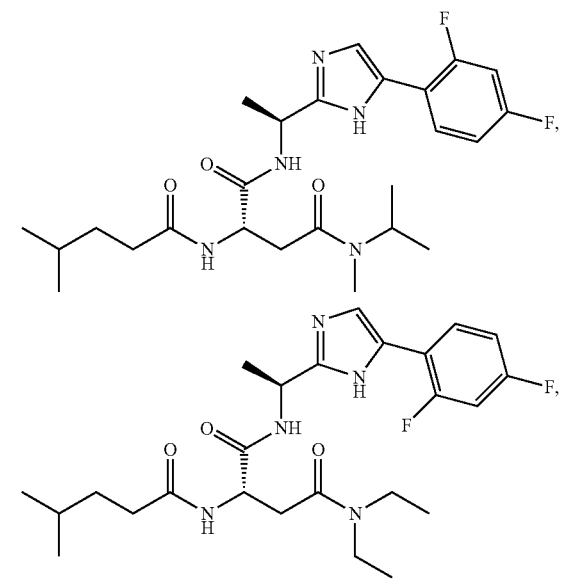
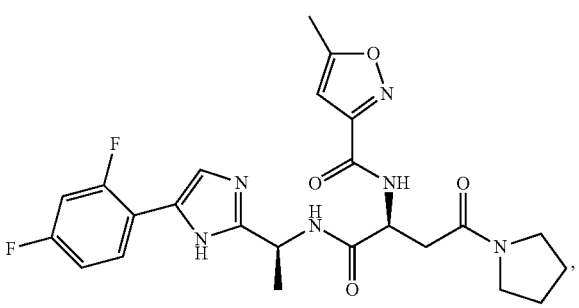
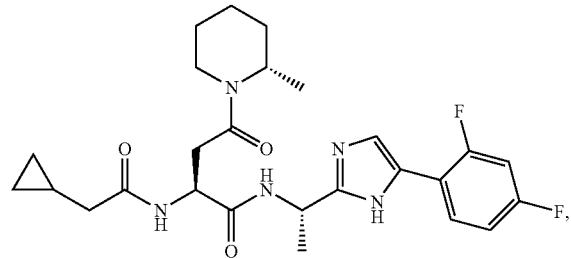
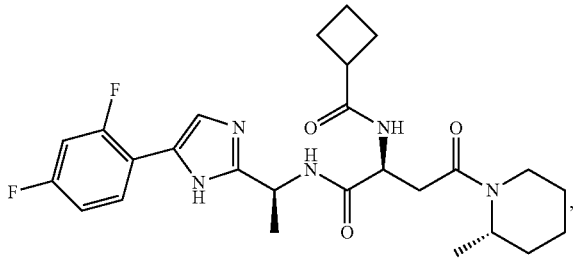
62
-continued
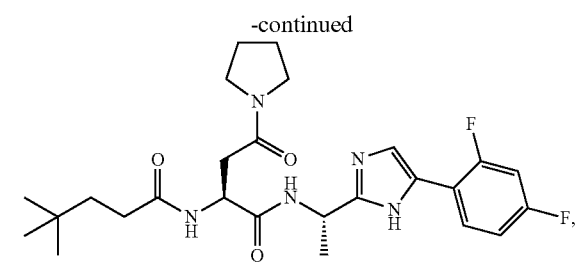
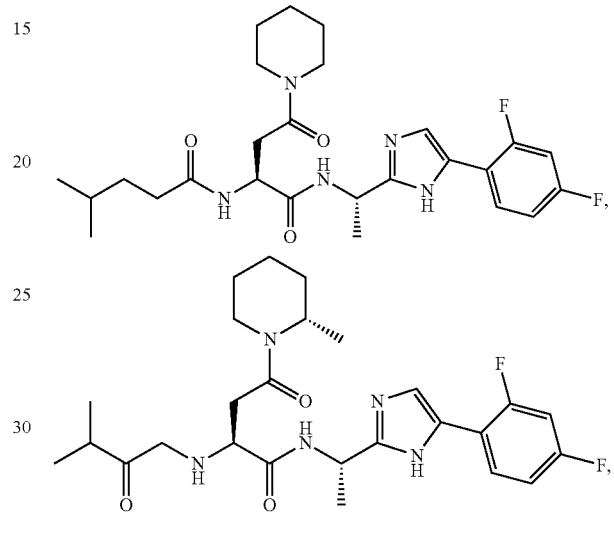
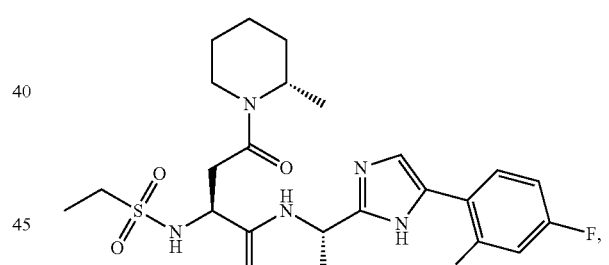
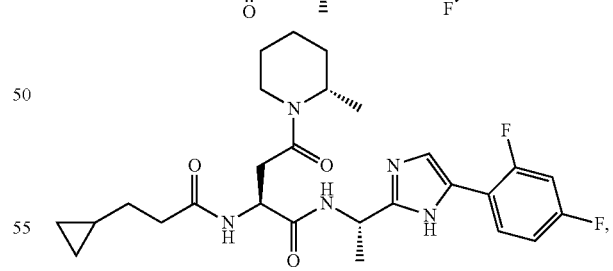
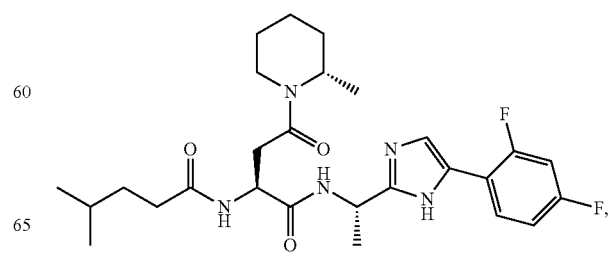

63
-continued
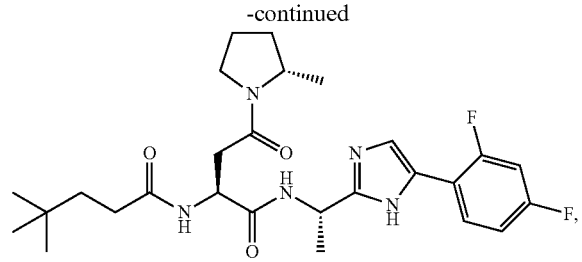
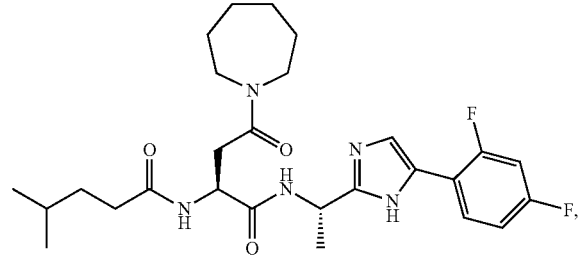
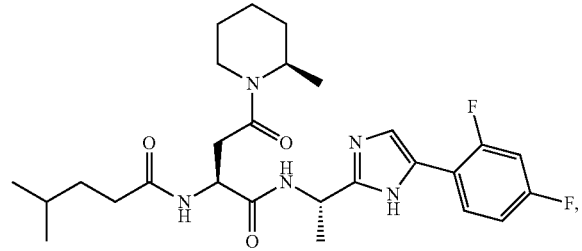
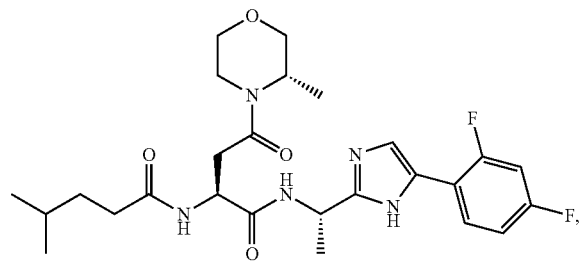
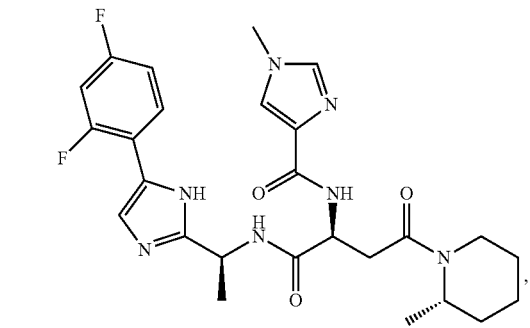
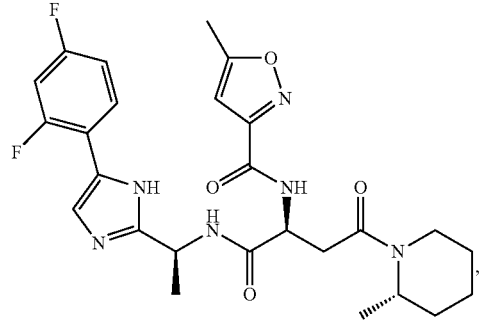
64
-continued
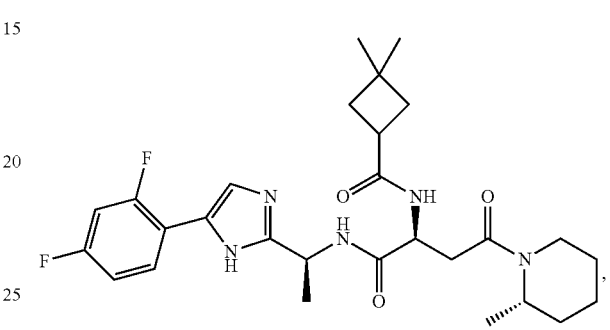
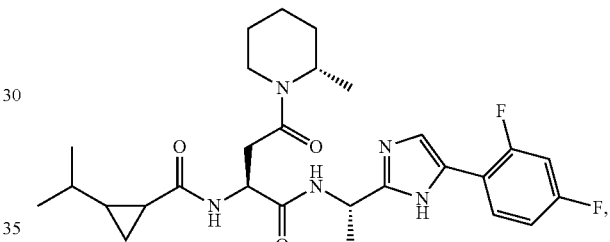
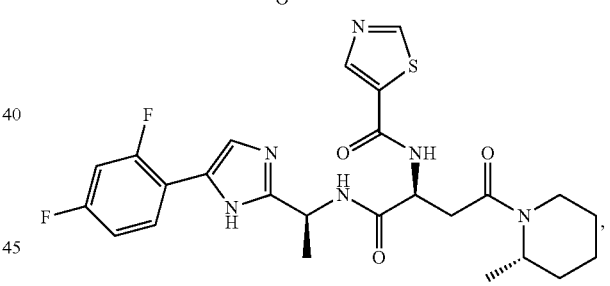
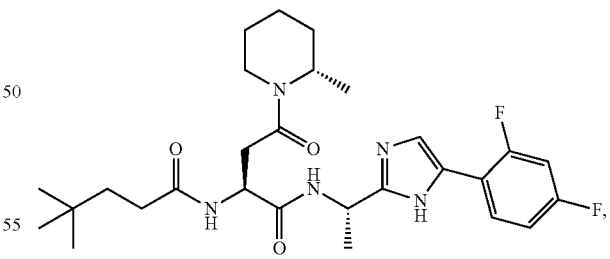
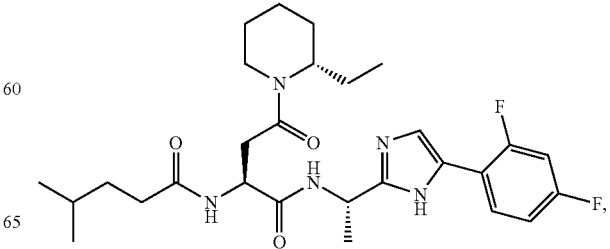

-continued
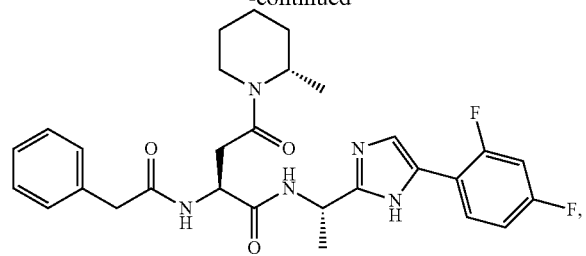
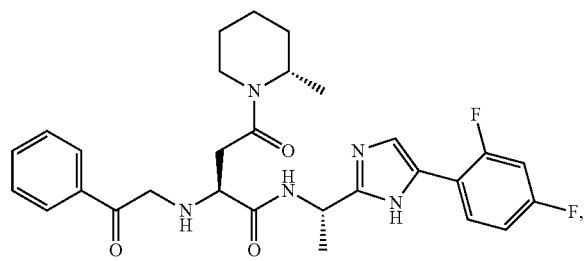
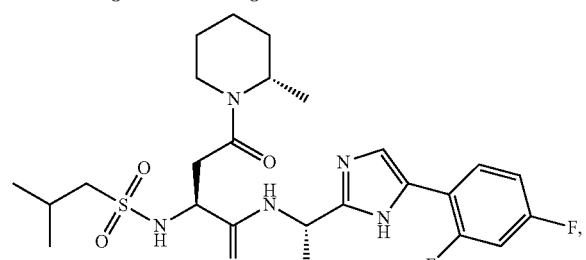
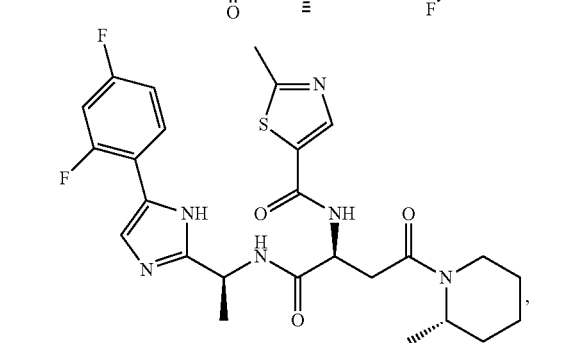
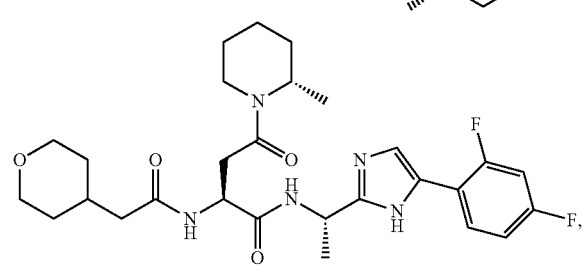
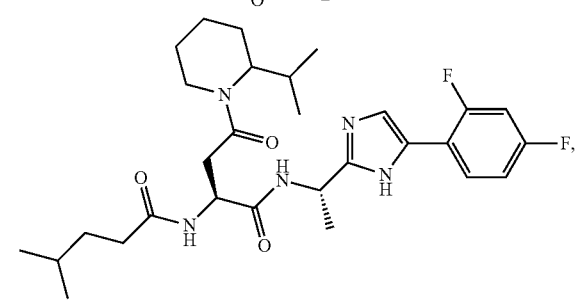
-continued
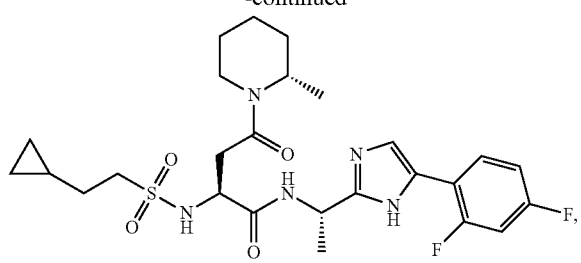
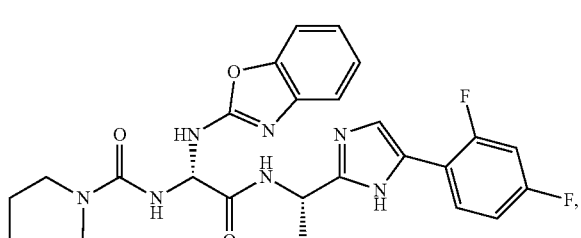
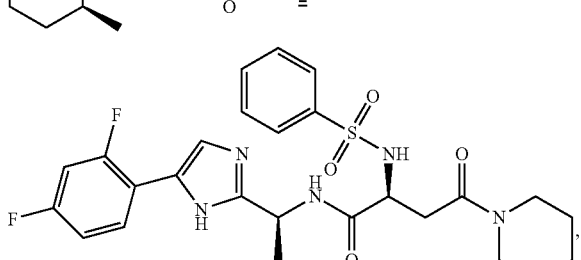
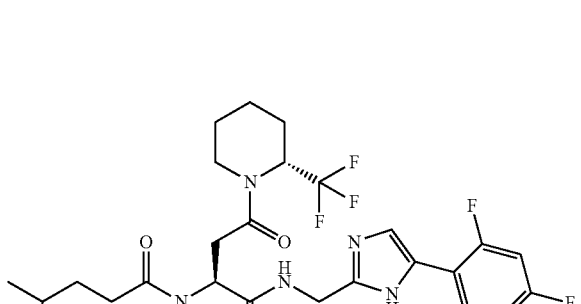
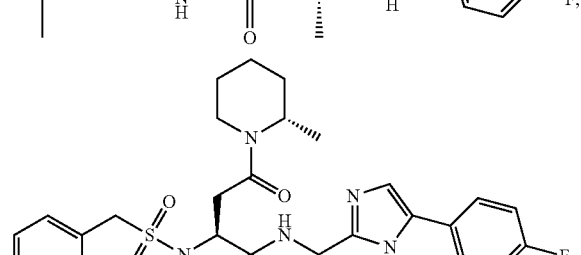
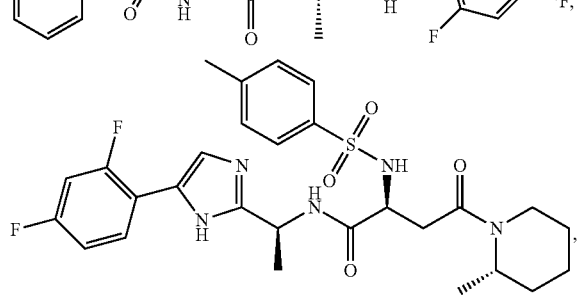

67
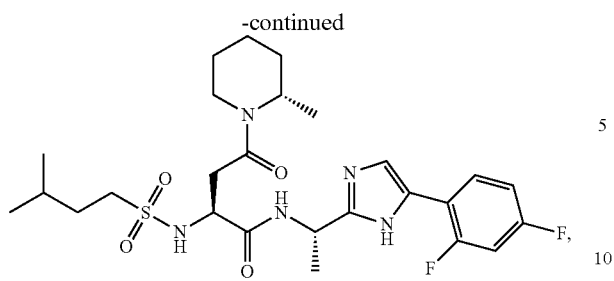
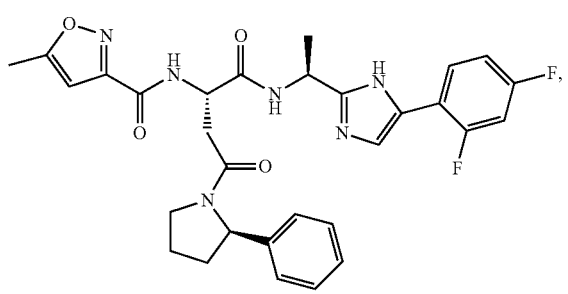
68
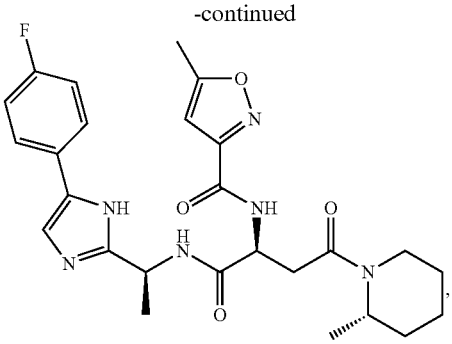
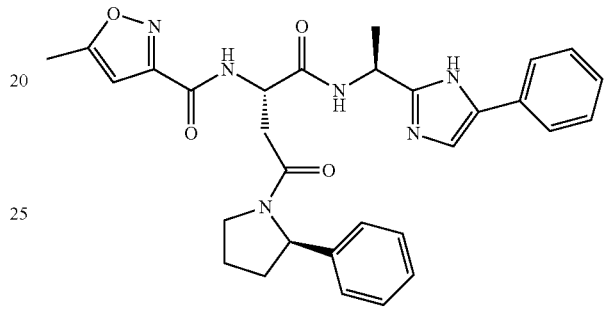
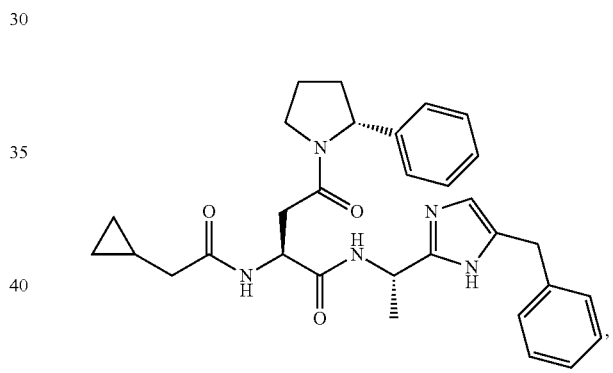
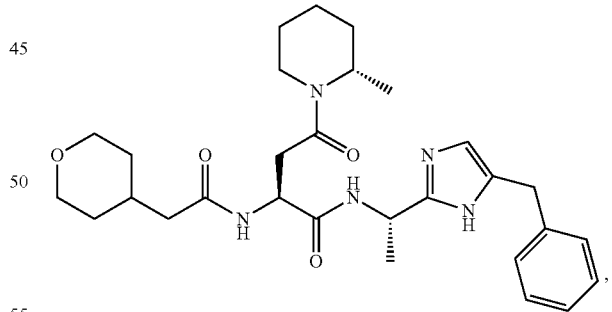
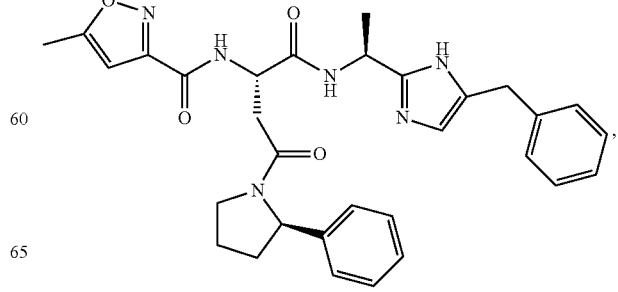

-continued

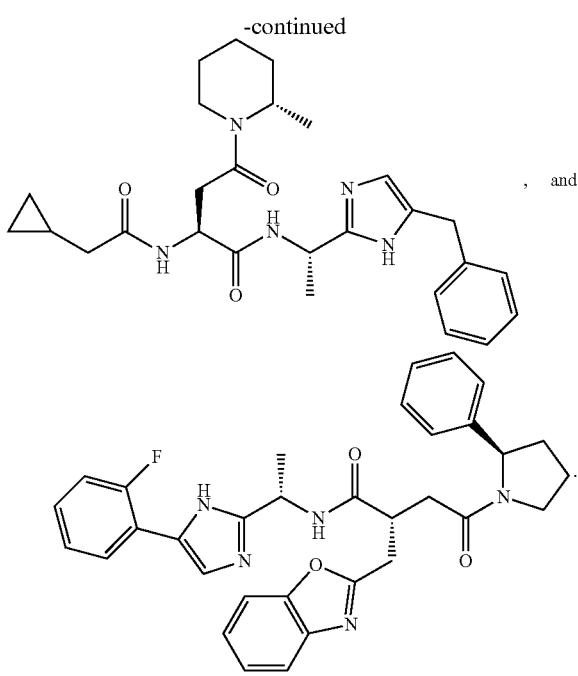, and

In one embodiment, compound has the Formula (I'):

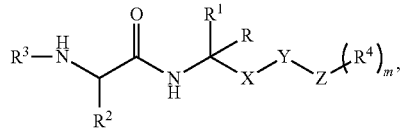

(I')

wherein
R is H or $C_{1-6}$ alkyl;
$R^1$ is H or $C_{1-6}$ alkyl;
or R and $R^1$ are taken together with the carbon to which they are attached to form a $C_{3-8}$ cycloalkyl ring;
$R^2$ is independently selected at each occurrence thereof from the group consisting of $C_{1-6}$ alkyl, and —$(CH_2)_nC(O)NR^6R^7$, wherein $C_{1-6}$ alkyl can be optionally substituted from 1 to 3 times with a substituent selected independently at each occurrence thereof from OH or $C(O)OR^{10}$;
$R^3$ is independently selected at each occurrence thereof from the group consisting of H, -Boc, —$C(O)(CH_2)R^5$, —$(CH_2)C(O)R^5$, —$C(O)OR^5$, —$C(O)(CH_2)NR^6R^7$, —$S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $C_{1-6}$ alkyl;
$R^4$ is H, $C_{1-12}$ alkyl, or halogen;
$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;

$R^6$, $R^7$ are each independently selected from the group consisting of H, $C_{1-6}$ alkyl, and arylalkyl;
or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;
$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;
$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;
$R^{10}$ is H or arylalkyl;
X is monocyclic and bicyclic heteroaryl, monocyclic and bicyclic heterocyclyl, or monocyclic and bicyclic non-aromatic heterocycle;
Y is optional and, if present, is —$(CH_2)_m$—;
Z is optional and, if present, is aryl;
m is 0, 1, or 2; and
n is 0, 1, 2, 3, or 4;
or an oxide thereof, a pharmaceutically acceptable salt thereof, a solvate thereof, or a prodrug thereof.

In another embodiment, compound has the Formula (I'A):

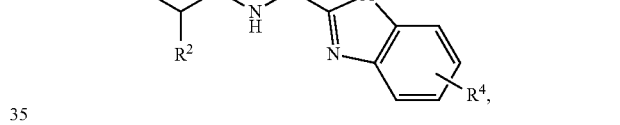

(I'A)

wherein
A is NH, N, O, or S.

In another embodiment, compound has the Formula (I'B):

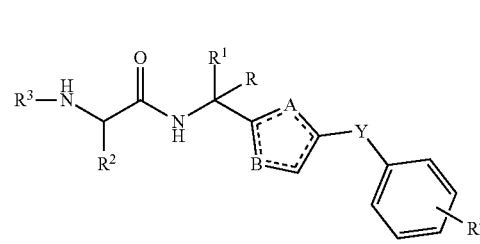

(I'B)

wherein
=== is a single or a double bond;
A is NH, N, O, or S; and
B is NH, N, O, or S.

In yet another embodiment, compound has the Formula (I'C):

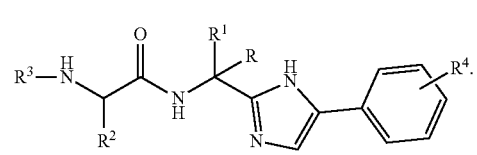

(I'C)

In yet another embodiment, compound has the Formula (I'D):

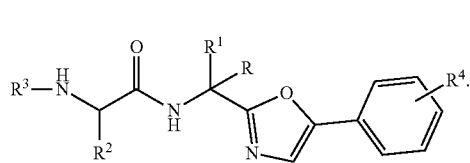
(I'D)

In another embodiment, compound has the Formula (I'E):

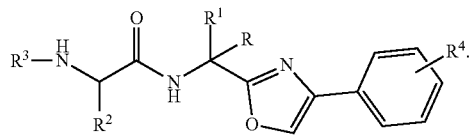
(I'E)

In yet another embodiment, compound has the Formula (I'F):

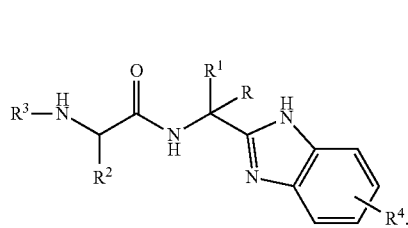
(I'F)

In a further embodiment, compound has the Formula (I'G):

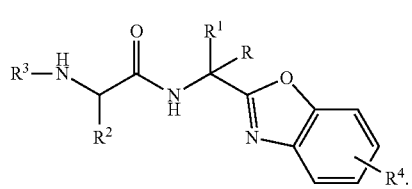
(I'G)

In another embodiment, compound has the Formula (I'C'):

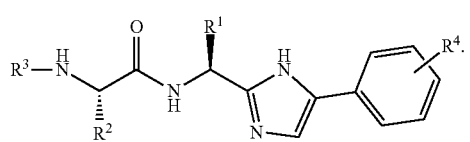
(I'C')

In yet another embodiment, compound has the Formula (I'D'):

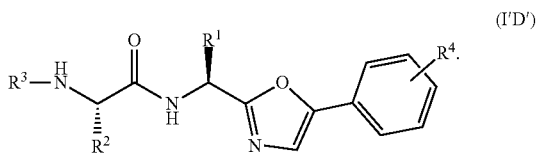
(I'D')

In a further embodiment, compound has the Formula (I'E'):

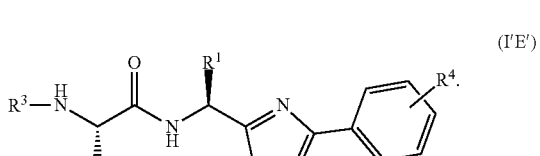
(I'E')

In another embodiment, compound has the Formula (I'F'):

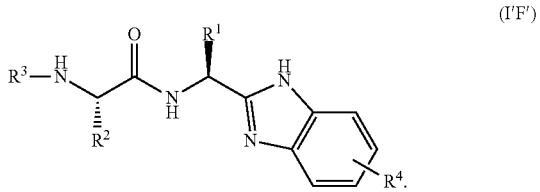
(I'F')

In yet another embodiment, compound has the Formula (I'G'):

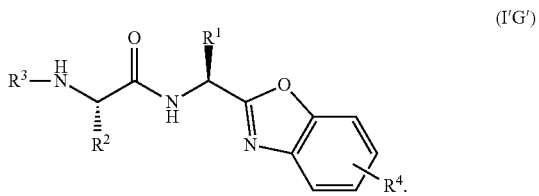
(I'G')

One embodiment relates to the compound of Formulae (I') where $R^1$ is H or Me.

Another embodiment relates to the compound of Formulae (I') where R and $R^1$ are taken together with the carbon to which they are attached to form

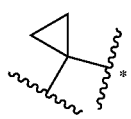

group, and wherein

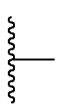

is the point of attachment to NH; and

is the point of attachment to X.

Another embodiment relates to the compound of Formulae (I') where R² is selected from the group consisting of

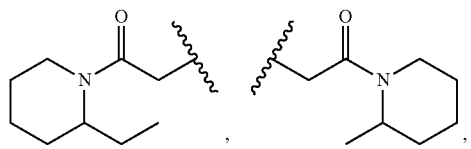

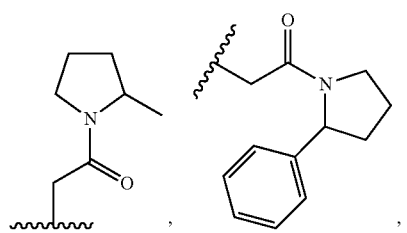

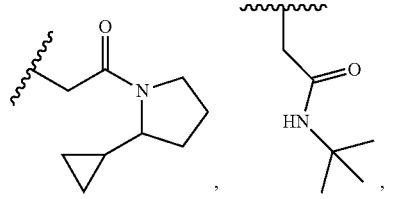

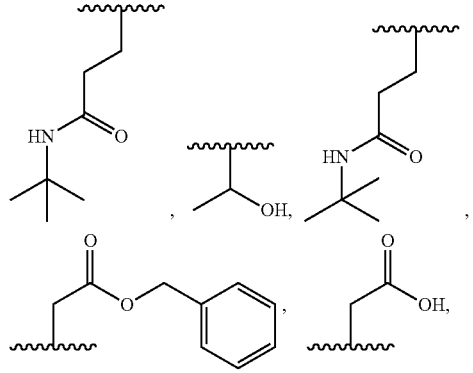

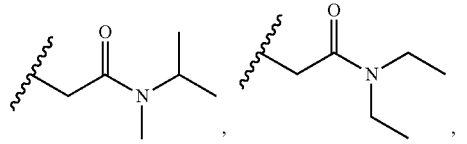

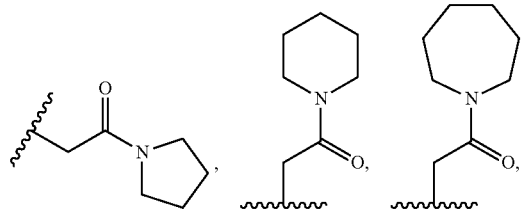

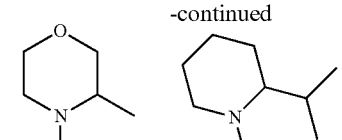

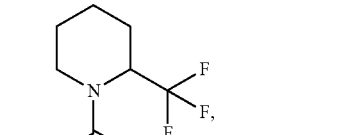

wherein

is the point of attachment to the corresponding carbon atom of the structure of Formula (I).

Yet another embodiment relates to the compound of Formulae (I') where R³ is selected from the group consisting of H, Boc,

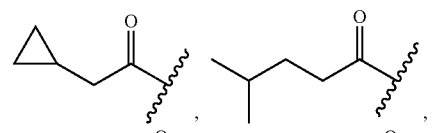

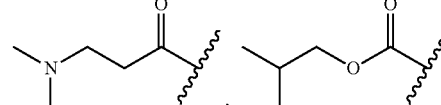

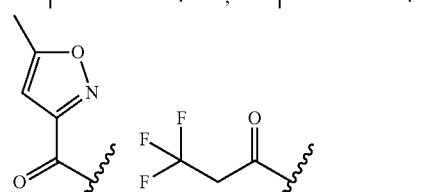

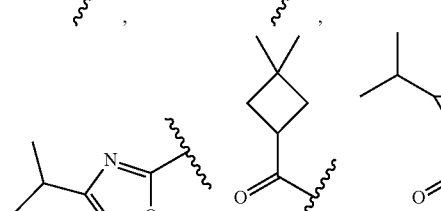

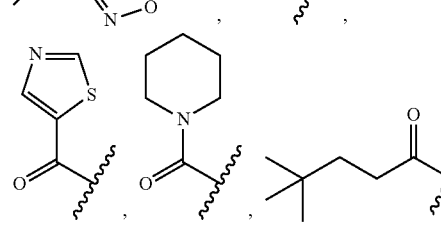

-continued
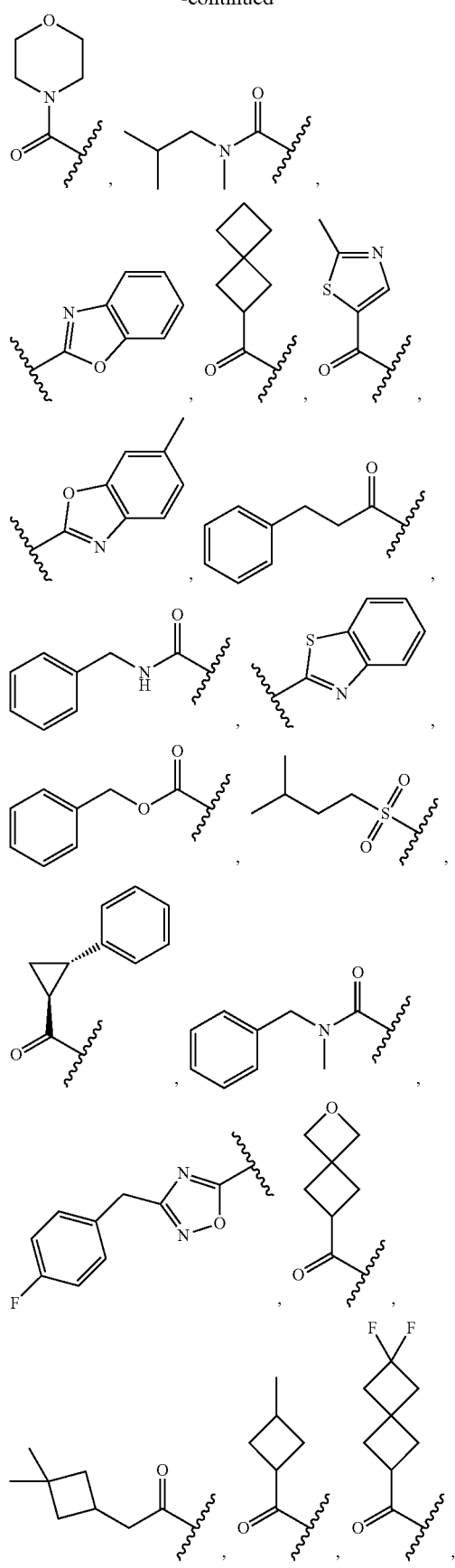
-continued
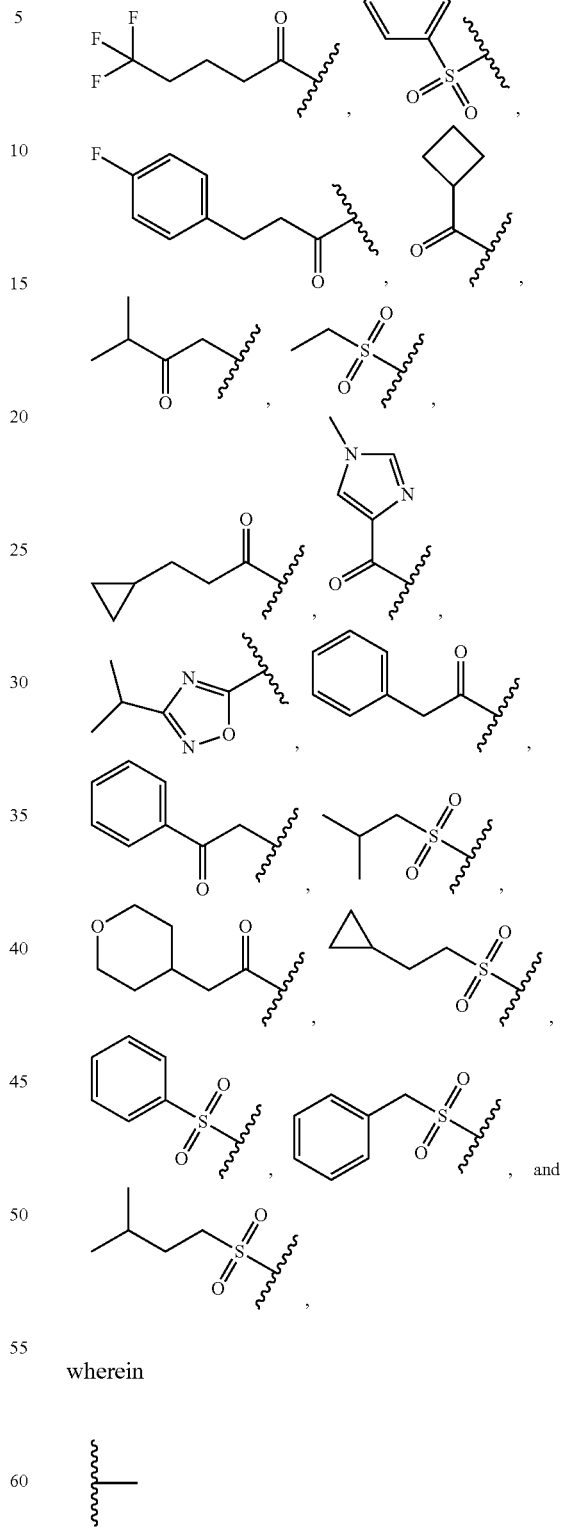
wherein
is the point of attachment to the corresponding carbon atom of the structure of Formula (I).
Another embodiment relates to the compound of Formulae (I') where $R^4$ is H, Me, or F.

Yet another embodiment relates to the compound of Formulae (I') where X is selected from the group consisting of

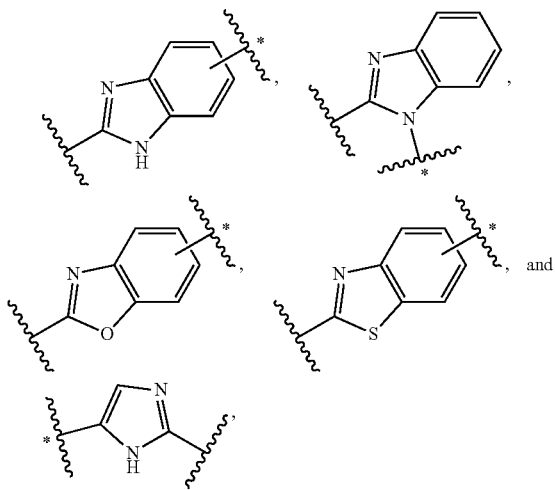

wherein

is the point of attachment to C(R¹)(R²) moiety;

is the point of attachment to Y, Z, or R⁴.

Yet another embodiment relates to the compound of Formulae (I') where Y is —CH₂—.

Another embodiment relates to the compound of Formulae (I') where n Z is

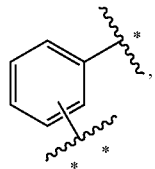

and
wherein

is the point of attachment to Y or X;

is the point of attachment to R⁴.

A further embodiment relates to the compound of Formulae (I') where the compound has a structure selected from the group consisting of:

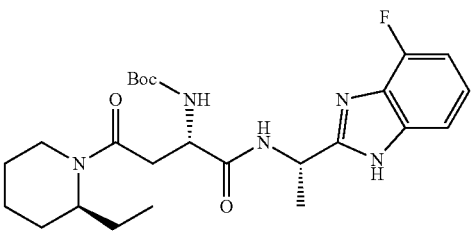

,

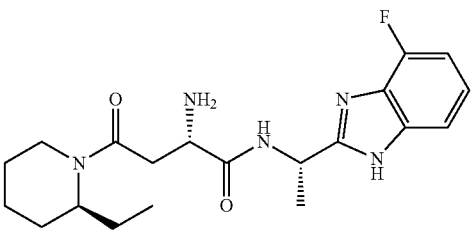

,

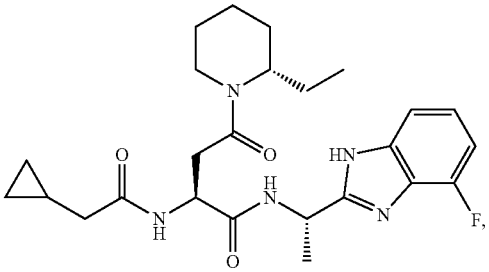

,

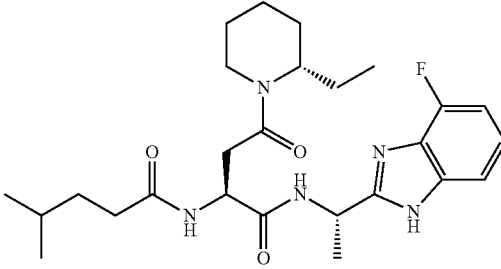

,

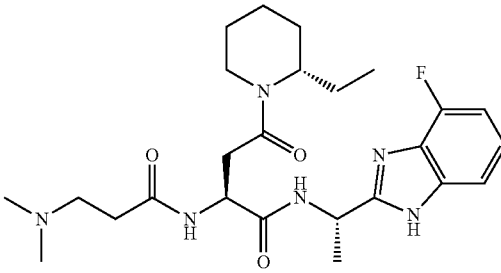

,

79
-continued
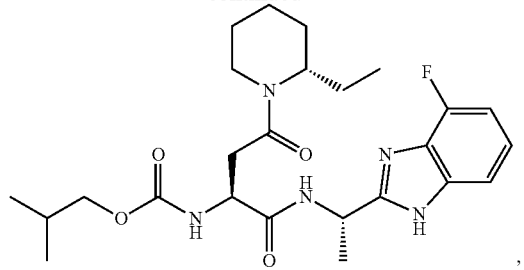
,
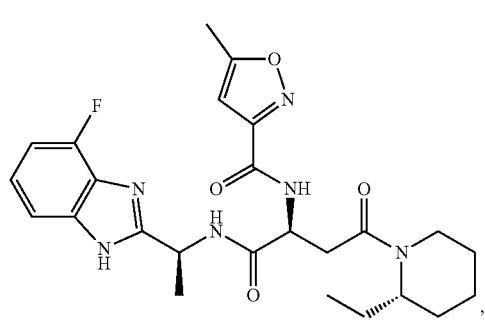
,
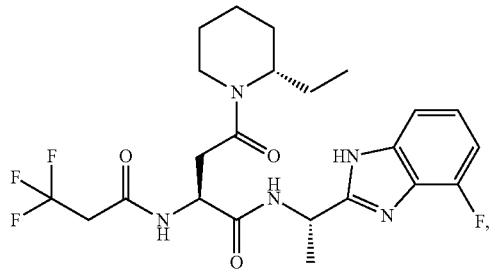
,
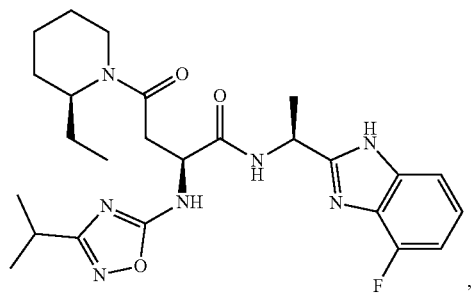
,
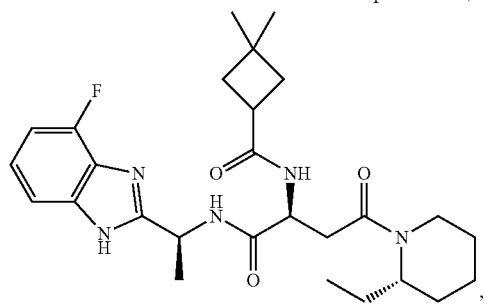
,
80
-continued
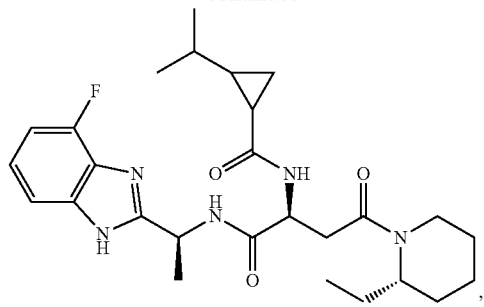
,
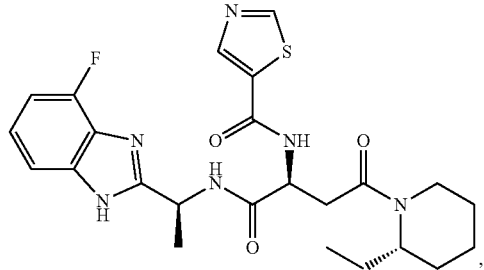
,
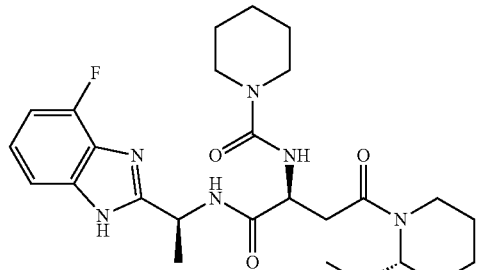
,
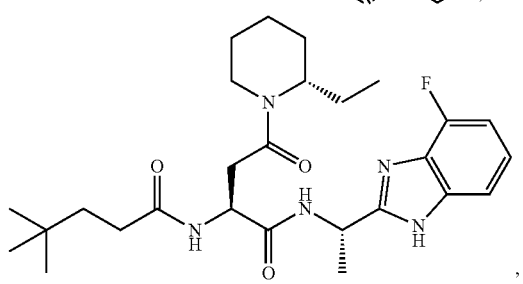
,
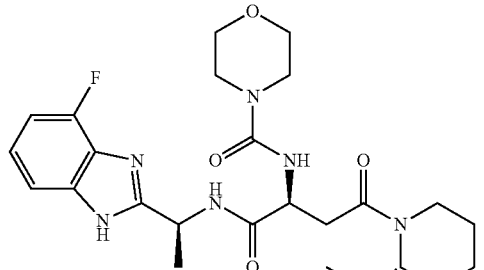
,
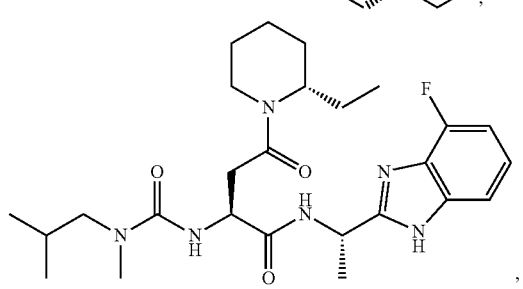
,

| 81 | 82 |
|---|---|
| -continued | -continued |
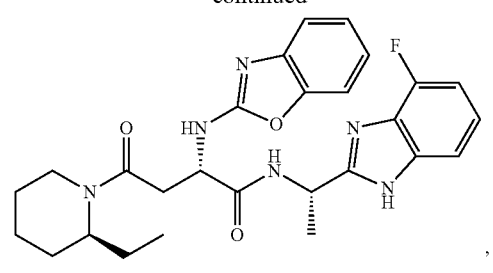
,
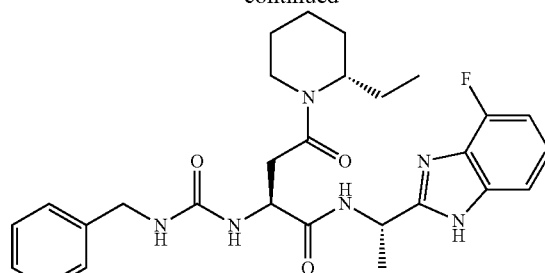
,
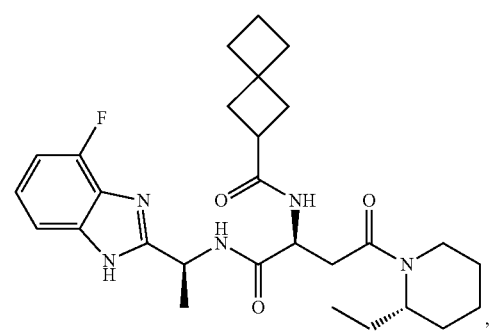
,
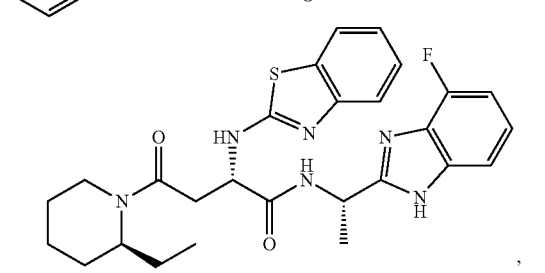
,
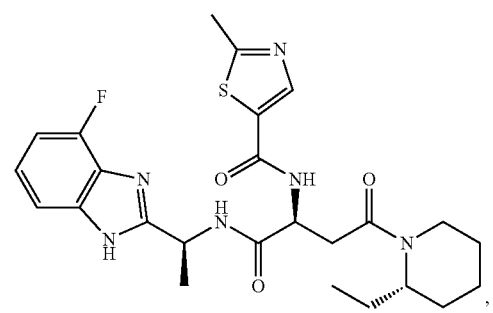
,
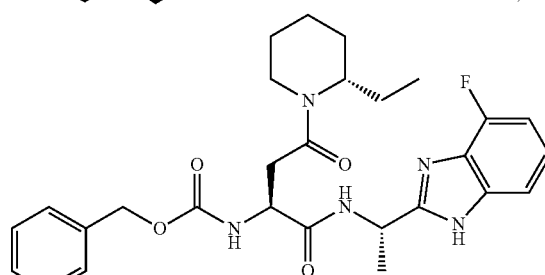
,
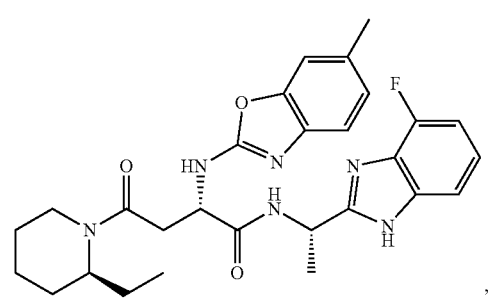
,
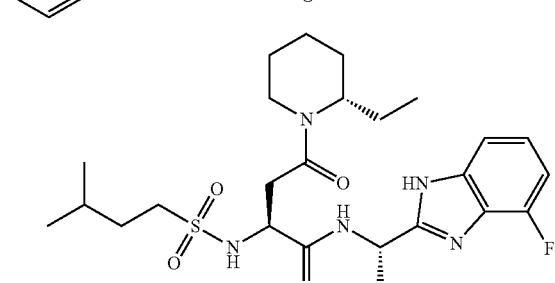
,
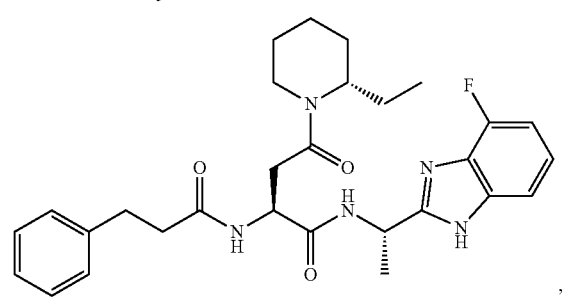
,
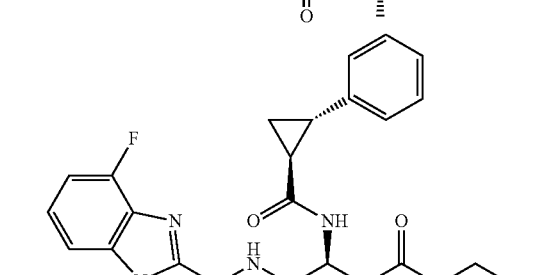
,
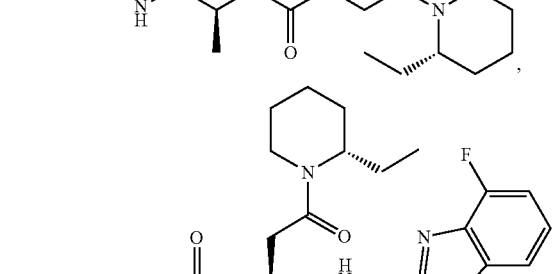
,

83
-continued
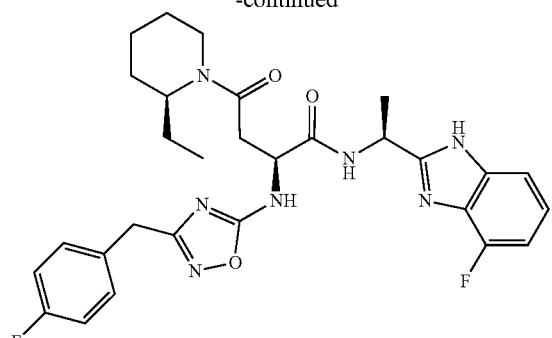
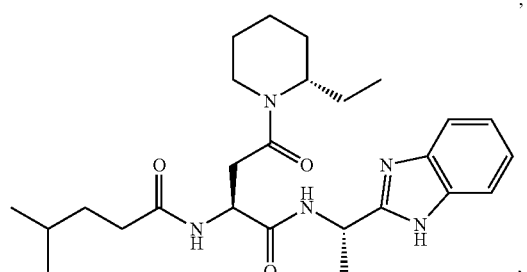
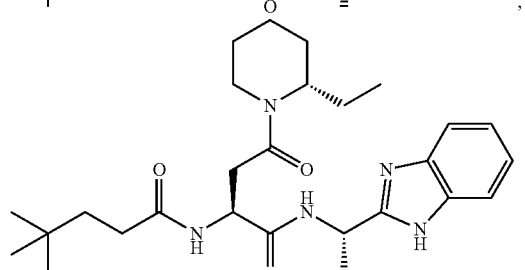
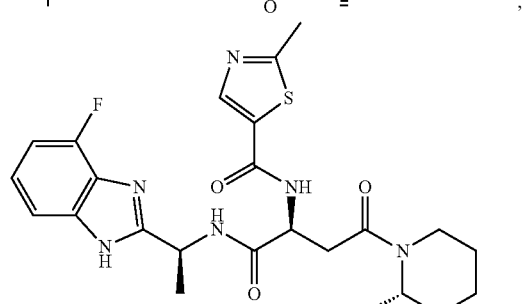
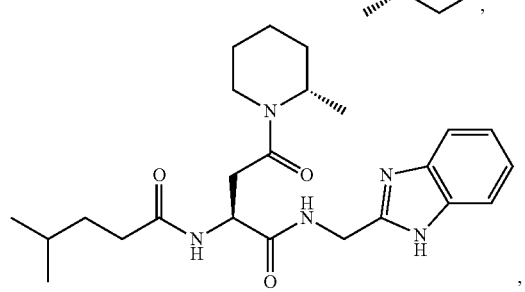
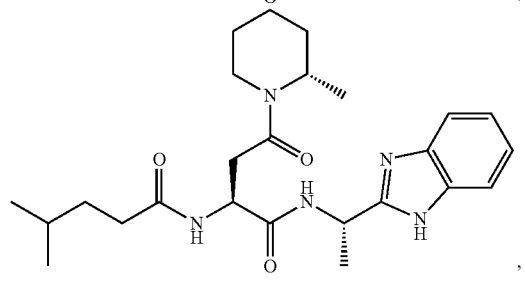
84
-continued
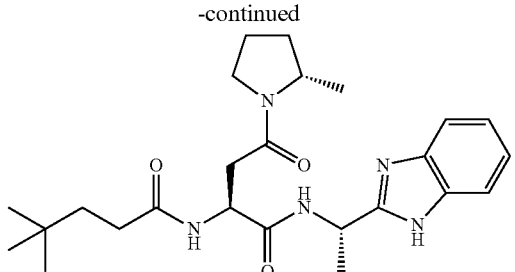
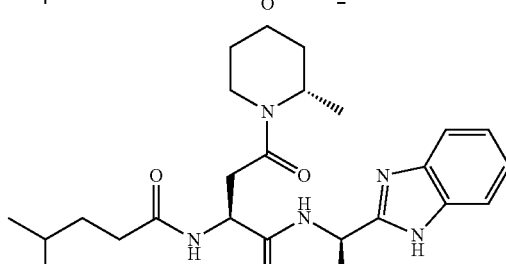
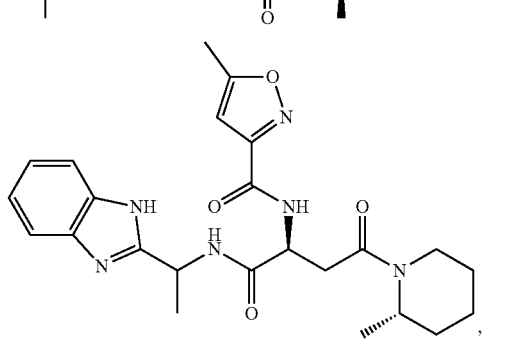
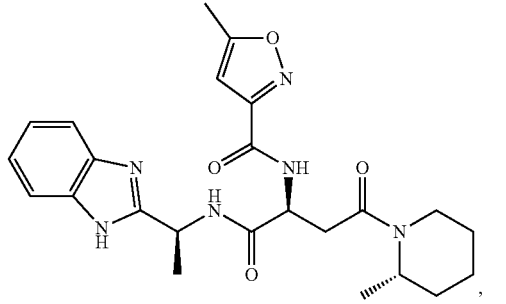
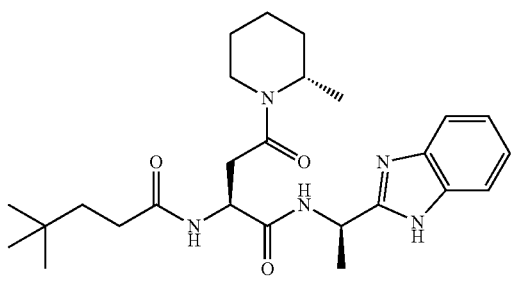
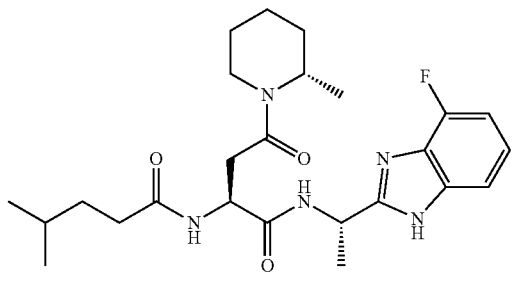

85
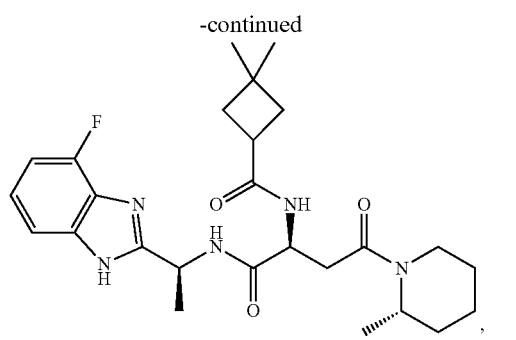
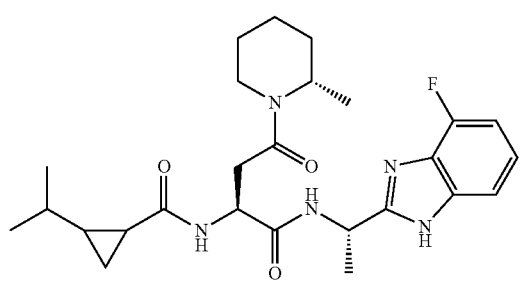
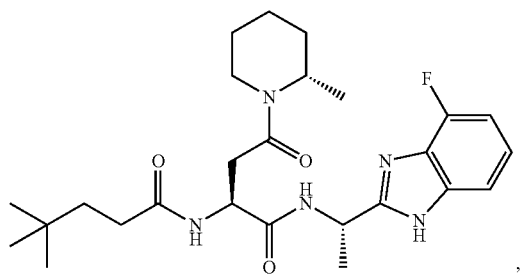
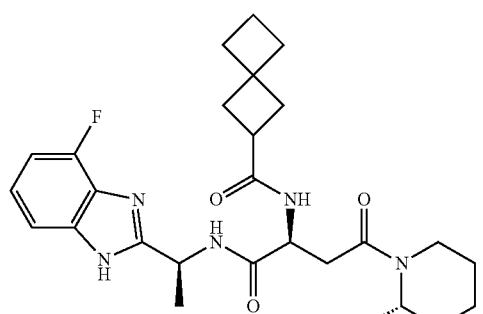
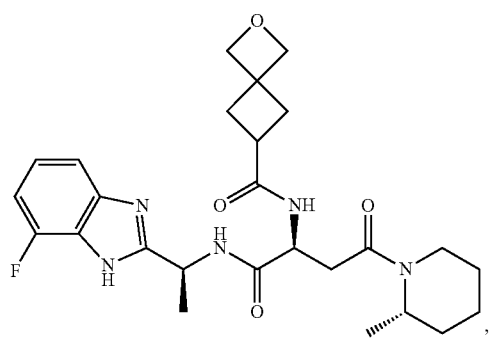
86
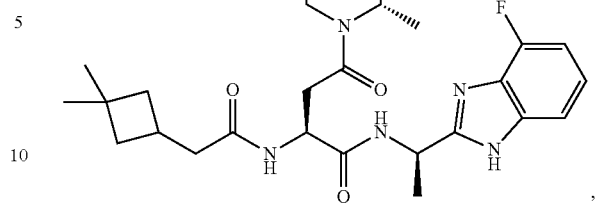
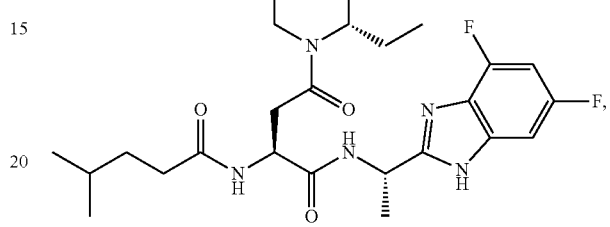
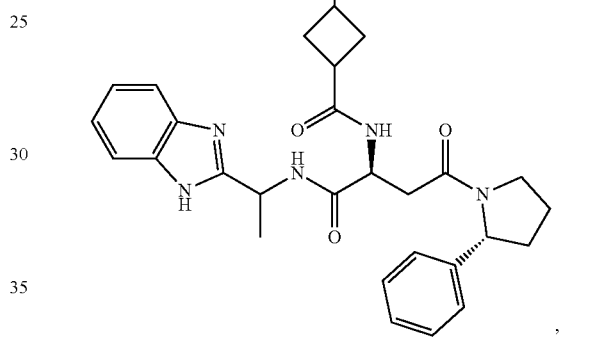
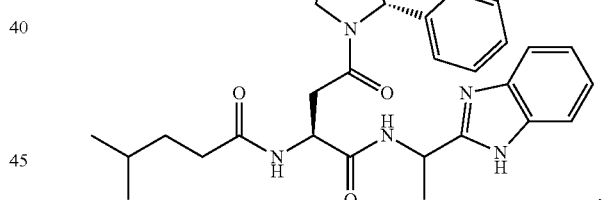
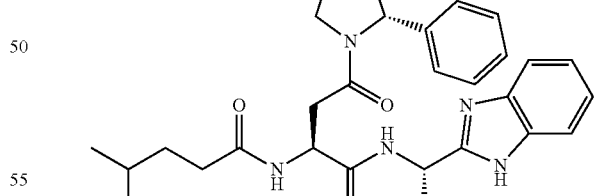
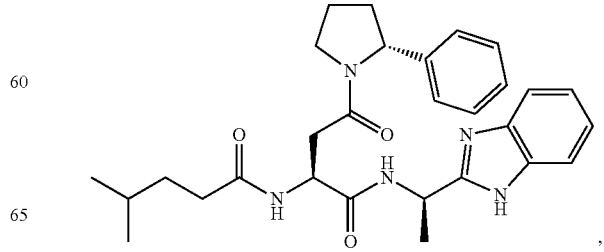

87
-continued
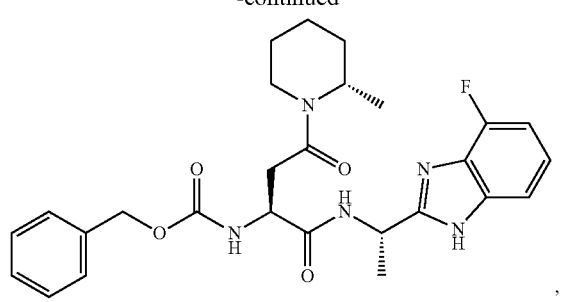
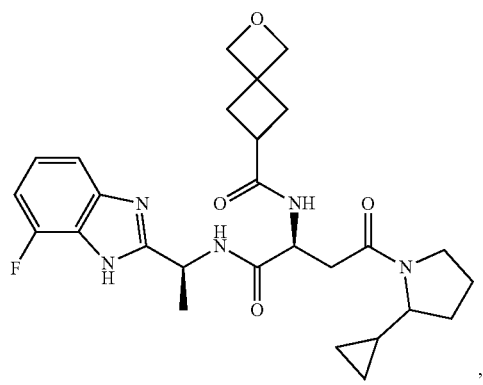
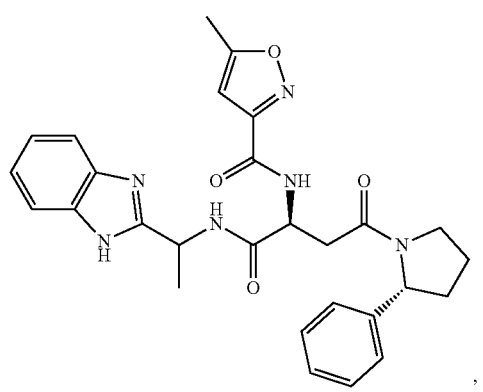
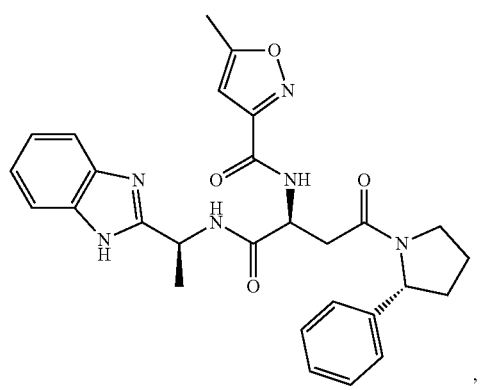
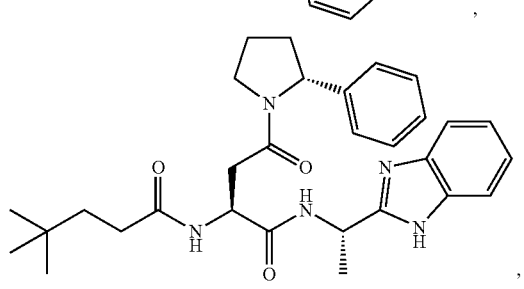
88
-continued
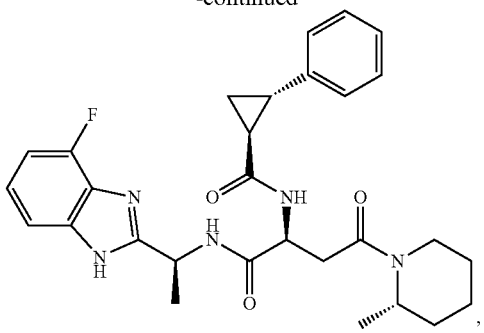
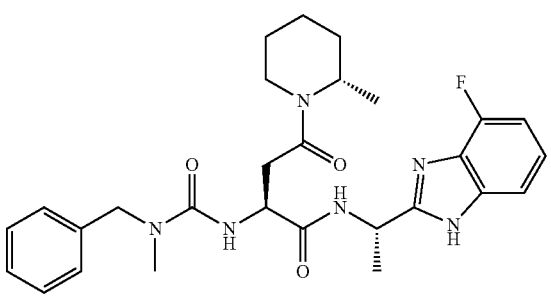
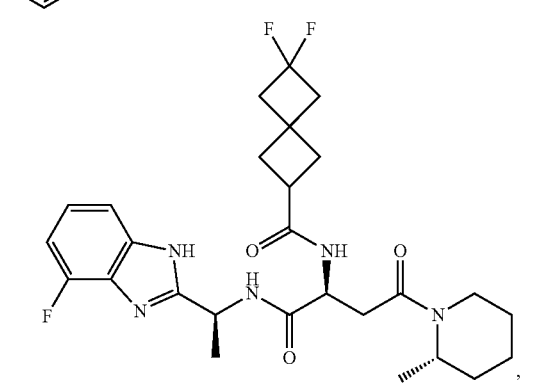
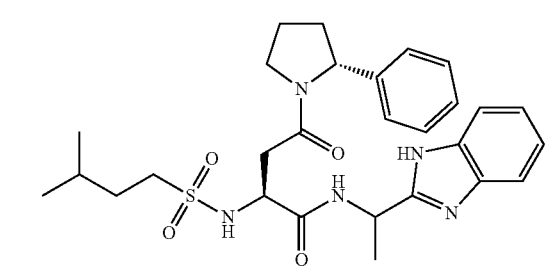
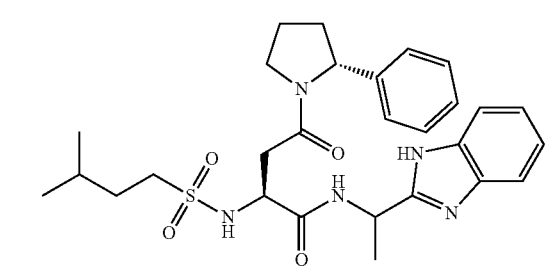

89
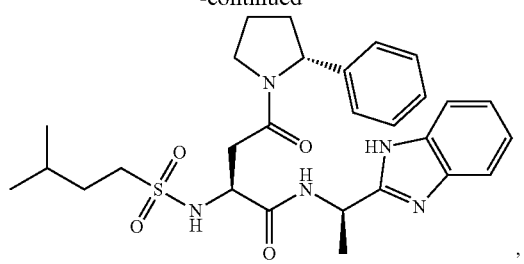
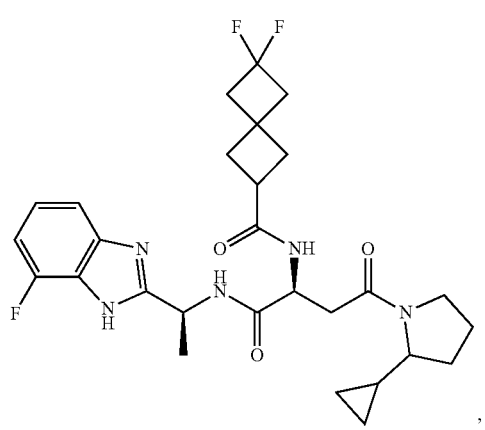
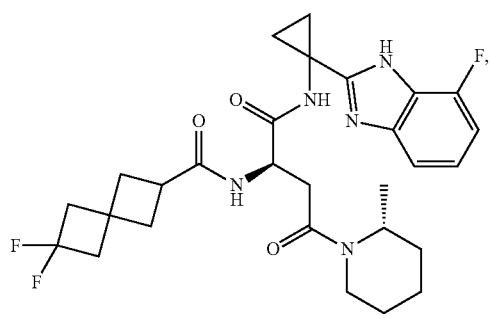
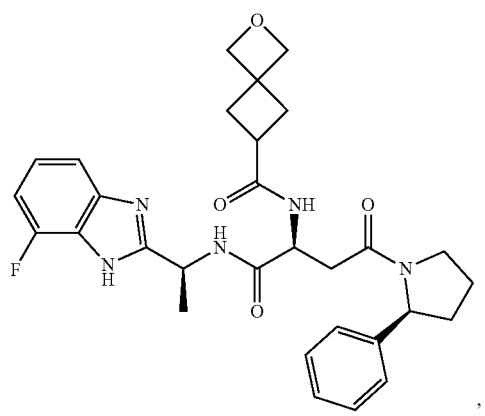
90
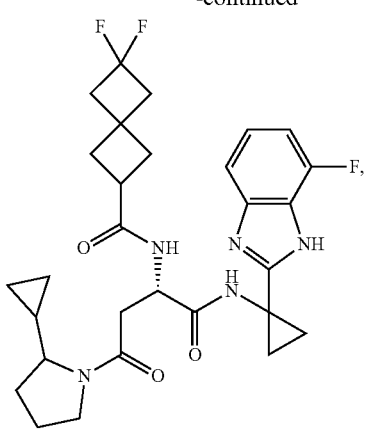
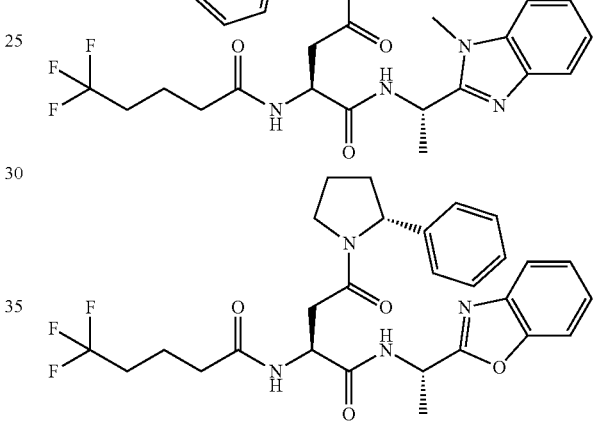
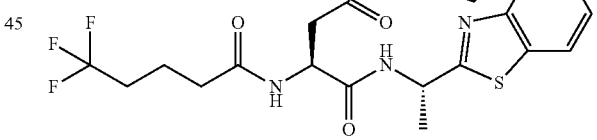
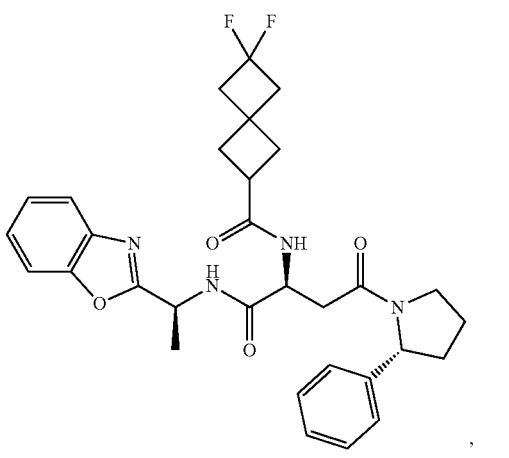

91
-continued
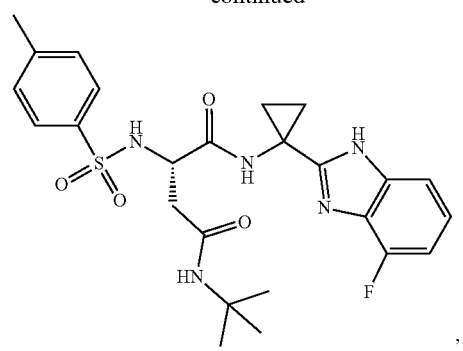
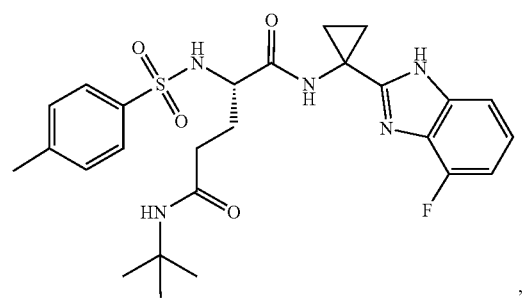
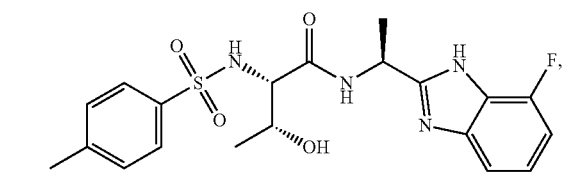
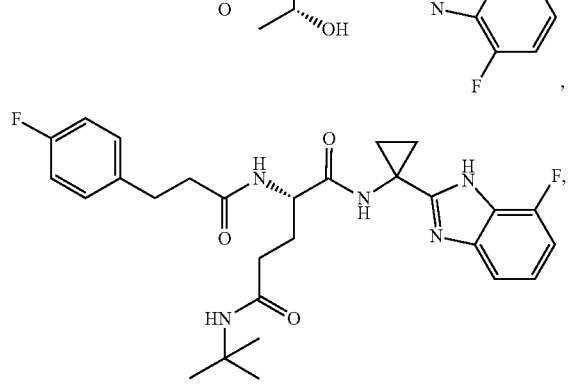
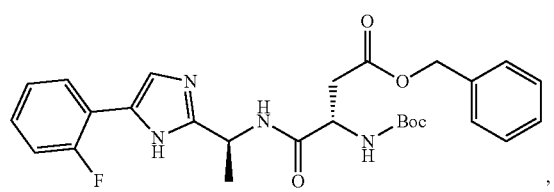
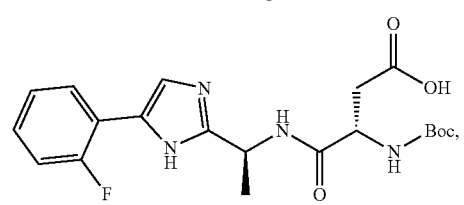
92
-continued
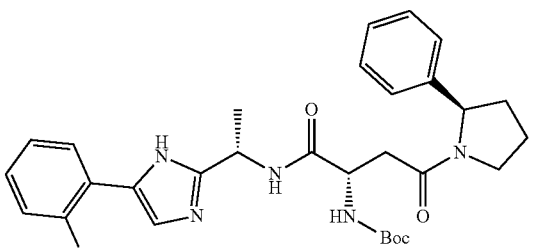
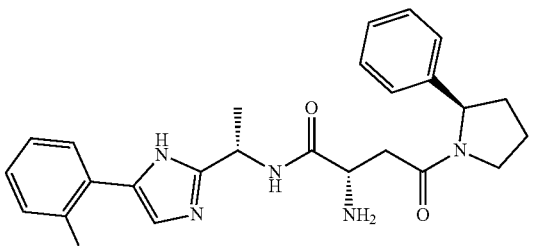
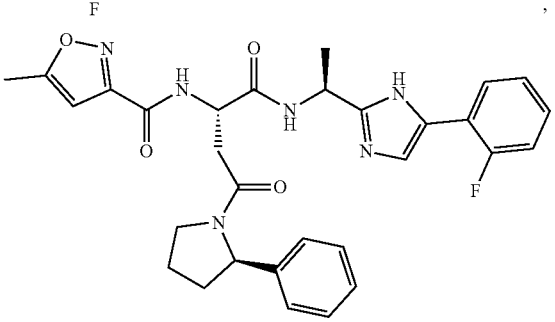
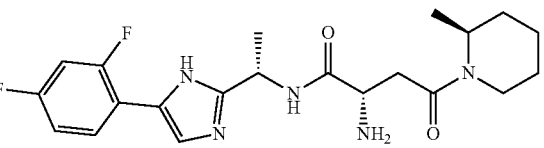
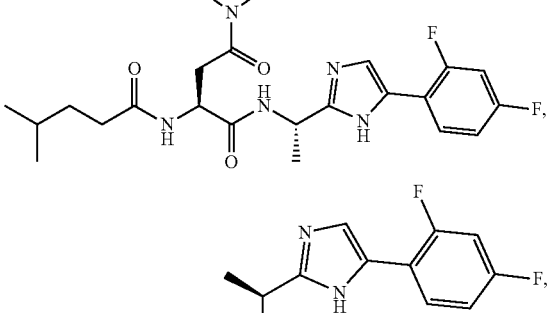

-continued
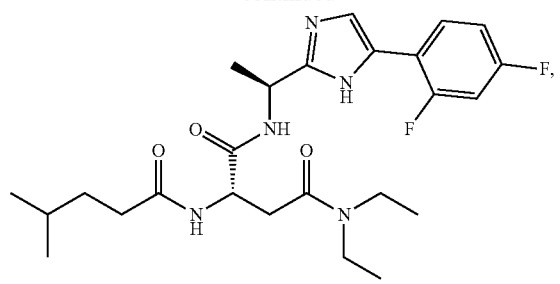
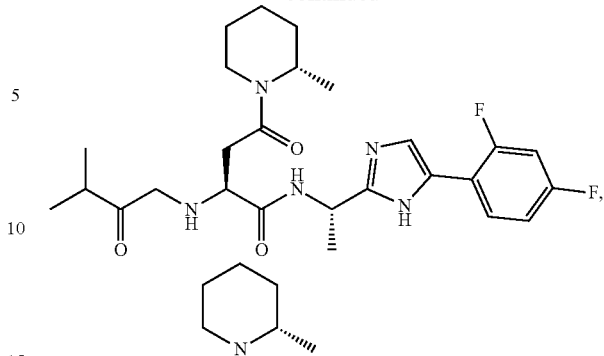
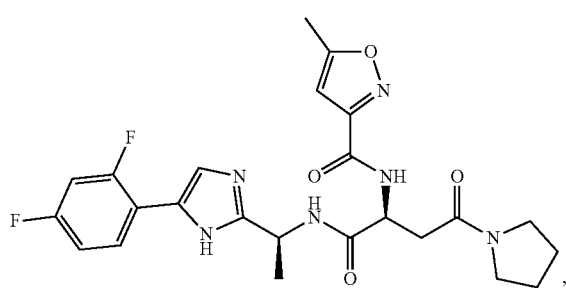
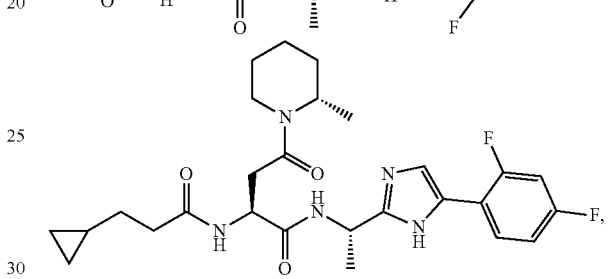
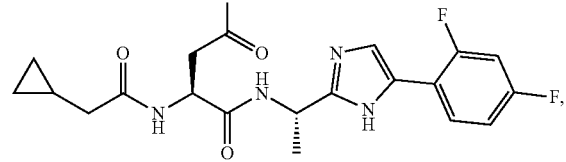
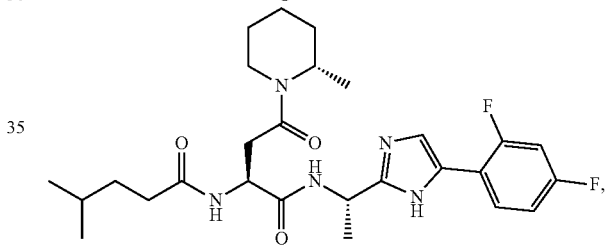
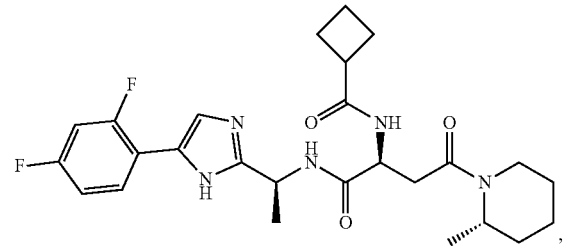
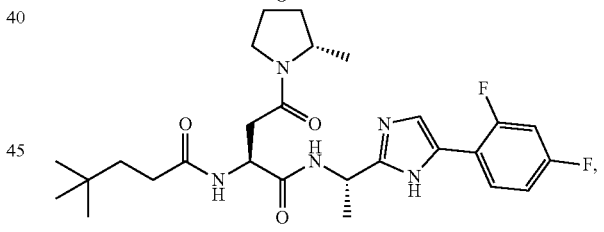
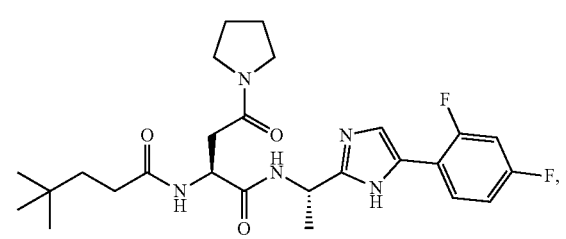
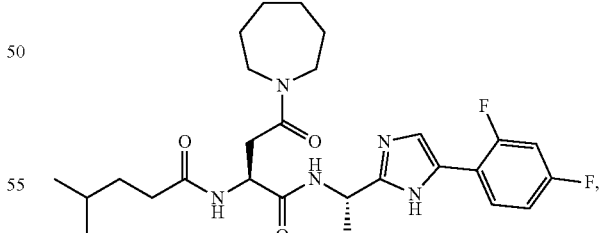
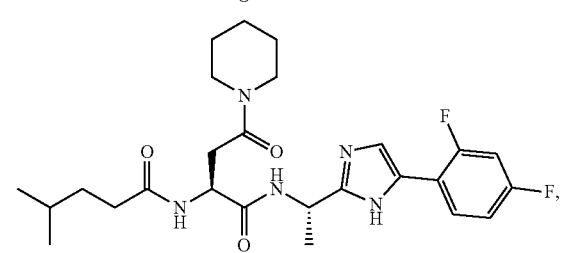
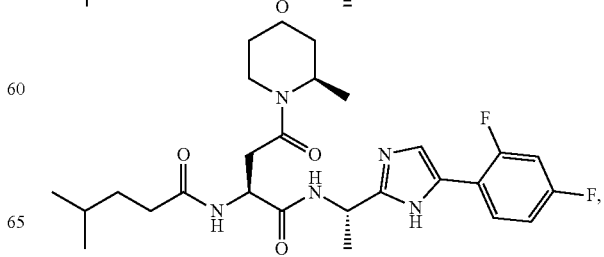

95
-continued
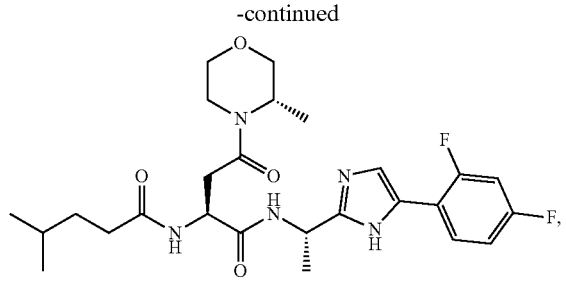
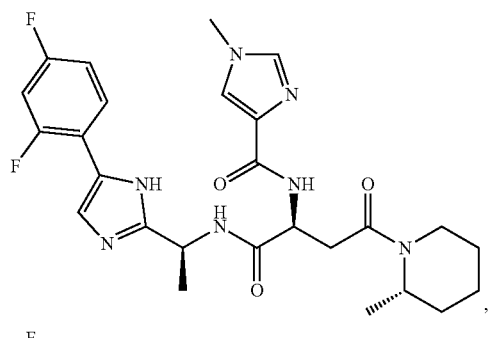
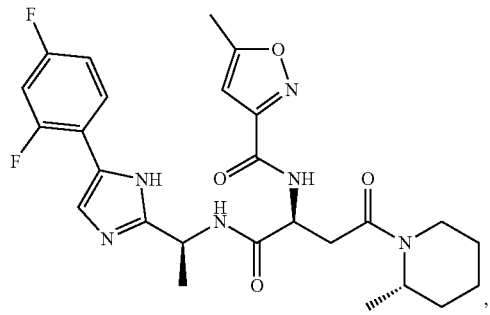
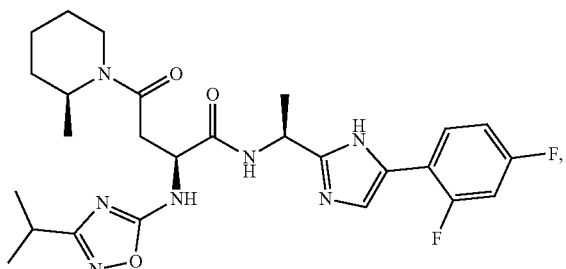
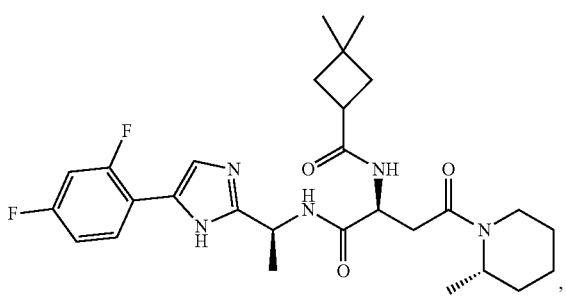
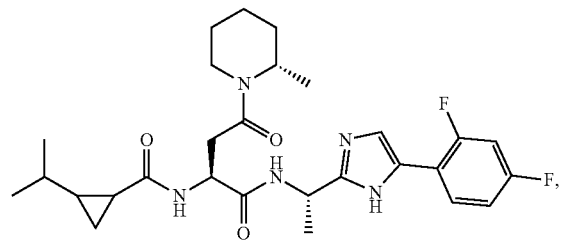
96
-continued
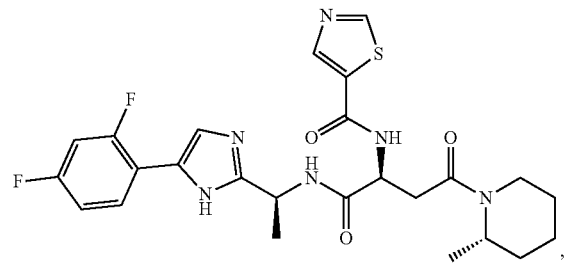
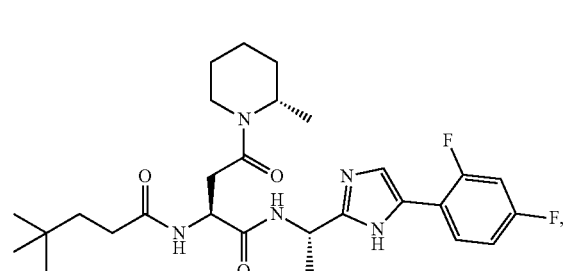
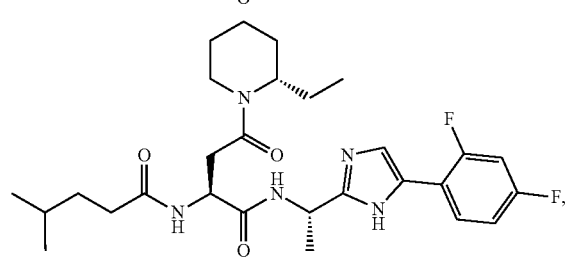
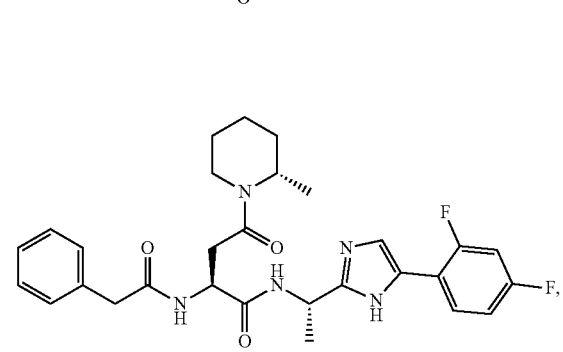
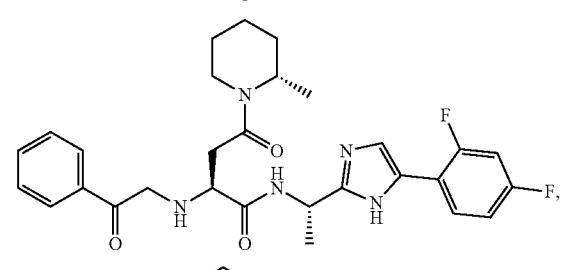
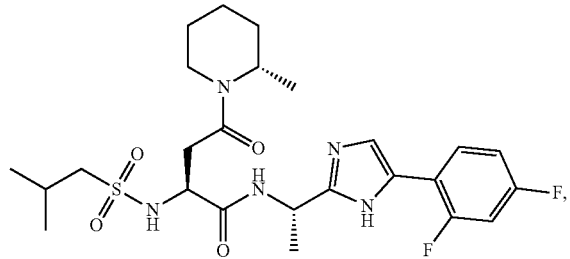

97
-continued
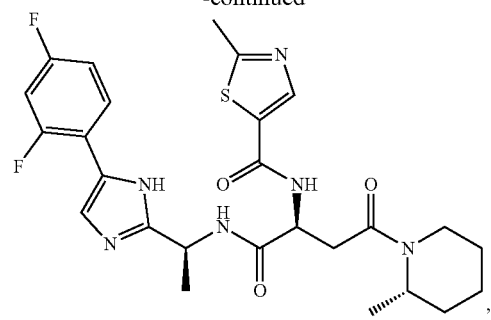
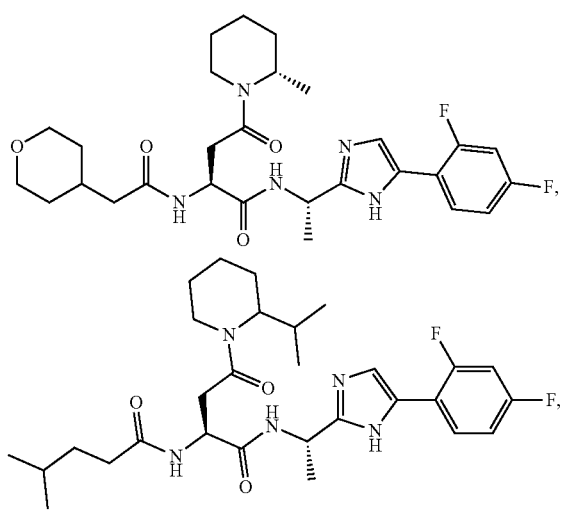
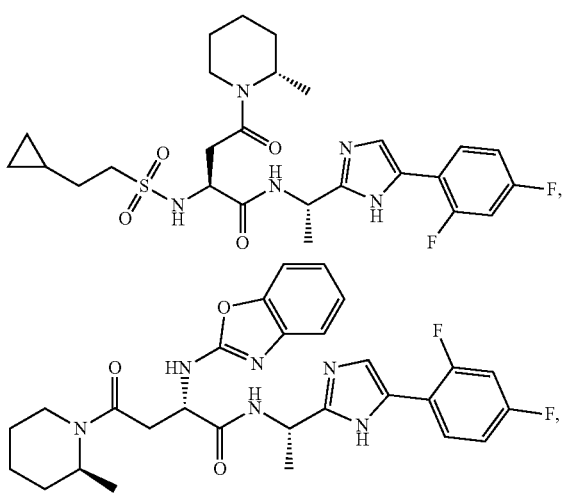
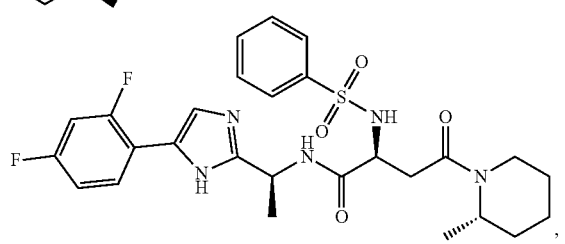
98
-continued
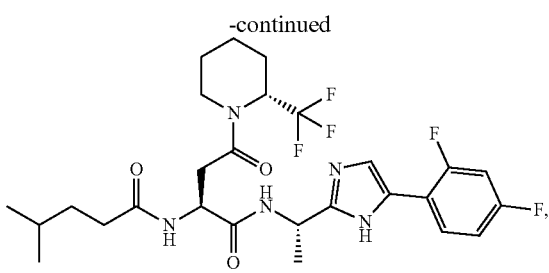
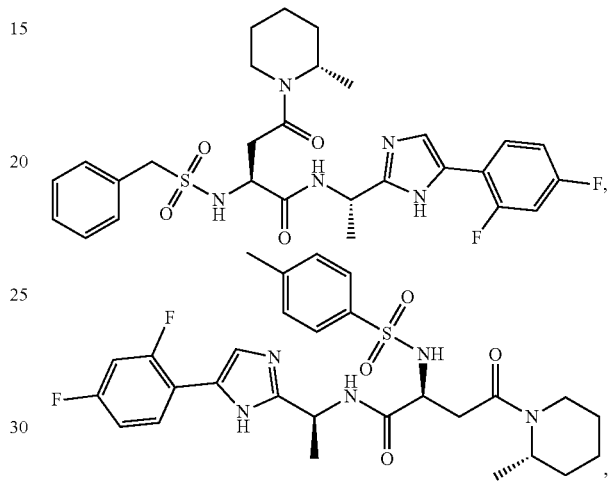
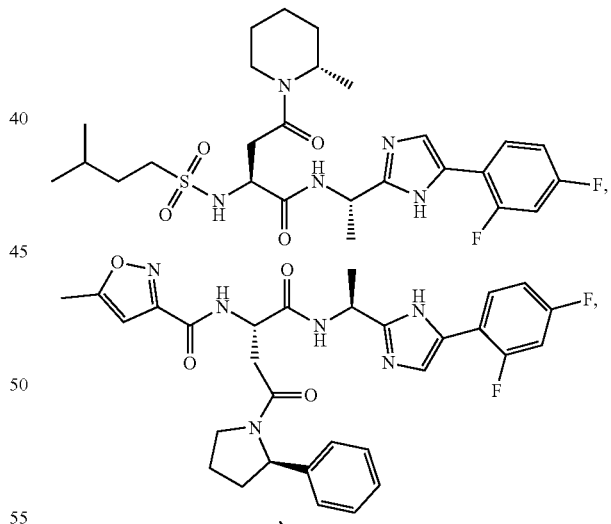
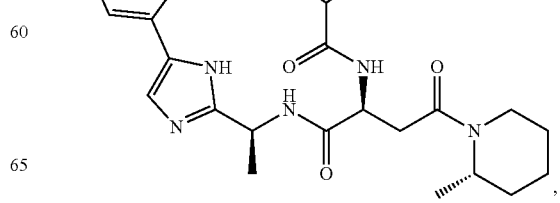

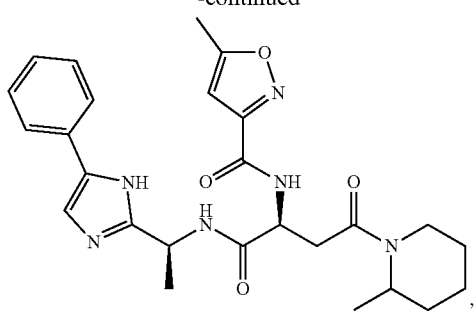
,
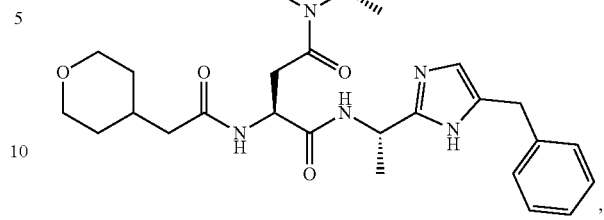
,
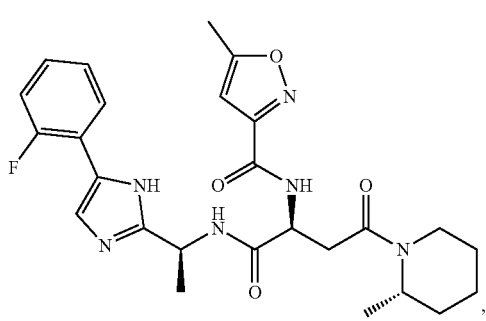
,
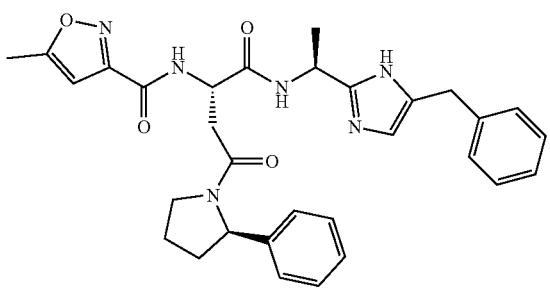
,
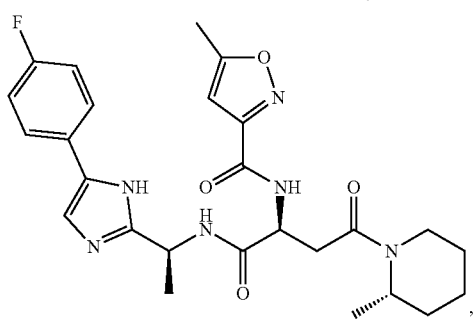
,
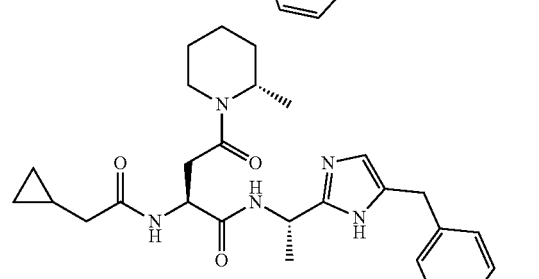
,
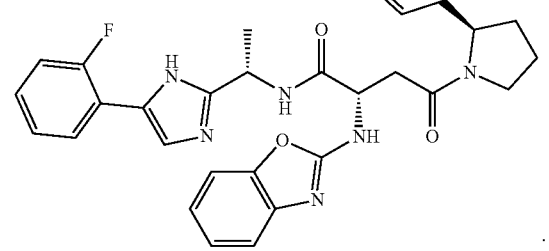
, and
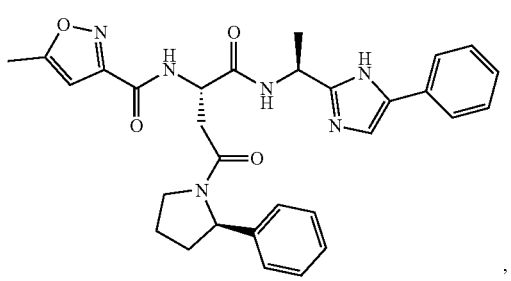
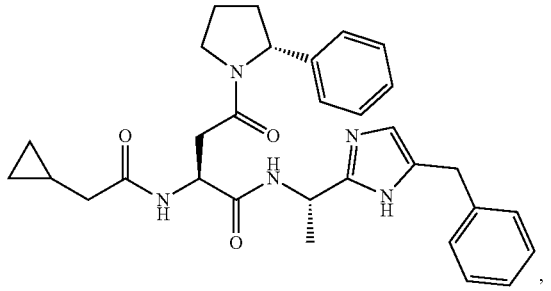
,
In another embodiment, compound has the Formula:
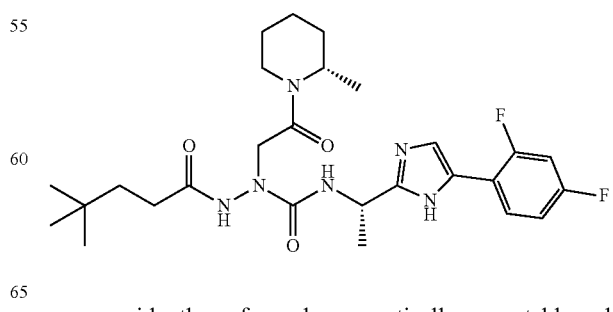
or an oxide thereof, a pharmaceutically acceptable salt thereof, a solvate thereof, or a prodrug thereof.

In yet another embodiment, compound has the Formula (II):

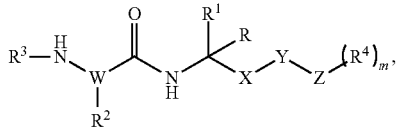

wherein
R is H or $C_{1-6}$ alkyl;
$R^1$ is H or $C_{1-6}$ alkyl;
or R and $R^1$ are taken together with the carbon to which they are attached to form a $C_{3-8}$ cycloalkyl ring;
$R^2$ is independently selected at each occurrence thereof from the group consisting of $C_{1-6}$ alkyl, and $-(CH_2)_nC(O)NR^6R^7$, wherein $C_{1-6}$ alkyl can be optionally substituted from 1 to 3 times with a substituent selected independently at each occurrence thereof from OH or $C(O)OR^{10}$;
$R^3$ is independently selected at each occurrence thereof from the group consisting of H, -Boc, $-C(O)(CH_2)R^5$, $-(CH_2)C(O)R^5$, $-C(O)OR^5$, $-C(O)(CH_2)NR^6R^7$, $-S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $C_{1-6}$ alkyl;
$R^4$ is H, $C_{1-12}$ alkyl, or halogen;
$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;
$R^6$, $R^7$ are each independently selected from the group consisting of H, $C_{1-6}$ alkyl, and arylalkyl;
or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;
$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;
$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;
$R^{10}$ is H or arylalkyl;
X is monocyclic and bicyclic heteroaryl, monocyclic and bicyclic heterocyclyl, or monocyclic and bicyclic non-aromatic heterocycle;
Y is optional and, if present, is $-(CH_2)_m-$;
Z is optional and, if present, is aryl;
W is N or CH;
m is 0, 1, or 2; and
n is 0, 1, 2, 3, or 4;

or an oxide thereof, a pharmaceutically acceptable salt thereof, a solvate thereof, or a prodrug thereof.

Another aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula (I):

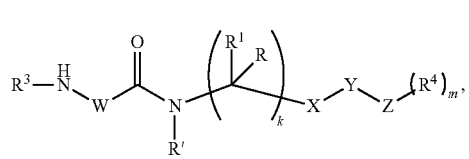

wherein
R is H or $C_{1-6}$ alkyl;
R' is H or $C_{1-6}$ alkyl;
$R^1$ is H or $C_{1-6}$ alkyl;
or R and $R^1$ are taken together with the carbon to which they are attached to form a $C_{3-8}$ cycloalkyl ring;
$R^2$ is independently selected at each occurrence thereof from

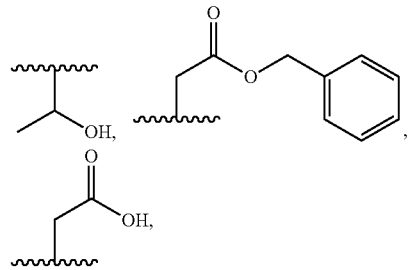

or $-(CH_2)_nC(O)NR^6R^7$;
$R^3$ is independently selected at each occurrence thereof from the group consisting of H, $C_{1-12}$ alkyl, -Boc, $-C(O)(CH_2)_nR^5$, $-(CH_2)C(O)R^5$, $-C(O)OR^5$, $-C(O)(CH_2)NR^6R^7$, $-S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $R^8$;
$R^4$ is H, halogen, $NH_2$, $NHCOOC_{1-12}$ alkyl, or $C_{1-12}$ alkyl;
$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;
$R^6$, $R^7$ are each independently selected from the group consisting of H, $C_{1-6}$ alkyl, and arylalkyl;
or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;

$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

W is $CHR^2$, $NR^2$, or

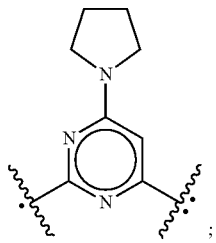

X is selected from the group consisting of —C(O)—NH—, monocyclic and bicyclic heteroaryl, monocyclic and bicyclic heterocyclyl, and monocyclic and bicyclic non-aromatic heterocycle;

Y is optional and, if present, is —$(CH_2)_m$—;

Z is optional and, if present, is aryl or bicyclic heteroaryl;

is the point of attachment to $NHR^3$ moiety;

is the point of attachment to C(O) moiety;

k is 1 or 2;

m is 0, 1, or 2; and n is 0, 1, 2, 3, or 4, with the proviso that $R^2$ is not —$CH_2C(O)NH_2$, —$CH_2C(O)NHCH_2C(CH_3)_3$, or —$(CH_2)_2C(O)NH_2$, or an oxide thereof, a pharmaceutically acceptable salt thereof, a solvate thereof, or a prodrug thereof.

One embodiment of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula (I'):

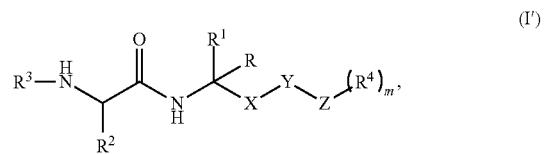

wherein

R is H or $C_{1-6}$ alkyl;

$R^1$ is H or $C_{1-6}$ alkyl;

or R and $R^1$ are taken together with the carbon to which they are attached to form a $C_{3-8}$ cycloalkyl ring;

$R^2$ is independently selected at each occurrence thereof from the group consisting of $C_{1-6}$ alkyl, and —$(CH_2)_nC(O)NR^6R^7$, wherein $C_{1-6}$ alkyl can be optionally substituted from 1 to 3 times with a substituent selected independently at each occurrence thereof from OH or $C(O)OR^{10}$;

$R^3$ is independently selected at each occurrence thereof from the group consisting of H, -Boc, —$C(O)(CH_2)_nR^5$, —$(CH_2)C(O)R^5$, —$C(O)OR^5$, —$C(O)(CH_2)NR^6R^7$, —$S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $C_{1-6}$ alkyl;

$R^4$ is H, $C_{1-12}$ alkyl, or halogen;

$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;

$R^6$, $R^7$ are each independently selected from the group consisting of H, $C_{1-6}$ alkyl, and arylalkyl;

or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;

$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

X is monocyclic and bicyclic heteroaryl, monocyclic and bicyclic heterocyclyl, or monocyclic and bicyclic non-aromatic heterocycle;

Y is optional and, if present, is —$(CH_2)_m$—;

Z is optional and, if present, is aryl;

m is 0, 1, or 2; and n is 0, 1, 2, 3, or 4;

or an oxide thereof, a pharmaceutically acceptable salt thereof, a solvate thereof, or a prodrug thereof.

Another aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula:

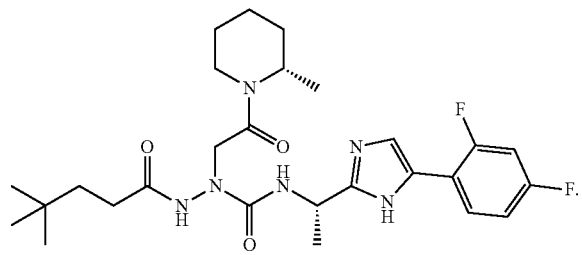 [SMILES: C[C@H](NC(=O)N(CC(=O)N1CCCC[C@@H]1C)NC(=O)CCC(C)(C)C)c1ncc(-c2ccc(F)cc2F)[nH]1]

Another aspect of the present invention relates to a method of treating bacterial infections, parasite infections, fungal infections, cancer, immunologic disorders, autoimmune disorders, neurodegenerative diseases and disorders, inflammatory disorders, or muscular dystrophy, in a subject or for achieving immunosuppression in transplanted organs or tissues in a subject. This method includes administering to the subject in need thereof a compound of Formula (II):

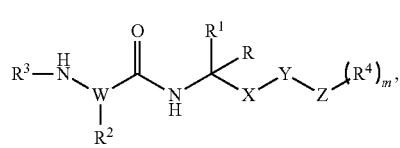

wherein

R is H or $C_{1-6}$ alkyl;

$R^1$ is H or $C_{1-6}$ alkyl;

or R and $R^1$ are taken together with the carbon to which they are attached to form a $C_{3-8}$ cycloalkyl ring;

$R^2$ is independently selected at each occurrence thereof from the group consisting of $C_{1-6}$ alkyl, and —$(CH_2)_nC(O)NR^6R^7$, wherein $C_{1-6}$ alkyl can be optionally substituted from 1 to 3 times with a substituent selected independently at each occurrence thereof from OH or $C(O)OR^{10}$;

$R^3$ is independently selected at each occurrence thereof from the group consisting of H, -Boc, —$C(O)(CH_2)_nR^5$, —$(CH_2)C(O)R^5$, —$C(O)OR^5$, —$C(O)(CH_2)NR^6R^7$, —$S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $C_{1-6}$ alkyl;

$R^4$ is H, $C_{1-12}$ alkyl, or halogen;

$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;

$R^6$, $R^7$ are each independently selected from the group consisting of H, $C_{1-6}$ alkyl, and arylalkyl;

or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;

$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

X is monocyclic and bicyclic heteroaryl, monocyclic and bicyclic heterocyclyl, or monocyclic and bicyclic non-aromatic heterocycle;

Y is optional and, if present, is —$(CH_2)_m$—;

Z is optional and, if present, is aryl;

W is N or CH;

m is 0, 1, or 2; and n is 0, 1, 2, 3, or 4;

or an oxide thereof, a pharmaceutically acceptable salt thereof, a solvate thereof, or a prodrug thereof.

In one embodiment, bacterial infection is treated. The bacterial infection is *Mycobacterium tuberculosis*.

In another embodiment, parasite infection is treated. The parasite infection is selected from, but not limited to, the group consisting of malaria, leishmaniasis, river blindness, Chagas disease, sleeping disease, cryptosporidiosis, amebiasis, cyclosporiasis, giardiasis, and toxoplasmosis.

In yet another embodiment, parasite infection is veterinary parasite infection. The veterinary parasite infection is caused by protozoan parasites, helminth parasites, arachnids, insects, or crustaceans. Exemplary protozoan parasites include, but are not limited to, *Babesia divergens, Balantidium coli, Eimeria tenella, Giardia lamblia (Giardia duodenalis), Hammondia hammondi, Histomonas meleagridis, Isospora canis, Leishmania donovani, Leishmania infantum, Neospora caninum, Toxoplasma gondii, Trichomonas gallinae, Tritrichomonas foetus, Trypanosoma brucei*, and *Trypanosoma equiperdum*. Exemplary helminth parasites include, but are not limited to, *Ancylostoma duodenale, Ascaris suum, Dicrocoelium dendriticum, Dictyocaulus viviparus, Dipylidium caninum, Echinococcus granulosus, Fasciola hepatica, Fascioloides magna, Habronema species, Haemonchus contortus, Metastrongylus, Muellerius capillaris, Ostertagia ostertagi, Paragonimus westermani, Schistosoma bovis, Strongyloides species, Strongylus vulgaris, Syngamus trachea* (Gapeworm), *Taenia pisiformis, Taenia saginata, Taenia solium, Toxocara canis, Trichinella spiralis, Trichobilharzia regenti, Trichostrongylus species*, and *Trichuris suis*. Exemplary arachnids, insects, and crustaceans include, but are not limited to, *Caligus* species, *Cimex colombarius, Cimex lectularius, Culex pipiens, Culicoides imicola, Demodex bovis, Dermacentor reticulatus, Gasterophilus intestinalis, Haematobia irritans, Hypoderma bovis, Ixodes ricinus, Knemidocoptes mutans, Lepeophtheirus salmonis, Lucilia sericata, Musca domestica, Nosema apis, Notoedres cati, Oestrus ovis, Otodectes cynotis, Phlebotomus species, Psoroptes ovis, Pulex irritans, Rhipicephalus sanguineus, Sarcoptes equi, Sarcophaga carnaria, Tabanus atratus, Triatoma species, Ctenocephalides canis*, and *Ctenocephalides felis*.

In another embodiment, an autoimmune disorder is treated. The autoimmune disorder is selected from the group consisting of arthritis, colitis, multiple sclerosis, lupus, Sjogren Syndrome, Systemic Lupus Erythematosus and lupus nephritis, glomerulonephritis, Rheumatoid Arthritis, Inflammatory bowel disease (IBD), ulcerative colitis, Crohn's diseases, Psoriasis, and asthma.

In yet another embodiment, immunosuppression is provided for transplanted organs or tissues. The immunosuppression is used to prevent transplant rejection and graft-verse-host disease.

In a further embodiment, an inflammatory disorder is treated. The inflammatory disorder is Crohn's disease.

The compounds and pharmaceutical compositions of the present invention are particularly useful for the treatment of cancer. As used herein, the term "cancer" refers to a cellular disorder characterized by uncontrolled or disregulated cell proliferation, decreased cellular differentiation, inappropriate ability to invade surrounding tissue, and/or ability to establish new growth at ectopic sites. The term "cancer" includes, but is not limited to, solid tumors and bloodborne tumors. The term "cancer" encompasses diseases of skin, tissues, organs, bone, cartilage, blood, and vessels. The term "cancer" further encompasses primary and metastatic cancers.

Non-limiting examples of solid tumors that can be treated with the disclosed proteasome inhibitors include pancreatic cancer; bladder cancer; colorectal cancer; breast cancer, including metastatic breast cancer; prostate cancer, including androgen-dependent and androgen-independent prostate cancer; renal cancer, including, e.g., metastatic renal cell carcinoma; hepatocellular cancer; lung cancer, including, e.g., non-small cell lung cancer (NSCLC), bronchioloalveolar carcinoma (BAC), and adenocarcinoma of the lung; ovarian cancer, including, e.g., progressive epithelial or primary peritoneal cancer; cervical cancer; gastric cancer; esophageal cancer; head and neck cancer, including, e.g., squamous cell carcinoma of the head and neck; melanoma; neuroendocrine cancer, including metastatic neuroendocrine tumors; brain tumors, including, e.g., glioma, anaplastic oligodendroglioma, adult glioblastoma multiforme, and adult anaplastic astrocytoma; bone cancer; and soft tissue sarcoma.

In one embodiment, cancer is treated. The cancer is selected from the group consisting of neoplastic disorders, hematologic malignancies, lymphocytic malignancies, mantel cell lymphoma, leukemia, Waldenstrom Macroglobulinemia, pancreatic cancer, bladder cancer, colorectal cancer, breast cancer, metastatic breast cancer, prostate cancer, androgen-dependent and androgen-independent prostate cancer, renal cancer, metastatic renal cell carcinoma, hepatocellular cancer, lung cancer, non-small cell lung cancer (NSCLC), bronchioloalveolar carcinoma (BAC), and adenocarcinoma of the lung, ovarian cancer, progressive epithelial or primary peritoneal cancer, cervical cancer, gastric cancer, esophageal cancer, head and neck cancer, squamous cell carcinoma of the head and neck, melanoma, neuroendocrine cancer, metastatic neuroendocrine tumors, brain tumors, glioma, anaplastic oligodendroglioma, adult glioblastoma multiforme, and adult anaplastic astrocytoma, bone cancer, and soft tissue sarcoma.

In another embodiment, a neurodegenerative disease or disorder is treated. The neurodegenerative disease or disorder is Amyotrophic Lateral Sclerosis (ALS) or Multiple Sclerosis (MS).

Another aspect of the present invention relates to a method of inhibiting proteasome activity. This method includes contacting a proteasome with a compound of Formula (I):

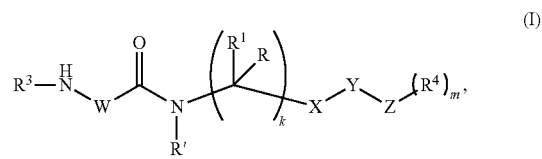

wherein
R is H or $C_{1-6}$ alkyl;
R' is H or $C_{1-6}$ alkyl;
$R^1$ is H or $C_{1-6}$ alkyl;
or R and $R^1$ are taken together with the carbon to which they are attached to form a $C_{3-8}$ cycloalkyl ring;
$R^2$ is independently selected at each occurrence thereof from

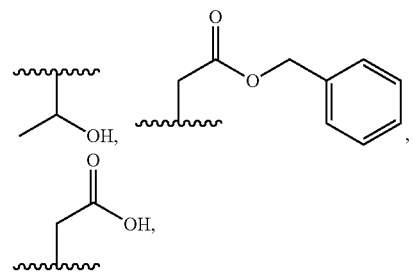

or —$(CH_2)_nC(O)NR^6R^7$;
$R^3$ is independently selected at each occurrence thereof from the group consisting of H, $C_{1-12}$ alkyl, -Boc, —C(O)$(CH_2)R^5$, —$(CH_2)C(O)R^5$, —C(O)OR$^5$, —C(O)(CH$_2$)NR$^6$R$^7$, —S(O)$_2$R$^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $R^8$;
$R^4$ is H, halogen, NH$_2$, NHCOOC$_{1-12}$ alkyl, or C$_{1-12}$ alkyl;
$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;
$R^6$, $R^7$ are each independently selected from the group consisting of H, $C_{1-6}$ alkyl, and arylalkyl;
or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;
$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

W is $CHR^2$, $NR^2$, or

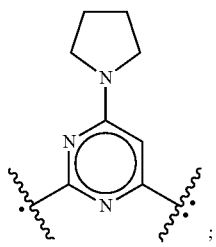
;

X is selected from the group consisting of —C(O)—NH—, monocyclic and bicyclic heteroaryl, monocyclic and bicyclic heterocyclyl, and monocyclic and bicyclic non-aromatic heterocycle;

Y is optional and, if present, is —$(CH_2)_m$—;

Z is optional and, if present, is aryl or bicyclic heteroaryl;

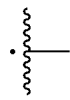

is the point of attachment to $NHR^3$ moiety;

is the point of attachment to C(O) moiety;

k is 1 or 2;

m is 0, 1, or 2; and n is 0, 1, 2, 3, or 4, with the proviso that $R^2$ is not —$CH_2C(O)NH_2$, —$CH_2C(O)NHCH_2C(CH_3)_3$, or —$(CH_2)_2C(O)NH_2$, or an oxide thereof, a pharmaceutically acceptable salt thereof, a solvate thereof, or a prodrug thereof under conditions effective to inhibit proteasome activity.

One embodiment of the present invention relates to a method of inhibiting proteasome activity. This method includes contacting a proteasome with a compound of Formula (I'):

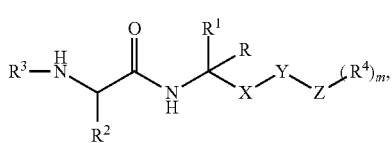
(I')

wherein

R is H or $C_{1-6}$ alkyl;

$R^1$ is H or $C_{1-6}$ alkyl;

or R and $R^1$ are taken together with the carbon to which they are attached to form a $C_{3-8}$ cycloalkyl ring;

$R^2$ is independently selected at each occurrence thereof from the group consisting of $C_{1-6}$ alkyl, and —$(CH_2)_nC(O)NR^6R^7$, wherein $C_{1-6}$ alkyl can be optionally substituted from 1 to 3 times with a substituent selected independently at each occurrence thereof from OH or $C(O)OR^{10}$;

$R^3$ is independently selected at each occurrence thereof from the group consisting of H, -Boc, —$C(O)(CH_2)_nR^5$, —$(CH_2)C(O)R^5$, —$C(O)OR^5$, —$C(O)(CH_2)NR^6R^7$, —$S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $C_{1-6}$ alkyl;

$R^4$ is H, $C_{1-12}$ alkyl, or halogen;

$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;

$R^6$, $R^7$ are each independently selected from the group consisting of H, $C_{1-6}$ alkyl, and arylalkyl;

or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;

$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

X is monocyclic and bicyclic heteroaryl, monocyclic and bicyclic heterocyclyl, or monocyclic and bicyclic non-aromatic heterocycle;

Y is optional and, if present, is —$(CH_2)_m$—;

Z is optional and, if present, is aryl;

m is 0, 1, or 2; and n is 0, 1, 2, 3, or 4;

or an oxide thereof, a pharmaceutically acceptable salt thereof, a solvate thereof, or a prodrug thereof under conditions effective to inhibit proteasome activity.

Another aspect of the present invention relates to a method of inhibiting proteasome activity. This method includes contacting a proteasome with a compound of Formula

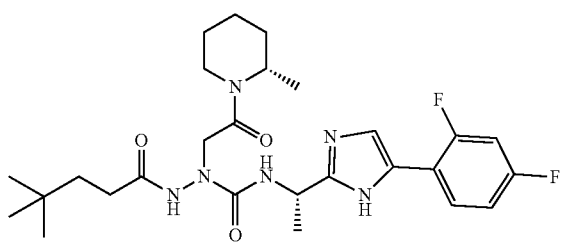

or an oxide thereof, a pharmaceutically acceptable salt thereof, a solvate thereof, or a prodrug thereof under conditions effective to inhibit proteasome activity.

Another aspect of the present invention relates to a method of inhibiting proteasome activity. This method includes contacting a proteasome with a compound of Formula (II):

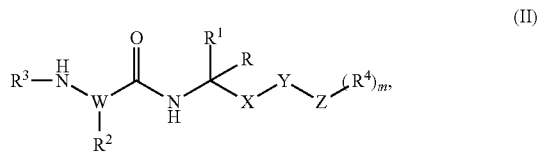

wherein

R is H or $C_{1-6}$ alkyl;

$R^1$ is H or $C_{1-6}$ alkyl;

or R and $R^1$ are taken together with the carbon to which they are attached to form a $C_{3-8}$ cycloalkyl ring;

$R^2$ is independently selected at each occurrence thereof from the group consisting of $C_{1-6}$ alkyl, and —$(CH_2)_nC(O)NR^6R^7$, wherein $C_{1-6}$ alkyl can be optionally substituted from 1 to 3 times with a substituent selected independently at each occurrence thereof from OH or $C(O)OR^{10}$;

$R^3$ is independently selected at each occurrence thereof from the group consisting of H, -Boc, —$C(O)(CH_2)_nR^5$, —$(CH_2)C(O)R^5$, —$C(O)OR^5$, —$C(O)(CH_2)NR^6R^7$, —$S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $C_{1-6}$ alkyl;

$R^4$ is H, $C_{1-12}$ alkyl, or halogen;

$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;

$R^6$, $R^7$ are each independently selected from the group consisting of H, $C_{1-6}$ alkyl, and arylalkyl;

or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;

$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;

$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;

$R^{10}$ is H or arylalkyl;

X is monocyclic and bicyclic heteroaryl, monocyclic and bicyclic heterocyclyl, or monocyclic and bicyclic non-aromatic heterocycle;

Y is optional and, if present, is —$(CH_2)_m$—;

Z is optional and, if present, is aryl;

W is N or CH;

m is 0, 1, or 2; and n is 0, 1, 2, 3, or 4;

or an oxide thereof, a pharmaceutically acceptable salt thereof, a solvate thereof, or a prodrug thereof under conditions effective to inhibit proteasome activity.

While it may be possible for compounds of Formula (I), Formula (IA), Formula (IB), Formula (IC), Formula (I'), Formula (I'A), Formula (I'B), Formula (I'C), Formula (I'D), Formula (I'E), Formula (I'F), Formula (I'G), Formula (I'C'), Formula (I'D'), Formula (I'E'), Formula (I'F'), Formula (I'G'), and Formula (II), to be administered as raw chemicals, it will often be preferable to present them as a part of a pharmaceutical composition. Accordingly, another aspect of the present invention is a pharmaceutical composition containing a therapeutically effective amount of the compound of Formula (I), Formula (IA), Formula (IB), Formula (IC), Formula (I'), Formula (I'A), Formula (I'B), Formula (I'C), Formula (I'D), Formula (I'E), Formula (I'F), Formula (I'G), Formula (I'C'), Formula (I'D'), Formula (I'E'), Formula (I'F'), Formula (I'G'), and Formula (II), or a pharmaceutically acceptable salt or solvate thereof, and a pharmaceutically acceptable carrier. The carrier must be "acceptable" in the sense of being compatible with the other ingredients of the formulation and not deleterious to the recipient thereof.

In practicing the method of the present invention, agents suitable for treating a subject can be administered using any method standard in the art. The agents, in their appropriate delivery form, can be administered orally, intradermally, intramuscularly, intraperitoneally, intravenously, subcutaneously, or intranasally. The compositions of the present invention may be administered alone or with suitable pharmaceutical carriers, and can be in solid or liquid form, such as tablets, capsules, powders, solutions, suspensions, or emulsions.

The agents of the present invention may be orally administered, for example, with an inert diluent, or with an assimilable edible carrier, or it may be enclosed in hard or soft shell capsules, or it may be compressed into tablets, or they may be incorporated directly with the food of the diet. Agents of the present invention may also be administered in a time release manner incorporated within such devices as time-release capsules or nanotubes. Such devices afford flexibility relative to time and dosage. For oral therapeutic administration, the agents of the present invention may be incorporated with excipients and used in the form of tablets, capsules, elixirs, suspensions, syrups, and the like. Such compositions and preparations should contain at least 0.1% of the agent, although lower concentrations may be effective and indeed optimal. The percentage of the agent in these compositions may, of course, be varied and may conveniently be between about 2% to about 60% of the weight of the unit. The amount of an agent of the present invention in such therapeutically useful compositions is such that a suitable dosage will be obtained.

Also specifically contemplated are oral dosage forms of the agents of the present invention. The agents may be chemically modified so that oral delivery of the derivative is efficacious. Generally, the chemical modification contemplated is the attachment of at least one moiety to the component molecule itself, where said moiety permits (a) inhibition of proteolysis; and (b) uptake into the blood stream from the stomach or intestine. Also desired is the increase in overall stability of the component or components and increase in circulation time in the body. Examples of such moieties include: polyethylene glycol, copolymers of ethylene glycol and propylene glycol, carboxymethyl cellulose, dextran, polyvinyl alcohol, polyvinyl pyrrolidone and polyproline (Abuchowski and Davis, "Soluble Polymer-Enzyme Adducts," In: *Enzymes as Drugs*, Hocenberg and Roberts, eds., Wiley-Interscience, New York, N.Y., pp. 367-383 (1981), which are hereby incorporated by reference in their entirety). Other polymers that could be used are poly-1,3-dioxolane and poly-1,3,6-tioxocane. Preferred for pharmaceutical usage, as indicated above, are polyethylene glycol moieties.

The tablets, capsules, and the like may also contain a binder such as gum tragacanth, acacia, corn starch, or gelatin; excipients such as dicalcium phosphate; a disintegrating agent such as corn starch, potato starch, alginic acid; a lubricant such as magnesium stearate; and a sweetening agent such as sucrose, lactose, sucralose, or saccharin. When the dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar, or both. A syrup may contain, in addition to active ingredient, sucrose as a sweetening agent, methyl and propylparabens as preservatives, a dye, and flavoring such as cherry or orange flavor.

The agents of the present invention may also be administered parenterally. Solutions or suspensions of the agent can be prepared in water suitably mixed with a surfactant such as hydroxypropylcellulose. Dispersions can also be prepared in glycerol, liquid polyethylene glycols, and mixtures thereof in oils. Illustrative oils are those of petroleum, animal, vegetable, or synthetic origin, for example, peanut oil, soybean oil, or mineral oil. In general, water, saline, aqueous dextrose and related sugar solution, and glycols, such as propylene glycol or polyethylene glycol, are preferred liquid carriers, particularly for injectable solutions. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol), suitable mixtures thereof, and vegetable oils.

When it is desirable to deliver the agents of the present invention systemically, they may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Intraperitoneal or intrathecal administration of the agents of the present invention can also be achieved using infusion pump devices such as those described by Medtronic, Northridge, Calif. Such devices allow continuous infusion of desired compounds avoiding multiple injections and multiple manipulations.

In addition to the formulations described previously, the agents may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The agents of the present invention may also be administered directly to the airways in the form of an aerosol. For use as aerosols, the agent of the present invention in solution or suspension may be packaged in a pressurized aerosol container together with suitable propellants, for example, hydrocarbon propellants like propane, butane, or isobutane with conventional adjuvants. The agent of the present invention also may be administered in a non-pressurized form such as in a nebulizer or atomizer.

Effective doses of the compositions of the present invention, for the treatment of cancer or pathogen infection vary depending upon many different factors, including type and stage of cancer or the type of pathogen infection, means of administration, target site, physiological state of the patient, other medications or therapies administered, and physical state of the patient relative to other medical complications. Treatment dosages need to be titrated to optimize safety and efficacy.

The percentage of active ingredient in the compositions of the present invention may be varied, it being necessary that it should constitute a proportion such that a suitable dosage shall be obtained. Obviously, several unit dosage forms may be administered at about the same time. The dose employed will be determined by the physician, and depends upon the desired therapeutic effect, the route of administration and the duration of the treatment, and the condition of the patient. In the adult, the doses are generally from about 0.01 to about 100 mg/kg body weight, preferably about 0.01 to about 10 mg/kg body weight per day by inhalation, from about 0.01 to about 100 mg/kg body weight, preferably 0.1 to 70 mg/kg body weight, more especially 0.1 to 10 mg/kg body weight per day by oral administration, and from about 0.01 to about 50 mg/kg body weight, preferably 0.01 to 10 mg/kg body weight per day by intravenous administration. In each particular case, the doses will be determined in accordance with the factors distinctive to the subject to be treated, such as age, weight, general state of health, and other characteristics which can influence the efficacy of the medicinal product.

The products according to the present invention may be administered as frequently as necessary in order to obtain the desired therapeutic effect. Some patients may respond rapidly to a higher or lower dose and may find much weaker maintenance doses adequate. For other patients, it may be necessary to have long-term treatments at the rate of 1 to 4 doses per day, in accordance with the physiological requirements of each particular patient. Generally, the active product may be administered orally 1 to 4 times per day. It goes without saying that, for other patients, it will be necessary to prescribe not more than one or two doses per day.

EXAMPLES

Example 1—General Procedure for HATU-Mediated Coupling Reaction

Carboxylic acid (1.0 eq.), 0-(7-azabenzotriazol-1-yl)-N,N,N,N'-tetramethyluronium hexafluorophosphate (HATU) (1.2 eq.), and 1-hydroxy-7-azabenzotriazole (HOAt) (0.6M in DMF) (1.0 eq.) were dissolved in DMF under argon atmosphere. The solution was cooled to 0° C. and amine was added. After stirring for 5 minutes at 0° C., Hunig's base (2-3 eq.) was added. The reaction mixture was stirred at 0° C. for 1 hour. After completion of the reaction (1 hour, monitored by LCMS), water (10 mL) was added to the reaction mixture and the mixture was stirred for 30 minutes. Product was isolated by either ethyl acetate extraction or by filtering the precipitate.

Example 2—General Procedure for Deprotection of Benzyl Group

The substance was dissolved in methanol. Palladium on carbon (10%) was added carefully. Air in the flask was exchanged with hydrogen. The mixture was stirred at room temperature for 3-4 hours under hydrogen atmosphere using a hydrogen balloon. After completion of reaction, the mixture was filtered through Celite. Filtrate was evaporated and dried under vacuum to give the product.

Example 3—General Procedure for N-Sulfonamide Preparation of Amines

The primary amine (generally TFA salt) was dissolved in dichloromethane. The solution was cooled to 0° C. and triethylamine (2.0-3.0 eq.) was added. Sulfonyl chloride (1.5 eq.) was added to the solution in one portion and the reaction mixture was warmed to room temperature (over 15 minutes). After completion of reaction (2-3 hours), dichloromethane was evaporated and crude product was isolated by ethyl acetate extraction.

Example 4—Preparation of tert-Butyl (S)-(1-((2-Amino-3-fluorophenyl)amino)-1-oxopropan-2-yl)carbamate (1-1)

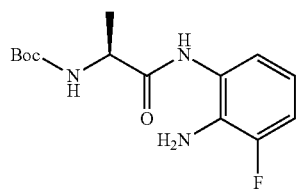 [SMILES: C[C@H](NC(=O)OC(C)(C)C)C(=O)Nc1cccc(F)c1N]

The title compound was synthesized by following the general protocol for HATU mediated coupling of (S)-2-(tert-butoxycarbonylamino)propanoic acid and 3-fluorobenzene-1,2-diamine on a 2.0 mmol scale. The product (600 mg, quant. ESI-MS (m/z): 298.22 (M+H$^+$)) was isolated and used directly in the next step.

Example 5—Preparation of (S)-1-(4-Fluoro-1H-benzo[d]imidazol-2-yl)ethan-1-amine (1-2)

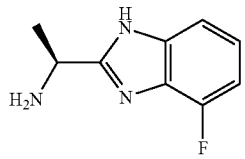

To a solution of tert-butyl (S)-(1-((2-amino-3-fluorophenyl)amino)-1-oxopropan-2-yl)carbamate (600 mg) in EtOH (4 ml) was added HCl (7 ml), and the reaction mixture was heated to reflux for 4 hours. Solvent was removed by evaporation to give a gum (400 mg) assumed diHCl salt. LC-MS (linear gradient 10→98% MeCN, 0.1% TFA, 6.5 min): t$_R$ (min): 2.13; ESI-MS (m/z): 180.10 (M+H$^+$).

Example 6—Preparation of Benzyl (S)-2-((tert-Butoxycarbonyl)amino)-4-((S)-2-ethylpiperidin-1-yl)-4-oxobutanoate (1-3)

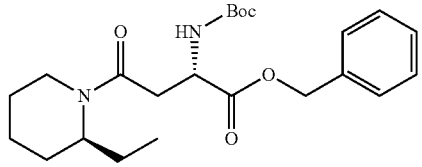 [SMILES: CC[C@H]1CCCCN1C(=O)C[C@H](NC(=O)OC(C)(C)C)C(=O)OCc1ccccc1]

The title compound was synthesized by following the general protocol for HATU mediated coupling of (S)-4-(benzyloxy)-3-(tert-butoxycarbonylamino)-4-oxobutanoic acid and (S)-2-ethylpiperidine hydrochloride on a 0.7 mmol scale, and isolated as a white solid in quant. yield. LC-MS (linear gradient 10→98% MeCN, 0.1% TFA, 6.5 min): t$_R$ (min): 4.58; ESI-MS (m/z): 419.24 (M+H$^+$).

Example 7—Preparation of (S)-2-((tert-Butoxycarbonyl)amino)-4-((S)-2-ethylpiperidin-1-yl)-4-oxobutanoic Acid (1-4)

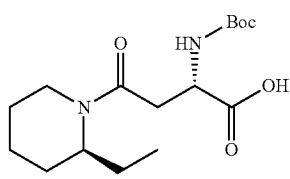 [SMILES: CC[C@H]1CCCCN1C(=O)C[C@H](NC(=O)OC(C)(C)C)C(=O)O]

The title compound was synthesized by following the O-Debenzylation protocol of 1-3 on a 0.7 mmol scale. LC-MS (linear gradient 10→98% MeCN, 0.1% TFA, 6.5 min): t$_R$ (min): 3.64; ESI-MS (m/z): 329.20 (M+H$^+$).

Example 8—Preparation of tert-Butyl ((S)-4-((S)-2-ethylpiperidin-1-yl)-1-(((S)-1-(4-fluoro-1H-benzo[d]imidazol-2-yl)ethyl)amino)-1,4-dioxobutan-2-yl)carbamate (1-5)

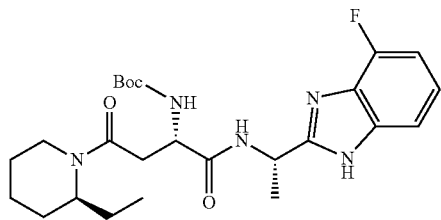 [SMILES: CC[C@H]1CCCCN1C(=O)C[C@H](NC(=O)OC(C)(C)C)C(=O)N[C@@H](C)c1nc2c(F)cccc2[nH]1]

The title compound was synthesized by following the general protocol for HATU mediated coupling of 1-4 and 1-2 on a 0.3 mmol scale. LC-MS (linear gradient 10→98% MeCN, 0.1% TFA, 6.5 min): $t_R$ (min): 3.97; ESI-MS (m/z): 490.22 (M+H$^+$).

Example 9—Preparation of (S)-2-Amino-4-((S)-2-ethylpiperidin-1-yl)-N—((S)-1-(4-fluoro-1H-benzo[d]imidazol-2-yl)ethyl)-4-oxobutanamide (CEN-1)

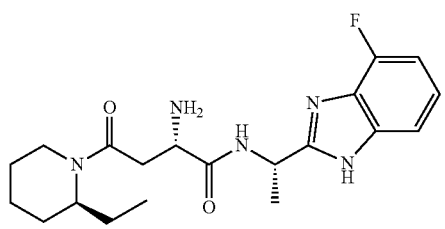 [SMILES: CC[C@H]1CCCCN1C(=O)C[C@H](N)C(=O)N[C@@H](C)c1nc2c(F)cccc2[nH]1]

The title compound was synthesized by following the general protocol for Boc-Deprotection protocol of 1-5 on a 0.1 mmol scale. LC-MS (linear gradient 10→98% MeCN, 0.1% TFA, 12 min): $t_R$ (min): 3.97; ESI-MS (m/z): 390.22 (M+H$^+$).

Example 10—Preparation of (S)-2-(2-Cyclopropylacetamido)-4-((S)-2-ethylpiperidin-1-yl)-N—((S)-1-(4-fluoro-1H-benzo[d]imidazol-2-yl)ethyl)-4-oxobutanamide (CEN-2)

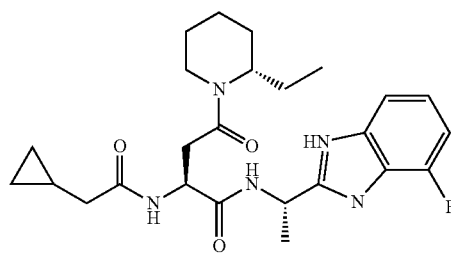

The title compound was synthesized by following the general protocol for HATU mediated coupling of CEN-1 and 2-cyclopropylacetic acid on a 0.01 mmol scale. LC-MS (linear gradient 10→98% MeCN, 0.1% TFA, 12 min): $t_R$ (min): 5.41; ESI-MS (m/z): 472.26 (M+H$^+$).

Example 11—Preparation of N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)-4-methylpentanamide (CEN-3)

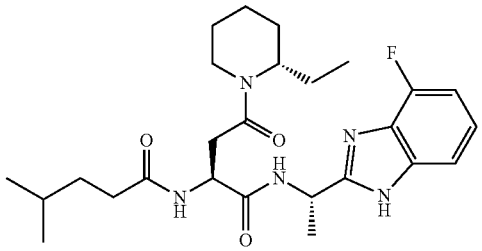 [SMILES: CC[C@H]1CCCCN1C(=O)C[C@H](NC(=O)CCC(C)C)C(=O)N[C@@H](C)c1nc2c(F)cccc2[nH]1]

The title compound was synthesized by following the general protocol for HATU mediated coupling of CEN-1 and 4-methylpentanoic acid on a 0.01 mmol scale. LC-MS (linear gradient 10→98% MeCN, 0.1% TFA, 12 min): $t_R$ (min): 5.97; ESI-MS (m/z): 488.29 (M+H$^+$).

Example 12—Preparation of (S)-2-(3-(Dimethylamino)propanamido)-4-((S)-2-ethylpiperidin-1-yl)-N—((S)-1-(4-fluoro-1H-benzo[d]imidazol-2-yl)ethyl)-4-oxobutanamide (CEN-4)

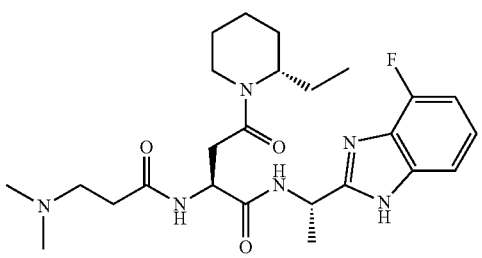 [SMILES: CC[C@H]1CCCCN1C(=O)C[C@H](NC(=O)CCN(C)C)C(=O)N[C@@H](C)c1nc2c(F)cccc2[nH]1]

The title compound was synthesized by following the general protocol for HATU mediated coupling of CEN-1 and 3-(dimethylamino)propanoic acid on a 0.01 mmol scale. LC-MS (linear gradient 10→98% MeCN, 0.1% TFA, 12 min): $t_R$ (min): 4.21; ESI-MS (m/z): 489.29 (M+H$^+$).

Example 13—Preparation of Isobutyl ((S)-4-((S)-2-Ethylpiperidin-1-yl)-1-(((S)-1-(4-fluoro-1H-benzo[d]imidazol-2-yl)ethyl)amino)-1,4-dioxobutan-2-yl)carbamate (CEN-5)

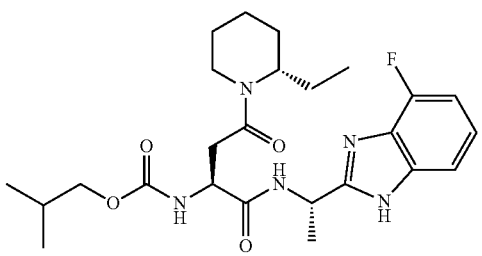 [SMILES: CC[C@H]1CCCCN1C(=O)C[C@H](NC(=O)OCC(C)C)C(=O)N[C@@H](C)c1nc2c(F)cccc2[nH]1]

To a solution of CEN-1 (4 mg) in DCM (0.5 mL) was added isobutyl carbonochloridate (1.403 mg) and triethylamine (3.58 μl), the reaction solution was stirred at room temperature for 15 min, and evaporated. The title product was purified by Prep-HPLC. LC-MS (linear gradient 10→98% MeCN, 0.1% TFA, 12 min): $t_R$ (min): 6.17; ESI-MS (m/z): 490.2 (M+H$^+$).

Example 14—Preparation of N—((S)-4-((S)-2-Ethylpiperidin-1-yl)-1-(((S)-1-(4-fluoro benzo[d]imidazol-2-yl)ethyl)amino)-1,4-dioxobutan-2-yl)-5-methylisoxazole-3-carboxamide (CEN-6)

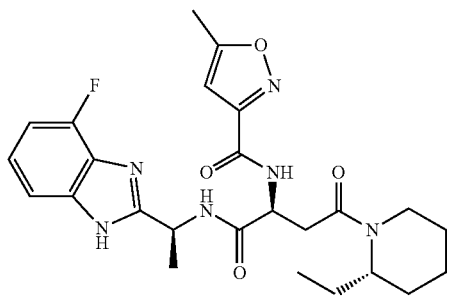 [SMILES: CC[C@H]1CCCCN1C(=O)C[C@H](NC(=O)c1cc(C)on1)C(=O)N[C@@H](C)c1nc2c(F)cccc2[nH]1]

The title compound was synthesized by following the general protocol for HATU mediated coupling of CEN-1 and 5-methylisoxazole-3-carboxylic acid on a 0.01 mmol scale. LC-MS (linear gradient 10→98% MeCN, 0.1% TFA, 12 min): $t_R$ (min): 5.67; ESI-MS (m/z): 499.23 (M+H$^+$).

Example 15—Preparation of (S)-4-((S)-2-Ethylpiperidin-1-yl)-N—((S)-1-(4-fluoro-1H-benzo[d]imidazol-2-yl)ethyl)-4-oxo-2-(3,3,3-trifluoropropanamido)butanamide (CEN-7)

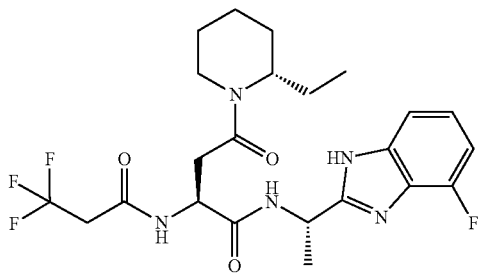 [SMILES: CC[C@H]1CCCCN1C(=O)C[C@H](NC(=O)CC(F)(F)F)C(=O)N[C@@H](C)c1nc2c(F)cccc2[nH]1]

The title compound was synthesized by following the general protocol for HATU mediated coupling of CEN-1 and 3,3,3-trifluoropropanoic acid on a 0.01 mmol scale. LC-MS (linear gradient 10→98% MeCN, 0.1% TFA, 12 min): $t_R$ (min): 5.57; ESI-MS (m/z): 500.22 (M+H$^+$).

Example 16—Preparation of (S)-4-((S)-2-Ethylpiperidin-1-yl)-N—((S)-1-(4-fluoro-1H-benzo[d]imidazol-2-yl)ethyl)-2-((3-isopropyl-1,2,4-oxadiazol-5-yl)amino) oxobutanamide (CEN-8)

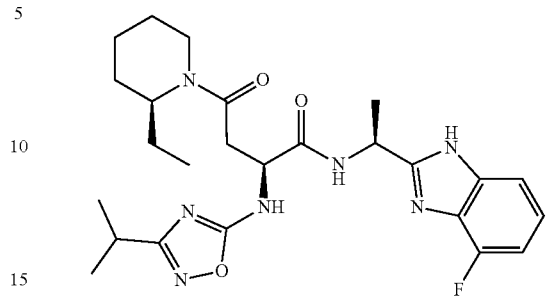

To a solution of CEN-1 (4 mg) in DMF (0.5 mL) was added 5-chloro-3-isopropyl-1,2,4-oxadiazole (2 mg), and the reaction mixture was stirred at 80° C. for 1 hour. The title product was purified by Prep-HPLC. LC-MS (linear gradient 10→98% MeCN, 0.1% TFA, 12 min): $t_R$ (min): 5.91; ESI-MS (m/z): 500.27 (M+H$^+$).

Example 17—Preparation of N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)-3,3-dimethylcyclobutane-1-carboxamide (CEN-9)

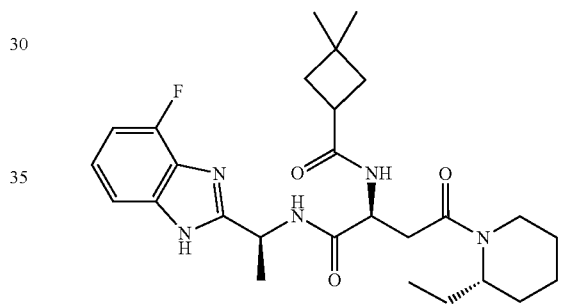

The title compound was synthesized by following the general protocol for HATU mediated coupling of CEN-1 and 3,3-dimethylcyclobutane-1-carboxylic acid on a 0.01 mmol scale. LC-MS (linear gradient 10→98% MeCN, 0.1% TFA, 12 min): $t_R$ (min): 6.49; ESI-MS (m/z): 500.29 (M+H$^+$).

Example 18—Preparation of N—((S)-4-((S)-2-Ethylpiperidin-1-yl)-1-(((S)-1-(4-fluoro benzo[d]imidazol-2-yl)ethyl)amino)-1,4-dioxobutan-2-yl)-2-isopropylcyclopropane-1-carboxamide (CEN-10)

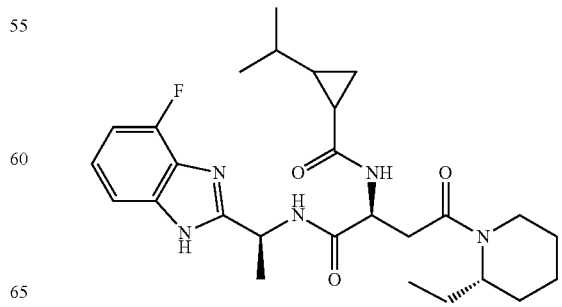

The title compound was synthesized by following the general protocol for HATU mediated coupling of CEN-1 and 2-isopropylcyclopropane-1-carboxylic acid on a 0.01 mmol scale. LC-MS (linear gradient 10→98% MeCN, 0.1% TFA, 12 min): $t_R$ (min): 6.15; ESI-MS (m/z): 500.29 (M+H$^+$).

Example 19—Preparation of N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)thiazole-5-carboxamide (CEN-11)

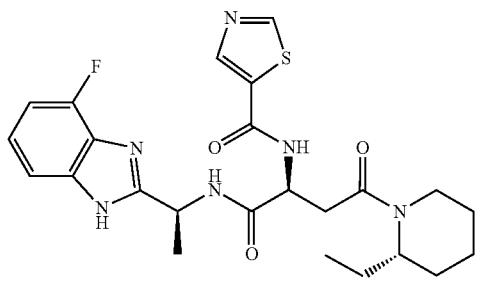 [SMILES: CC[C@H]1CCCCN1C(=O)C[C@H](NC(=O)c1cncs1)C(=O)N[C@@H](C)c1nc2c(F)cccc2[nH]1]

The title compound was synthesized by following the general protocol for HATU mediated coupling of CEN-1 and thiazole-5-carboxylic acid on a 0.01 mmol scale. LC-MS (linear gradient 10→98% MeCN, 0.1% TFA, 12 min): $t_R$ (min): 4.91; ESI-MS (m/z): 501.2 (M+H$^+$).

Example 20—Preparation of N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)piperidine carboxamide (CEN-12)

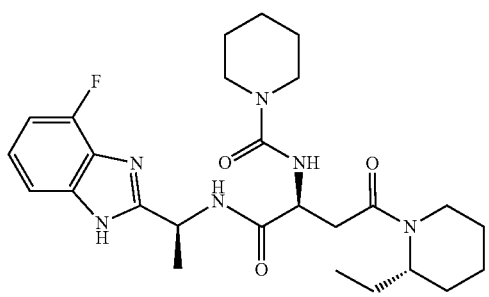 [SMILES: CC[C@H]1CCCCN1C(=O)C[C@H](NC(=O)N1CCCCC1)C(=O)N[C@@H](C)c1nc2c(F)cccc2[nH]1]

To a solution of CEN-1 (5 mg) in DCM (0.5 mL) was added piperidine-1-carbonyl chloride (2 mg) and triethylamine (5 µl), the reaction solution was stirred at room temperature for 60 min, and evaporated. The title product was purified by Prep-HPLC. LC-MS (linear gradient 10→98% MeCN, 0.1% TFA, 12 min): $t_R$ (min): 5.82; ESI-MS (m/z): 501.29 (M+H$^+$).

Example 21—Preparation of N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)-4,4-dimethylpentanamide (CEN-13)

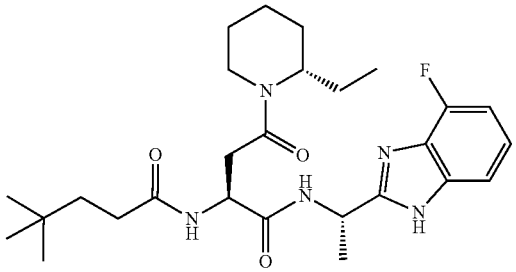 [SMILES: CC[C@H]1CCCCN1C(=O)C[C@H](NC(=O)CCC(C)(C)C)C(=O)N[C@@H](C)c1nc2c(F)cccc2[nH]1]

The title compound was synthesized by following the general protocol for HATU mediated coupling of CEN-1 and 4,4-dimethylpentanoic acid on a 0.01 mmol scale. LC-MS (linear gradient 10→98% MeCN, 0.1% TFA, 12 min): $t_R$ (min): 6.26; ESI-MS (m/z): 502.31 (M+H$^+$).

Example 22—preparation of N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)morpholine-4-carboxamide (CEN-14)

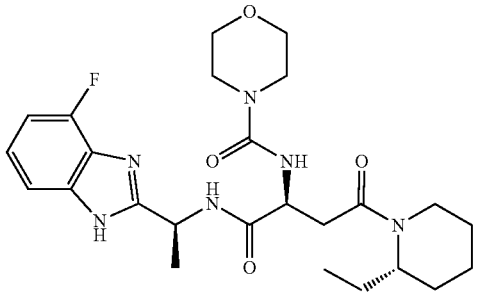 [SMILES: CC[C@H]1CCCCN1C(=O)C[C@H](NC(=O)N1CCOCC1)C(=O)N[C@@H](C)c1nc2c(F)cccc2[nH]1]

To a solution of CEN-1 (5 mg) in DCM (0.5 mL) was added morpholine-4-carbonyl chloride (2 mg) and triethylamine (5 µl), the reaction solution was stirred at r.t. for 60 min, and evaporated. The title product was purified by Prep-HPLC. LC-MS (linear gradient 10→98% MeCN, 0.1% TFA, 12 min): $t_R$ (min): 5.13; ESI-MS (m/z): 503.26 (M+H$^+$).

Example 23—Preparation of (S)-4-((S)-2-Ethylpiperidin-1-yl)-N—((S)-1-(4-fluoro-1H-benzo[d]imidazol-2-yl)ethyl)-2-(3-isobutyl-3-methylureido)-4-oxobutanamide (CEN-15)

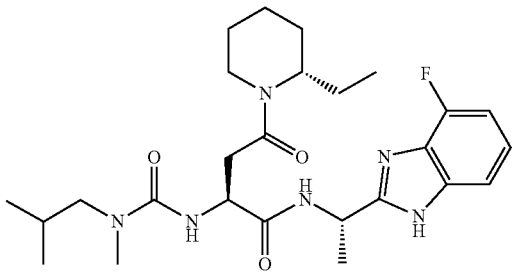 [SMILES: CC[C@H]1CCCCN1C(=O)C[C@H](NC(=O)N(C)CC(C)C)C(=O)N[C@@H](C)c1nc2c(F)cccc2[nH]1]

To a solution of CEN-1 (5 mg) in DCM (0.5 mL) was added isobutyl(methyl)carbamic chloride (2 mg) and triethylamine (3 μl), the reaction solution was stirred at room temperature for 20 min, and evaporated. The title product was purified by Prep-HPLC. LC-MS (linear gradient 10→98% MeCN, 0.1% TFA, 12 min): $t_R$ (min): 6.07; ESI-MS (m/z): 503.30 (M+H$^+$).

Example 24—Preparation of (S)-2-(Benzo[d]oxazol-2-ylamino)-4-((S)-2-ethylpiperidin yl)-N—((S)-1-(4-fluoro-1H-benzo[d]imidazol-2-yl)ethyl)-4-oxobutanamide (CEN-16)

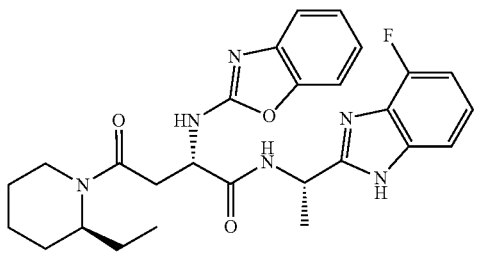 [SMILES: CC[C@H]1CCCCN1C(=O)C[C@H](Nc1nc2ccccc2o1)C(=O)N[C@@H](C)c1nc2c(F)cccc2[nH]1]

To a solution of CEN-1 (3 mg) in NMP (0.5 mL) was added 2-chlorobenzo[d]oxazole (2 mg), the reaction solution was stirred at 150° C. for 10 min. The title product was purified by Prep-HPLC. LC-MS (linear gradient 10→98% MeCN, 0.1% TFA, 12 min): $t_R$ (min): 6.00; ESI-MS (m/z): 507.24 (M+H$^+$).

Example 25—Preparation of N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)spiro[3.3]heptane-2-carboxamide (CEN-17)

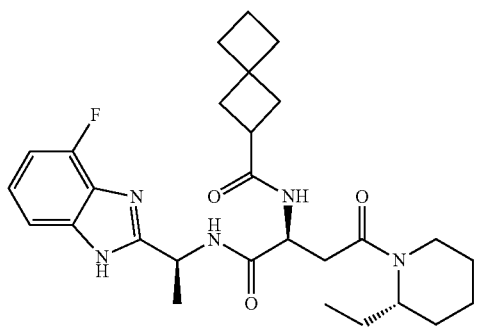 [SMILES: CC[C@H]1CCCCN1C(=O)C[C@H](NC(=O)C1CC2(CCC2)C1)C(=O)N[C@@H](C)c1nc2c(F)cccc2[nH]1]

The title compound was synthesized by following the general protocol for HATU mediated coupling of CEN-1 and spiro[3.3]heptane-2-carboxylic acid on a 0.01 mmol scale. LC-MS (linear gradient 10→98% MeCN, 0.1% TFA, 12 min): $t_R$ (min): 6.51; ESI-MS (m/z): 512.29 (M+H$^+$).

Example 26—Preparation of N—((S)-4-((S)-2-Ethylpiperidin-1-yl)-1-(((S)-1-(4-fluoro benzo[d]imidazol-2-yl)ethyl)amino)-1,4-dioxobutan-2-yl)-2-methylthiazole carboxamide (CEN-18)=

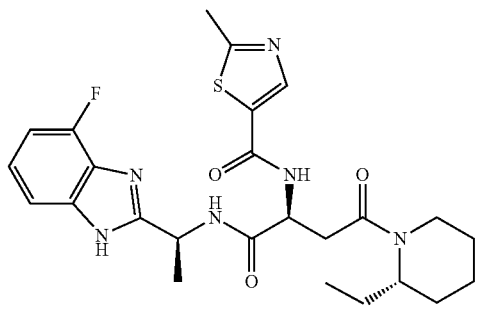 [SMILES: CC[C@H]1CCCCN1C(=O)C[C@H](NC(=O)c1cnc(C)s1)C(=O)N[C@@H](C)c1nc2c(F)cccc2[nH]1]

The title compound was synthesized by following the general protocol for HATU mediated coupling of CEN-1 and 2-methylthiazole-5-carboxylic acid on a 0.01 mmol scale. LC-MS (linear gradient 10→98% MeCN, 0.1% TFA, 12 min): $t_R$ (min): 5.03; ESI-MS (m/z): 515.21 (M+H$^+$).

Example 27—Preparation of (S)-4-((S)-2-Ethylpiperidin-1-yl)-N—((S)-1-(4-fluoro-1H-benzo[d]imidazol-2-yl)ethyl)-2-((6-methylbenzo[d]oxazol-2-yl)amino)-4-oxobutanamide (CEN-19)

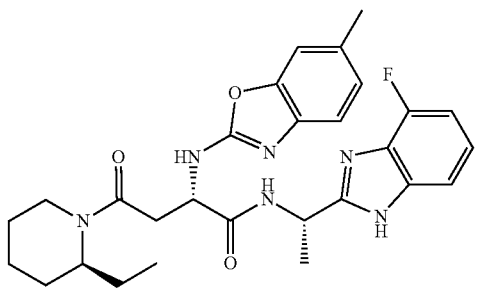 [SMILES: CC[C@H]1CCCCN1C(=O)C[C@H](Nc1nc2ccc(C)cc2o1)C(=O)N[C@@H](C)c1nc2c(F)cccc2[nH]1]

To a solution of CEN-1 (4 mg) in NMP (0.5 mL) was added 2-chloro-6-methylbenzo[d]oxazole (2 mg), the reaction solution was stirred at 150° C. for 10 min. The title product was purified by Prep-HPLC. LC-MS (linear gradient 10→98% MeCN, 0.1% TFA, 12 min): $t_R$ (min): 6.35; ESI-MS (m/z): 521.25 (M+H$^+$).

Example 28—Preparation of (S)-4-((S)-2-Ethylpiperidin-1-yl)-N—((S)-1-(4-fluoro-1H-benzo[d]imidazol-2-yl)ethyl)-4-oxo-2-(3-phenylpropanamido)butanamide (CEN-20)

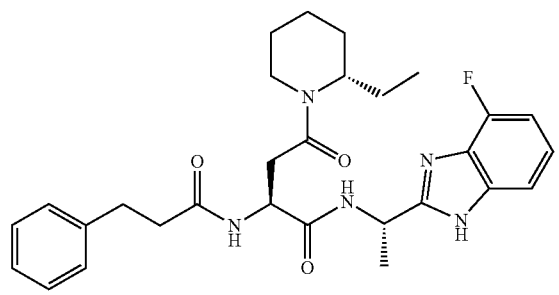 [SMILES: CC[C@H]1CCCCN1C(=O)C[C@H](NC(=O)CCc1ccccc1)C(=O)N[C@@H](C)c1nc2c(F)cccc2[nH]1]

The title compound was synthesized by following the general protocol for HATU mediated coupling of CEN-1 and 3-phenylpropanoic acid on a 0.01 mmol scale. LC-MS (linear gradient 10→98% MeCN, 0.1% TFA, 12 min): $t_R$ (min): 5.98; ESI-MS (m/z): 522.27 (M+H$^+$).

Example 29—Preparation of (S)-2-(3-Benzylureido)-4-((S)-2-ethylpiperidin-1-yl)-N—((S)-1-(4-fluoro-1H-benzo[d]imidazol-2-yl)ethyl)-4-oxobutanamide (CEN-21)

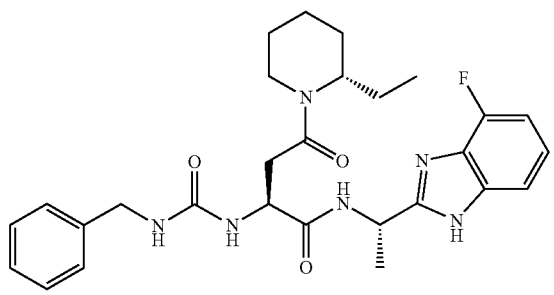 [SMILES: CC[C@H]1CCCCN1C(=O)C[C@H](NC(=O)NCc1ccccc1)C(=O)N[C@@H](C)c1nc2c(F)cccc2[nH]1]

To a solution of CEN-1 (5 mg) in DCM (0.5 mL) was added benzylcarbamic chloride (2 mg) and triethylamine (3 μl), the reaction solution was stirred at room temperature for 10 min, and evaporated. The title product was purified by Prep-HPLC. LC-MS (linear gradient 10→98% MeCN, 0.1% TFA, 12 min): $t_R$ (min): 5.66; ESI-MS (m/z): 523.27 (M+H$^+$).

Example 30—Preparation of (S)-2-(Benzo[d]thiazol-2-ylamino)-4-((S)-2-ethylpiperidin yl)-N—((S)-1-(4-fluoro-1H-benzo[d]imidazol-2-yl)ethyl)-4-oxobutanamide (CEN-22)

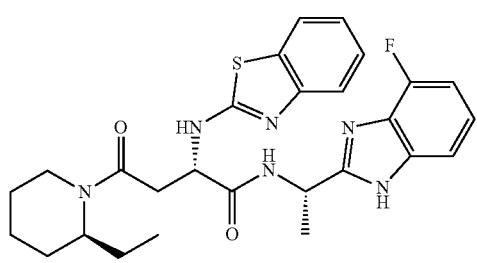 [SMILES: CC[C@H]1CCCCN1C(=O)C[C@H](Nc1nc2ccccc2s1)C(=O)N[C@@H](C)c1nc2c(F)cccc2[nH]1]

To a solution of CEN-1 (4 mg) in NMP (0.5 mL) was added 2-chlorobenzo[d]thiazole (2 mg), the reaction solution was stirred at 150° C. for 10 min. The title product was purified by Prep-HPLC. LC-MS (linear gradient 10→98% MeCN, 0.1% TFA, 12 min): $t_R$ (min): 6.34; ESI-MS (m/z): 523.22 (M+H$^+$).

Example 31—Preparation of Benzyl ((S)-4-((S)-2-Ethylpiperidin-1-yl)-1-(((S)-1-(4-fluoro-1H-benzo[d]imidazol-2-yl)ethyl)amino)-1,4-dioxobutan-2-yl) carbamate (CEN-23)

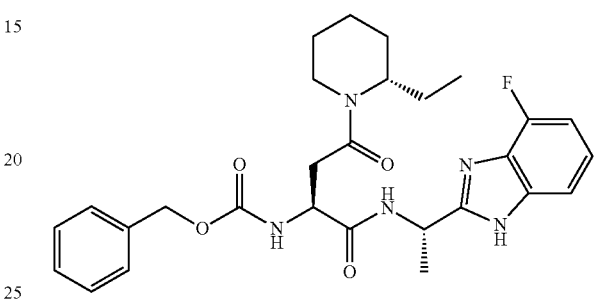

To a solution of CEN-1 (5 mg) in DCM (0.5 mL) was added benzyl carbonochloridate (2 mg) and triethylamine (5 μl), the reaction solution was stirred at room temperature for 10 min, and evaporated. The title product was purified by Prep-HPLC. LC-MS (linear gradient 10→98% MeCN, 0.1% TFA, 12 min): $t_R$ (min): 6.42; ESI-MS (m/z): 524.25 (M+H$^+$).

Example 32—Preparation of (S)-4-((S)-2-Ethylpiperidin-1-yl)-N—((S)-1-(4-fluoro-1H-benzo[d]imidazol-2-yl)ethyl)-2-((3-methylbutyl)sulfonamido)-4-oxobutanamide (CEN-24)

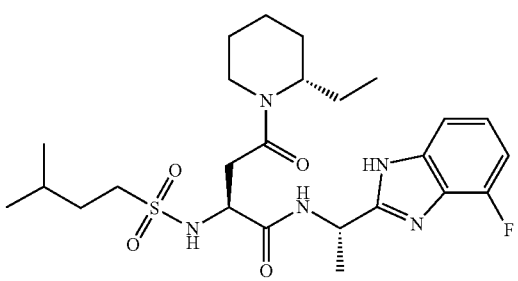 [SMILES: CC[C@H]1CCCCN1C(=O)C[C@H](NS(=O)(=O)CCC(C)C)C(=O)N[C@@H](C)c1nc2c(F)cccc2[nH]1]

The title compound was synthesized by following the general procedure for N-Sulfonamide formation of CEN-1 with 3-methylbutane-1-sulfonyl chloride on a 0.01 mmol scale. LC-MS (linear gradient 10→98% MeCN, 0.1% TFA, 12 min): $t_R$ (min): 6.21; ESI-MS (m/z): 524.26 (M+H$^+$).

Example 33—Preparation of (1S,2S)—N—((S)-4-((S)-2-Ethylpiperidin-1-yl)-1-(((S)-1-(4-fluoro-1H-benzo[d]imidazol-2-yl)ethyl)amino)-1,4-dioxobutan-2-yl)-2-phenylcyclopropane-1-carboxamide (CEN-25)

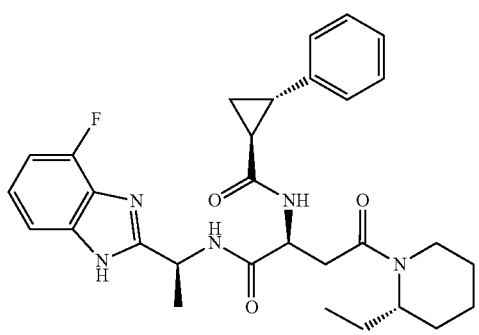 [SMILES: CC[C@H]1CCCCN1C(=O)C[C@H](NC(=O)[C@H]1C[C@@H]1c1ccccc1)C(=O)N[C@@H](C)c1nc2c(F)cccc2[nH]1]

The title compound was synthesized by following the general protocol for HATU mediated coupling of CEN-1 and (1S,2S)-2-phenylcyclopropane-1-carboxylic acid on a 0.01 mmol scale. LC-MS (linear gradient 10→98% MeCN, 0.1% TFA, 12 min): $t_R$ (min): 6.36; ESI-MS (m/z): 534.27 (M+H$^+$).

Example 34—Preparation of (S)-2-(3-Benzyl-3-methylureido)-4-((S)-2-ethylpiperidin-1-yl)-N—((S)-1-(4-fluoro-1H-benzo[d]imidazol-2-yl)ethyl)-4-oxobutanamide (CEN-26)

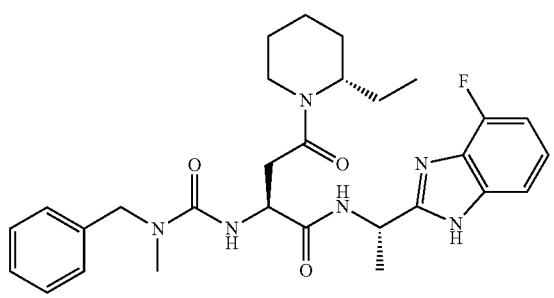 [SMILES: CC[C@H]1CCCCN1C(=O)C[C@H](NC(=O)N(C)Cc1ccccc1)C(=O)N[C@@H](C)c1nc2c(F)cccc2[nH]1]

To a solution of CEN-1 (5 mg) in DCM (0.5 mL) was added benzyl(methyl)carbamic chloride (3 mg) and triethylamine (5 μl), the reaction solution was stirred at r.t. for 15 min, and evaporated. The title product was purified by Prep-HPLC. LC-MS (linear gradient 10→98% MeCN, 0.1% TFA, 12 min): $t_R$ (min): 6.19; ESI-MS (m/z): 537.29 (M+H$^+$).

Example 35—Preparation of (S)-4-((S)-2-Ethylpiperidin-1-yl)-N—((S)-1-(4-fluoro-1H-benzo[d]imidazol-2-yl)ethyl)-2-((3-(4-fluorobenzyl)-1,2,4-oxadiazol-5-yl)amino)-4-oxobutanamide (CEN-27)

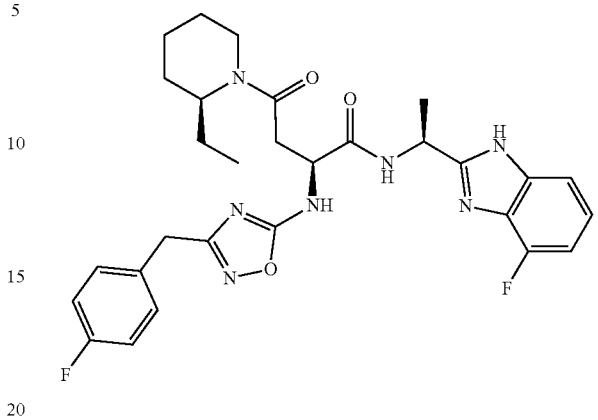

To a solution of CEN-1 (2 mg) in NMP (0.25 mL) was added 5-chloro-3-(4-fluorobenzyl)-1,2,4-oxadiazole (1 mg), the reaction solution was stirred at 150° C. for 10 min. The title product was purified by Prep-HPLC. LC-MS (linear gradient 10→98% MeCN, 0.1% TFA, 12 min): $t_R$ (min): 6.46; ESI-MS (m/z): 566.26 (M+H$^+$).

Example 36—Preparation of N—((S)-1-(((S)-1-(1H-Benzo[d]imidazol-2-yl)ethyl)amino) ((S)-2-ethylpiperidin-1-yl)-1,4-dioxobutan-2-yl)-4-methylpentanamide (CEN-28)

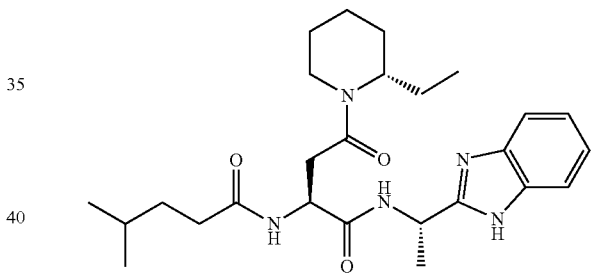

The title compound was synthesized by the similar method described for CEN-2. LC-MS (linear gradient 10→98% MeCN, 0.1% TFA, 12 min): $t_R$ (min): 5.59; ESI-MS (m/z): 470.30 (M+H$^+$).

Example 37—Preparation of N—((S)-1-(((S)-1-(1H-Benzo[d]imidazol-2-yl)ethyl)amino)-4-((S)-2-ethylpiperidin-1-yl)-1,4-dioxobutan-2-yl)-4,4-dimethylpentanamide (CEN-29)

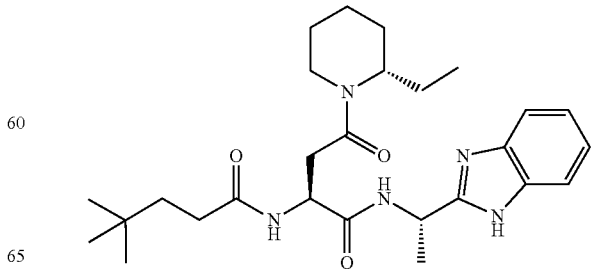

The title compound was synthesized by the similar method described for CEN-2. LC-MS (linear gradient 10→98% MeCN, 0.1% TFA, 12 min): t_R (min): 5.93; ESI-MS (m/z): 484.32 (M+H⁺).

Example 38—Preparation of N—((S)-1-(((S)-1-(4-Fluoro-1H-benzo[d]imidazol-2-yl)ethyl)amino)-4-((S)-2-methylpiperidin-1-yl)-1,4-dioxobutan-2-yl)-2-methylthiazole-5-carboxamide (CEN-30)

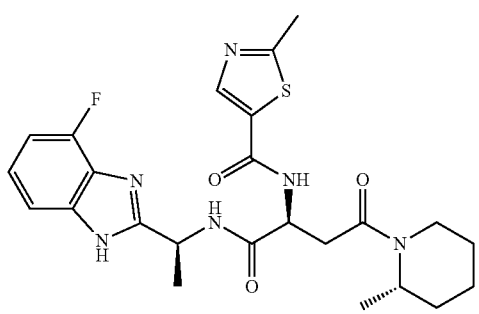 [SMILES: Cc1ncc(C(=O)N[C@@H](CC(=O)N2CCCC[C@@H]2C)C(=O)N[C@@H](C)c2nc3c(F)cccc3[nH]2)s1]

The title compound was synthesized by the similar method described for CEN-2. LC-MS (linear gradient 10→98% MeCN, 0.1% TFA, 12 min): t_R (min): 4.75; ESI-MS (m/z): 501.2 (M+H⁺).

Example 39—Preparation of N—((S)-1-(01H-Benzo[d]imidazol-2-yl)methyl)amino)-4-((S)-2-methylpiperidin-1-yl)-1,4-dioxobutan-2-yl)-4-methylpentanamide (CEN-31)

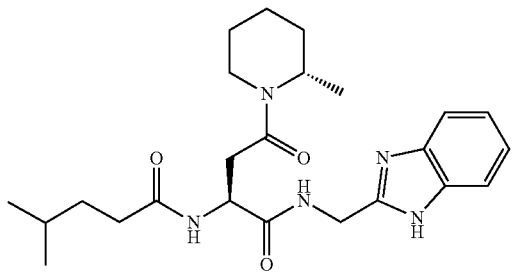 [SMILES: CC(C)CCC(=O)N[C@@H](CC(=O)N1CCCC[C@@H]1C)C(=O)NCc1nc2ccccc2[nH]1]

The title compound was synthesized by the similar method described for CEN-2. LC-MS (linear gradient 10→98% MeCN, 0.1% TFA, 12 min): t_R (min): 5.19; ESI-MS (m/z): 442.27 (M+H⁺).

Example 40—Preparation of N—((S)-1-(((S)-1-(1H-Benzo[d]imidazol-2-yl)ethyl)amino) ((S)-2-methylpiperidin-1-yl)-1,4-dioxobutan-2-yl)-4-methylpentanamide (CEN-32)

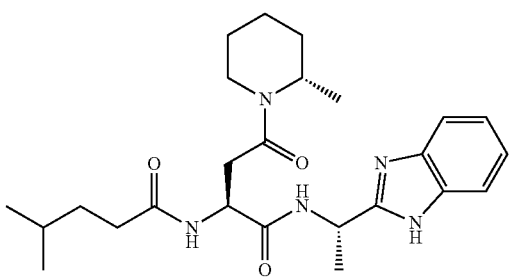 [SMILES: CC(C)CCC(=O)N[C@@H](CC(=O)N1CCCC[C@@H]1C)C(=O)N[C@@H](C)c1nc2ccccc2[nH]1]

The title compound was synthesized by the similar method described for CEN-2. LC-MS (linear gradient 10→98% MeCN, 0.1% TFA, 12 min): t_R (min): 5.15; ESI-MS (m/z): 456.28 (M+H⁺).

Example 41—Preparation of N—((S)-1-(((S)-1-(1H-Benzo[d]imidazol-2-yl)ethyl)amino)-4-((S)-2-methylpyrrolidin-1-yl)-1,4-dioxobutan-2-yl)-4,4-dimethylpentanamide (CEN-33)

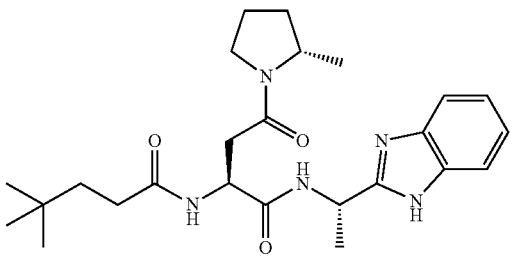 [SMILES: C[C@H](NC(=O)[C@H](CC(=O)N1CCC[C@@H]1C)NC(=O)CCC(C)(C)C)c1nc2ccccc2[nH]1]

The title compound was synthesized by the similar method described for CEN-2. LC-MS (linear gradient 10→98% MeCN, 0.1% TFA, 12 min): t_R (min): 5.16; ESI-MS (m/z): 456.28 (M+H⁺).

Example 42—Preparation of N—((S)-1-(((R)-1-(1H-Benzo[d]imidazol-2-yl)ethyl)amino) ((S)-2-methylpiperidin-1-yl)-1,4-dioxobutan-2-yl)-4-methylpentanamide (CEN-34)

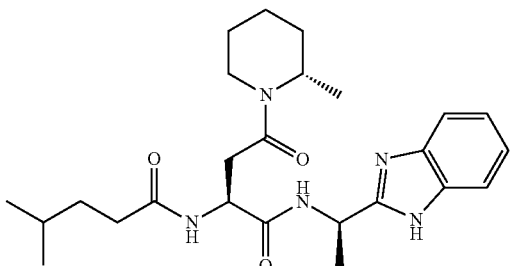

The title compound was synthesized by the similar method described for CEN-2. LC-MS (linear gradient 10→98% MeCN, 0.1% TFA, 12 min): $t_R$ (min): 5.29; ESI-MS (m/z): 456.28 (M+H$^+$).

Example 43—Preparation of N-((2S)-1-((1-(1H-Benzo[d]imidazol-2-yl)ethyl)amino)-4-((S)-2-methylpiperidin-1-yl)-1,4-dioxobutan-2-yl)-5-methylisoxazole-3-carboxamide (CEN-35)

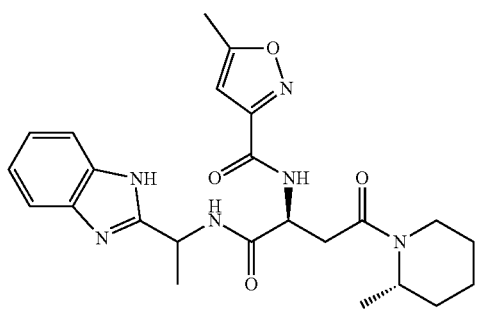 [SMILES: Cc1cc(C(=O)N[C@@H](CC(=O)N2CCCC[C@@H]2C)C(=O)NC(C)c2nc3ccccc3[nH]2)no1]

The title compound was synthesized by the similar method described for CEN-2. LC-MS (linear gradient 10→98% MeCN, 0.1% TFA, 12 min): $t_R$ (min): 4.81; ESI-MS (m/z): 467.23 (M+H$^+$).

Example 44—Preparation of N—((S)-1-(((S)-1-(1H-Benzo[d]imidazol-2-yl)ethyl)amino) ((S)-2-methylpiperidin-1-yl)-1,4-dioxobutan-2-yl)-5-methylisoxazole-3-carboxamide (CEN-36)

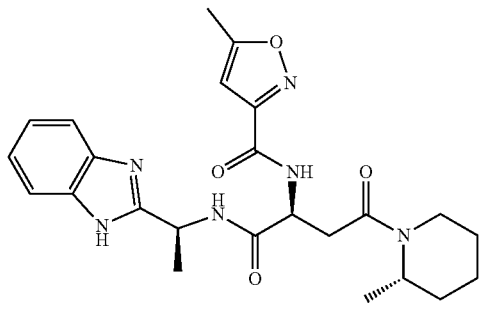 [SMILES: Cc1cc(C(=O)N[C@@H](CC(=O)N2CCCC[C@@H]2C)C(=O)N[C@@H](C)c2nc3ccccc3[nH]2)no1]

The title compound was synthesized by the similar method described for CEN-2. LC-MS (linear gradient 10→98% MeCN, 0.1% TFA, 12 min): $t_R$ (min): 4.83; ESI-MS (m/z): 467.23 (M+H$^+$).

Example 45—Preparation of N—((S)-1-(((R)-1-(1H-Benzo[d]imidazol-2-yl)ethyl)amino)-4-((S)-2-methylpiperidin-1-yl)-1,4-dioxobutan-2-yl)-4,4-dimethylpentanamide (CEN-37)

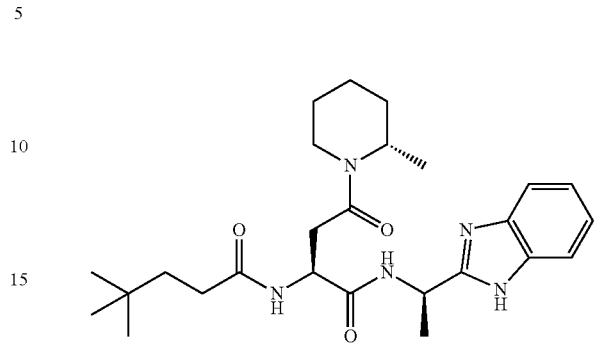

The title compound was synthesized by the similar method described for CEN-2. LC-MS (linear gradient 10→98% MeCN, 0.1% TFA, 12 min): $t_R$ (min): 5.54; ESI-MS (m/z): 470.30 (M+H$^+$).

Example 46—Preparation of N—((S)-1-(((S)-1-(4-Fluoro-1H-benzo[d]imidazol-2-yl)ethyl)amino)-4-((S)-2-methylpiperidin-1-yl)-1,4-dioxobutan-2-yl)-4-methylpentanamide (CEN-38)

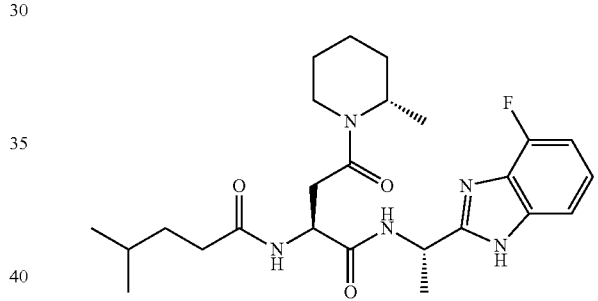

The title compound was synthesized by the similar method described for CEN-2. LC-MS (linear gradient 10→98% MeCN, 0.1% TFA, 12 min): $t_R$ (min): 5.67; ESI-MS (m/z): 474.27 (M+H$^+$).

Example 47—Preparation of N—((S)-1-(((S)-1-(4-Fluoro-1H-benzo[d]imidazol-2-yl)ethyl)amino)-4-((S)-2-methylpiperidin-1-yl)-1,4-dioxobutan-2-yl)-3,3-dimethylcyclobutane-1-carboxamide (CEN-39)

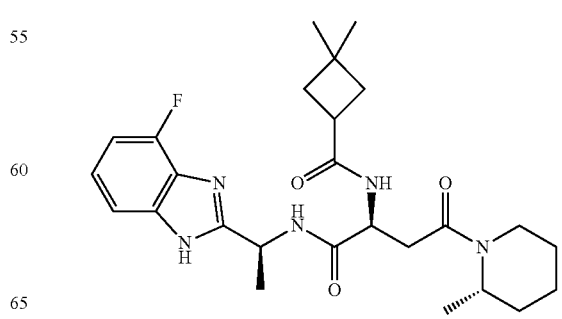

The title compound was synthesized by the similar method described for CEN-2. LC-MS (linear gradient 10→98% MeCN, 0.1% TFA, 12 min): $t_R$ (min): 6.18; ESI-MS (m/z): 486.27 (M+H$^+$).

Example 48—Preparation of N—((S)-1-(((S)-1-(4-Fluoro-1H-benzo[d]imidazol-2-yl)ethyl)amino)-4-((S)-2-methylpiperidin-1-yl)-1,4-dioxobutan-2-yl)-2-isopropylcyclopropane-1-carboxamide (CEN-40)

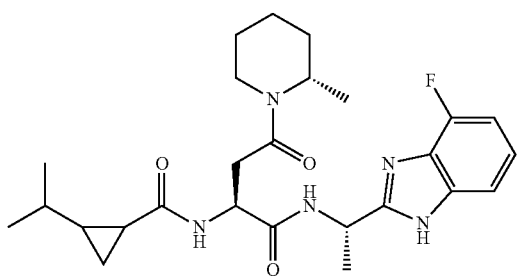 [SMILES: CC(C)C1CC1C(=O)N[C@@H](CC(=O)N1CCCC[C@@H]1C)C(=O)N[C@@H](C)c1nc2c(F)cccc2[nH]1]

The title compound was synthesized by the similar method described for CEN-2. LC-MS (linear gradient 10→98% MeCN, 0.1% TFA, 12 min): $t_R$ (min): 6.00; ESI-MS (m/z): 486.27 (M+H$^+$).

Example 49—Preparation of N—((S)-1-(((S)-1-(4-Fluoro-1H-benzo[d]imidazol-2-yl)ethyl)amino)-4-((S)-2-methylpiperidin-1-yl)-1,4-dioxobutan-2-yl)-4,4-dimethylpentanamide (CEN-41)

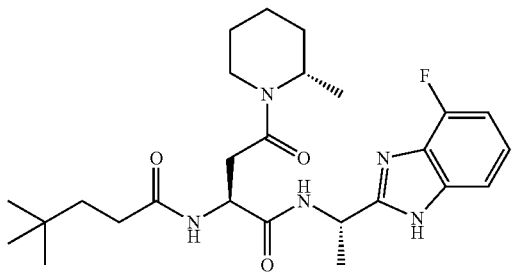 [SMILES: C[C@H](NC(=O)[C@H](CC(=O)N1CCCC[C@@H]1C)NC(=O)CCC(C)(C)C)c1nc2c(F)cccc2[nH]1]

The title compound was synthesized by the similar method described for CEN-2. LC-MS (linear gradient 10→98% MeCN, 0.1% TFA, 12 min): $t_R$ (min): 6.01; ESI-MS (m/z): 488.29 (M+H$^+$).

Example 50—Preparation of N—((S)-1-(((S)-1-(4-Fluoro-1H-benzo[d]imidazol-2-yl)ethyl)amino)-4-((S)-2-methylpiperidin-1-yl)-1,4-dioxobutan-2-yl)spiro[3.3]heptane-2-carboxamide (CEN-42)

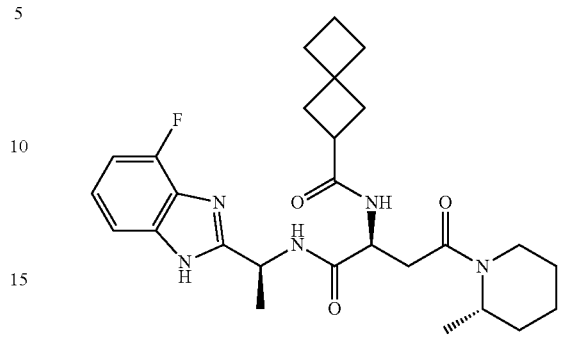

The title compound was synthesized by the similar method described for CEN-2. LC-MS (linear gradient 10→98% MeCN, 0.1% TFA, 12 min): $t_R$ (min): 6.18; ESI-MS (m/z): 498.27 (M+H$^+$).

Example 51—Preparation of N—((S)-1-(((S)-1-(7-Fluoro-1H-benzo[d]imidazol-2-yl)ethyl)amino)-4-((S)-2-methylpiperidin-1-yl)-1,4-dioxobutan-2-yl)-2-oxaspiro[3.3]heptane-6-carboxamide (CEN-43)

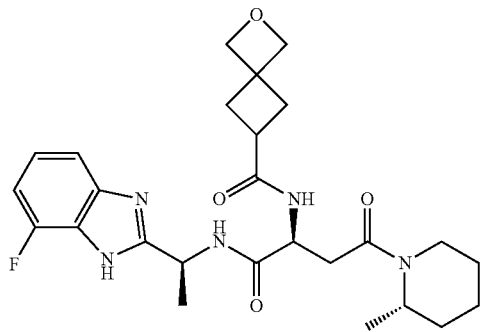 [SMILES: C[C@H](NC(=O)[C@H](CC(=O)N1CCCC[C@@H]1C)NC(=O)C1CC2(COC2)C1)c1nc2cccc(F)c2[nH]1]

The title compound was synthesized by the similar method described for CEN-2. LC-MS (linear gradient 10→98% MeCN, 0.1% TFA, 12 min): $t_R$ (min): 5.72; ESI-MS (m/z): 500.26 (M+H$^+$).

Example 52—Preparation of (S)-2-(2-(3,3-Dimethylcyclobutyl)acetamido)-N—((R)-1-(4-fluoro-1H-benzo[d]imidazol-2-yl)ethyl)-4-((S)-2-methylpiperidin-1-yl)-4-oxobutanamide (CEN-44)

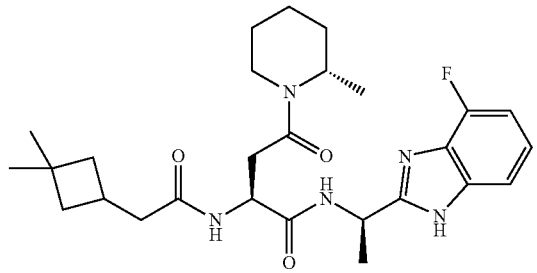 [SMILES: C[C@@H](NC(=O)[C@H](CC(=O)N1CCCC[C@@H]1C)NC(=O)CC1CC(C)(C)C1)c1nc2c(F)cccc2[nH]1]

The title compound was synthesized by the similar method described for CEN-2. LC-MS (linear gradient 10→98% MeCN, 0.1% TFA, 12 min): $t_R$ (min): 6.69; ESI-MS (m/z): 500 (M+H$^+$).

Example 53—Preparation of N—((S)-1-(((S)-1-(4,6-Difluoro-1H-benzo[d]imidazol-2-yl)ethyl)amino)-4-((S)-2-ethylpiperidin-1-yl)-1,4-dioxobutan-2-yl)-4-methylpentanamide (CEN-45)

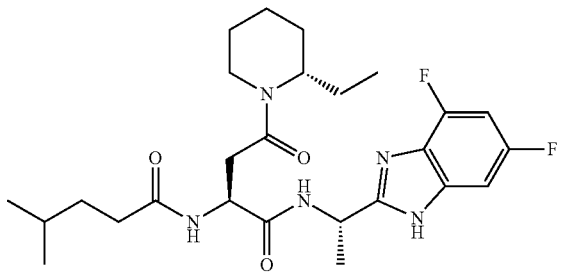 [SMILES: CC[C@H]1CCCCN1C(=O)C[C@H](NC(=O)CCC(C)C)C(=O)N[C@@H](C)c1nc2c(F)cc(F)cc2[nH]1]

The title compound was synthesized by the similar method described for CEN-2. LC-MS (linear gradient 10→98% MeCN, 0.1% TFA, 12 min): $t_R$ (min): 6.75; ESI-MS (m/z): 506.28 (M+H$^+$).

Example 54—Preparation of N-((2S)-1-((1-(1H-Benzo[d]imidazol-2-yl)ethyl)amino)-1,4-dioxo-4-((R)-2-phenylpyrrolidin-1-yl)butan-2-yl)-3-methylcyclobutane carboxamide (CEN-46)

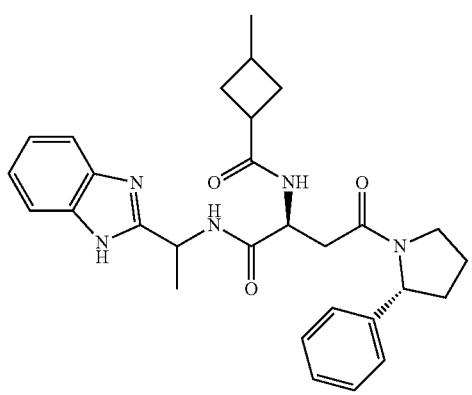 [SMILES: CC1CC(C(=O)N[C@@H](CC(=O)N2CCC[C@@H]2c2ccccc2)C(=O)NC(C)c2nc3ccccc3[nH]2)C1]

The title compound was synthesized by the similar method described for CEN-2. LC-MS (linear gradient 10→98% MeCN, 0.1% TFA, 12 min): $t_R$ (min): 5.48; ESI-MS (m/z): 502.27 (M+H$^+$).

Example 55—Preparation of N-((2S)-1-((1-(1H-Benzo[d]imidazol-2-yl)ethyl)amino)-1,4-dioxo-4-((R)-2-phenylpyrrolidin-1-yl)butan-2-yl)-4-methylpentanamide (CEN-47)

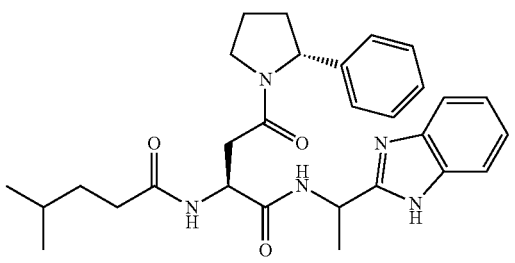 [SMILES: CC(C)CCC(=O)N[C@@H](CC(=O)N1CCC[C@@H]1c1ccccc1)C(=O)NC(C)c1nc2ccccc2[nH]1]

The title compound was synthesized by the similar method described for CEN-2. LC-MS (linear gradient 10→98% MeCN, 0.1% TFA, 9 min): $t_R$ (min): 5.57; ESI-MS (m/z): 504.28 (M+H$^+$).

Example 56—Preparation of N—((S)-1-(((S)-1-(1H-Benzo[d]imidazol-2-yl)ethyl)amino)-1,4-dioxo-4-((R)-2-phenylpyrrolidin-1-yl)butan-2-yl)-4-methylpentanamide (CEN-48)

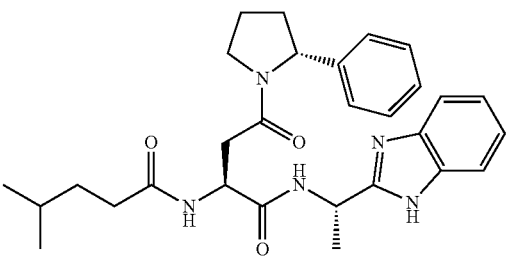 [SMILES: CC(C)CCC(=O)N[C@@H](CC(=O)N1CCC[C@@H]1c1ccccc1)C(=O)N[C@@H](C)c1nc2ccccc2[nH]1]

The title compound was synthesized by the similar method described for CEN-2. LC-MS (linear gradient 10→98% MeCN, 0.1% TFA, 12 min): $t_R$ (min): 6.36; ESI-MS (m/z): 504.28 (M+H$^+$).

Example 57—Preparation of N—((S)-1-(((R)-1-(1H-Benzo[d]imidazol-2-yl)ethyl)amino)-1,4-dioxo-4-((R)-2-phenylpyrrolidin-1-yl)butan-2-yl)-4-methylpentanamide (CEN-49)

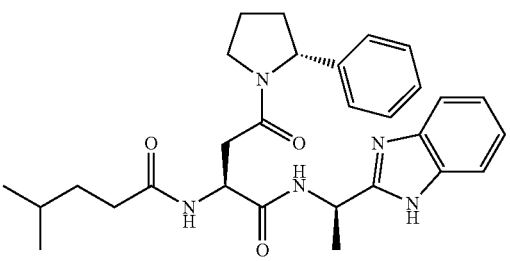 [SMILES: CC(C)CCC(=O)N[C@@H](CC(=O)N1CCC[C@@H]1c1ccccc1)C(=O)N[C@H](C)c1nc2ccccc2[nH]1]

The title compound was synthesized by the similar method described for CEN-2. LC-MS (linear gradient 10→98% MeCN, 0.1% TFA, 12 min): $t_R$ (min): 6.77; ESI-MS (m/z): 504.28 (M+H$^+$).

Example 58—Preparation of benzyl ((S)-1-(((S)-1-(4-Fluoro-1H-benzo[d]imidazol-2-yl)ethyl)amino)-4-((S)-2-methylpiperidin-1-yl)-1,4-dioxobutan-2-yl) carbamate (CEN-50)

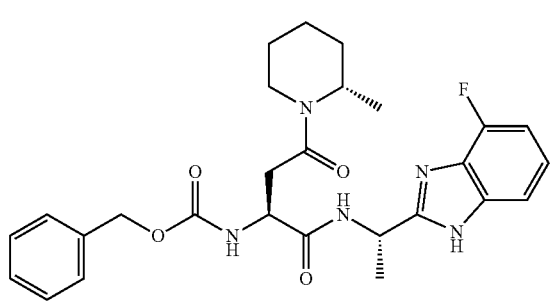 [SMILES: C[C@H](NC(=O)[C@H](CC(=O)N1CCCC[C@@H]1C)NC(=O)OCc1ccccc1)c1nc2c(F)cccc2[nH]1]

The title compound was synthesized by the similar method described for CEN-5. LC-MS (linear gradient 10→98% MeCN, 0.1% TFA, 12 min): $t_R$ (min): 6.12; ESI-MS (m/z): 510.24 (M+H$^+$).

Example 59—Preparation of N-((2S)-4-(2-Cyclopropylpyrrolidin-1-yl)-1-(((S)-1-(7-fluoro-1H-benzo[d]imidazol-2-yl)ethyl)amino)-1,4-dioxobutan-2-yl)-2-oxaspiro[3.3]heptane-6-carboxamide (CEN-51)

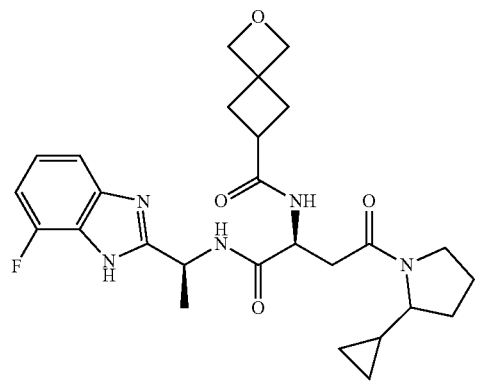 [SMILES: C[C@H](NC(=O)[C@H](CC(=O)N1CCCC1C1CC1)NC(=O)C1CC2(COC2)C1)c1nc2cccc(F)c2[nH]1]

The title compound was synthesized by the similar method described for CEN-2. LC-MS (linear gradient 10→98% MeCN, 0.1% TFA, 12 min): $t_R$ (min): 5.80; ESI-MS (m/z): 512.26 (M+H$^+$).

Example 60—Preparation of N-((2S)-1-((1-(1H-Benzo[d]imidazol-2-yl)ethyl)amino)-1,4-dioxo-4-((R)-2-phenylpyrrolidin-1-yl)butan-2-yl)-5-methylisoxazole-3-carboxamide (CEN-52)

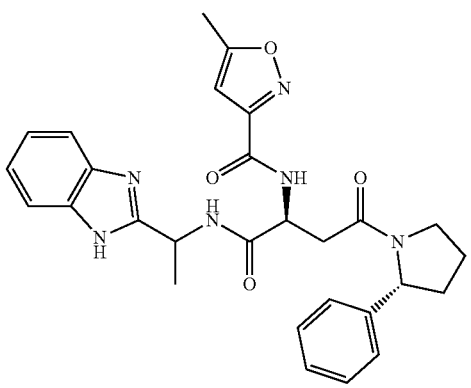 [SMILES: Cc1cc(C(=O)N[C@@H](CC(=O)N2CCC[C@@H]2c2ccccc2)C(=O)NC(C)c2nc3ccccc3[nH]2)no1]

The title compound was synthesized by the similar method described for CEN-2. LC-MS (linear gradient 10→98% MeCN, 0.1% TFA, 12 min): $t_R$ (min): 5.37; ESI-MS (m/z): 515.23 (M+H$^+$).

Example 61—Preparation of N—((S)-1-(((S)-1-(1H-Benzo[d]imidazol-2-yl)ethyl)amino)-1,4-dioxo-4-((R)-2-phenylpyrrolidin-1-yl)butan-2-yl)-5-methylisoxazole-3-carboxamide (CEN-53)

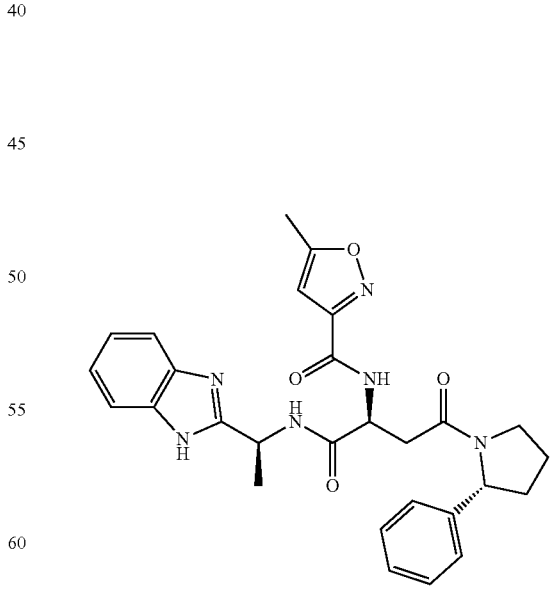

The title compound was synthesized by the similar method described for CEN-2. LC-MS (linear gradient 10→98% MeCN, 0.1% TFA, 12 min): $t_R$ (min): 5.28; ESI-MS (m/z): 515.23 (M+H$^+$).

Example 62—Preparation of N—((S)-1-(((S)-1-(1H-Benzo[d]imidazol-2-yl)ethyl)amino)-1,4-dioxo-4-((R)-2-phenylpyrrolidin-1-yl)butan-2-yl)-4,4-dimethylpentanamide (CEN-54)

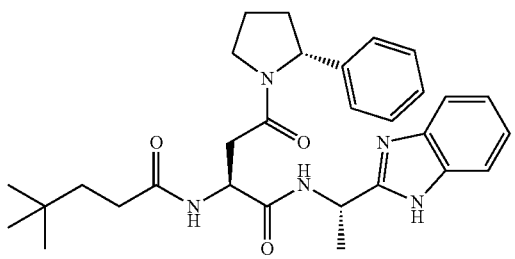 [SMILES: C[C@H](NC(=O)[C@H](CC(=O)N1CCC[C@@H]1c1ccccc1)NC(=O)CCC(C)(C)C)c1nc2ccccc2[nH]1]

The title compound was synthesized by the similar method described for CEN-2. LC-MS (linear gradient 10→98% MeCN, 0.1% TFA, 12 min): $t_R$ (min): 5.09; ESI-MS (m/z): 518.30 (M+H⁺).

Example 63—Preparation of (1S,2S)—N—((S)-1-(((S)-1-(4-Fluoro-1H-benzo[d]imidazol-2-yl)ethyl)amino)-4-((S)-2-methylpiperidin-1-yl)-1,4-dioxobutan-2-yl)-2-phenylcyclopropane-1-carboxamide (CEN-55)

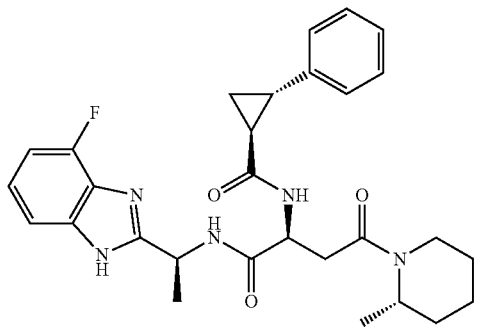 [SMILES: C[C@H](NC(=O)[C@H](CC(=O)N1CCCC[C@@H]1C)NC(=O)[C@H]1C[C@@H]1c1ccccc1)c1nc2c(F)cccc2[nH]1]

The title compound was synthesized by the similar method described for CEN-2. LC-MS (linear gradient 10→98% MeCN, 0.1% TFA, 12 min): $t_R$ (min): 6.10; ESI-MS (m/z): 520.26 (M+H⁺).

Example 64—Preparation of (S)-2-(3-Benzyl-3-methylureido)-N—((S)-1-(4-fluoro-1H-benzo[d]imidazol-2-yl)ethyl)-4-((S)-2-methylpiperidin-1-yl)-4-oxobutanamide (CEN-56)

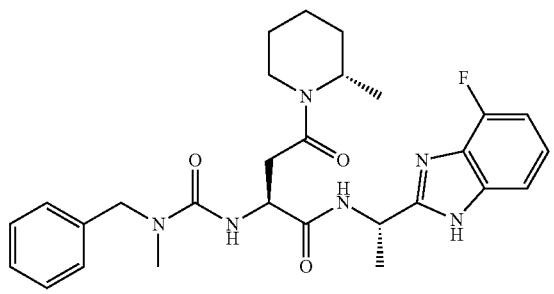 [SMILES: C[C@H](NC(=O)[C@H](CC(=O)N1CCCC[C@@H]1C)NC(=O)N(C)Cc1ccccc1)c1nc2c(F)cccc2[nH]1]

The title compound was synthesized by the similar method described for CEN-15. LC-MS (linear gradient 10→98% MeCN, 0.1% TFA, 12 min): $t_R$ (min): 5.88; ESI-MS (m/z): 523.27 (M+H⁺).

Example 65—Preparation of 6,6-Difluoro-N—((S)-1-(((S)-1-(4-fluoro-1H-benzo[d]imidazol-2-yl)ethyl)amino)-4-((S)-2-methylpiperidin-1-yl)-1,4-dioxobutan-2-yl)spiro[3.3]heptane-2-carboxamide (CEN-57)

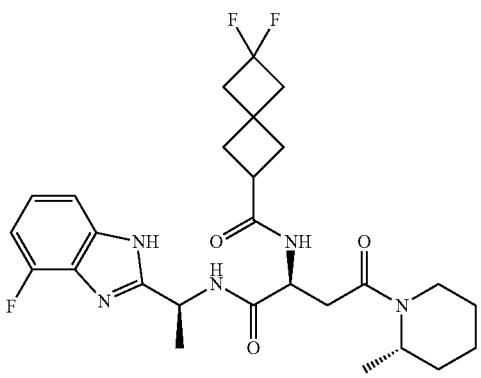 [SMILES: C[C@H](NC(=O)[C@H](CC(=O)N1CCCC[C@@H]1C)NC(=O)C1CC2(C1)CC(F)(F)C2)c1nc2c(F)cccc2[nH]1]

The title compound was synthesized by the similar method described for CEN-2. LC-MS (linear gradient 10→98% MeCN, 0.1% TFA, 12 min): $t_R$ (min): 7.07; ESI-MS (m/z): 534.26 (M+H⁺).

Example 66—Preparation of (2S)—N-(1-(1H-Benzo[d]imidazol-2-yl)ethyl)-2-((3-methylbutyl)sulfonamido)-4-oxo-4-((R)-2-phenylpyrrolidin-1-yl)butanamide (CEN-58)

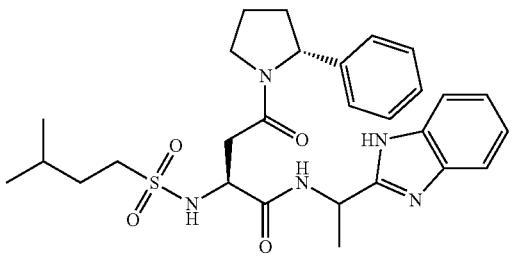 [SMILES: CC(C)CCS(=O)(=O)N[C@@H](CC(=O)N1CCC[C@@H]1c1ccccc1)C(=O)NC(C)c1nc2ccccc2[nH]1]

The title compound was synthesized by the similar method described for CEN-24. LC-MS (linear gradient 10→98% MeCN, 0.1% TFA, 12 min): $t_R$ (min): 5.67; ESI-MS (m/z): 540.25 (M+H⁺).

Example 67—Preparation of (S)—N—((S)-1-(1H-Benzo[d]imidazol-2-yl)ethyl)-2-((3-methylbutyl)sulfonamido)-4-oxo-4-((R)-2-phenylpyrrolidin-1-yl)butanamide (CEN-59)

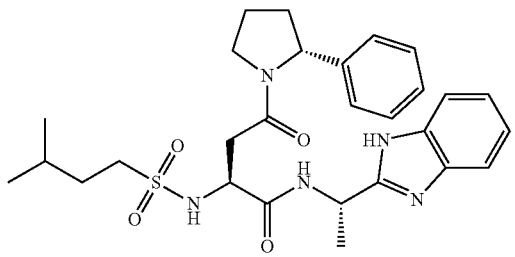 [SMILES: CC(C)CCS(=O)(=O)N[C@@H](CC(=O)N1CCC[C@@H]1c1ccccc1)C(=O)N[C@@H](C)c1nc2ccccc2[nH]1]

The title compound was synthesized by the similar method described for CEN-24. LC-MS (linear gradient 10→98% MeCN, 0.1% TFA, 12 min): $t_R$ (min): 4.94; ESI-MS (m/z): 540 (M+H$^+$).

Example 68—Preparation of (S)—N—((R)-1-(1H-Benzo[d]imidazol-2-yl)ethyl)-2-((3-methylbutyl)sulfonamido)-4-oxo-4-((R)-2-phenylpyrrolidin-1-yl)butanamide (CEN-60)

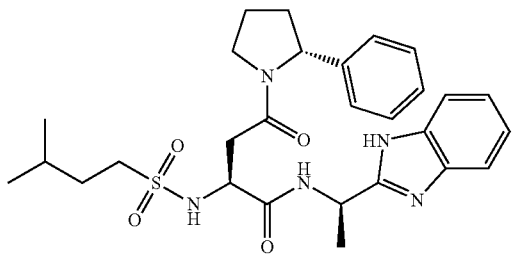 [SMILES: CC(C)CCS(=O)(=O)N[C@@H](CC(=O)N1CCC[C@@H]1c1ccccc1)C(=O)N[C@H](C)c1nc2ccccc2[nH]1]

The title compound was synthesized by the similar method described for CEN-24. LC-MS (linear gradient 10→98% MeCN, 0.1% TFA, 12 min): $t_R$ (min): 5.76; ESI-MSf (m/z): 540.25 (M+H$^+$).

Example 69—Preparation of N-((2S)-4-(2-Cyclopropylpyrrolidin-1-yl)-1-(((S)-1-(7-fluoro-1H-benzo[d]imidazol-2-yl)ethyl)amino)-1,4-dioxobutan-2-yl)-6,6-difluorospiro[3.3]heptane-2-carboxamide (CEN-61)

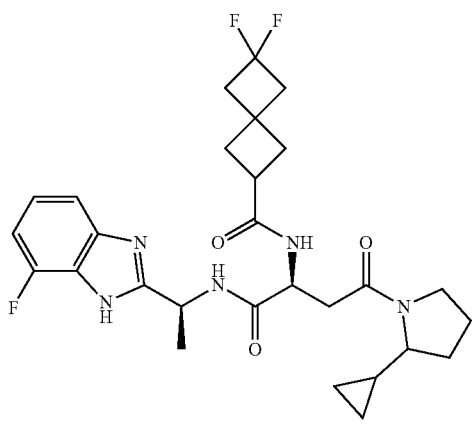 [SMILES: C[C@H](NC(=O)[C@H](CC(=O)N1CCCC1C1CC1)NC(=O)C1CC2(C1)CC(F)(F)C2)c1nc2cccc(F)c2[nH]1]

The title compound was synthesized by the similar method described for CEN-2. LC-MS (linear gradient 10→98% MeCN, 0.1% TFA, 12 min): $t_R$ (min): 7.16; ESI-MS (m/z): 546.26 (M+H$^+$).

Example 70—Preparation of 6,6-Difluoro-N—((S)-1-((1-(7-fluoro-1H-benzo[d]imidazol-2-yl)cyclopropyl)amino)-4-((S)-2-methylpiperidin-1-yl)-1,4-dioxobutan-2-yl)spiro[3.3]heptane-2-carboxamide (CEN-62)

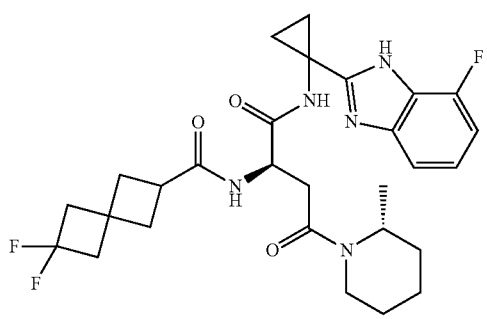 [SMILES: C[C@@H]1CCCCN1C(=O)C[C@@H](NC(=O)C1CC2(C1)CC(F)(F)C2)C(=O)NC1(c2nc3cccc(F)c3[nH]2)CC1]

The title compound was synthesized by the similar method described for CEN-2. LC-MS (linear gradient 10→98% MeCN, 0.1% TFA, 12 min): $t_R$ (min): 7.32; ESI-MS (m/z): 546.26 (M+H$^+$).

Example 71—Preparation of N—((S)-1-(((S)-1-(7-Fluoro-1H-benzo[d]imidazol-2-yl)ethyl)amino)-1,4-dioxo-4-((S)-2-phenylpyrrolidin-1-yl)butan-2-yl)-2-oxaspiro[3.3]heptane-6-carboxamide (CEN-63)

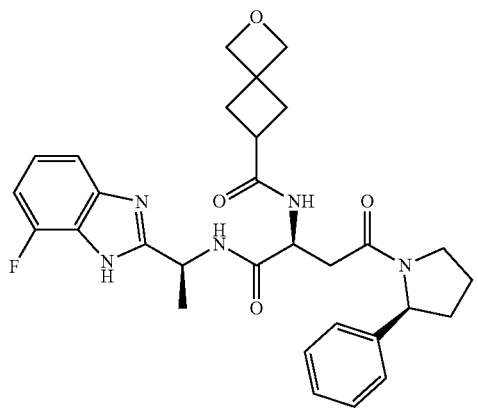 [SMILES: C[C@H](NC(=O)[C@H](CC(=O)N1CCC[C@H]1c1ccccc1)NC(=O)C1CC2(COC2)C1)c1nc2cccc(F)c2[nH]1]

The title compound was synthesized by the similar method described for CEN-2. LC-MS (linear gradient 10→98% MeCN, 0.1% TFA, 12 min): $t_R$ (min): 6.13; ESI-MS (m/z): 548.26 (M+H$^+$).

Example 72—Preparation of N-((2S)-4-(2-Cyclopropylpyrrolidin-1-yl)-1-((1-(7-fluoro-1H-benzo[d]imidazol-2-yl)cyclopropyl)amino)-1,4-dioxobutan-2-yl)-6,6-difluorospiro[3.3]heptane-2-carboxamide (CEN-64)

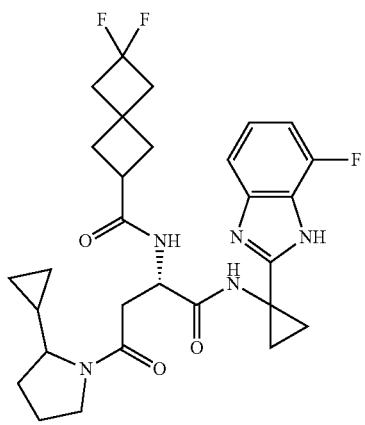 [SMILES: O=C(N[C@@H](CC(=O)N1CCCC1C1CC1)C(=O)NC1(c2nc3cccc(F)c3[nH]2)CC1)C1CC2(C1)CC(F)(F)C2]

The title compound was synthesized by the similar method described for CEN-2. LC-MS (linear gradient 10→98% MeCN, 0.1% TFA, 12 min): $t_R$ (min): 7.40; ESI-MS (m/z): 558.2 (M+H$^+$).

Example 73—Preparation of 5,5,5-Trifluoro-N—((S)-1-(((S)-1-(1-methyl-1H-benzo[d]imidazol-2-yl)ethyl)amino)-1,4-dioxo-4-((R)-2-phenylpyrrolidin yl)butan-2-yl)pentanamide (CEN-65)

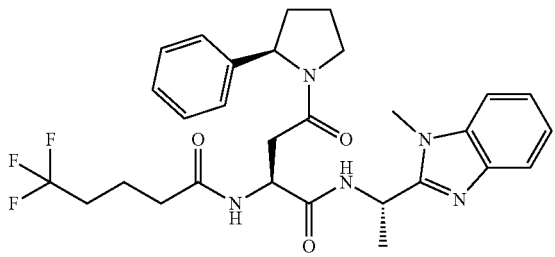 [SMILES: C[C@H](NC(=O)[C@H](CC(=O)N1CCC[C@@H]1c1ccccc1)NC(=O)CCCC(F)(F)F)c1nc2ccccc2n1C]

The title compound was synthesized by the similar method described for CEN-2. LC-MS (linear gradient 10→98% MeCN, 0.1% TFA, 12 min): $t_R$ (min): 4.81; ESI-MS (m/z): 558 (M+H$^+$).

Example 74—Preparation of N—((S)-1-(((S)-1-(Benzo[d]oxazol-2-yl)ethyl)amino)-1,4-dioxo-4-((R)-2-phenylpyrrolidin-1-yl)butan-2-yl)-5,5,5-trifluoropentanamide (CEN-66)

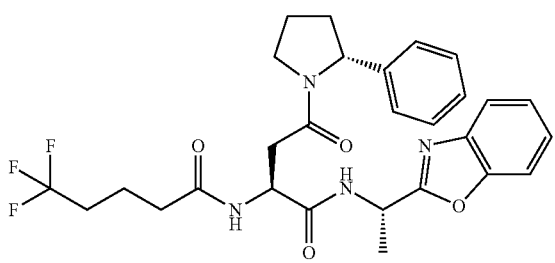 [SMILES: C[C@H](NC(=O)[C@H](CC(=O)N1CCC[C@@H]1c1ccccc1)NC(=O)CCCC(F)(F)F)c1nc2ccccc2o1]

The title compound was synthesized by the similar method described for CEN-2. LC-MS (linear gradient 10→98% MeCN, 0.1% TFA, 12 min): $t_R$ (min): 7.07; ESI-MS (m/z): 545 (M+H$^+$).

Example 75—Preparation of N—((S)-1-(((S)-1-(Benzo[d]thiazol-2-yl)ethyl)amino)-1,4-dioxo-4-((R)-2-phenylpyrrolidin-1-yl)butan-2-yl)-5,5,5-trifluoropentanamide (CEN-67)

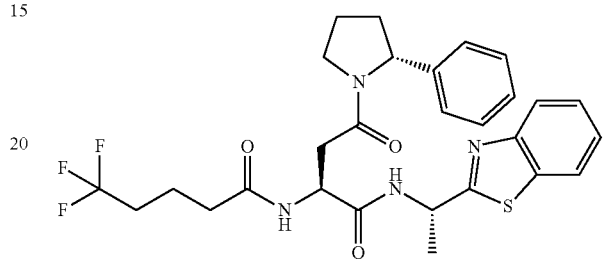

The title compound was synthesized by the similar method described for CEN-2. LC-MS (linear gradient 10→98% MeCN, 0.1% TFA, 12 min): $t_R$ (min): 7.24; ESI-MS (m/z): 561 (M+H$^+$).

Example 76—Preparation of N—((S)-1-(((S)-1-(Benzo[d]oxazol-2-yl)ethyl)amino)-1,4-dioxo-4-((R)-2-phenylpyrrolidin-1-yl)butan-2-yl)-6,6-difluorospiro[3.3]heptane-2-carboxamide (CEN-68)

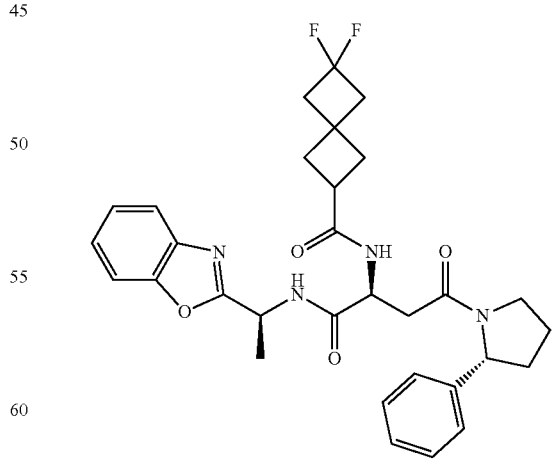

The title compound was synthesized by the similar method described for CEN-2. LC-MS (linear gradient 10→98% MeCN, 0.1% TFA, 12 min): $t_R$ (min): 7.26; ESI-MS (m/z): 565 (M+H$^+$).

Example 77—Preparation of (S)—N⁴-(tert-Butyl)-N¹-(1-(4-fluoro-1H-benzo[d]imidazol-2-yl)cyclopropyl)-2-((4-methylphenyl)sulfonamido)succinamide (CEN-69)

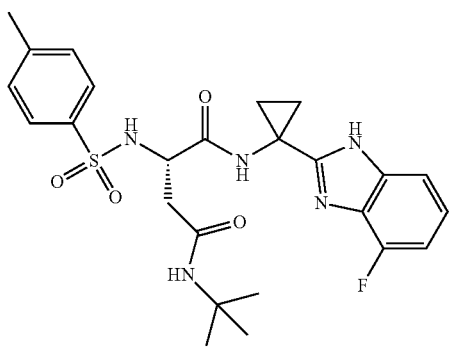 [SMILES: Cc1ccc(S(=O)(=O)N[C@@H](CC(=O)NC(C)(C)C)C(=O)NC2(c3nc4c(F)cccc4[nH]3)CC2)cc1]

The title compound was synthesized by the similar method described for CEN-24. LC-MS (linear gradient 10→95% MeCN, 0.1% TFA, 5 min): $t_R$ (min): 3.19; ESI-MS (m/z): 516.40 (M+H⁺).

Example 78—Preparation of (S)—N⁵-(tert-Butyl)-N¹-(1-(4-fluoro-1H-benzo[d]imidazol-2-yl)cyclopropyl)-2-((4-methylphenyl)sulfonamido)pentanediamide (CEN-70)

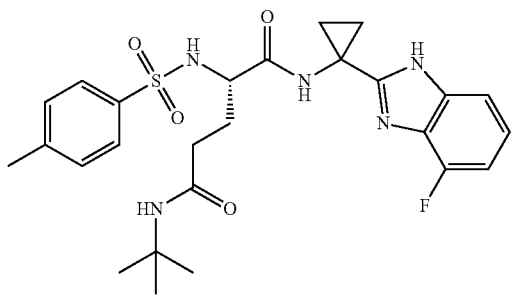 [SMILES: Cc1ccc(S(=O)(=O)N[C@@H](CCC(=O)NC(C)(C)C)C(=O)NC2(c3nc4c(F)cccc4[nH]3)CC2)cc1]

The title compound was synthesized by the similar method described for CEN-24. LC-MS (linear gradient 10→95% MeCN, 0.1% TFA, 5 min): $t_R$ (min): 3.17; ESI-MS (m/z): 530.45 (M+H⁺).

Example 79—Preparation of (2S,3R)—N—((S)-1-(7-Fluoro-1H-benzo[d]imidazol-2-yl)ethyl)-3-hydroxy-2-((4-methylphenyl)sulfonamido)butanamide (CEN-71)

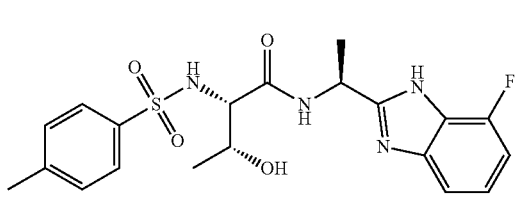 [SMILES: Cc1ccc(S(=O)(=O)N[C@H](C(=O)N[C@@H](C)c2nc3cccc(F)c3[nH]2)[C@@H](C)O)cc1]

The title compound was synthesized by the similar method described for CEN-24. LC-MS (linear gradient 10→95% MeCN, 0.1% TFA, 5 min): $t_R$ (min): 2.66; ESI-MS (m/z): 435.28 (M+H⁺).

Example 80—Preparation of (2S,3R)—N—((S)-1-(4-Fluoro-1H-benzo[d]imidazol-2-yl)ethyl)-2-(3-(4-fluorophenyl)propanamido)-3-hydroxybutanamide (CEN-72)

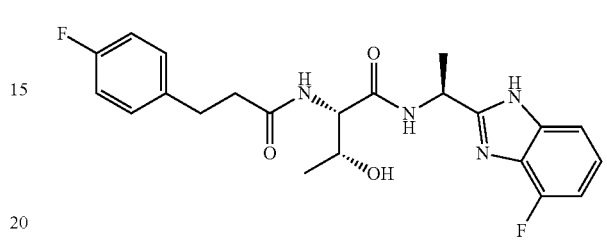

The title compound was synthesized by the similar method described for CEN-24. LC-MS (linear gradient 10→95% MeCN, 0.1% TFA, 5 min): $t_R$ (min): 2.65; ESI-MS (m/z): 431.34 (M+H⁺).

Example 81—Preparation of (S)—N5-(tert-Butyl)-N1-(1-(7-fluoro-1H-benzo[d]imidazol-2-yl)cyclopropyl)-2-(3-(4-fluorophenyl)propanamido)pentanediamide (CEN-73)

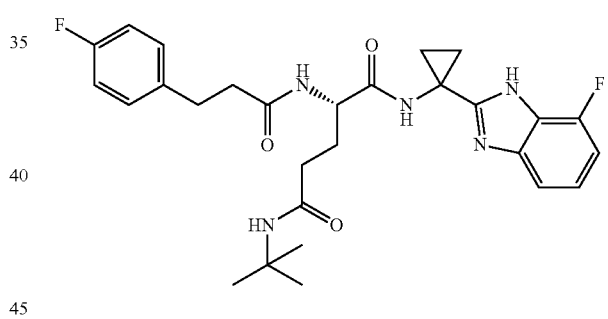

The title compound was synthesized by the similar method described for CEN-24. LC-MS (linear gradient 10→95% MeCN, 0.1% TFA, 5 min): $t_R$ (min): 3.12; ESI-MS (m/z): 526.45 (M+H⁺).

Example 82—Preparation of Benzyl (S)-(1-Oxo-1-((2-oxo-2-phenylethyl)amino)propan-2-yl)carbamate (2-1)

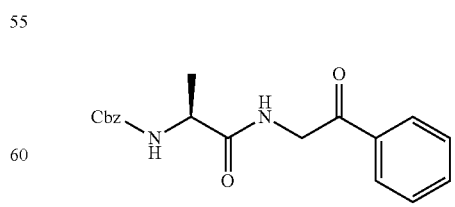

The title compound was synthesized by following the general protocol for HATU mediated coupling of ((benzyloxy)carbonyl)-L-alanine and 2-amino-1-phenylethan-1-one hydrochloride on a 1.3 mmol scale, and isolated as a white solid in quant. yield. LC-MS (linear gradient 10→98% MeCN, 0.1% TFA, 6.5 min): $t_R$ (min): 3.53; ESI-MS (m/z): 363.13 (M+Na⁺).

Example 83—Preparation of Benzyl (S)-(1-(5-Phenyl-1H-imidazol-2-yl)ethyl)carbamate (2-2)

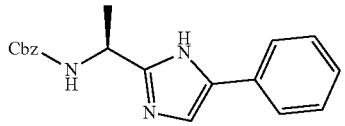 [SMILES: C[C@H](NC(=O)OCc1ccccc1)c1ncc(-c2ccccc2)[nH]1]

To a solution of 2-1 (450 mg, 1.32 mmol) in AcOH (4 mL) was added ammonium acetate (2.04 g, 26.4 mmol), and the reaction mixture was heated to reflux for 2 hours. After the reaction was completed, the mixture was poured into H₂O (15 mL) and extracted with DCM (10 mL×3). The combined organic layers were washed with saturated brine (50 mL×2), dried over Na₂SO₄, and concentrated under vacuum to give title product (400 mg) as a gum. LC-MS (linear gradient 10→98% MeCN, 0.1% TFA, 6.5 min): $t_R$ (min): 2.55; ESI-MS (m/z): 322.14 (M+H⁺).

Example 84—Preparation of (S)-1-(5-Phenyl-1H-imidazol-2-yl)ethan-1-amine (2-3)

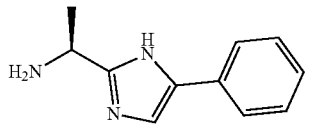

The title compound was synthesized by following the O-Debenzylation protocol of 2-2 on a 1.0 mmol scale. LC-MS (linear gradient 10→98% MeCN, 0.1% TFA, 6.5 min): $t_R$ (min): 2.12; ESI-MS (m/z): 188.10 (M+H⁺).

Example 85—Preparation of (S)-1-(5-(2-Fluorophenyl)-1H-imidazol-2-yl)ethan-1-amine (2-4)

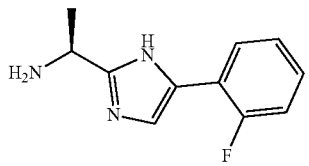

The title compound was synthesized by the similar method described for 2-3. LC-MS (linear gradient 10→98% MeCN, 0.1% TFA, 6.5 min): $t_R$ (min): 2.29; ESI-MS (m/z): 206.1 (M+H⁺).

Example 86—Preparation of (S)-1-(5-(4-Fluorophenyl)-1H-imidazol-2-yl)ethan-1-amine (2-5)

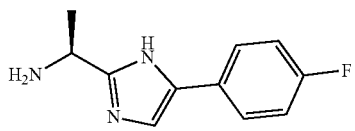

The title compound was synthesized by the similar method described for 2-3. LC-MS (linear gradient 10→98% MeCN, 0.1% TFA, 6.5 min): $t_R$ (min): 2.20; ESI-MS (m/z): 206.1 (M+H⁺).

Example 87—Preparation of (S)-1-(5-(2,4-Difluorophenyl)-1H-imidazol-2-yl)ethan-1-amine (2-6)

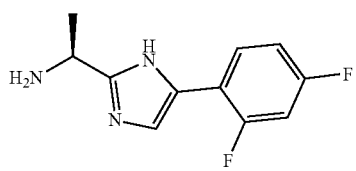 [SMILES: C[C@H](N)c1ncc(-c2ccc(F)cc2F)[nH]1]

The title compound was synthesized by the similar method described for 2-3. LC-MS (linear gradient 10→98% MeCN, 0.1% TFA, 6.5 min): $t_R$ (min): 2.35; ESI-MS (m/z): 224.1 (M+H⁺).

Example 88—Preparation of (S)-1-(5-Benzyl-1H-imidazol-2-yl)ethan-1-amine (2-7)

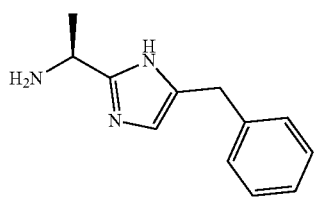

The title compound was synthesized by the similar method described for 2-3. LC-MS (linear gradient 10→98% MeCN, 0.1% TFA, 6.5 min): $t_R$ (min): 1.81; ESI-MS (m/z): 202.1 (M+H⁺).

Example 89—Preparation of Benzyl (S)-3-((tert-Butoxycarbonyl)amino)-4-(((S)-1-(5-(2-fluorophenyl)-1H-imidazol-2-yl)ethyl)amino)-4-oxobutanoate (2-8)

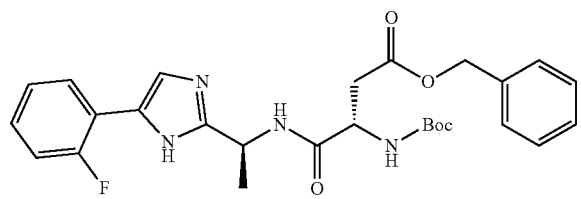 [SMILES: C[C@H](NC(=O)[C@H](CC(=O)OCc1ccccc1)NC(=O)OC(C)(C)C)c1ncc(-c2ccccc2F)[nH]1]

The title compound was synthesized by following the general protocol for HATU mediated coupling of 2-4 and (S)-4-(benzyloxy)-2-(tert-butoxycarbonylamino)-4-oxobutanoic acid on a 0.7 mmol scale, and isolated as a white solid (160 mg). LC-MS (linear gradient 10-98% MeCN, 0.1% TFA, 6.5 min): $t_R$ (min): 2.90; ESI-MS (m/z): 511.21 (M+H⁺).

Example 90—Preparation of (S)-3-((tert-Butoxycarbonyl)amino)-4-(((S)-1-(5-(2-fluorophenyl)-1H-imidazol-2-yl)ethyl)amino)-4-oxobutanoic Acid (2-9)

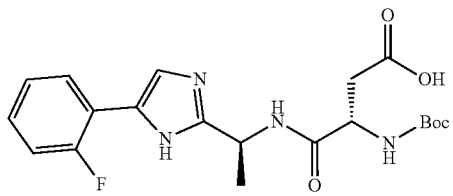 [SMILES: C[C@H](NC(=O)[C@H](CC(=O)O)NC(=O)OC(C)(C)C)c1ncc(-c2ccccc2F)[nH]1]

The title compound was synthesized by following the O-Debenzylation protocol of 2-8 on a 1.0 mmol scale. LC-MS (linear gradient 10→98% MeCN, 0.1% TFA, 6.5 min): $t_R$ (min): 2.51; ESI-MS (m/z): 421.10 (M+H$^+$).

Example 91—Preparation of tert-Butyl ((S)-1-(((S)-1-(5-(2-Fluorophenyl)-1H-imidazol-2-yl)ethyl)amino)-1,4-dioxo-4-((R)-2-phenylpyrrolidin-1-yl)butan-2-yl)carbamate (2-10)

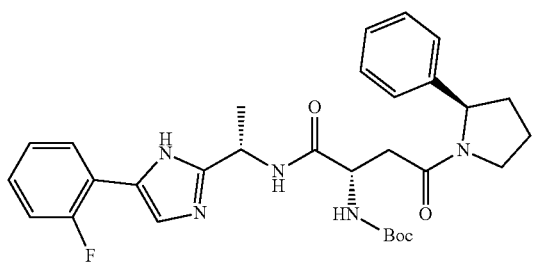 [SMILES: C[C@H](NC(=O)[C@H](CC(=O)N1CCC[C@@H]1c1ccccc1)NC(=O)OC(C)(C)C)c1ncc(-c2ccccc2F)[nH]1]

The title compound was synthesized by following the general protocol for HATU mediated coupling of 2-9 and (R)-2-phenylpyrrolidine on a 0.1 mmol scale. LC-MS (linear gradient 10→98% MeCN, 0.1% TFA, 6.5 min): $t_R$ (min): 2.83; ESI-MS (m/z): 550.1 (M+H$^+$).

Example 92—Preparation of (S)-2-Amino-N—((S)-1-(5-(2-fluorophenyl)-1H-imidazol-2-yl)ethyl)-4-oxo-4-((R)-2-phenylpyrrolidin-1-yl)butanamide (CEN-74)

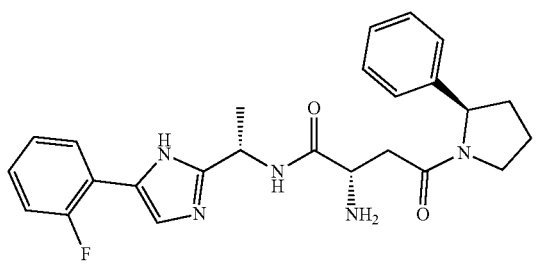 [SMILES: C[C@H](NC(=O)[C@@H](N)CC(=O)N1CCC[C@@H]1c1ccccc1)c1ncc(-c2ccccc2F)[nH]1]

The title compound was synthesized by following the general protocol for Boc-Deprotection protocol of 2-10 on a 0.05 mmol scale. LC-MS (linear gradient 10→98% MeCN, 0.1% TFA, 12 min): $t_R$ (min): 4.25; ESI-MS (m/z): 450.22 (M+H$^+$).

Example 93—Preparation of N—((S)-1-(((S)-1-(5-(2-Fluorophenyl)-1H-imidazol-2-yl)ethyl)amino)-1,4-dioxo-4-((R)-2-phenylpyrrolidin-1-yl)butan-2-yl)-5-methylisoxazole-3-carboxamide (CEN-75)

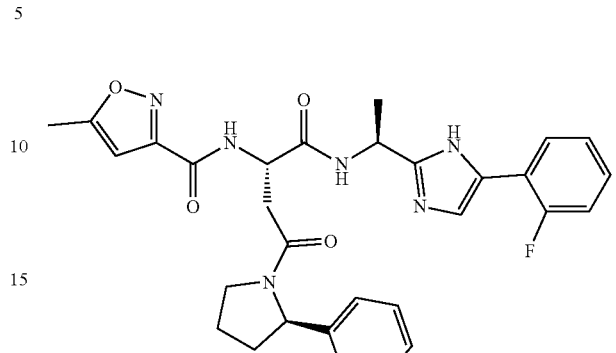

The title compound was synthesized by following the general protocol for HATU mediated coupling of CEN-74 and 5-methylisoxazole-3-carboxylic acid on a 0.1 mmol scale. LC-MS (linear gradient 10→98% MeCN, 0.1% TFA, 12 min): $t_R$ (min): 4.72; ESI-MS (m/z): 559.20 (M+H$^+$).

Example 94—Preparation of (S)-2-Amino-N—((S)-1-(5-(2,4-difluorophenyl)-1H-imidazol-2-yl)ethyl)-4-((S)-2-methylpiperidin-1-yl)-4-oxobutanamide (CEN-76)

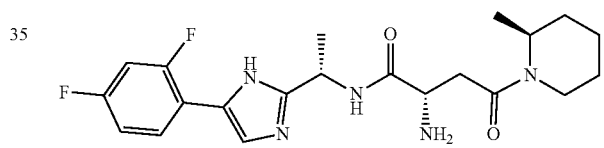

The title compound was synthesized by the similar method described for CEN-74. LC-MS (linear gradient 10→98% MeCN, 0.1% TFA, 12 min): $t_R$ (min): 3.81; ESI-MS (m/z): 420.21 (M+H$^+$).

Example 95—Preparation of N—((S)-1-(((S)-1-(5-(2,4-Difluorophenyl)-1H-imidazol-2-yl)ethyl)amino)-1,4-dioxo-4-(pyrrolidin-1-yl)butan-2-yl)-4-methylpentanamide (CEN-77)

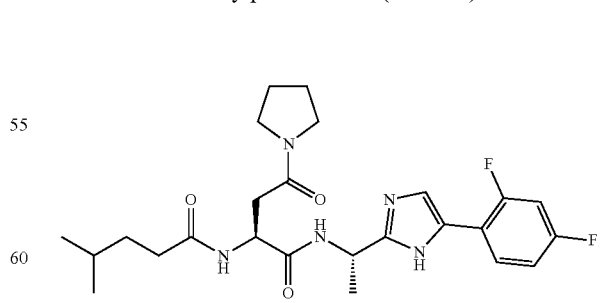

The title compound was synthesized by the similar method described for CEN-75. LC-MS (linear gradient 10→98% MeCN, 0.1% TFA, 12 min): $t_R$ (min): 5.30; ESI-MS (m/z): 490.25 (M+H$^+$).

Example 96—Preparation of (S)—N1-((S)-1-(5-(2, 4-Difluorophenyl)-1H-imidazol-2-yl)ethyl)-N4-isopropyl-N4-methyl-2-(4-methylpentanamido)succinamide (CEN-78)

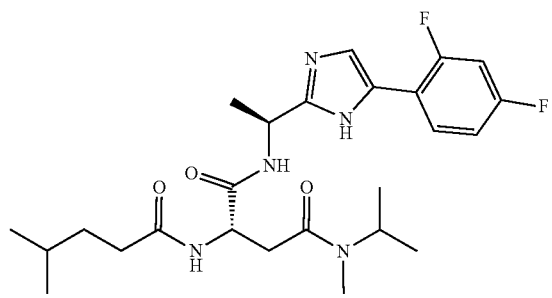 [SMILES: CC(C)CCC(=O)N[C@@H](CC(=O)N(C)C(C)C)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 6.5 min): $t_R$ (min): 2.77; ESI-MS (m/z): 492.27 (M+H$^+$).

Example 97—Preparation of (S)—N1-((S)-1-(5-(2, 4-Difluorophenyl)-1H-imidazol-2-yl)ethyl)-N4,N4-diethyl-2-(4-methylpentanamido)succinamide (CEN-79)

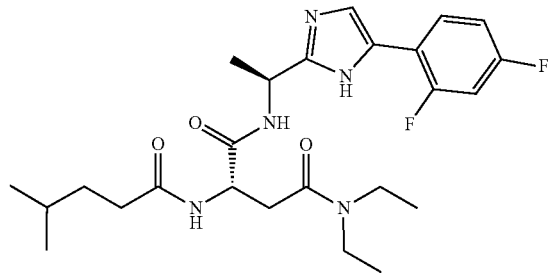 [SMILES: CCN(CC)C(=O)C[C@H](NC(=O)CCC(C)C)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.51; ESI-MS (m/z): 492.27 (M+H$^+$).

Example 98—Preparation of N—((S)-1-(((S)-1-(5-(2,4-Difluorophenyl)-1H-imidazol-2-yl)ethyl) amino)-1,4-dioxo-4-(pyrrolidin-1-yl)butan-2-yl)-5-methylisoxazole-3-carboxamide (CEN-80)

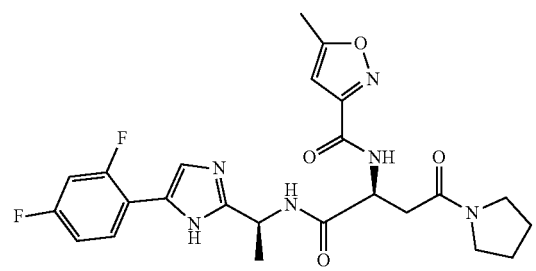 [SMILES: Cc1cc(C(=O)N[C@@H](CC(=O)N2CCCC2)C(=O)N[C@@H](C)c2ncc(-c3ccc(F)cc3F)[nH]2)no1]

The title compound was synthesized by the similar method described for CEN-75. LC-MS (linear gradient 10→98% MeCN, 0.1% TFA, 12 min): $t_R$ (min): 4.24; ESI-MS (m/z): 501 (M+H$^+$).

Example 99—Preparation of (S)-2-(2-Cyclopropylacetamido)-N—((S)-1-(5-(2,4-difluorophenyl)-1H-imidazol-2-yl)ethyl)-4-((S)-2-methylpiperidin-1-yl)-4-oxobutanamide (CEN-81)

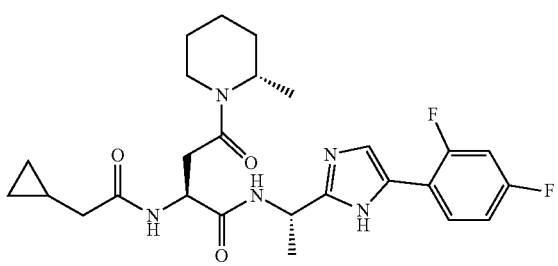 [SMILES: C[C@H](NC(=O)[C@H](CC(=O)N1CCCC[C@@H]1C)NC(=O)CC1CC1)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.20; ESI-MS (m/z): 502.25 (M+H$^+$).

Example 100—Preparation of N—((S)-1-(((S)-1-(5-(2,4-Difluorophenyl)-1H-imidazol-2-yl)ethyl) amino)-4-((S)-2-methylpiperidin-1-yl)-1,4-dioxobutan-2-yl)cyclobutanecarboxamide (CEN-82)

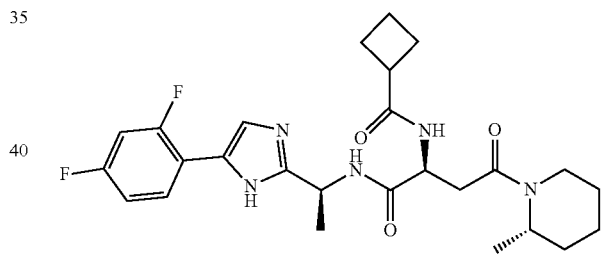

The title compound was synthesized by the similar method described for CEN-75. LC-MS (linear gradient 10→98% MeCN, 0.1% TFA, 12 min): $t_R$ (min): 4.48; ESI-MS (m/z): 502 (M+H$^+$).

Example 101—Preparation of N—((S)-1-(((S)-1-(5-(2,4-Difluorophenyl)-1H-imidazol-2-yl)ethyl) amino)-1,4-dioxo-4-(pyrrolidin-1-yl)butan-2-yl)-4,4-dimethylpentanamide (CEN-83)

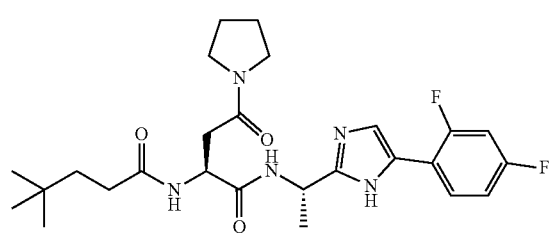 [SMILES: C[C@H](NC(=O)[C@H](CC(=O)N1CCCC1)NC(=O)CCC(C)(C)C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.41; ESI-MS (m/z): 504.27 (M+H$^+$).

Example 102—Preparation of N—((S)-1-(((S)-1-(5-(2,4-Difluorophenyl)-1H-imidazol-2-yl)ethyl)amino)-1,4-dioxo-4-(piperidin-1-yl)butan-2-yl)-4-methylpentanamide (CEN-84)

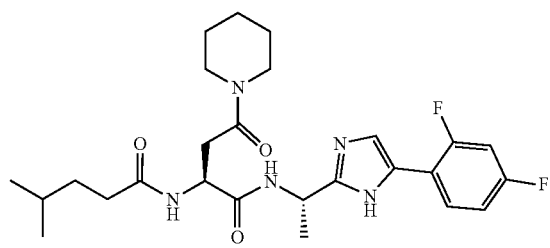 [SMILES: CC(C)CCC(=O)N[C@@H](CC(=O)N1CCCCC1)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.59; ESI-MS (m/z): 504.27 (M+H$^+$).

Example 103—Preparation of (S)—N—((S)-1-(5-(2,4-Difluorophenyl)-1H-imidazol-2-yl)ethyl)-2-((3-methyl-2-oxobutyl)amino)-4-((S)-2-methylpiperidin-1-yl)-4-oxobutanamide (CEN-85)

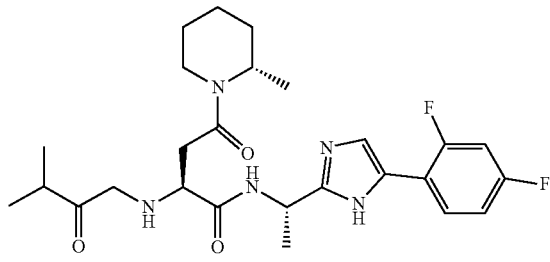 [SMILES: CC(C)C(=O)CN[C@@H](CC(=O)N1CCCC[C@@H]1C)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 4.54; ESI-MS (m/z): 504.27 (M+H$^+$).

Example 104—Preparation of (S)—N—((S)-1-(5-(2,4-Difluorophenyl)-1H-imidazol-2-yl)ethyl)-2-(ethylsulfonamido)-4-((S)-2-methylpiperidin-1-yl)-4-oxobutanamide (CEN-86)

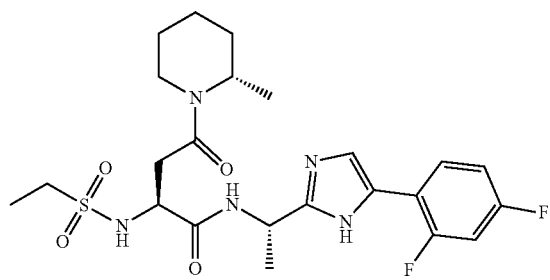 [SMILES: CCS(=O)(=O)N[C@@H](CC(=O)N1CCCC[C@@H]1C)C(=O)N[C@@H](C)c1ncc(-c2ccc(F)cc2F)[nH]1]

The title compound was synthesized by the similar method described for CEN-24. LC-MS (linear gradient 10→98% MeCN, 0.1% TFA, 12 min): $t_R$ (min): 4.88; ESI-MS (m/z): 512.20 (M+H$^+$).

Example 105—Preparation of (S)-2-(3-Cyclopropylpropanamido)-N—((S)-1-(5-(2,4-difluorophenyl)-1H-imidazol-2-yl)ethyl)-4-((S)-2-methylpiperidin-1-yl)-4-oxobutanamide (CEN-87)

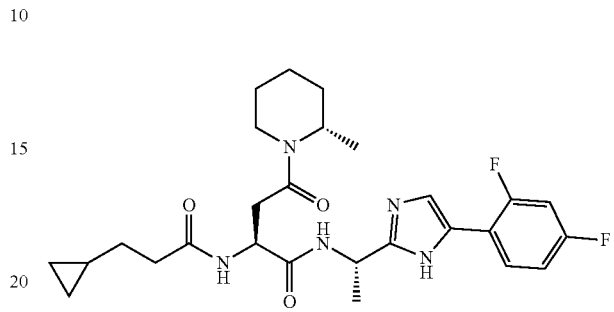

The title compound was synthesized by the similar method described for CEN-75. LC-MS (linear gradient 10→98% MeCN, 0.1% TFA, 12 min): $t_R$ (min): 5.52; ESI-MS (m/z): 516.27 (M+H$^+$).

Example 106—Preparation of N—((S)-1-(((S)-1-(5-(2,4-Difluorophenyl)-1H-imidazol-2-yl)ethyl)amino)-4-((S)-2-methylpiperidin-1-yl)-1,4-dioxobutan-2-yl)-4-methylpentanamide (CEN-88)

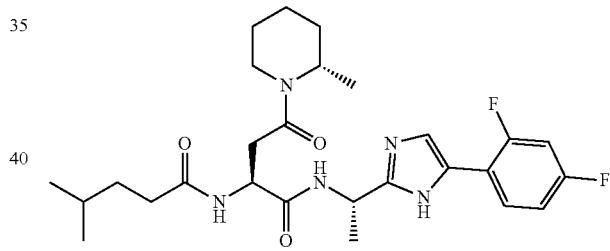

The title compound was synthesized by the similar method described for CEN-75. LC-MS (linear gradient 10→98% MeCN, 0.1% TFA, 12 min): $t_R$ (min): 5.67; ESI-MS (m/z): 518.28 (M+H$^+$).

Example 107—Preparation of N—((S)-1-(((S)-1-(5-(2,4-Difluorophenyl)-1H-imidazol-2-yl)ethyl)amino)-4-((S)-2-methylpyrrolidin-1-yl)-1,4-dioxobutan-2-yl)-4,4-dimethylpentanamide (CEN-89)

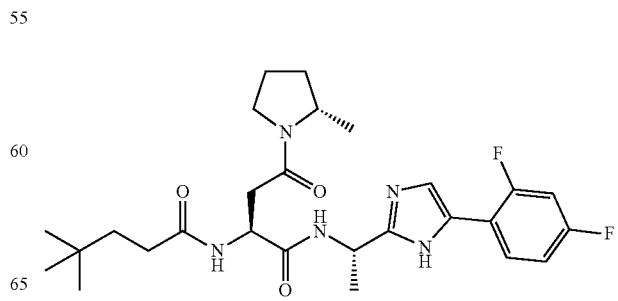

The title compound was synthesized by the similar method described for CEN-75. LC-MS (linear gradient 10→98% MeCN, 0.1% TFA, 12 min): $t_R$ (min): 5.75; ESI-MS (m/z): 518.28 (M+H$^+$).

Example 108—Preparation of N—((S)-4-(Azepan-1-yl)-1-(((S)-1-(5-(2,4-difluorophenyl)-1H-imidazol-2-yl)ethyl)amino)-1,4-dioxobutan-2-yl)-4-methylpentanamide (CEN-90)

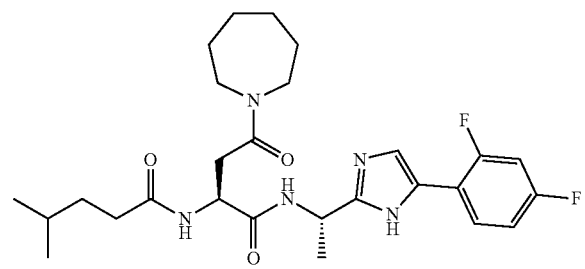 [SMILES: CC(C)CCC(=O)N[C@@H](CC(=O)N1CCCCCC1)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.77; ESI-MS (m/z): 518.26 (M+H$^+$).

Example 109—Preparation of N—((S)-1-(((S)-1-(5-(2,4-Difluorophenyl)-1H-imidazol-2-yl)ethyl)amino)-4-((R)-2-methylpiperidin-1-yl)-1,4-dioxobutan-2-yl)-4-methylpentanamide (CEN-91)

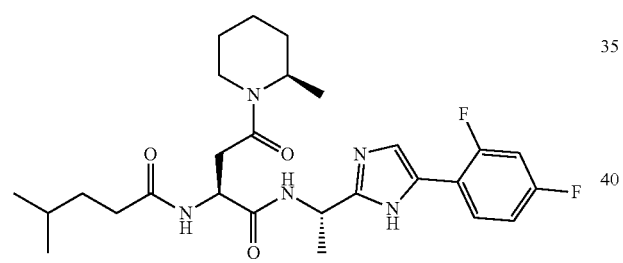

The title compound was synthesized by the similar method described for CEN-75. LC-MS (linear gradient 10→98% MeCN, 0.1% TFA, 12 min): $t_R$ (min): 5.83; ESI-MS (m/z): 518.28 (M+H$^+$).

Example 110—Preparation of N—((S)-1-(((S)-1-(5-(2,4-Difluorophenyl)-1H-imidazol-2-yl)ethyl)amino)-4-((S)-3-methylmorpholino)-1,4-dioxobutan-2-yl)-4-methylpentanamide (CEN-92)

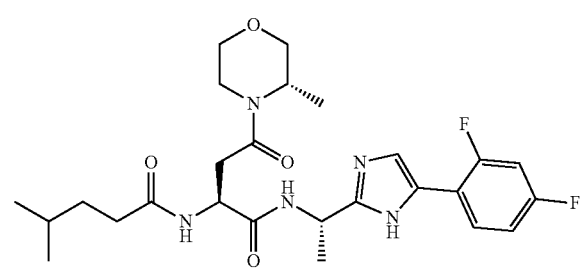 [SMILES: CC(C)CCC(=O)N[C@@H](CC(=O)N1CCOC[C@@H]1C)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.04; ESI-MS (m/z): 520.26 (M+H$^+$).

Example 111—Preparation of N—((S)-1-(((S)-1-(5-(2,4-Difluorophenyl)-1H-imidazol-2-yl)ethyl)amino)-4-((S)-2-methylpiperidin-1-yl)-1,4-dioxobutan-2-yl)-1-methyl-1H-imidazole-4-carboxamide (CEN-93)

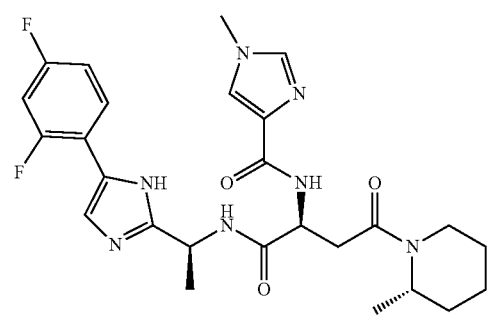 [SMILES: C[C@H](NC(=O)[C@H](CC(=O)N1CCCC[C@@H]1C)NC(=O)c1cn(C)cn1)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 4.30; ESI-MS (m/z): 528.24 (M+H$^+$).

Example 112—Preparation of N—((S)-1-(((S)-1-(5-(2,4-Difluorophenyl)-1H-imidazol-2-yl)ethyl)amino)-4-((S)-2-methylpiperidin-1-yl)-1,4-dioxobutan-2-yl)-5-methylisoxazole-3-carboxamide (CEN-94)

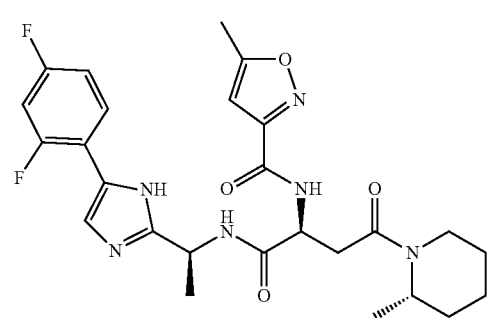 [SMILES: Cc1cc(C(=O)N[C@@H](CC(=O)N2CCCC[C@@H]2C)C(=O)N[C@@H](C)c2ncc(-c3ccc(F)cc3F)[nH]2)no1]

The title compound was synthesized by the similar method described for CEN-75. LC-MS (linear gradient 10→98% MeCN, 0.1% TFA, 12 min): $t_R$ (min): 5.47; ESI-MS (m/z): 529.22 (M+H$^+$).

Example 113—Preparation of (S)—N—((S)-1-(5-(2,4-Difluorophenyl)-1H-imidazol-2-yl)ethyl)-2-((3-isopropyl-1,2,4-oxadiazol-5-yl)amino)-4-((S)-2-methylpiperidin-1-yl)-4-oxobutanamide (CEN-95)

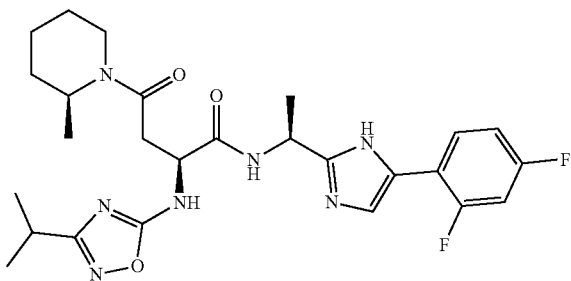 [SMILES: CC(C)c1noc(N[C@@H](CC(=O)N2CCCC[C@@H]2C)C(=O)N[C@@H](C)c2ncc(-c3ccc(F)cc3F)[nH]2)n1]

The title compound was synthesized by the similar method described for CEN-8. LC-MS (linear gradient 10→98% MeCN, 0.1% TFA, 12 min): $t_R$ (min): 5.81; ESI-MS (m/z): 530.26 (M+H$^+$).

Example 114—Preparation of N—((S)-1-(((S)-1-(5-(2,4-difluorophenyl)-1H-imidazol-2-yl)ethyl)amino)-4-((S)-2-methylpiperidin-1-yl)-1,4-dioxobutan-2-yl)-3,3-dimethylcyclobutane-1-carboxamide (CEN-96)

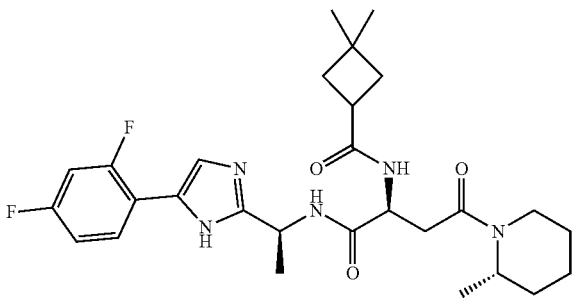 [SMILES: C[C@H](NC(=O)[C@H](CC(=O)N1CCCC[C@@H]1C)NC(=O)C1CC(C)(C)C1)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 6.01; ESI-MS (m/z): 530.28 (M+H$^+$).

Example 115—Preparation of N—((S)-1-(((S)-1-(5-(2,4-Difluorophenyl)-1H-imidazol-2-yl)ethyl)amino)-4-((S)-2-methylpiperidin-1-yl)-1,4-dioxobutan-2-yl)-2-isopropylcyclopropane-1-carboxamide (CEN-97)

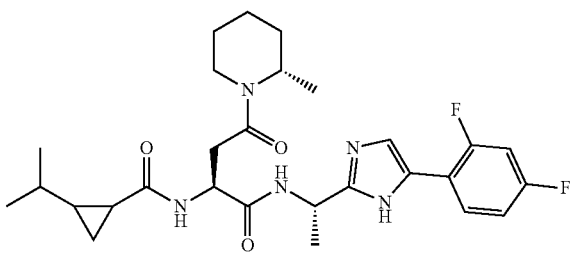 [SMILES: CC(C)C1CC1C(=O)N[C@@H](CC(=O)N1CCCC[C@@H]1C)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 6.02; ESI-MS (m/z): 530.28 (M+H$^+$).

Example 116—Preparation of N—((S)-1-(((S)-1-(5-(2,4-Difluorophenyl)-1H-imidazol-2-yl)ethyl)amino)-4-((S)-2-methylpiperidin-1-yl)-1,4-dioxobutan-2-yl)thiazole-5-carboxamide (CEN-98)

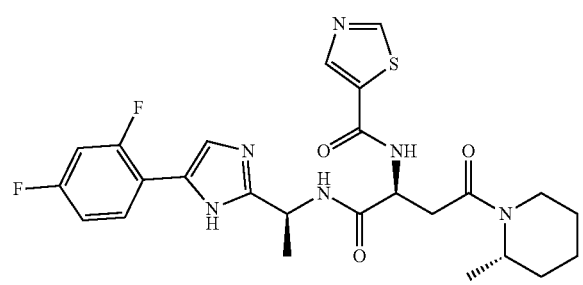 [SMILES: C[C@H](NC(=O)[C@H](CC(=O)N1CCCC[C@@H]1C)NC(=O)c1cncs1)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 4.81; ESI-MS (m/z): 531.19 (M+H$^+$).

Example 117—Preparation of N—((S)-1-(((S)-1-(5-(2,4-Difluorophenyl)-1H-imidazol-2-yl)ethyl)amino)-4-((S)-2-methylpiperidin-1-yl)-1,4-dioxobutan-2-yl)-4,4-dimethylpentanamide (CEN-99)

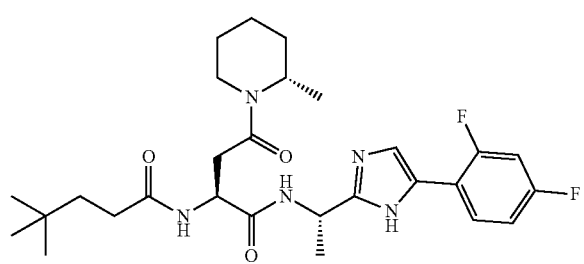 [SMILES: C[C@H](NC(=O)[C@H](CC(=O)N1CCCC[C@@H]1C)NC(=O)CCC(C)(C)C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.96; ESI-MS (m/z): 532.30 (M+H$^+$).

Example 118—Preparation of N—((S)-1-(((S)-1-(5-(2,4-Difluorophenyl)-1H-imidazol-2-yl)ethyl)amino)-4-((S)-2-ethylpiperidin-1-yl)-1,4-dioxobutan-2-yl)-4-methylpentanamide (CEN-100)

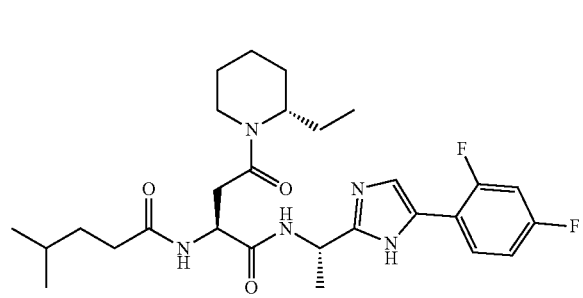 [SMILES: CC[C@H]1CCCCN1C(=O)C[C@H](NC(=O)CCC(C)C)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 6.16; ESI-MS (m/z): 532.30 (M+H⁺).

Example 119—Preparation of N—((S)-1-(5-(2,4-Difluorophenyl)-1H-imidazol-2-yl)ethyl)-2-(4,4-dimethylpentanoyl)-1-(2-((S)-2-methylpiperidin-1-yl)-2-oxoethyl)hydrazine-1-carboxamide (CEN-101)

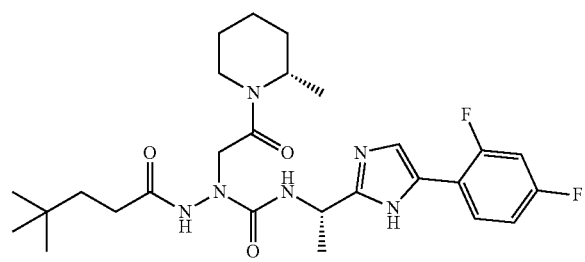 [SMILES: C[C@H](NC(=O)N(CC(=O)N1CCCC[C@@H]1C)NC(=O)CCC(C)(C)C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.73; ESI-MS (m/z): 533.3 (M+H⁺).

Example 120—Preparation of (S)—N—((S)-1-(5-(2,4-Difluorophenyl)-1H-imidazol-2-yl)ethyl)-4-((S)-2-methylpiperidin-1-yl)-4-oxo-2-(2-phenylacetamido)butanamide (CEN-102)

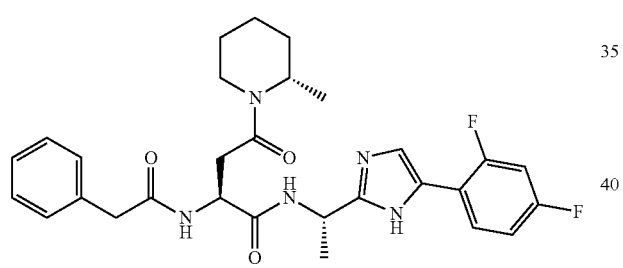

The title compound was synthesized by the similar method described for CEN-75. LC-MS (linear gradient 10→98% MeCN, 0.1% TFA, 12 min): $t_R$ (min): 5.47; ESI-MS (m/z): 538.25 (M+H⁺).

Example 121—Preparation of (S)—N—((S)-1-(5-(2,4-Difluorophenyl)-1H-imidazol-2-yl)ethyl)-4-((S)-2-methylpiperidin-1-yl)-4-oxo-2-((2-oxo phenylethyl)amino)butanamide (CEN-103)

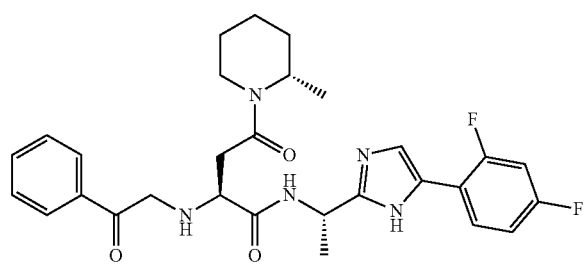 [SMILES: C[C@H](NC(=O)[C@H](CC(=O)N1CCCC[C@@H]1C)NCC(=O)c1ccccc1)c1ncc(-c2ccc(F)cc2F)[nH]1]

The title compound was synthesized by the similar method described for CEN-8. LC-MS (linear gradient 10→98% MeCN, 0.1% TFA, 12 min): $t_R$ (min): 4.70; ESI-MS (m/z): 538.25 (M+H⁺).

Example 122—Preparation of (S)—N—((S)-1-(5-(2,4-Difluorophenyl)-1H-imidazol-2-yl)ethyl)-4-((S)-2-methylpiperidin-1-yl)-2-((2-methylpropyl)sulfonamido)-4-oxobutanamide (CEN-104)

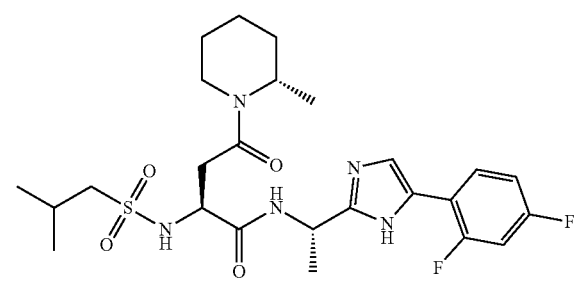 [SMILES: CC(C)CS(=O)(=O)N[C@@H](CC(=O)N1CCCC[C@@H]1C)C(=O)N[C@@H](C)c1ncc(-c2ccc(F)cc2F)[nH]1]

The title compound was synthesized by the similar method described for CEN-24. LC-MS (linear gradient 10→98% MeCN, 0.1% TFA, 12 min): $t_R$ (min): 4.83; ESI-MS (m/z): 540 (M+H⁺).

Example 123—Preparation of N—((S)-1-(((S)-1-(5-(2,4-Difluorophenyl)-1H-imidazol-2-yl)ethyl)amino)-4-((S)-2-methylpiperidin-1-yl)-1,4-dioxobutan-2-yl)-2-methylthiazole-5-carboxamide (CEN-105)

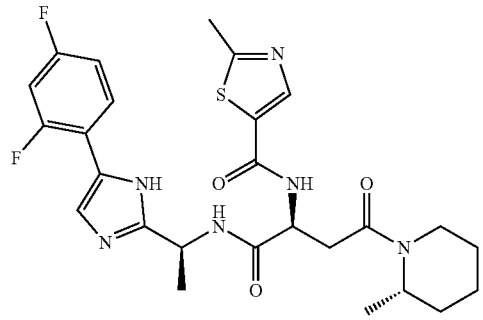 [SMILES: Cc1ncc(C(=O)N[C@@H](CC(=O)N2CCCC[C@@H]2C)C(=O)N[C@@H](C)c2ncc(-c3ccc(F)cc3F)[nH]2)s1]

The title compound was synthesized by the similar method described for CEN-75. LC-MS (linear gradient 10→98% MeCN, 0.1% TFA, 12 min): $t_R$ (min): 4.98; ESI-MS (m/z): 545.20 (M+H⁺).

Example 124—Preparation of (S)—N—((S)-1-(5-(2,4-Difluorophenyl)-1H-imidazol-2-yl)ethyl)-4-((S)-2-methylpiperidin-1-yl)-4-oxo-2-(2-(tetrahydro-2H-pyran-4-yl)acetamido)butanamide (CEN-106)

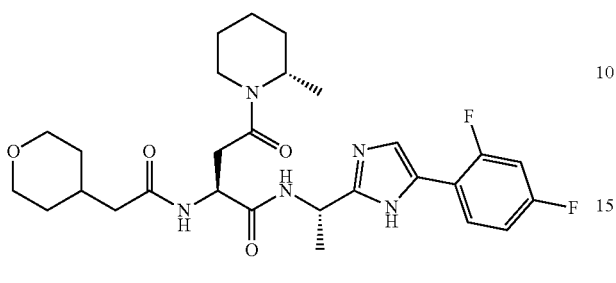

The title compound was synthesized by the similar method described for CEN-75. LC-MS (linear gradient 10→98% MeCN, 0.1% TFA, 12 min): $t_R$ (min): 4.92; ESI-MS (m/z): 546.28 (M+H$^+$).

Example 125—Preparation of N-((2S)-1-(((S)-1-(5-(2,4-Difluorophenyl)-1H-imidazol-2-yl)ethyl)amino)-4-(2-isopropylpiperidin-1-yl)-1,4-dioxobutan-2-yl)-4-methylpentanamide (CEN-107)

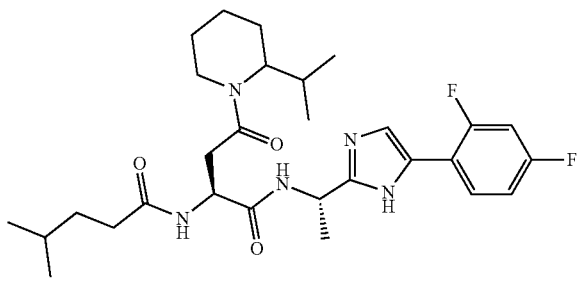 [SMILES: CC(C)CCC(=O)N[C@@H](CC(=O)N1CCCCC1C(C)C)C(=O)N[C@@H](C)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 6.41; ESI-MS (m/z): 546.31 (M+H$^+$).

Example 126—Preparation of (S)-2-((2-Cyclopropylethyl)sulfonamido)-N—((S)-1-(5-(2,4-difluorophenyl)-1H-imidazol-2-yl)ethyl)-4-((S)-2-methylpiperidin-1-yl)-4-oxobutanamide (CEN-108)

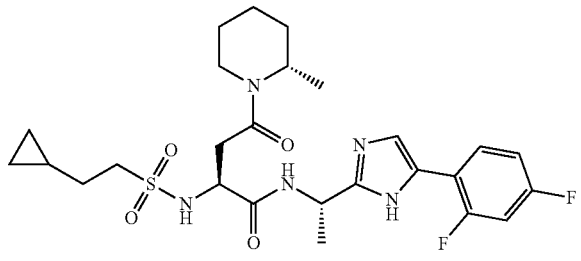 [SMILES: C[C@H](NC(=O)[C@H](CC(=O)N1CCCC[C@@H]1C)NS(=O)(=O)CCC1CC1)c1ncc(-c2ccc(F)cc2F)[nH]1]

The title compound was synthesized by the similar method described for CEN-24. LC-MS (linear gradient 10→98% MeCN, 0.1% TFA, 12 min): $t_R$ (min): 5.78; ESI-MS (m/z): 552.23 (M+H$^+$).

Example 127—Preparation of (S)-2-(Benzo[d]oxazol-2-ylamino)-N—((S)-1-(5-(2,4-difluorophenyl)-1H-imidazol-2-yl)ethyl)-4-((S)-2-methylpiperidin-1-yl)-4-oxobutanamide (CEN-109)

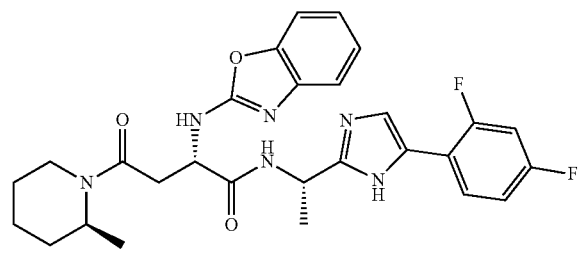 [SMILES: C[C@H](NC(=O)[C@H](CC(=O)N1CCCC[C@@H]1C)Nc1nc2ccccc2o1)c1ncc(-c2ccc(F)cc2F)[nH]1]

The title compound was synthesized by the similar method described for CEN-16. LC-MS (linear gradient 10→98% MeCN, 0.1% TFA, 12 min): $t_R$ (min): 5.80; ESI-MS (m/z): 537.23 (M+H$^+$).

Example 128—Preparation of (S)—N—((S)-1-(5-(2,4-Difluorophenyl)-1H-imidazol-2-yl)ethyl)-4-((S)-2-methylpiperidin-1-yl)-4-oxo-2-(phenylsulfonamido)butanamide (CEN-110)

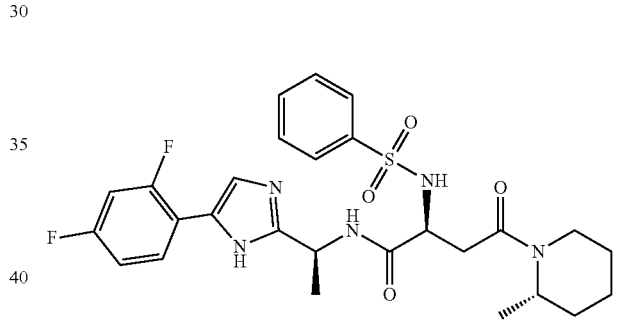

The title compound was synthesized by the similar method described for CEN-24. LC-MS (linear gradient 10→98% MeCN, 0.1% TFA, 12 min): $t_R$ (min): 5.54; ESI-MS (m/z): 560.20 (M+H$^+$).

Example 129—Preparation of N—((S)-1-(((S)-1-(5-(2,4-Difluorophenyl)-1H-imidazol-2-yl)ethyl)amino)-1,4-dioxo-4-((R)-2-(trifluoromethyl)piperidin-1-yl)butan-2-yl)-4-methylpentanamide (CEN-111)

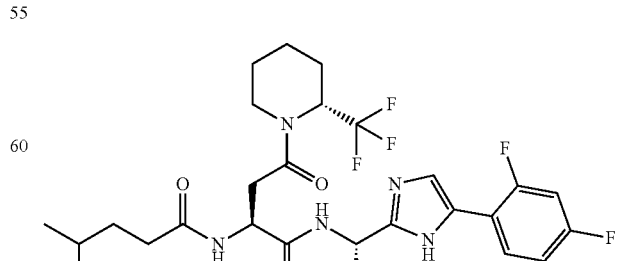

The title compound was synthesized by the similar method described for CEN-75. LC-MS (linear gradient 10→98% MeCN, 0.1% TFA, 12 min): $t_R$ (min): 5.17; ESI-MS (m/z): 572.25 (M+H$^+$).

Example 130—Preparation of (S)—N—((S)-1-(5-(2,4-Difluorophenyl)-1H-imidazol-2-yl)ethyl)-4-((S)-2-methylpiperidin-1-yl)-4-oxo ((phenylmethyl)sulfonamido)butanamide (CEN-112)

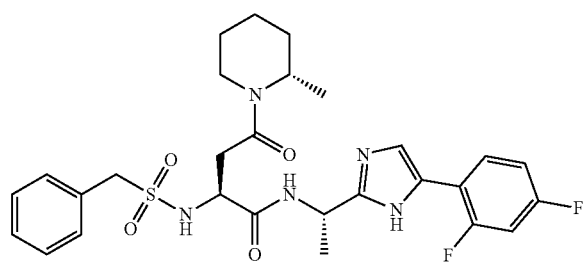 [SMILES: C[C@H](NC(=O)[C@H](CC(=O)N1CCCC[C@@H]1C)NS(=O)(=O)Cc1ccccc1)c1ncc(-c2ccc(F)cc2F)[nH]1]

The title compound was synthesized by the similar method described for CEN-75. LC-MS (linear gradient 10→98% MeCN, 0.1% TFA, 12 min): $t_R$ (min): 5.75; ESI-MS (m/z): 574.22 (M+H$^+$).

Example 131—Preparation of (S)—N—((S)-1-(5-(2,4-Difluorophenyl)-1H-imidazol-2-yl)ethyl)-2-((4-methylphenyl)sulfonamido)-4-((S)-2-methylpiperidin-1-yl)-4-oxobutanamide (CEN-113)

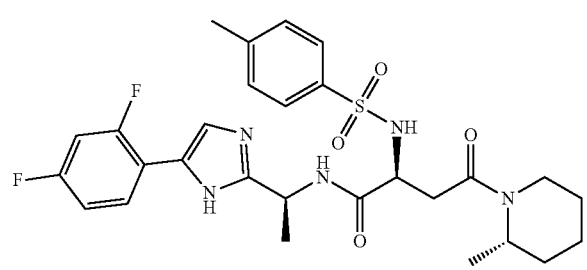 [SMILES: Cc1ccc(S(=O)(=O)N[C@@H](CC(=O)N2CCCC[C@@H]2C)C(=O)N[C@@H](C)c2ncc(-c3ccc(F)cc3F)[nH]2)cc1]

The title compound was synthesized by the similar method described for CEN-24. LC-MS (linear gradient 10→98% MeCN, 0.1% TFA, 12 min): $t_R$ (min): 5.81; ESI-MS (m/z): 574.22 (M+H$^+$).

Example 132—Preparation of (S)—N—((S)-1-(5-(2,4-Difluorophenyl)-1H-imidazol-2-yl)ethyl)-2-((3-methylbutyl)sulfonamido)-4-((S)-2-methylpiperidin-1-yl)-4-oxobutanamide (CEN-114)

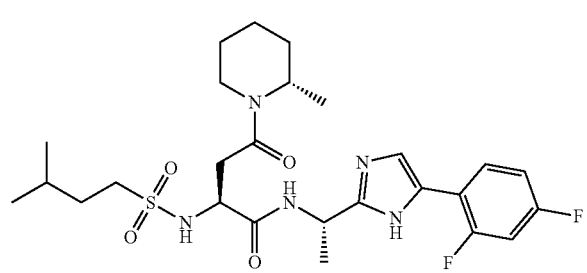 [SMILES: CC(C)CCS(=O)(=O)N[C@@H](CC(=O)N1CCCC[C@@H]1C)C(=O)N[C@@H](C)c1ncc(-c2ccc(F)cc2F)[nH]1]

The title compound was synthesized by the similar method described for CEN-24. LC-MS (linear gradient 10→98% MeCN, 0.1% TFA, 12 min): $t_R$ (min): 5.80; ESI-MS (m/z): 554.25 (M+H$^+$).

Example 133—Preparation of N—((S)-1-(((S)-1-(5-(2,4-Difluorophenyl)-1H-imidazol-2-yl)ethyl)amino)-1,4-dioxo-4-((R)-2-phenylpyrrolidin-1-yl)butan-2-yl)-5-methylisoxazole-3-carboxamide (CEN-115)

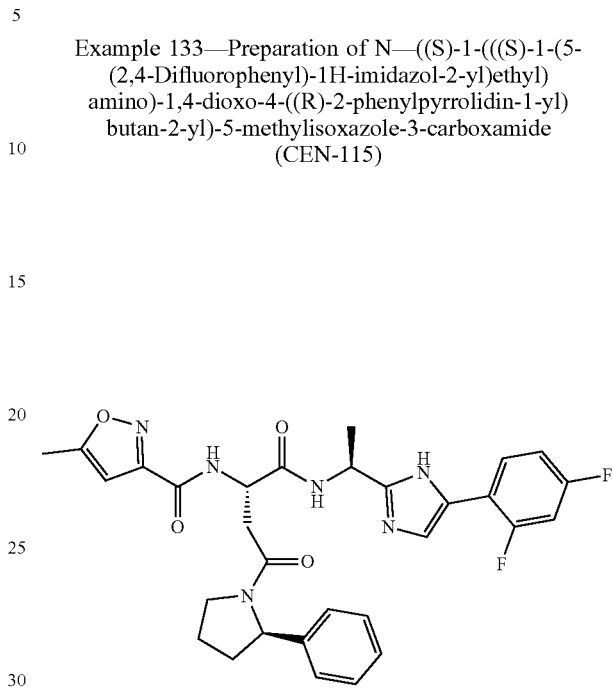

The title compound was synthesized by the similar method described for CEN-75. LC-MS (linear gradient 5→95% MeCN, 0.1% TFA, 8 min): $t_R$ (min): 3.56; ESI-MS (m/z): 577.3 (M+H$^+$).

Example 134—Preparation of 5-Methyl-N—((S)-4-((S)-2-methylpiperidin-1-yl)-1,4-dioxo-1-(((S)-1-(5-phenyl-1H-imidazol-2-yl)ethyl)amino)butan-2-yl)isoxazole-3-carboxamide (CEN-116)

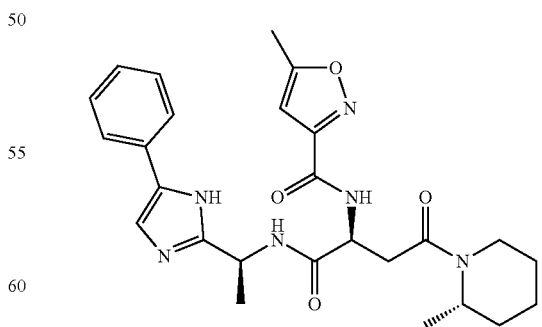

The title compound was synthesized by the similar method described for CEN-75. LC-MS (linear gradient 10→98% MeCN, 0.1% TFA, 12 min): $t_R$ (min): 5.39; ESI-MS (m/z): 493.34 (M+H$^+$).

Example 135—Preparation of 5-Methyl-N-((2S)-4-(2-methylpiperidin-1-yl)-1,4-dioxo (((S)-1-(5-phenyl-1H-imidazol-2-yl)ethyl)amino)butan-2-yl)isoxazole-3-carboxamide (CEN-117)

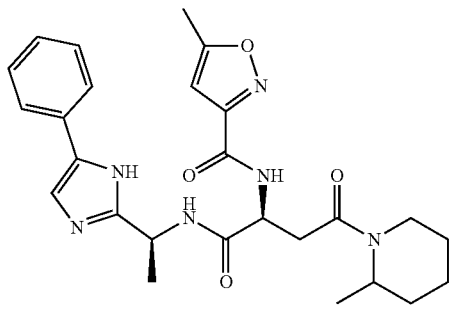 [SMILES: Cc1cc(C(=O)N[C@@H](CC(=O)N2CCCCC2C)C(=O)N[C@@H](C)c2ncc(-c3ccccc3)[nH]2)no1]

The title compound was synthesized by the similar method described for CEN-75. LC-MS (linear gradient 10→98% MeCN, 0.1% TFA, 12 min): $t_R$ (min): 5.37; ESI-MS (m/z): 493.24 (M+H$^+$).

Example 136—Preparation of N—((S)-1-(((S)-1-(5-(2-Fluorophenyl)-1H-imidazol-2-yl)ethyl)amino)-4-((S)-2-methylpiperidin-1-yl)-1,4-dioxobutan-2-yl)-5-methylisoxazole-3-carboxamide (CEN-118)

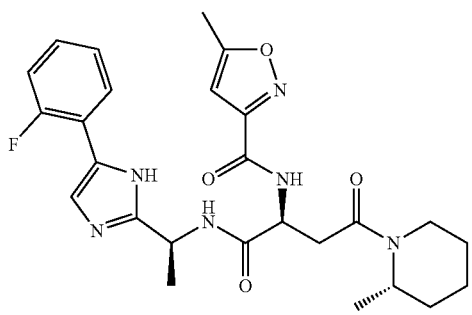 [SMILES: Cc1cc(C(=O)N[C@@H](CC(=O)N2CCCC[C@@H]2C)C(=O)N[C@@H](C)c2ncc(-c3ccccc3F)[nH]2)no1]

The title compound was synthesized by the similar method described for CEN-75. LC-MS (linear gradient 10→98% MeCN, 0.1% TFA, 12 min): $t_R$ (min): 5.36; ESI-MS (m/z): 511.23 (M+H$^+$).

Example 137—Preparation of N—((S)-1-(((S)-1-(5-(4-Fluorophenyl)-1H-imidazol-2-yl)ethyl)amino)-4-((S)-2-methylpiperidin-1-yl)-1,4-dioxobutan-2-yl)-5-methylisoxazole-3-carboxamide (CEN-119)

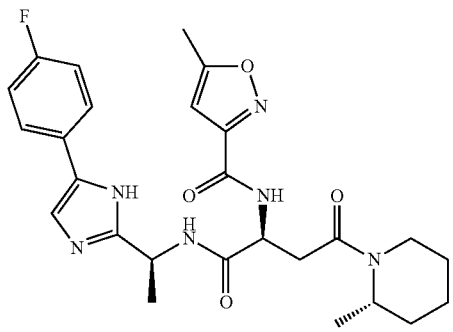 [SMILES: Cc1cc(C(=O)N[C@@H](CC(=O)N2CCCC[C@@H]2C)C(=O)N[C@@H](C)c2ncc(-c3ccc(F)cc3)[nH]2)no1]

The title compound was synthesized by the similar method described for CEN-75. LC-MS (linear gradient 10→98% MeCN, 0.1% TFA, 12 min): $t_R$ (min): 5.43; ESI-MS (m/z): 511.23 (M+H$^+$).

Example 138—Preparation of N—((S)-1,4-Dioxo-1-(((S)-1-(5-phenyl-1H-imidazol-2-yl)ethyl)amino)-4-((R)-2-phenylpyrrolidin-1-yl)butan-2-yl)-5-methylisoxazole-3-carboxamide (CEN-120)

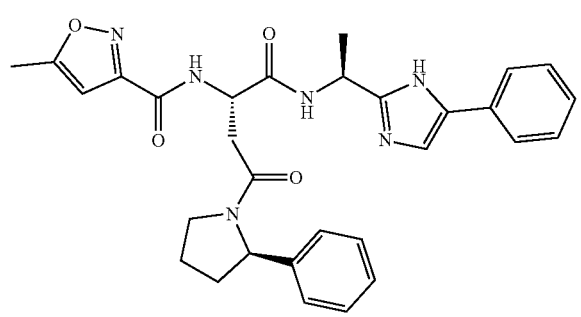 [SMILES: Cc1cc(C(=O)N[C@@H](CC(=O)N2CCC[C@@H]2c2ccccc2)C(=O)N[C@@H](C)c2ncc(-c3ccccc3)[nH]2)no1]

The title compound was synthesized by the similar method described for CEN-75. LC-MS (linear gradient 5→95% MeCN, 0.1% TFA, 8 min): $t_R$ (min): 3.47; ESI-MS (m/z): 541.5 (M+H$^+$).

Example 139—Preparation of (S)—N—((S)-1-(5-Benzyl-1H-imidazol-2-yl)ethyl)-2-(2-cyclopropylacetamido)-4-oxo-4-((R)-2-phenylpyrrolidin-1-yl)butanamide (CEN-121)

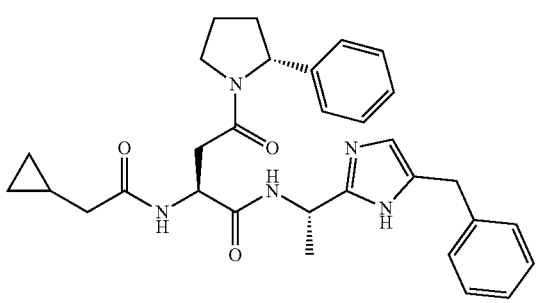 [SMILES: C[C@H](NC(=O)[C@H](CC(=O)N1CCC[C@@H]1c1ccccc1)NC(=O)CC1CC1)c1ncc(Cc2ccccc2)[nH]1]

The title compound was synthesized by the similar method described for CEN-75. LC-MS (linear gradient 10→98% MeCN, 0.1% TFA, 12 min): $t_R$ (min): 5.61; ESI-MS (m/z): 528.29 (M+H$^+$).

Example 140—Preparation of (S)—N—((S)-1-(5-Benzyl-1H-imidazol-2-yl)ethyl)-4-((S)-2-methylpiperidin-1-yl)-4-oxo-2-(2-(tetrahydro-2H-pyran-4-yl)acetamido)butanamide (CEN-122)

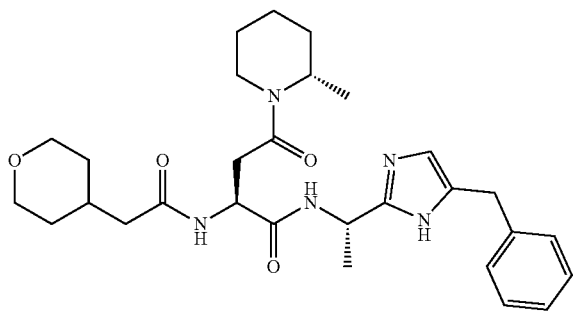 [SMILES: C[C@H](NC(=O)[C@H](CC(=O)N1CCCC[C@@H]1C)NC(=O)CC1CCOCC1)c1ncc(Cc2ccccc2)[nH]1]

The title compound was synthesized by the similar method described for CEN-75. LC-MS (linear gradient 10→98% MeCN, 0.1% TFA, 12 min): t$_R$ (min): 4.94; ESI-MS (m/z): 524.31 (M+H$^+$).

Example 141—Preparation of N—((S)-1-(((S)-1-(5-Benzyl-1H-imidazol-2-yl)ethyl)amino)-1,4-dioxo-4-((R)-2-phenylpyrrolidin-1-yl)butan-2-yl)-5-methylisoxazole-3-carboxamide (CEN-123)

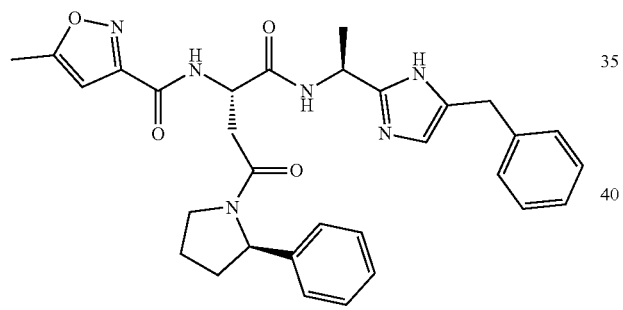

The title compound was synthesized by the similar method described for CEN-75. LC-MS (linear gradient 10→98% MeCN, 0.1% TFA, 12 min): t$_R$ (min): 5.84; ESI-MS (m/z): 555.26 (M+H$^+$).

Example 142—Preparation of (S)—N—((S)-1-(5-Benzyl-1H-imidazol-2-yl)ethyl)-2-(2-cyclopropylacetamido)-4-((S)-2-methylpiperidin-1-yl)-4-oxobutanamide (CEN-124)

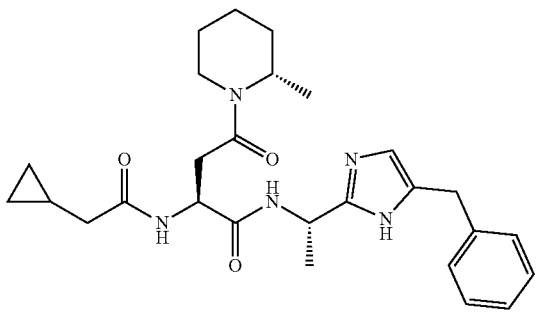 [SMILES: C[C@H](NC(=O)[C@H](CC(=O)N1CCCC[C@@H]1C)NC(=O)CC1CC1)c1ncc(Cc2ccccc2)[nH]1]

The title compound was synthesized by the similar method described for CEN-75. LC-MS (linear gradient 10→98% MeCN, 0.1% TFA, 12 min): t$_R$ (min): 5.27; ESI-MS (m/z): 480.29 (M+H$^+$).

Example 143—Preparation of (S)-2-(benzo[d]oxazol-2-ylamino)-N—((S)-1-(5-(2-fluorophenyl)-1H-imidazol-2-yl)ethyl)-4-oxo-4-((R)-2-phenylpyrrolidin yl)butanamide (CEN-125)

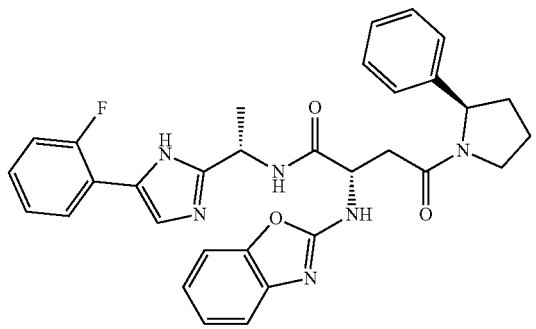 [SMILES: C[C@H](NC(=O)[C@H](CC(=O)N1CCC[C@@H]1c1ccccc1)Nc1nc2ccccc2o1)c1ncc(-c2ccccc2F)[nH]1]

The title compound was synthesized by the similar method described for CEN-16. LC-MS (linear gradient 10→98% MeCN, 0.1% TFA, 12 min): t$_R$ (min): 5.73; ESI-MS (m/z): 567.24 (M+H$^+$).

Synthesized compounds are shown in Table 1.

TABLE 1

| Formula | Molecular Weight | Structure IUPAC Name |
|---|---|---|
|  | 492.6 | 5-methyl-N-[(1S)-3-(2-methyl-1-piperidyl)-3-oxo-1-[[(1S)-1-(5-phenyl-1H-imidazol-2-yl)ethyl]carbamoyl]propyl]isoxazole-3-carboxamide |

TABLE 1-continued

| Formula | Molecular Weight | Structure IUPAC Name |
|---|---|---|
| 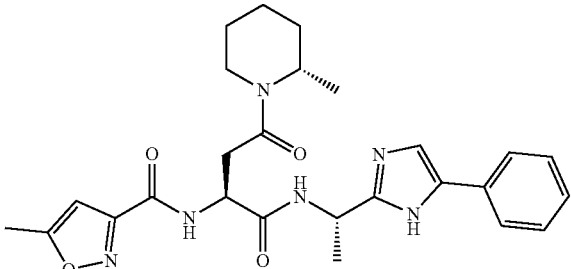 | 492.6 | 5-methyl-N-((S)-4-((S)-2-methylpiperidin-1-yl)-1,4-dioxo-1-(((S)-1-(5-phenyl-1H-imidazol-2-yl)ethyl)amino)butan-2-yl)isoxazole-3-carboxamide |
| 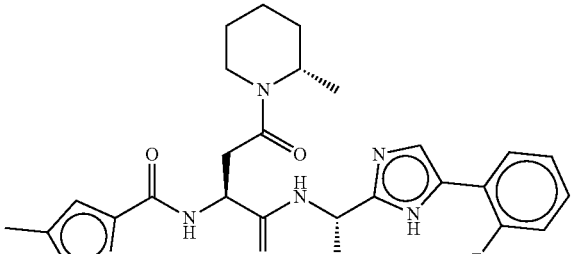 | 510.6 | N-((S)-1-(((S)-1-(5-(2-fluorophenyl)-1H-imidazol-2-yl)ethyl)amino)-4-((S)-2-methylpiperidin-1-yl)-1,4-dioxobutan-2-yl)-5-methylisoxazole-3-carboxamide |
| 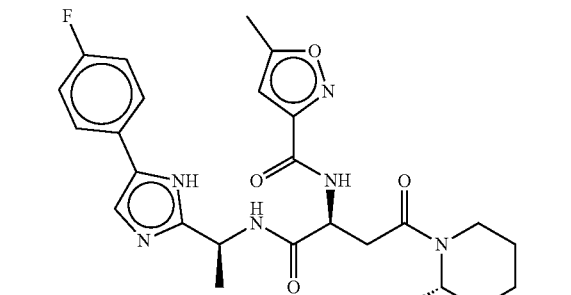 | 510.6 | N-((S)-1-(((S)-1-(5-(4-fluorophenyl)-1H-imidazol-2-yl)ethyl)amino)-4-((S)-2-methylpiperidin-1-yl)-1,4-dioxobutan-2-yl)-5-methylisoxazole-3-carboxamide |
| 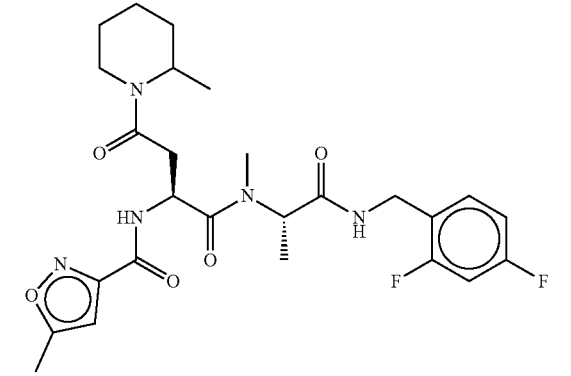 | 533.6 | N-((2S)-1-(((S)-1-((2,4-difluorobenzyl)amino)-1-oxopropan-2-yl)(methyl)amino)-4-(2-methylpiperidin-1-yl)-1,4-dioxobutan-2-yl)-5-methylisoxazole-3-carboxamide |
| 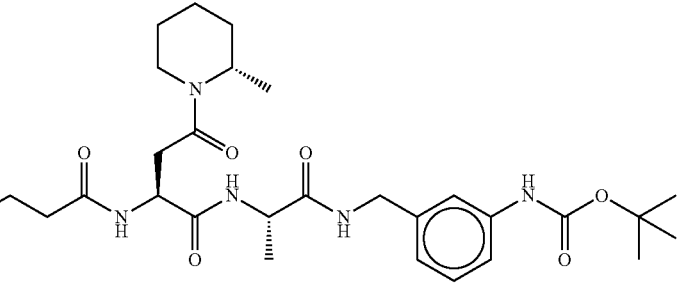 | 621.8 | tert-butyl (3-(((S)-2-((S)-4-((S)-2-methylpiperidin-1-yl)-4-oxo-2-(3-phenylpropanamido)butanamido)propanamido)methyl)phenyl)carbamate |

TABLE 1-continued

| Formula | Molecular Weight | Structure IUPAC Name |
|---|---|---|
| | 521.7 | (S)-N-((S)-1-((3-aminobenzyl)amino)-1-oxopropan-2-yl)-4-((S)-2-methylpiperidin-1-yl)-4-oxo-2-(3-phenylpropanamido)butanamide |
| | 466.5 | N-((2S)-1-((1-(1H-benzo[d]imidazol-2-yl)ethyl)amino)-4-((S)-2-methylpiperidin-1-yl)-1,4-dioxobutan-2-yl)-5-methylisoxazole-3-carboxamide |
| | 558.6 | N-[(1S)-1-[[(1S)-1-[5-(2-fluorophenyl)-1H-imidazol-2-yl]ethyl]carbamoyl]-3-oxo-3-[(2S)-2-phenylpyrrolidin-1-yl]propyl]-5-methyl-isoxazole-3-carboxamide |
| | 566.6 | (2S)-2-(1,3-benzoxazol-2-ylamino)-N-[(1S)-1-[4-(2-fluorophenyl)-1H-imidazol-2-yl]ethyl]-4-oxo-4-[(2R)-2-phenylpyrrolidin-1-yl]butanamide |
| | 449.5 | (2S)-2-amino-N-[(1S)-1-[5-(2-fluorophenyl)-2,5-dihydro-1H-imidazol-2-yl]ethyl]-4-oxo-4-[(2R)-2-phenylpyrrolidin-1-yl]butanamide |

TABLE 1-continued

| Formula | Molecular Weight | Structure IUPAC Name |
|---|---|---|
| | 528.6 | N-[(1S)-1-[[(1S)-1-[5-(2,4-difluorophenyl)-1H-imidazol-2-yl]ethyl]carbamoyl]-3-[(2S)-2-methyl-1-piperidyl]-3-oxo-propyl]-5-methyl-isoxazole-3-carboxamide |
| | 514.6 | N-[(1S)-1-[1-(1H-benzimidazol-2-yl)ethylcarbamoyl]-3-oxo-3-[(2S)-2-phenylpyrrolidin-1-yl]propyl]-5-methyl-isoxazole-3-carboxamide |
| | 506.6 | N-[(1S)-1-[[(1S)-1-(5-benzyl-1H-imidazol-2-yl)ethyl]carbamoyl]-3-[(2S)-2-methyl-1-piperidyl]-3-oxo-propyl]-5-methyl-isoxazole-3-carboxamide |
| | 554.64 | N-[(1S)-1-[[(1S)-1-(5-benzyl-1H-imidazol-2-yl)ethyl]carbamoyl]-3-oxo-3-[(2S)-2-phenylpyrrolidin-1-yl]propyl]-5-methyl-isoxazole-3-carboxamide |

TABLE 1-continued

| Formula | Molecular Weight | Structure IUPAC Name |
|---|---|---|
| | 523.67 | (2S)-N-[(1S)-1-(5-benzyl-1H-imidazol-2-yl)ethyl]-4-[(2S)-2-methyl-1-piperidyl]-4-oxo-2-[(2-tetrahydropyran-4-ylacetyl)amino]butanamide |
| | 479.61 | (2S)-N-[(1S)-1-(5-benzyl-1H-imidazol-2-yl)ethyl]-2-[(2-cyclopropylacetyl)amino]-4-[(2S)-2-methyl-1-piperidyl]-4-oxo-butanamide |
| | 527.66 | (2S)-N-[(1S)-1-(5-benzyl-1H-imidazol-2-yl)ethyl]-2-[(2-cyclopropylacetyl)amino]-4-oxo-4-[(2S)-2-phenylpyrrolidin-1-yl]butanamide |
| | 501.57 | (2S)-2-[(2-cyclopropylacetyl)amino]-N-[(1S)-1-[5-(2,4-difluorophenyl)-1H-imidazol-2-yl]ethyl]-4-[(2S)-2-methyl-1-piperidyl]-4-oxo-butanamide |
| | 545.62 | (2S)-N-[(1S)-1-[5-(2,4-difluorophenyl)-1H-imidazol-2-yl]ethyl]-4-[(2S)-2-methyl-1-piperidyl]-4-oxo-2-[(2-tetrahydropyran-4-ylacetyl)amino]butanamide |

TABLE 1-continued

| Formula | Molecular Weight | Structure IUPAC Name |
|---|---|---|
| | 573.65 | (2S)-2-(benzylsulfonylamino)-N-[(1S)-1-[5-(2,4-difluorophenyl)-1H-imidazol-2-yl]ethyl]-4-[(2S)-2-methyl-1-piperidyl]-4-oxo-butanamide |
| | 539.64 | (2S)-N-[(1S)-1-[5-(2,4-difluorophenyl)-1H-imidazol-2-yl]ethyl]-2-(isobutylsulfonylamino)-4-[(2S)-2-methyl-1-piperidyl]-4-oxo-butanamide |
| | 559.63 | (2S)-2-(benzenesulfonamido)-N-[(1S)-1-[5-(2,4-difluorophenyl)-1H-imidazol-2-yl]ethyl]-4-[(2S)-2-methyl-1-piperidyl]-4-oxo-butanamide |
| | 573.65 | (2S)-N-[(1S)-1-[5-(2,4-difluorophenyl)-1H-imidazol-2-yl]ethyl]-4-[(2S)-2-methyl-1-piperidyl]-4-oxo-2-(p-tolylsulfonylamino)butanamide |
| | 511.59 | (2S)-N-[(1S)-1-[5-(2,4-difluorophenyl)-1H-imidazol-2-yl]ethyl]-2-(ethylsulfonylamino)-4-[(2S)-2-methyl-1-piperidyl]-4-oxo-butanamide |

TABLE 1-continued

| Formula | Molecular Weight | Structure IUPAC Name |
|---|---|---|
| | 537.6 | (2S)-N-[(1S)-1-[5-(2,4-difluorophenyl)-1H-imidazol-2-yl]ethyl]-4-[(2S)-2-methyl-1-piperidyl]-4-oxo-2-(phenacylamino)butanamide |
| | 501.57 | N-[(1S)-1-[[(1S)-1-[5-(2,4-difluorophenyl)-1H-imidazol-2-yl]ethyl]carbamoyl]-3-[(2S)-2-methyl-1-piperidyl]-3-oxo-propyl]cyclobutanecarboxamide |
| | 517.61 | N-[(1S)-1-[[(1S)-1-[5-(2,4-difluorophenyl)-1H-imidazol-2-yl]ethyl]carbamoyl]-3-[(2S)-2-methyl-1-piperidyl]-3-oxo-propyl]-4-methyl-pentanamide |
| | 466.53 | N-[(1S)-1-[[(1S)-1-(1H-benzimidazol-2-yl)ethyl]carbamoyl]-3-[(2S)-2-methyl-1-piperidyl]-3-oxo-propyl]-5-methyl-isoxazole-3-carboxamide |
| | 455.59 | N-[(1S)-1-[[(1S)-1-(1H-benzimidazol-2-yl)ethyl]carbamoyl]-3-[(2S)-2-methyl-1-piperidyl]-3-oxo-propyl]-4-methyl-pentanamide |

TABLE 1-continued

| Formula | Molecular Weight | Structure IUPAC Name |
|---|---|---|
| | 503.64 | N-[(1S)-1-[[(1S)-1-(1H-benzimidazol-2-yl)ethyl]carbamoyl]-3-oxo-3-[(2S)-2-phenylpyrrolidin-1-yl]propyl]-4-methyl-pentanamide |
| | 503.64 | N-((S)-1-(((R)-1-(1H-benzo[d]imidazol-2-yl)ethyl)amino)-1,4-dioxo-4-((R)-2-phenylpyrrolidin-1-yl)butan-2-yl)-4-methylpentanamide |
| | 503.58 | (2S)-N-[(1S)-1-[5-(2,4-difluorophenyl)-1H-imidazol-2-yl]ethyl]-2-[(3-methyl-2-oxo-butyl)amino]-4-[(2S)-2-methyl-1-piperidyl]-4-oxo-butanamide |
| | 514.58 | N-[(1S)-1-[[(1S)-1-(1H-benzimidazol-2-yl)ethyl]carbamoyl]-3-oxo-3-[(2S)-2-phenylpyrrolidin-1-yl]propyl]-5-methyl-isoxazole-3-carboxamide |
| | 503.64 | N-[(1S)-1-[1-(1H-benzimidazol-2-yl)ethylcarbamoyl]-3-oxo-3-[(2S)-2-phenylpyrrolidin-1-yl]propyl]-4-methyl-pentanamide |
| | 539.69 | (2S)-N-[1-(1H-benzimidazol-2-yl)ethyl]-2-(isopentylsulfonylamino)-4-oxo-4-[(2S)-2-phenylpyrrolidin-1-yl]butanamide |

TABLE 1-continued

| Formula | Molecular Weight | Structure IUPAC Name |
|---|---|---|
| | 501.62 | N-[(1S)-1-[1-(1H-benzimidazol-2-yl)ethylcarbamoyl]-3-oxo-3-[(2S)-2-phenylpyrrolidin-1-yl]propyl]-3-methyl-cyclobutanecarboxamide |
| | 517.66 | N-[(1S)-1-[[(1S)-1-(1H-benzimidazol-2-yl)ethyl]carbamoyl]-3-oxo-3-[(2S)-2-phenylpyrrolidin-1-yl]propyl]-4,4-dimethyl-pentanamide |
| | 553.66 | (2S)-N-[(1S)-1-[5-(2,4-difluorophenyl)-1H-imidazol-2-yl]ethyl]-2-(isopentylsulfonylamino)-4-[(2S)-2-methyl-1-piperidyl]-4-oxo-butanamide |
| | 531.64 | N-[(1S)-1-[[(1S)-1-[5-(2,4-difluorophenyl)-1H-imidazol-2-yl]ethyl]carbamoyl]-3-[(2S)-2-methyl-1-piperidyl]-3-oxo-propyl]-4,4-dimethyl-pentanamide |
| | 489.56 | N-[(1S)-1-[[(1S)-1-[5-(2,4-difluorophenyl)-1H-imidazol-2-yl]ethyl]carbamoyl]-3-oxo-3-pyrrolidin-1-yl-propyl]-4-methyl-pentanamide |

TABLE 1-continued

| Formula | Molecular Weight | Structure IUPAC Name |
|---|---|---|
| 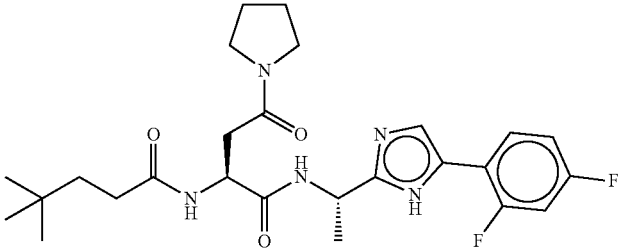 | 503.58 | N-[(1S)-1-[[(1S)-1-[5-(2,4-difluorophenyl)-1H-imidazol-2-yl]ethyl]carbamoyl]-3-oxo-3-pyrrolidin-1-yl-propyl]-4,4-dimethyl-pentanamide |
| 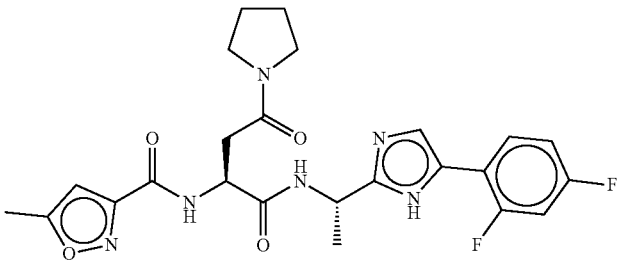 | 500.5 | N-[(1S)-1-[[(1S)-1-[5-(2,4-difluorophenyl)-1H-imidazol-2-yl]ethyl]carbamoyl]-3-oxo-3-pyrrolidin-1-yl-propyl]-5-methyl-isoxazole-3-carboxamide |
| 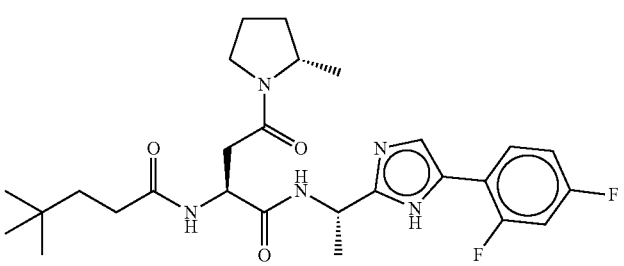 | 517.61 | N-[(1S)-1-[[(1S)-1-[5-(2,4-difluorophenyl)-1H-imidazol-2-yl]ethyl]carbamoyl]-3-[(2R)-2-methylpyrrolidin-1-yl]-3-oxo-propyl]-4,4-dimethyl-pentanamide |
| 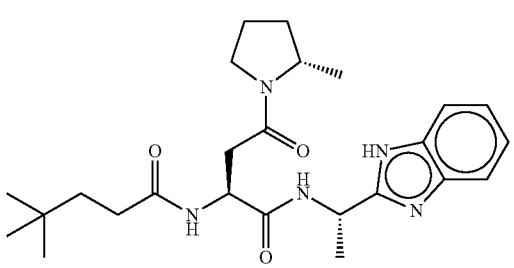 | 455.59 | N-[(1S)-1-[[(1S)-1-(1H-benzimidazol-2-yl)ethyl]carbamoyl]-3-[(2R)-2-methylpyrrolidin-1-yl]-3-oxo-propyl]-4,4-dimethyl-pentanamide |
| 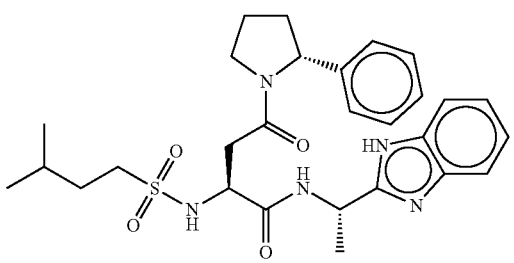 | 539.70 | (2S)-N-[(1S)-1-(1H-benzimidazol-2-yl)ethyl]-2-(isopentylsulfonylamino)-4-oxo-4-[(2R)-2-phenylpyrrolidin-1-yl]butanamide |
| 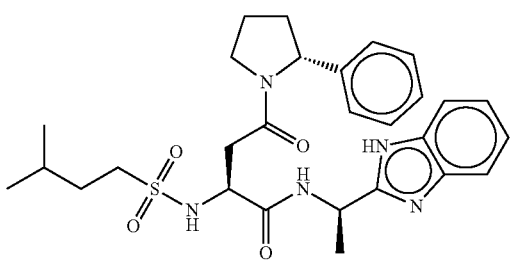 | 539.70 | (2S)-N-[(1R)-1-(1H-benzimidazol-2-yl)ethyl]-2-(isopentylsulfonylamino)-4-oxo-4-[(2R)-2-phenylpyrrolidin-1-yl]butanamide |

TABLE 1-continued

| Formula | Molecular Weight | Structure IUPAC Name |
|---|---|---|
| | 474.55 | N-[(1S)-2-[(2,4-difluorophenyl)methylamino]-1-methyl-2-oxo-ethyl]-2-(isopentylamino)-6-pyrrolidin-1-yl-pyrimidine-4-carboxamide |
| | 511.57 | tert-butyl 2-(((S)-1-((2,4-difluorobenzyl)amino)-1-oxopropan-2-yl)carbamoyl)-2-(2-((S)-2-methylpiperidin-1-yl)-2-oxoethyl)hydrazine-1-carboxylate |
| | 523.63 | (2S)-N-[(2,4-difluorophenyl)methyl]-2-[[(4,4-dimethylpentanoylamino)-[2-[(2S)-2-methyl-1-piperidyl]-2-oxoethyl]carbamoyl]amino]propanamide |
| | 532.63 | 3-[(1S)-1-[5-(2,4-difluorophenyl)-1H-imidazol-2-yl]ethyl]-1-(4,4-dimethylpentanoylamino)-1-[2-[(2S)-2-methyl-1-piperidyl]-2-oxo-ethyl]urea |
| | 469.62 | N-[(1S)-1-[[(1R)-1-(1H-benzimidazol-2-yl)ethyl]carbamoyl]-3-[(2S)-2-methyl-1-piperidyl]-3-oxo-propyl]-4,4-dimethyl-pentanamide |

TABLE 1-continued

| Formula | Molecular Weight | Structure IUPAC Name |
|---|---|---|
| | 455.59 | N-[(1S)-1-(1H-benzimidazol-2-ylmethylcarbamoyl)-3-[(2S)-2-methyl-1-piperidyl]-3-oxo-propyl]-4,4-dimethyl-pentanamide |
| | 455.59 | N-[(1S)-1-[[(1R)-1-(1H-benzimidazol-2-yl)ethyl]carbamoyl]-3-[(2S)-2-methyl-1-piperidyl]-3-oxo-propyl]-4-methyl-pentanamide |
| | 441.57 | N-[(1S)-1-(1H-benzimidazol-2-ylmethylcarbamoyl)-3-[(2S)-2-methyl-1-piperidyl]-3-oxo-propyl]-4-methyl-pentanamide |
| | 491.57 | (2S)-N-[(1S)-1-[5-(2,4-difluorophenyl)-1H-imidazol-2-yl]ethyl]-N',N'-diethyl-2-(4-methylpentanoylamino)butanediamide |
| | 503.58 | N-[(1S)-1-[[(1S)-1-[5-(2,4-difluorophenyl)-1H-imidazol-2-yl]ethyl]carbamoyl]-3-oxo-3-(1-piperidyl)propyl]-4-methyl-pentanamide |

TABLE 1-continued

| Formula | Molecular Weight | Structure IUPAC Name |
|---|---|---|
| | 517.61 | N-[(1S)-1-[[(1S)-1-[5-(2,4-difluorophenyl)-1H-imidazol-2-yl]ethyl]carbamoyl]-3-[(2R)-2-methyl-1-piperidyl]-3-oxo-propyl]-4-methyl-pentanamide |
| | 491.57 | (2S)-N-[(1S)-1-[5-(2,4-difluorophenyl)-1H-imidazol-2-yl]ethyl]-N'-isopropyl-N'-methyl-2-(4-methylpentanoylamino)butanediamide |
| | 515.6 | (2S)-2-(3-cyclopropylpropanoylamino)-N-[(1S)-1-[5-(2,4-difluorophenyl)-1H-imidazol-2-yl]ethyl]-4-[(2S)-2-methyl-1-piperidyl]-4-oxo-butanamide |
| | 551.65 | (2S)-2-(2-cyclopropylethylsulfonylamino)-N-[(1S)-1-[5-(2,4-difluorophenyl)-1H-imidazol-2-yl]ethyl]-4-[(2S)-2-methyl-1-piperidyl]-4-oxo-butanamide |
| | 519.58 | N-[(1S)-1-[[(1S)-1-[5-(2,4-difluorophenyl)-1H-imidazol-2-yl]ethyl]carbamoyl]-3-[(3S)-3-methylmorpholin-4-yl]-3-oxo-propyl]-4-methyl-pentanamide |

TABLE 1-continued

| Formula | Molecular Weight | Structure IUPAC Name |
|---|---|---|
| | 571.58 | N-[(1S)-1-[[(1S)-1-[5-(2,4-difluorophenyl)-1H-imidazol-2-yl]ethyl]carbamoyl]-3-oxo-3-[(2R)-2-(trifluoromethyl)-1-piperidyl]propyl]-4-methyl-pentanamide |
| | 531.64 | N-[(1S)-1-[[(1S)-1-[5-(2,4-difluorophenyl)-1H-imidazol-2-yl]ethyl]carbamoyl]-3-[(2S)-2-ethyl-1-piperidyl]-3-oxo-propyl]-4-methyl-pentanamide |
| | 517.61 | N-[(1S)-3-(azepan-1-yl)-1-[[(1S)-1-[5-(2,4-difluorophenyl)-1H-imidazol-2-yl]ethyl]carbamoyl]-3-oxo-propyl]-4-methyl-pentanamide |
| | 469.62 | N-[(1S)-1-[[(1S)-1-(1H-benzimidazol-2-yl)ethyl]carbamoyl]-3-[(2S)-2-ethyl-1-piperidyl]-3-oxo-propyl]-4-methyl-pentanamide |
| | 483.65 | N-[(1S)-1-[[(1S)-1-(1H-benzimidazol-2-yl)ethyl]carbamoyl]-3-[(2S)-2-ethyl-1-piperidyl]-3-oxo-propyl]-4,4-dimethyl-pentanamide |

TABLE 1-continued

| Formula | Molecular Weight | Structure IUPAC Name |
|---|---|---|
| | 545.66 | N-[(1S)-1-[[(1S)-1-[5-(2,4-difluorophenyl)-1H-imidazol-2-yl]ethyl]carbamoyl]-3-(2-isopropyl-1-piperidyl)-3-oxo-propyl]-4-methyl-pentanamide |
| | 505.6 | N-[(1S)-1-[[(1S)-1-(4,6-difluoro-1H-benzimidazol-2-yl)ethyl]carbamoyl]-3-[(2S)-2-ethyl-1-piperidyl]-3-oxo-propyl]-4-methyl-pentanamide |
| | 501.64 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]-4,4-dimethyl-pentanamide |
| | 487.61 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]-4-methyl-pentanamide |
| | 473.58 | N-[(1S)-1-[[(1S)-1-(4-fluoro-1H-benzimidazol-2-yl)ethyl]carbamoyl]-3-[(2S)-2-methyl-1-piperidyl]-3-oxo-propyl]-4-methyl-pentanamide |

TABLE 1-continued

| Formula | Molecular Weight | Structure IUPAC Name |
|---|---|---|
| | 487.61 | N-[(1S)-1-[[(1S)-1-(4-fluoro-1H-benzimidazol-2-yl)ethyl]carbamoyl]-3-[(2S)-2-methyl-1-piperidyl]-3-oxo-propyl]-4,4-dimethyl-pentanamide |
| | 523.66 | (2S)-4-[(2S)-2-ethyl-1-piperidyl]-N-[(1S)-1-(4-fluoro-1H-benzimidazol-2-yl)ethyl]-2-(isopentylsulfonylamino)-4-oxo-butanamide |
| | 505.6 | N-[(1S)-1-[[(1S)-1-(5,6-difluoro-1H-benzimidazol-2-yl)ethyl]carbamoyl]-3-[(2S)-2-ethyl-1-piperidyl]-3-oxo-propyl]-4-methyl-pentanamide |
| | 498.55 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]-5-methyl-isoxazole-3-carboxamide |
| | 522.61 | (2S)-2-(benzylcarbamoylamino)-4-[(2S)-2-ethyl-1-piperidyl]-N-[(1S)-1-(4-fluoro-1H-benzimidazol-2-yl)ethyl]-4-oxo-butanamide |

TABLE 1-continued

| Formula | Molecular Weight | Structure IUPAC Name |
|---|---|---|
| | 521.63 | (2S)-4-[(2S)-2-ethyl-1-piperidyl]-N-[(1S)-1-(4-fluoro-1H-benzimidazol-2-yl)ethyl]-4-oxo-2-(3-phenylpropanoylamino) butanamide |
| | 571.7 | N-[(1S)-1-[[(1R,2R)-2-[5-(2,4-difluorophenyl)-1H-imidazol-2-yl]cyclopentyl]carbamoyl]-3-[(2S)-2-ethyl-1-piperidyl]-3-oxo-propyl]-4-methyl-pentanamide |
| | 517.62 | (2S)-N-[(1S)-2-(1H-indol-7-ylmethylamino)-1-methyl-2-oxo-ethyl]-4-oxo-2-(3-phenylpropanoylamino)-4-pyrrolidin-1-yl-butanamide |
| | 471.57 | (2S)-2-[(2-cyclopropylacetyl)amino]-4-[(2S)-2-ethyl-1-piperidyl]-N-[(1S)-1-(4-fluoro-1H-benzimidazol-2-yl)ethyl]-4-oxo-butanamide |
| | 499.5 | (2S)-4-[(2S)-2-ethyl-1-piperidyl]-N-[(1S)-1-(4-fluoro-1H-benzimidazol-2-yl)ethyl]-4-oxo-2-(3,3,3-trifluoropropanoylamino) butanamide |

TABLE 1-continued

| Formula | Molecular Weight | Structure IUPAC Name |
|---|---|---|
| | 506.57 | (2S)-2-(1,3-benzoxazol-2-ylamino)-4-[(2S)-2-ethyl-1-piperidyl]-N-[(1S)-1-(4-fluoro-1H-benzimidazol-2-yl)ethyl]-4-oxo-butanamide |
| | 488.6 | (2S)-2-[3-(dimethylamino)propanoylamino]-4-[(2S)-2-ethyl-1-piperidyl]-N-[(1S)-1-(4-fluoro-1H-benzimidazol-2-yl)ethyl]-4-oxo-butanamide |
| | 520.6 | (2S)-4-[(2S)-2-ethyl-1-piperidyl]-N-[(1S)-1-(4-fluoro-1H-benzimidazol-2-yl)ethyl]-2-[(5-methyl-1,3-benzoxazol-2-yl)amino]-4-oxo-butanamide |
| | 520.6 | (2S)-4-[(2S)-2-ethyl-1-piperidyl]-N-[(1S)-1-(4-fluoro-1H-benzimidazol-2-yl)ethyl]-2-[(6-methyl-1,3-benzoxazol-2-yl)amino]-4-oxo-butanamide |
| | 533.65 | (1S,2S)-N-((S)-4-((S)-2-ethylpiperidin-1-yl)-1-(((S)-1-(4-fluoro-1H-benzo[d]imidazol-2-yl)ethyl)amino)-1,4-dioxobutan-2-yl)-2-phenylcyclopropane-1-carboxamide |

TABLE 1-continued

| Formula | Molecular Weight | Structure IUPAC Name |
|---|---|---|
| 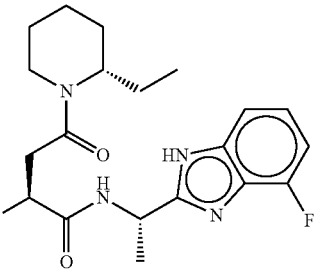 | 499.62 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]-2-isopropyl-cyclopropanecarboxamide |
| 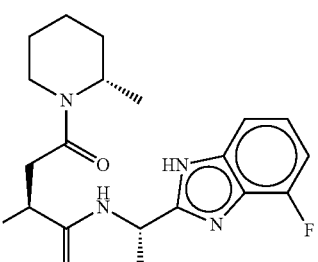 | 485.59 | N-[(1S)-1-[[(1S)-1-(4-fluoro-1H-benzimidazol-2-yl)ethyl]carbamoyl]-3-[(2S)-2-methyl-1-piperidyl]-3-oxo-propyl]-2-isopropyl-cyclopropanecarboxamide |
| 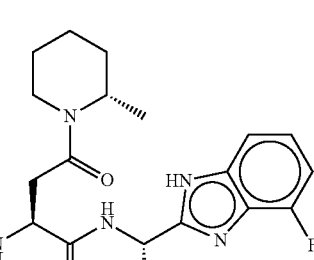 | 519.62 | (1S,2S)-N-((S)-1-(((S)-1-(4-fluoro-1H-benzo[d]imidazol-2-yl)ethyl)amino)-4-((S)-2-methylpiperidin-1-yl)-1,4-dioxobutan-2-yl)-2-phenylcyclopropane-1-carboxamide |
| 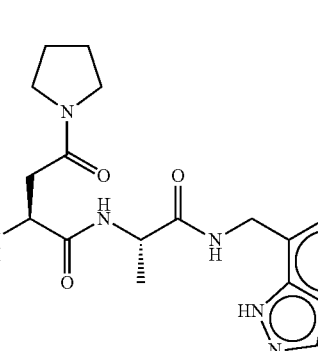 | 518.61 | (2S)-N-[(1S)-2-(1H-indazol-7-ylmethylamino)-1-methyl-2-oxo-ethyl]-4-oxo-2-(3-phenylpropanoylamino)-4-pyrrolidin-1-yl-butanamide |
| 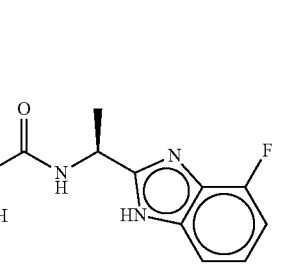 | 499.58 | (2S)-4-[(2S)-2-ethyl-1-piperidyl]-N-[(1S)-1-(4-fluoro-1H-benzimidazol-2-yl)ethyl]-2-[(3-isopropyl-1,2,4-oxadiazol-5-yl)amino]-4-oxo-butanamide |

TABLE 1-continued

| Formula | Molecular Weight | Structure IUPAC Name |
|---|---|---|
| 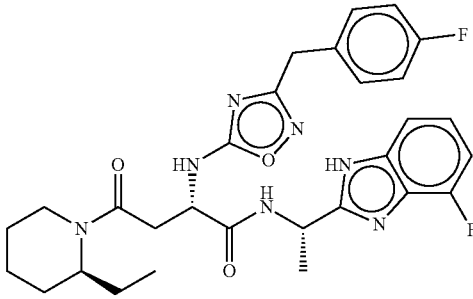 | 565.61 | (2S)-4-[(2S)-2-ethyl-1-piperidyl]-N-[(1S)-1-(4-fluoro-1H-benzimidazol-2-yl)ethyl]-2-[[3-[(4-fluorophenyl)methyl]-1,2,4-oxadiazol-5-yl]amino]-4-oxo-butanamide |
| 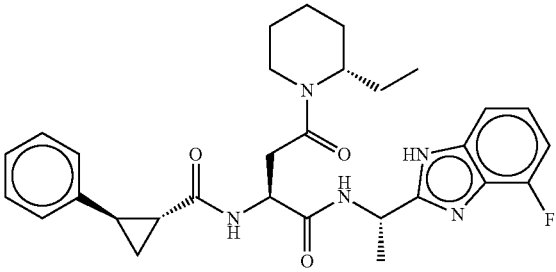 | 533.64 | (1S,2R)-N-[(1S)-3-[(2S)-2-ethyl-1-piperidyl]-1-[[(1S)-1-(4-fluoro-1H-benzimidazol-2-yl)ethyl]carbamoyl]-3-oxo-propyl]-2-phenyl-cyclopropanecarboxamide |
| 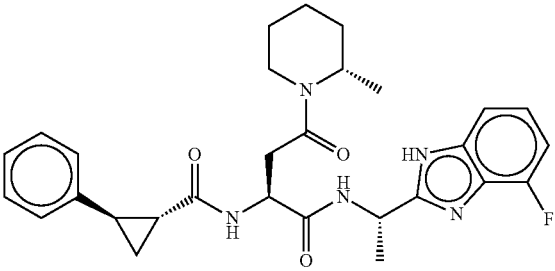 | 519.61 | (1S,2R)-N-[(1S)-1-[[(1S)-1-(4-fluoro-1H-benzimidazol-2-yl)ethyl]carbamoyl]-3-[(2S)-2-methyl-1-piperidyl]-3-oxo-propyl]-2-phenyl-cyclopropanecarboxamide |
| 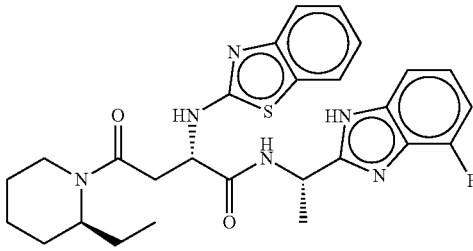 | 522.64 | (2S)-2-(1,3-benzothiazol-2-ylamino)-4-[(2S)-2-ethyl-1-piperidyl]-N-[(1S)-1-(4-fluoro-1H-benzimidazol-2-yl)ethyl]-4-oxo-butanamide |
| 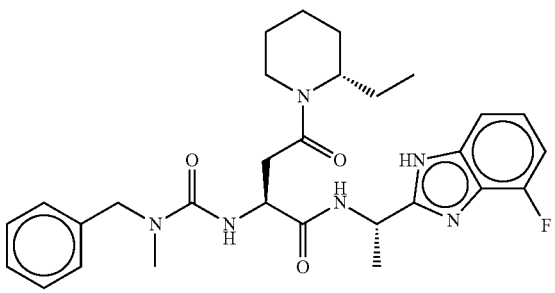 | 536.64 | (2S)-2-[[benzyl(methyl)carbamoyl]amino]-4-[(2S)-2-ethyl-1-piperidyl]-N-[(1S)-1-(4-fluoro-1H-benzimidazol-2-yl)ethyl]-4-oxo-butanamide |

TABLE 1-continued

| Formula | Molecular Weight | Structure IUPAC Name |
|---|---|---|
| 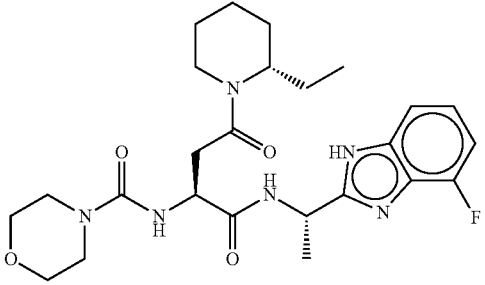 | 502.58 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]morpholine-4-carboxamide |
| 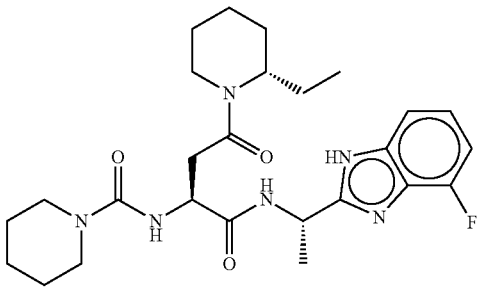 | 500.61 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]piperidine-1-carboxamide |
| 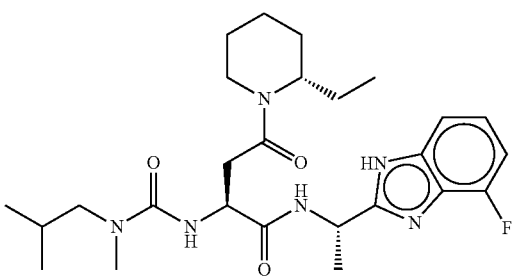 | 502.62 | (2S)-4-[(2S)-2-ethyl-1-piperidyl]-N-[(1S)-1-(4-fluoro-1H-benzimidazol-2-yl)ethyl]-2-[[isobutyl(methyl)carbamoyl]amino]-4-oxo-butanamide |
| 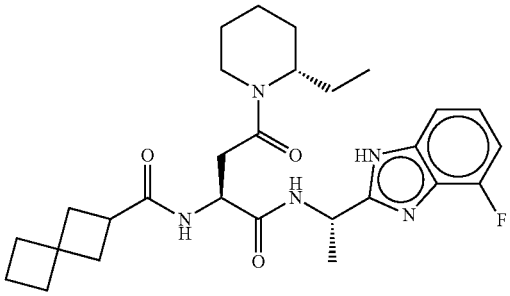 | 511.63 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]spiro[3.3]heptane-2-carboxamide |
| 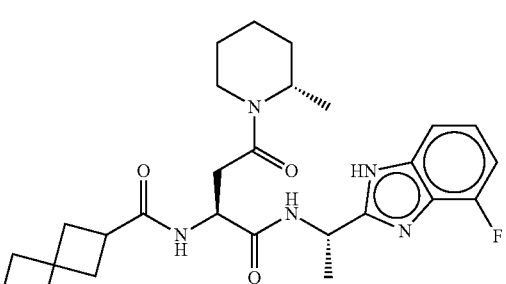 | 497.6 | N-[(1S)-1-[[(1S)-1-(4-fluoro-1H-benzimidazol-2-yl)ethyl]carbamoyl]-3-[(2S)-2-methyl-1-piperidyl]-3-oxo-propyl]spiro[3.3]heptane-2-carboxamide |

TABLE 1-continued

| Formula | Molecular Weight | Structure IUPAC Name |
|---|---|---|
| | 522.61 | (2S)-2-[[benzyl(methyl)carbamoyl]amino]-N-[(1S)-1-(4-fluoro-1H-benzimidazol-2-yl)ethyl]-4-[(2S)-2-methyl-1-piperidyl]-4-oxo-butanamide |
| | 523.6 | benzyl N-[(1S)-3-[(2S)-2-ethyl-1-piperidyl]-1-[[(1S)-1-(4-fluoro-1H-benzimidazol-2-yl)ethyl]carbamoyl]-3-oxo-propyl]carbamate |
| | 509.57 | benzyl N-[(1S)-1-[[(1S)-1-(4-fluoro-1H-benzimidazol-2-yl)ethyl]carbamoyl]-3-[(2S)-2-methyl-1-piperidyl]-3-oxo-propyl]carbamate |
| | 489.58 | isobutyl N-[(1S)-3-[(2S)-2-ethyl-1-piperidyl]-1-[[(1S)-1-(4-fluoro-1H-benzimidazol-2-yl)ethyl]carbamoyl]-3-oxo-propyl]carbamate |
| | 499.62 | N-[(1S)-3-[(2S)-2-ethyl-1-piperidyl]-1-[[(1S)-1-(4-fluoro-1H-benzimidazol-2-yl)ethyl]carbamoyl]-3-oxo-propyl]-3,3-dimethyl-cyclobutanecarboxamide |

TABLE 1-continued

| Formula | Molecular Weight | Structure IUPAC Name |
|---|---|---|
| | 485.59 | N-[(1S)-1-[[(1S)-1-(4-fluoro-1H-benzimidazol-2-yl)ethyl]carbamoyl]-3-[(2S)-2-methyl-1-piperidyl]-3-oxo-propyl]-3,3-dimethyl-cyclobutanecarboxamide |
| | 529.62 | N-[(1S)-1-[[(1S)-1-[5-(2,4-difluorophenyl)-1H-imidazol-2-yl]ethyl]carbamoyl]-3-[(2S)-2-methyl-1-piperidyl]-3-oxo-propyl]-3,3-dimethyl-cyclobutanecarboxamide |
| | 529.62 | N-[(1S)-1-[[(1S)-1-[5-(2,4-difluorophenyl)-1H-imidazol-2-yl]ethyl]carbamoyl]-3-[(2S)-2-methyl-1-piperidyl]-3-oxo-propyl]-2-isopropyl-cyclopropanecarboxamide |
| | 536.57 | (2S)-2-(1,3-benzoxazol-2-ylamino)-N-[(1S)-1-[5-(2,4-difluorophenyl)-1H-imidazol-2-yl]ethyl]-4-[(2S)-2-methyl-1-piperidyl]-4-oxo-butanamide |
| | 529.58 | (2S)-N-[(1S)-1-[5-(2,4-difluorophenyl)-1H-imidazol-2-yl]ethyl]-2-[(3-isopropyl-1,2,4-oxadiazol-5-yl)amino]-4-[(2S)-2-methyl-1-piperidyl]-4-oxo-butanamide |

Example 144—IC$_{50}$ Determination

Experiments to determine IC$_{50}$ values against β5i and β5c for compounds were carried out in 96-well plates. In brief, 1 μL of compound in a 3× series dilution in DMSO at concentration ranging from 100 μM-0.0017 μM were spotted to the bottom of a black 96-well plate with solid bottom. 100 μL of reaction buffer (20 mM HEPES, 0.5 mM EDTA, pH7.5, 0.1% BSA) containing enzyme (final concentration was 0.2 nM for c-20S, and 0.4 nM for i-20S) and substrate (25 μM for suc-LLVY-AMC for 135c and 15 μM for Ac-ANW-AMC) were dispensed into each well, and the plate was then spun at 1000× rpm for 1 minute and then shaked on a shaker for 1 minute. Time course of the hydrolysis of each well was followed by recording the fluorescence of product AMC (Ex 360 nm and Em 460 nm) on a SpectraMax M5 plate reader for 1.5-2 hours. Initial reaction velocity of each well was fit to a dose-dependent inhibition equation using PRISM to determine the IC$_{50}$. IC$_{50}$s were determined only for 135i and 135c (Table 2). SDS was used as activator for both enzymes at concentration 0.02%.

TABLE 2

IC$_{50}$ values

| Formula | ID | Hu c-20S IC50 (μM) | Mtb20SOG IC50 (μM) | Selectivity |
|---|---|---|---|---|
|  | CF-503094 | 12<br>11 | 0.471<br>0.726 | 25<br>15 |
|  | CF-503102 | 14<br>10 | 0.717<br>0.44 | 20<br>23 |
|  | CF-503103 | >15<br>>15 | 0.16<br>0.306 | >90<br>>49 |
|  | CF-503105 | >18<br>19 | 0.259<br>0.256 | >69<br>74 |

TABLE 2-continued
IC$_{50}$ values
| Formula | ID | Hu c-20S IC50 (μM) | Mtb20SO G IC50 (μM) | Selectivity |
|---|---|---|---|---|
| 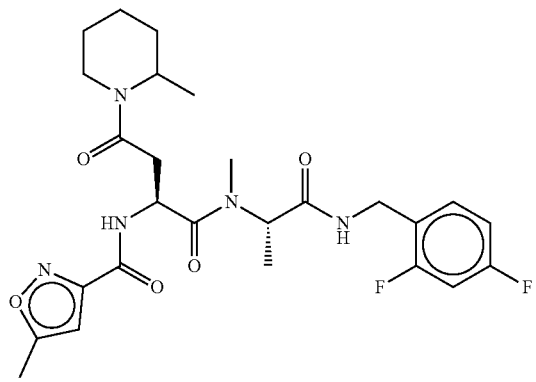 | Not Registered | 19 | 10 | 1.9 |
| 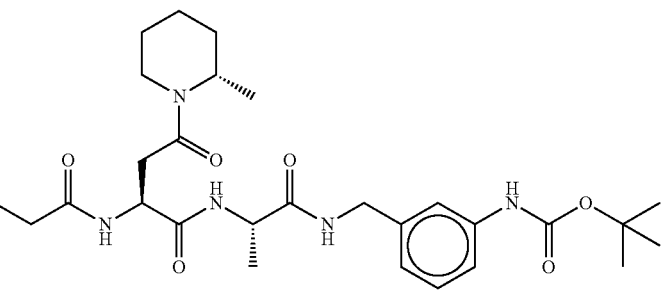 | Not Registered | 50.2 | 24.7 | 2 |
| 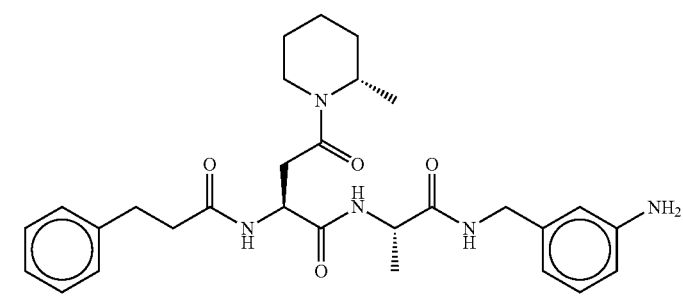 | Not Registered | 0.69 | 0.005 | 138 |
| 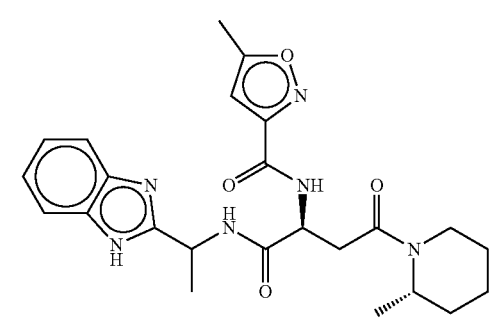 | Not Registered | 71.6<br>19.6 | 0.549<br>0.331 | 130<br>59 |

TABLE 2-continued
IC₅₀ values
| Formula | ID | Hu c-20S IC50 (μM) | Mtb20SOG IC50 (μM) | Selectivity |
|---|---|---|---|---|
| 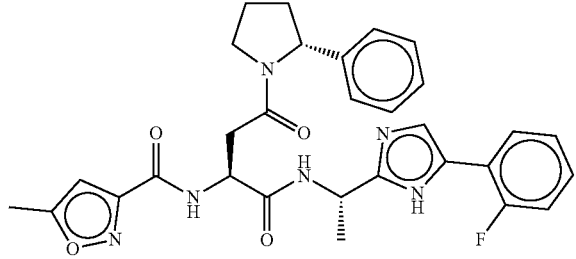 | CF-503108 | 100<br>0.07<br>13.3 | 0.013<br>0.004<br>0.013 | 7692<br>17<br>1023 |
| 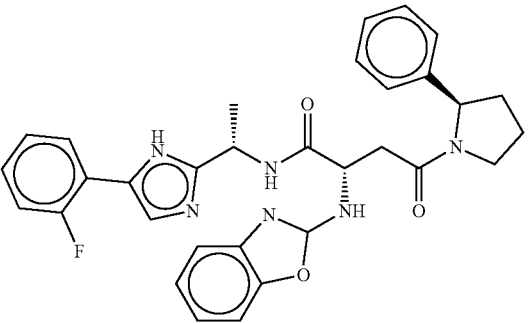 | CF-503242 | 16.8<br>20.6 | 0.753<br>0.677 | 22<br>30 |
| 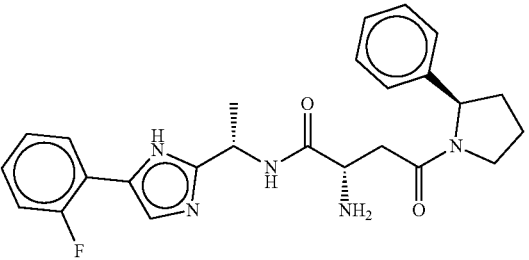 | CF-503240 | 94 | 8.5 | 11 |
| 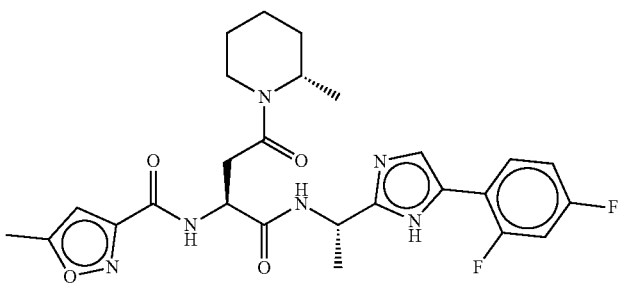 | CF-503111 | 7.2<br>5.48 | 0.041<br>0.034 | 175<br>161 |

TABLE 2-continued

| | | IC$_{50}$ values | | |
|---|---|---|---|---|
| Formula | ID | Hu c-20S IC50 (μM) | Mtb20SOG IC50 (μM) | Selectivity |
| | CF-503127 | 7 | 0.084 0.1 | 70 |
| | CF-503133 | 5.59 7.08 | 0.266 0.231 | 21 30 |
| | CF-503134 | 7.4 7.6 | 0.09 0.057 | 82 133 |
| | CF-503135 | 9.12 13.5 | 0.45 0.386 | 20 35 |

TABLE 2-continued
IC$_{50}$ values
| Formula | ID | Hu c-20S IC50 (μM) | Mtb20SO G IC50 (μM) | Selectivity |
|---|---|---|---|---|
| 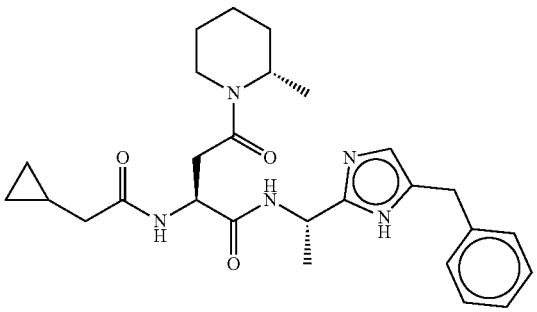 | CF-503136 | 10.4 | 0.925 | 11 |
| 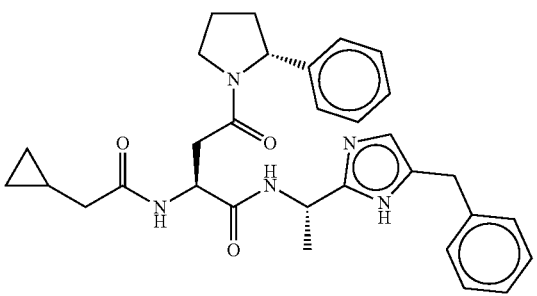 | CF-503137 | 12.6<br>10.6 | 0.078<br>0.064 | 161<br>165 |
| 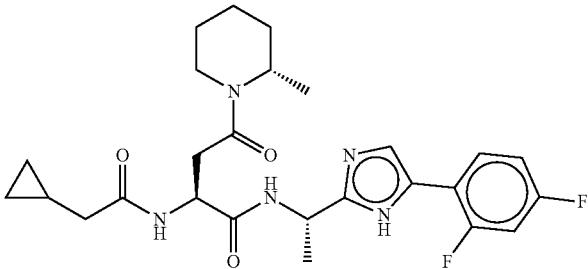 | CF-503138 | 11.8<br>10.5 | 0.169<br>0.085 | 70<br>123 |
| 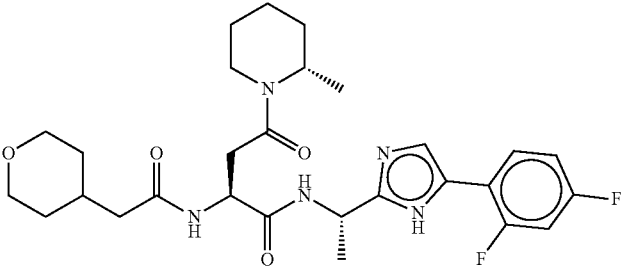 | CF-503139 | 12.8<br>10.26 | 0.089<br>0.148 | 144<br>69 |
| 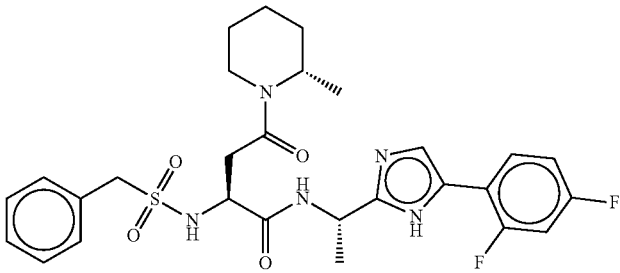 | CF-503140 | 6.13 | 0.379 | 16 |

TABLE 2-continued

IC$_{50}$ values

| Formula | ID | Hu c-20S IC50 (μM) | Mtb20SOG IC50 (μM) | Selectivity |
|---|---|---|---|---|
| | CF-503141 | 4.9 | 0.368 | 13 |
| | CF-503142 | 8.13 | 0.65 | 12 |
| | CF-503143 | 6.47 | 0.494 | 13 |
| | CF-503144 | 28.2 | 1.904 | 15 |
| | CF-503145 | 15.2 | 10 | 1.5 |

TABLE 2-continued

| Formula | ID | Hu c-20S IC50 (μM) | Mtb20SOG IC50 (μM) | Selectivity |
|---|---|---|---|---|
| | CF-503146 | 2.41 | 0.163 | 15 |
| | CF-503147 | 6.36 | 0.049 | 130 |
| | | 9.66 | 0.053 | 182 |
| | | 10.7 | 0.037 | 289 |
| | | 15.1 | 0.032 | 471 |
| | | . | . | . |
| | | . | . | . |
| | | . | . | . |
| | | 8.73 | 0.045 | 194 |
| | CF-503148 | 17.45 | 0.906 | 19 |
| | CF-503149 | 18.95 | 0.136 | 139 |
| | | 23.5 | 0.118 | 199 |
| | CF-503150 | 16.77 | 0.047 | 357 |
| | | 13.7 | 0.045 | 304 |
| | | 53.1 | 0.05 | 1062 |
| | | 9.3 | 0.069 | 134 |
| | | 10.6 | 0.059 | 179 |
| | | 50 | 0.042 | 1190 |

TABLE 2-continued

| | | IC50 values | | |
|---|---|---|---|---|
| Formula | ID | Hu c-20S IC50 (μM) | Mtb20SOG IC50 (μM) | Selectivity |
| | CF-503185 proposed enantiomer of CF-503150 | 8.96 50 | 0.636 0.42 | 14 119 |
| | CF-503151 | 9.9 | 11.4 | 0.9 |
| | CF-503152 | 10.97 9.7 | 0.184 0.127 | 60 76 |
| | CF-503153 | 29.4 19.78 | 0.029 0.053 | 1013 373 |
| | CF-503154 | 13.9 11.8 | 0.116 0.202 | 119 58 |

TABLE 2-continued

IC₅₀ values

| Formula | ID | Hu c-20S IC50 (μM) | Mtb20SOG IC50 (μM) | Selectivity |
|---|---|---|---|---|
| | CF-503155 | 8.4 | 0.125 | 67 |
| | CF-503156 | 16.6 | 0.088 | 188 |
| | CF-503157 | 7.5<br>9.66 | 1.066<br>0.691 | 7<br>14 |
| | CF-503158 | 5.3<br>8.5 | 0.027<br>0.022 | 196<br>386 |
| | CF-503159 | 10.4 | 3.47 | 3 |

TABLE 2-continued

| | | Hu c-20S IC50 (μM) | Mtb20SOG IC50 (μM) | |
|---|---|---|---|---|
| Formula | ID | | | Selectivity |
| (structure) | CF-503160 | 10.3 | 0.796 | 13 |
| (structure) | CF-503161 | 16.7 | 3.34 | 5 |
| (structure) | CF-503162 | 6.3<br>5.7 | 0.173<br>0.128 | 36<br>44 |
| (structure) | CF-503163 | 16.49 | 3.5 | 5 |
| (structure) | CF-503183 | 10.14<br>9.7<br>10 | 0.224<br>0.242<br>0.124 | 45<br>40<br>80 |

TABLE 2-continued
| Formula | ID | Hu c-20S IC50 (μM) | Mtb20SOG IC50 (μM) | Selectivity |
|---|---|---|---|---|
| 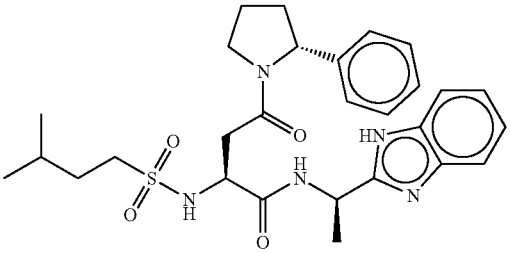 | CF-503184 | 10.7 | 2.6 | 4 |
| 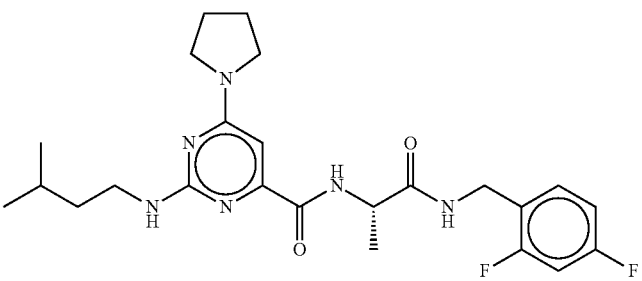 | CF-503175 | 4.59<br>5.46 | 4.6<br>5.6 | 1<br>1 |
| 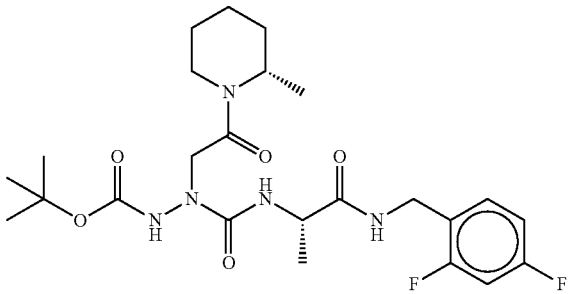 | CF-503201 | 8.5<br>>8 | 8.4<br>>8 | 1<br>1 |
| 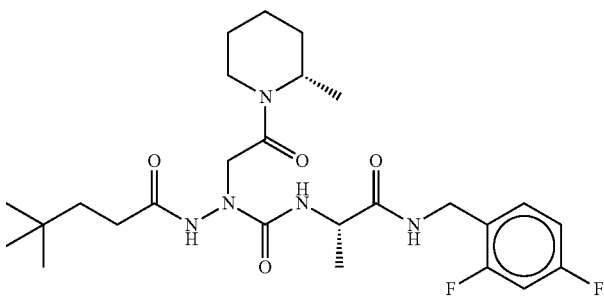 | CF-503202 | 8.5<br>9.12 | 8.32<br>8.8 | 1<br>1 |
| 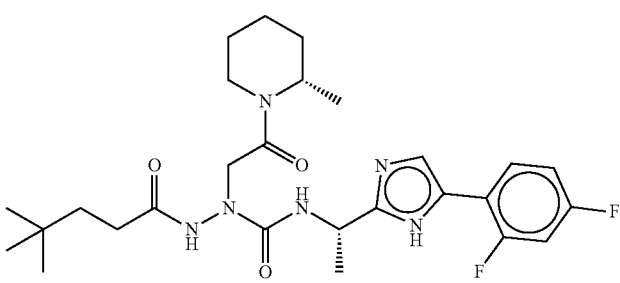 | CF-503189 | 7.61<br>10.24 | 7.38<br>8.04 | 1<br>1.3 |

TABLE 2-continued
| Formula | ID | Hu c-20S IC50 (μM) | Mtb20SOG IC50 (μM) | Selectivity |
|---|---|---|---|---|
| 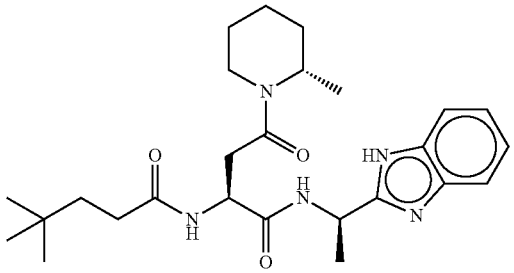 | CF-503190 | 17.32 | 2.66 | 7 |
| 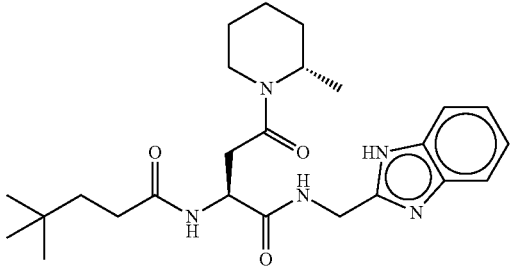 | CF-503191 | 10.35 | 0.456 | 23 |
| 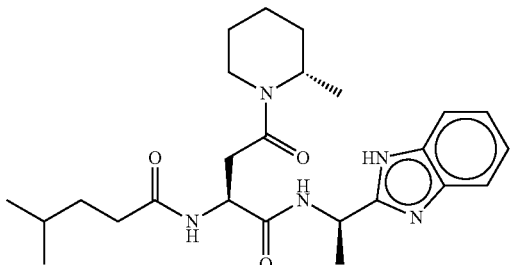 | CF-503192 | 15.56 | 4.9 | 3 |
| 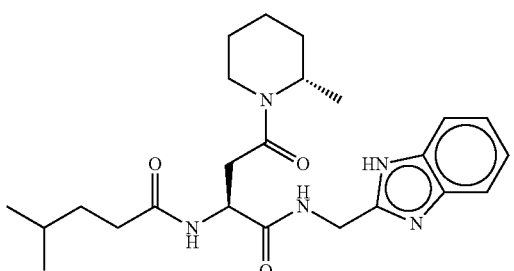 | CF-503193 | 17.6 | 0.647 | 27 |
| 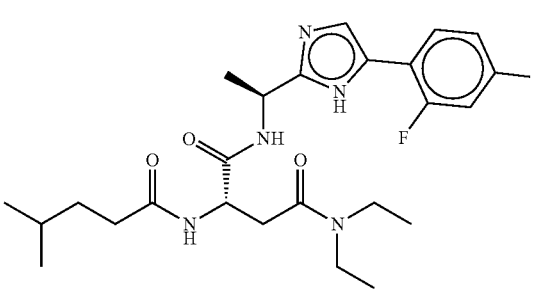 | CF-503197 | 7.28 | 1.11 | 7 |

TABLE 2-continued
| Formula | ID | Hu c-20S IC50 (μM) | Mtb20SOG IC50 (μM) | Selectivity |
|---|---|---|---|---|
| 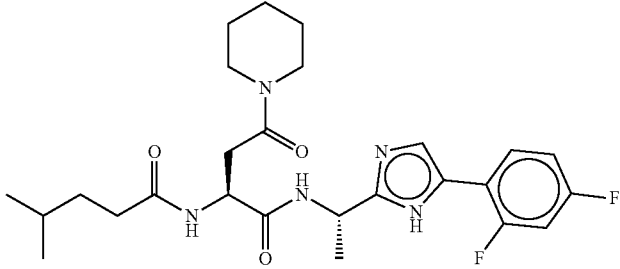 | CF-503198 | 7.25 | 1.57 | 5 |
| 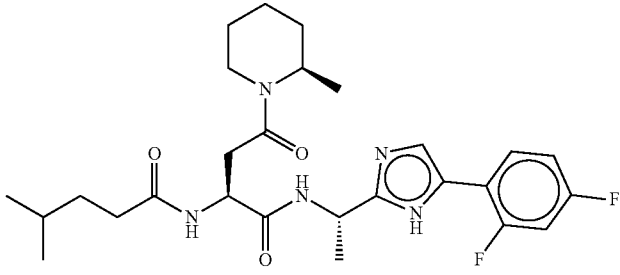 | CF-503199 | 10.47 | 1 | 10 |
| 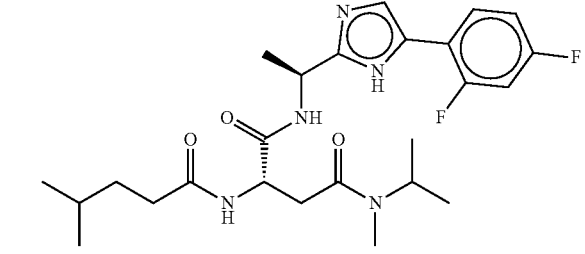 | CF-503200 | 14.87 | 0.919 | 16 |
| 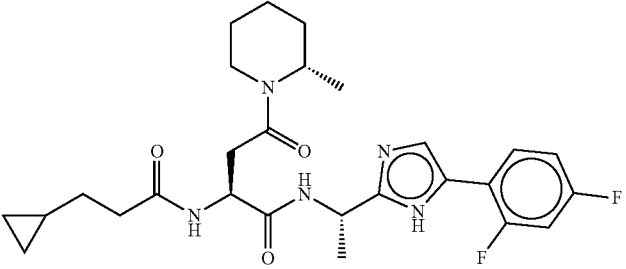 | CF-503204 | 11.65 | 0.098 | 119 |
| 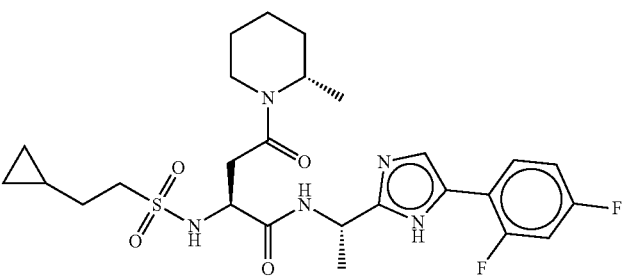 | CF-503206 | 6.16 | 0.506 | 12 |

TABLE 2-continued

IC₅₀ values

| Formula | ID | Hu c-20S IC50 (μM) | Mtb20SOG IC50 (μM) | Selectivity |
|---|---|---|---|---|
| | CF-503210 | 15.18 | 0.407 | 37 |
| | CF-503212 | 4.87 | 0.346 | 14 |
| | CF-503213 | 4.49 | 0.033 | 136 |
| | | 4.43 | 0.029 | 153 |
| | CF-503214 | 10.18 | 0.667 | 15 |
| | CF-503216 | 14.8 | 0.296 | 50 |
| | | 14.47 | 0.333 | 43 |

TABLE 2-continued

IC₅₀ values

| Formula | ID | Hu c-20S IC50 (μM) | Mtb20SOG IC50 (μM) | Selectivity |
|---|---|---|---|---|
| | CF-503217 | 6.85<br>8.99 | 0.127<br>0.835 | 54<br>11 |
| | CF-503218 | 2.78<br>3.18 | 0.136<br>0.168 | 20<br>19 |
| | CF-503219 | 4.06<br>4.5 | 0.793<br>0.84 | 5<br>5 |
| | CF-503222 | 11.24<br>12.33<br>11.7 | 0.015<br>0.029<br>0.041 | 749<br>425<br>285 |
| | CF-503223 | 10.62<br>10.18 | 0.028<br>0.033 | 379<br>308 |

TABLE 2-continued

IC$_{50}$ values

| Formula | ID | Hu c-20S IC50 (μM) | Mtb20SOG IC50 (μM) | Selectivity |
|---|---|---|---|---|
| (structure) | CF-503225 | 16.16<br>16.86 | 0.097<br>0.118 | 197<br>143 |
| (structure) | CF-503227 | 4.83<br>6.49 | 0.079<br>0.081 | 61<br>80 |
| (structure) | CF-503230 | 17.8<br>8.6 | 0.4<br>0.52 | 44<br>17 |
| (structure) | CF-503229 | 5 | 6 | 1 |
| (structure) | CF-503274 | 7.09 | 0.069 | 103 |

TABLE 2-continued

| | | Hu c-20S IC50 | Mtb20SO G IC50 | |
|---|---|---|---|---|
| Formula | ID | (μM) | (μM) | Selectivity |
| *(structure)* | CF-503304 | 9.36 | 0.359 | 26 |
| | | 9.4 | 0.327 | 29 |
| *(structure)* | CF-503291 | 2.64 | 0.007 | 377 |
| | | 3.39 | 0.006 | 565 |
| *(structure)* | CF-503292 | 4.95 | 0.657 | 7.5 |
| | | 9.23 | 4.6 | 2 |
| | | 8.19 | 0.522 | 16 |
| | | 8.6 | 0.561 | 15 |
| *(structure)* | CF-503293 | 4.06 | 0.095 | 43 |
| | | 11.58 | 2.21 | 5 |
| | | 19.08 | 0.047 | 406 |
| | | 36.7 | 0.035 | 1049 |

TABLE 2-continued

IC₅₀ values

| Formula | ID | Hu c-20S IC50 (μM) | Mtb20SOG IC50 (μM) | Selectivity |
|---|---|---|---|---|
| (structure) | CF-503318 | 16.9 | 0.112 | 150 |
| (structure) | CF-503319 | 4.2 | 0.32 | 13 |
| (structure) | CF-503321 | 4.5<br>5.2 | 0.271<br>0.374 | 17<br>14 |
| (structure) | CF-503356 | 6.4 | 6.4 | 1 |
| (structure) | CF-503357 | 1.9 | 0.26 | 7 |

TABLE 2-continued

| Formula | ID | Hu c-20S IC50 (μM) | Mtb20SO G IC50 (μM) | Selectivity |
|---|---|---|---|---|
| | CF-503360 | 1.12 | 0.125 | 9 |
| | | 1.43 | 0.19 | 7 |
| | | 1.42 | 0.353 | 4 |
| | | 1.44 | 0.361 | 4 |
| | | 8.14 | 0.051 | 160 |
| | CF-503373 | 37.7 | 0.011 | 3427 |
| | | 2.3 | 0.023 | 100 |
| | | 1.72 | 0.021 | 82 |
| | CF-503381 | 2.47 | 0.0.036 | 60 |
| | | 2.7 | 041 | 75 |
| | | 12.34 | 0.166 | 74 |

TABLE 2-continued
IC$_{50}$ values
| Formula | ID | Hu c-20S IC50 (μM) | Mtb20SOG IC50 (μM) | Selectivity |
|---|---|---|---|---|
| 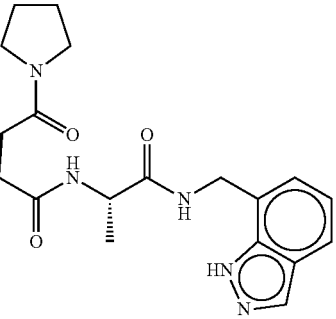 | CF-503390 | 5.5<br>2.72 | 0.121<br>0.088 | 45<br>31 |
| 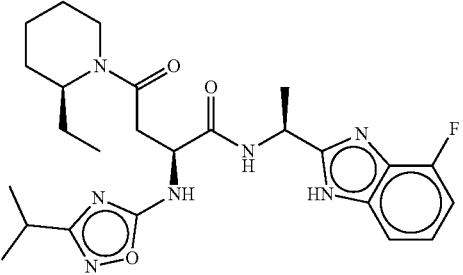 | CF-503417 | 3.6<br>2.99 | 1.35<br>1.77 | 3<br>2 |
| 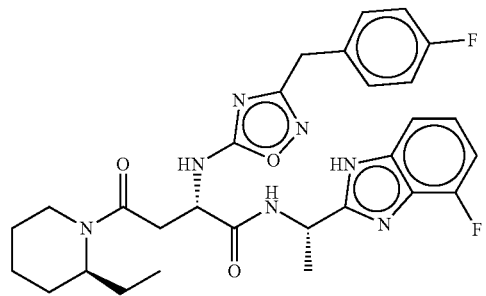 | CF-503419 | 1.36<br>1.2 | 0.257<br>0.319 | 5<br>4 |
| 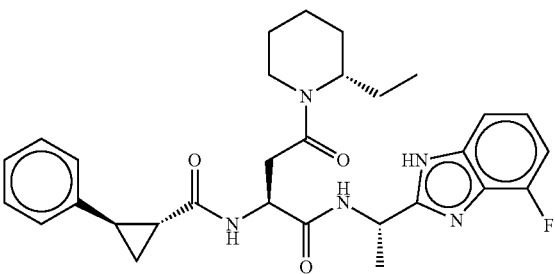 | CF-503363 | 8 | 0.0507 | 158 |
| 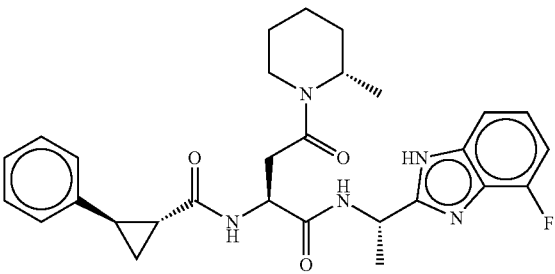 | CF-503382 | 12 | 0.166 | 72 |

TABLE 2-continued

IC$_{50}$ values

| Formula | ID | Hu c-20S IC50 (μM) | Mtb20SOG IC50 (μM) | Selectivity |
|---|---|---|---|---|
| | CF-503445 | 1.19 | 1.18 | 1 |
| | CF-503451 | 3.33<br>3.7 | 0.176<br>0.184 | 19<br>20 |
| | CF-503453 | 4.45 | 4.69 | 1 |
| | CF-503454 | 3 | 0.765 | 4 |
| | CF-503457 | 5.03 | 2.36 | 2 |

TABLE 2-continued

IC50 values

| Formula | ID | Hu c-20S IC50 (μM) | Mtb20SOG IC50 (μM) | Selectivity |
|---|---|---|---|---|
| | CF-503458 | 13.44<br>1.24 | 0.007<br>0.011 | 1920<br>112 |
| | CF-503459 | 27.4<br>2.1 | 0.013<br>0.02 | 2107<br>105 |
| | CF-503460 | 17.2 | 0.272 | 63 |
| | CF-503461 | 5.8<br>8.2 | 0.068<br>0.075 | 85<br>109 |
| | CF-503462 | 14.8 | 0.12 | 123 |

TABLE 2-continued
IC$_{50}$ values
| Formula | ID | Hu c-20S IC50 (μM) | Mtb20SOG IC50 (μM) | Selectivity |
|---|---|---|---|---|
| 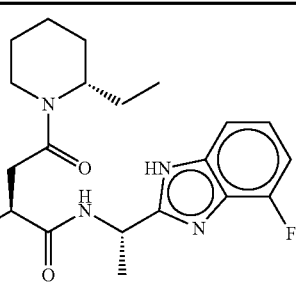 | CF-503463 | 2.5 | 1.14 | 2 |
| 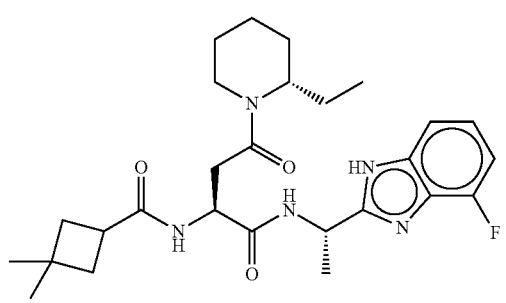 | CF-503464 | 4.41<br>1.26 | 0.01<br>0.019 | 441<br>66 |
| 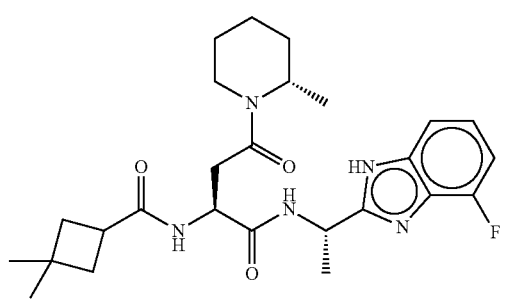 | CF-503465 | 7.62<br>1.92 | 0.025<br>0.032 | 305<br>60 |
| 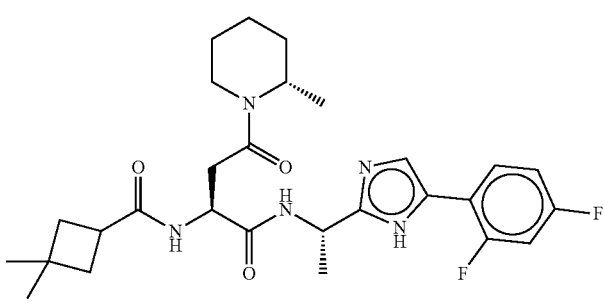 | CF-503474 | 5.65 | 0.014 | 404 |
| 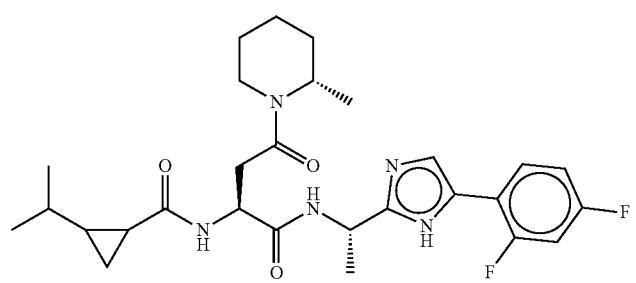 | CF-503475 | 4.77 | 0.034 | 140 |

TABLE 2-continued

IC$_{50}$ values

| Formula | ID | Hu c-20S IC50 (μM) | Mtb20SOG IC50 (μM) | Selectivity |
|---|---|---|---|---|
| | CF-503476 | 7.26 | 2.49 | 3 |
| | CF-503477 | 2.29 | 2.05 | 1 |

The results of the 20S proteasome inhibitor assays are presented in Table 3.

TABLE 3

IC$_{50}$ of Compounds Against Human Constitutive (Hu C-20S) β5 Active Subunit

| ID | Formula | Hu-C20S β5 (μM) |
|---|---|---|
| CEN-1 | | 14.2 |
| CEN-2 | | 16.9 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-3 | | 10.6 |
| CEN-4 | | 6.4 |
| CEN-5 | | 2.5 |
| CEN-6 | | 7.1 |
| CEN-7 | | 4.2 |

TABLE 3-continued

IC$_{50}$ of Compounds Against Human Constitutive (Hu C-20S) β5 Active Subunit

| ID | Formula | Hu-C20S β5 (μM) |
| --- | --- | --- |
| CEN-8 | | 3.6 |
| CEN-9 | | 4.4 |
| CEN-10 | | 37.7 |
| CEN-11 | | 19.2 |
| CEN-12 | | 3.0 |

TABLE 3-continued

IC$_{50}$ of Compounds Against Human Constitutive (Hu C-20S) β5 Active Subunit

| ID | Formula | Hu-C20S β5 (μM) |
| --- | --- | --- |
| CEN-13 | | 11.2 |
| CEN-14 | | 4.5 |
| CEN-15 | | 5.0 |
| CEN-16 | | 4.5 |
| CEN-17 | | 13.4 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-18 | | 9.5 |
| CEN-19 | | 1.1 |
| CEN-20 | | 2.6 |
| CEN-21 | | 9.4 |
| CEN-22 | | 1.2 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-23 | | 5.8 |
| CEN-24 | | 17.8 |
| CEN-25 | | 8.1 |
| CEN-26 | | 3.3 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-27 | | 1.4 |
| CEN-28 | | 14.8 |
| CEN-29 | | 6.9 |
| CEN-30 | | 4.5 |
| CEN-31 | | 17.6 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-32 | | 23.5 |
| CEN-33 | | 16.5 |
| CEN-34 | | 15.6 |
| CEN-35 | | 19.6 |
| CEN-36 | | 17.5 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-37 | | 17.3 |
| CEN-38 | | 16.2 |
| CEN-39 | | 7.6 |
| CEN-40 | | 2.7 |
| CEN-41 | | 4.8 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-42 | | 27.4 |
| CEN-43 | | 13.8 |
| CEN-44 | | 0.9 |
| CEN-45 | | 4.1 |

TABLE 3-continued

IC$_{50}$ of Compounds Against Human Constitutive (Hu C-20S) β5 Active Subunit

| ID | Formula | Hu-C20S β5 (µM) |
|---|---|---|
| CEN-46 | | 8.4 |
| CEN-47 | | 29.4 |
| CEN-48 | | 50.0 |
| CEN-49 | | 50.0 |
| CEN-50 | | 14.8 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-51 | 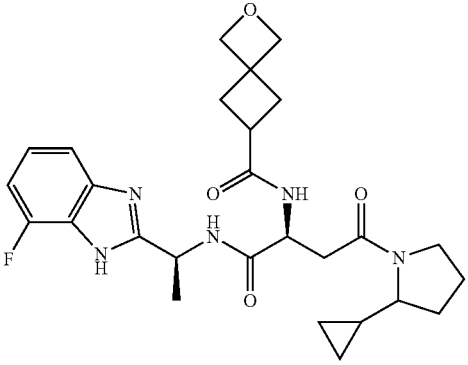 [SMILES: C[C@H](NC(=O)[C@H](CC(=O)N1CCCC1C1CC1)NC(=O)C1CC2(COC2)C1)c1nc2cccc(F)c2[nH]1] | 15.0 |
| CEN-52 | 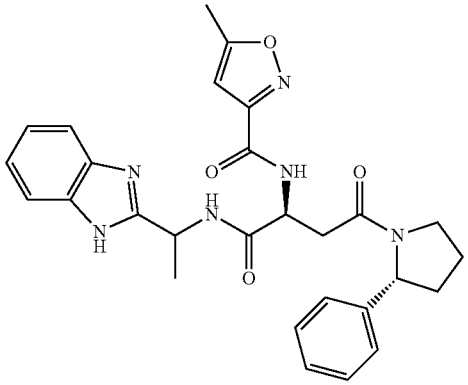 [SMILES: Cc1cc(C(=O)N[C@@H](CC(=O)N2CCC[C@@H]2c2ccccc2)C(=O)NC(C)c2nc3ccccc3[nH]2)no1] | 7.5 |
| CEN-53 | 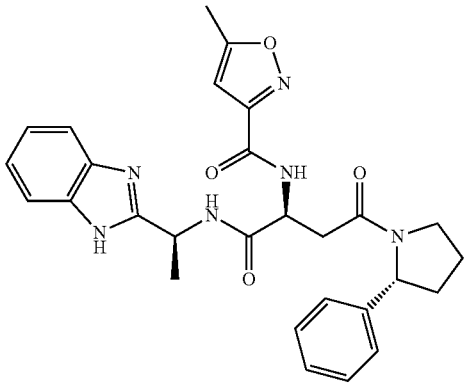 [SMILES: Cc1cc(C(=O)N[C@@H](CC(=O)N2CCC[C@@H]2c2ccccc2)C(=O)N[C@@H](C)c2nc3ccccc3[nH]2)no1] | 9.7 |
| CEN-54 | 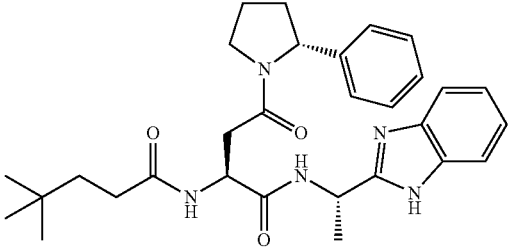 [SMILES: C[C@H](NC(=O)[C@H](CC(=O)N1CCC[C@@H]1c1ccccc1)NC(=O)CCC(C)(C)C)c1nc2ccccc2[nH]1] | 16.6 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-55 | 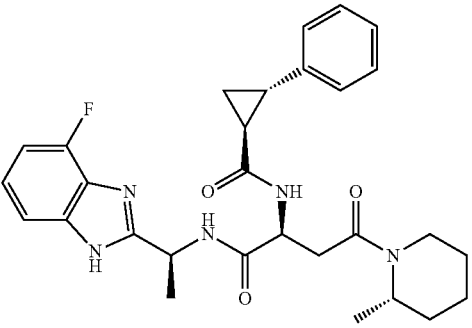 [SMILES: C[C@H](NC(=O)[C@H](CC(=O)N1CCCC[C@@H]1C)NC(=O)[C@H]1C[C@@H]1c1ccccc1)c1nc2c(F)cccc2[nH]1] | 12.3 |
| CEN-56 | 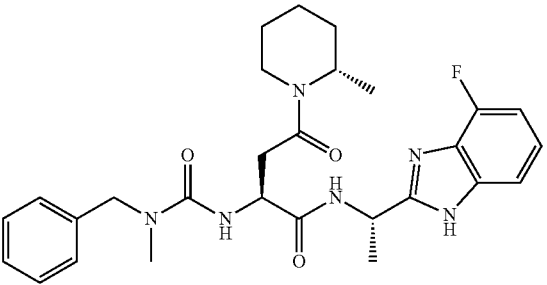 [SMILES: C[C@H](NC(=O)[C@H](CC(=O)N1CCCC[C@@H]1C)NC(=O)N(C)Cc1ccccc1)c1nc2c(F)cccc2[nH]1] | 17.2 |
| CEN-57 | 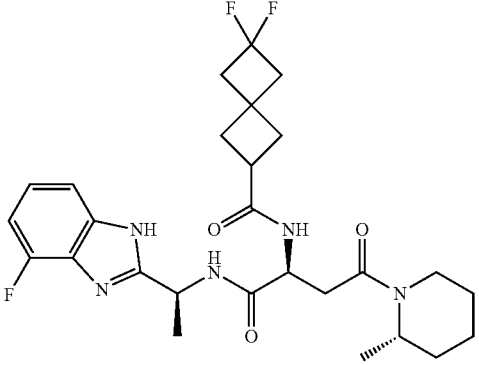 [SMILES: C[C@H](NC(=O)[C@H](CC(=O)N1CCCC[C@@H]1C)NC(=O)C1CC2(C1)CC(F)(F)C2)c1nc2c(F)cccc2[nH]1] | 28.0 |
| CEN-58 | 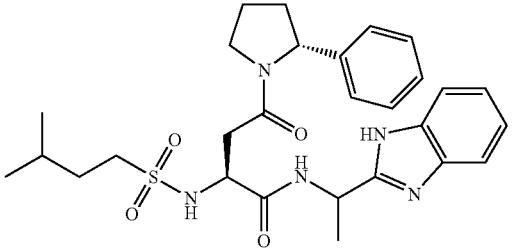 [SMILES: CC(C)CCS(=O)(=O)N[C@@H](CC(=O)N1CCC[C@@H]1c1ccccc1)C(=O)NC(C)c1nc2ccccc2[nH]1] | 13.9 |
| CEN-59 | 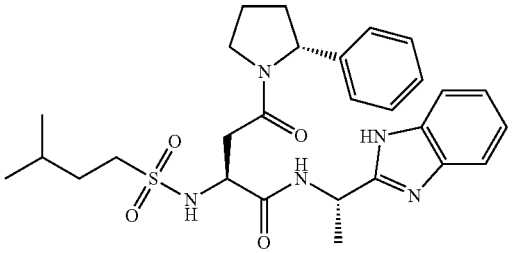 [SMILES: CC(C)CCS(=O)(=O)N[C@@H](CC(=O)N1CCC[C@@H]1c1ccccc1)C(=O)N[C@@H](C)c1nc2ccccc2[nH]1] | 10.0 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-60 | | 10.7 |
| CEN-61 | | 8.8 |
| CEN-62 | | 2.4 |
| CEN-63 | | 6.8 |

TABLE 3-continued

IC$_{50}$ of Compounds Against Human Constitutive (Hu C-20S) β5 Active Subunit

| ID | Formula | Hu-C20S β5 (μM) |
| --- | --- | --- |
| CEN-64 | | 2.4 |
| CEN-65 | | >100.0 |
| CEN-66 | | >100.0 |
| CEN-67 | | >100.0 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-68 | 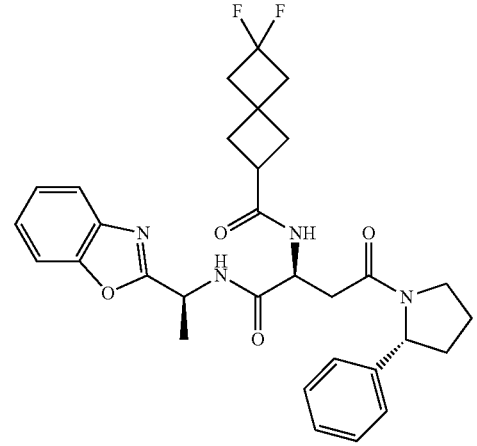 [SMILES: C[C@H](NC(=O)[C@H](CC(=O)N1CCC[C@@H]1c1ccccc1)NC(=O)C1CC2(C1)CC(F)(F)C2)c1nc2ccccc2o1] | >100.0 |
| CEN-69 | 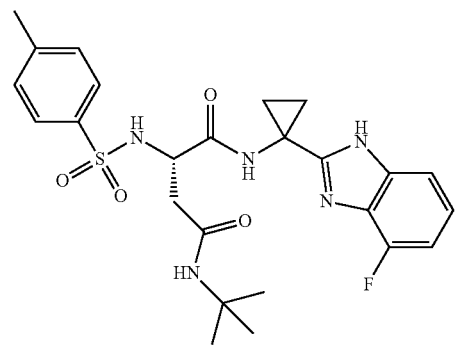 [SMILES: Cc1ccc(S(=O)(=O)N[C@@H](CC(=O)NC(C)(C)C)C(=O)NC2(c3nc4c(F)cccc4[nH]3)CC2)cc1] | >100.0 |
| CEN-70 | 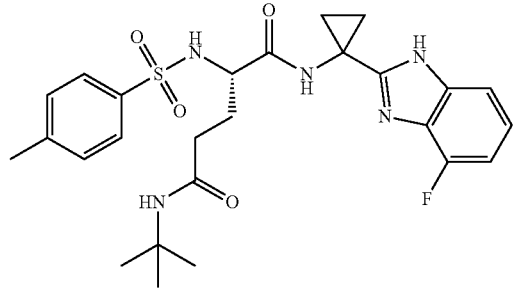 [SMILES: Cc1ccc(S(=O)(=O)N[C@@H](CCC(=O)NC(C)(C)C)C(=O)NC2(c3nc4c(F)cccc4[nH]3)CC2)cc1] | >100.0 |
| CEN-71 | 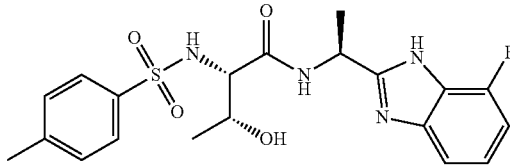 | >100.0 |
| CEN-72 | 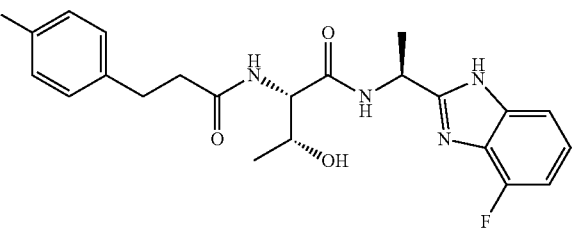 | >100.0 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-73 | 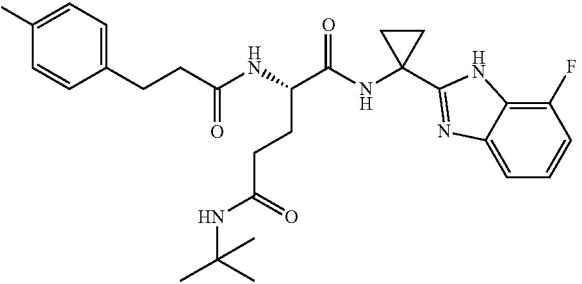 | >100.0 |
| CEN-74 | 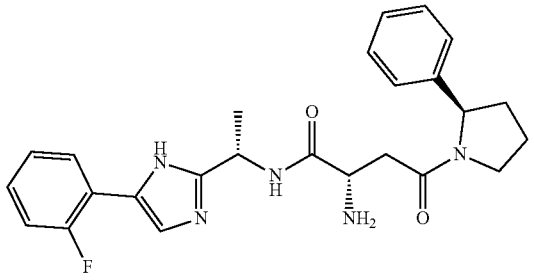 [SMILES: C[C@H](NC(=O)[C@@H](N)CC(=O)N1CCC[C@@H]1c1ccccc1)c1ncc(-c2ccccc2F)[nH]1] | 94.0 |
| CEN-75 | 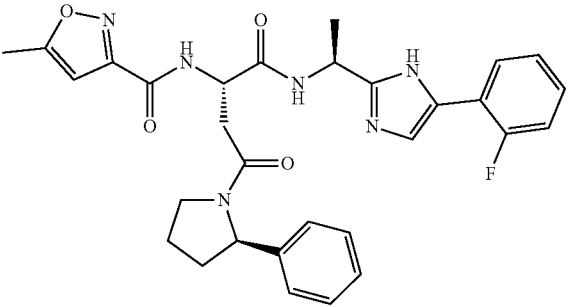 [SMILES: Cc1cc(C(=O)N[C@@H](CC(=O)N2CCC[C@@H]2c2ccccc2)C(=O)N[C@@H](C)c2ncc(-c3ccccc3F)[nH]2)no1] | >100.0 |
| CEN-76 | 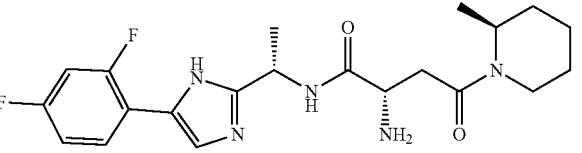 | 14.2 |
| CEN-77 | 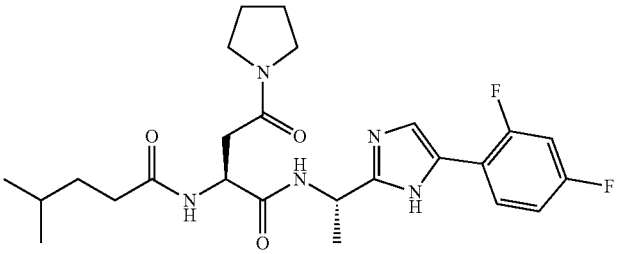 [SMILES: CC(C)CCC(=O)N[C@@H](CC(=O)N1CCCC1)C(=O)N[C@@H](C)c1ncc(-c2ccc(F)cc2F)[nH]1] | 10.4 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-78 | | 14.9 |
| CEN-79 | | 7.3 |
| CEN-80 | | 16.7 |
| CEN-81 | | 10.5 |
| CEN-82 | | 2.4 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-83 | | 10.3 |
| CEN-84 | | 7.3 |
| CEN-85 | | 9.9 |
| CEN-86 | | 28.2 |
| CEN-87 | | 11.7 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-88 | 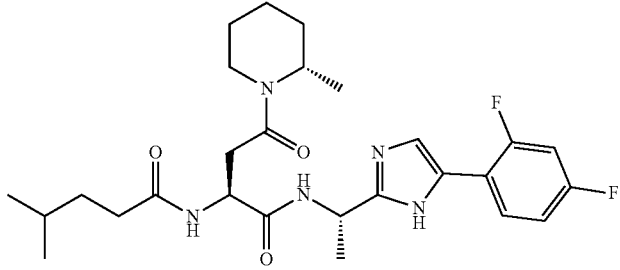 [SMILES: CC(C)CCC(=O)N[C@@H](CC(=O)N1CCCC[C@@H]1C)C(=O)N[C@@H](C)c1ncc(-c2ccc(F)cc2F)[nH]1] | 15.1 |
| CEN-89 | 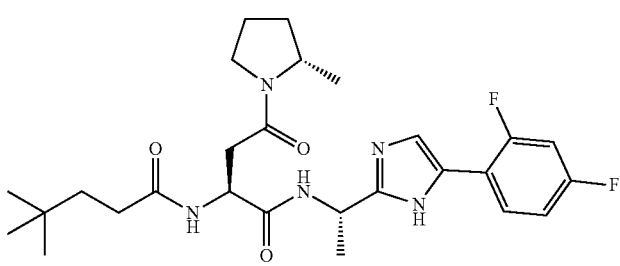 [SMILES: C[C@H](NC(=O)[C@H](CC(=O)N1CCC[C@@H]1C)NC(=O)CCC(C)(C)C)c1ncc(-c2ccc(F)cc2F)[nH]1] | 5.7 |
| CEN-90 | 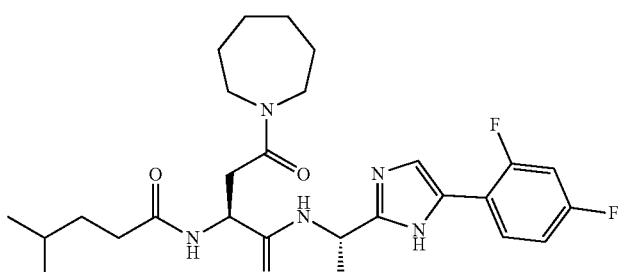 | 10.2 |
| CEN-91 | 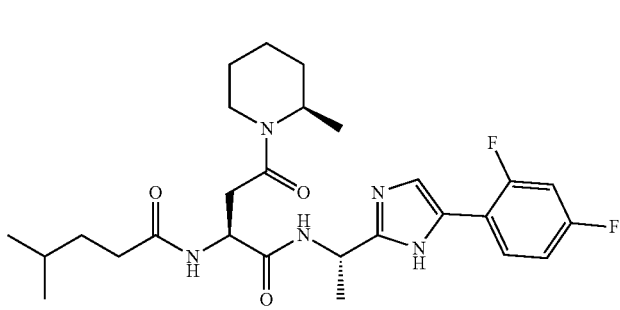 [SMILES: CC(C)CCC(=O)N[C@@H](CC(=O)N1CCCC[C@H]1C)C(=O)N[C@@H](C)c1ncc(-c2ccc(F)cc2F)[nH]1] | 10.5 |
| CEN-92 | 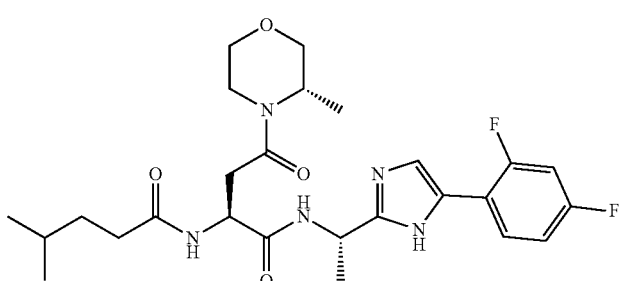 | 15.2 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-93 | | 10.9 |
| CEN-94 | | 5.5 |
| CEN-95 | | 2.3 |
| CEN-96 | | 5.7 |
| CEN-97 | | 4.8 |

TABLE 3-continued

IC$_{50}$ of Compounds Against Human Constitutive (Hu C-20S) β5 Active Subunit

| ID | Formula | Hu-C20S β5 (µM) |
| --- | --- | --- |
| CEN-98 | | 7.1 |
| CEN-99 | | 8.5 |
| CEN-100 | | 4.4 |
| CEN-101 | | 7.6 |
| CEN-102 | | 10.2 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-103 | 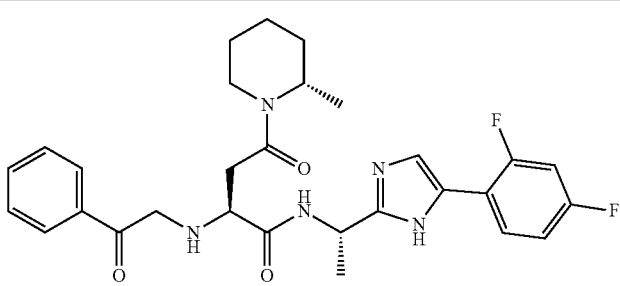 [SMILES: C[C@H](NC(=O)[C@H](CC(=O)N1CCCC[C@@H]1C)NCC(=O)c1ccccc1)c1ncc(-c2ccc(F)cc2F)[nH]1] | 15.2 |
| CEN-104 | 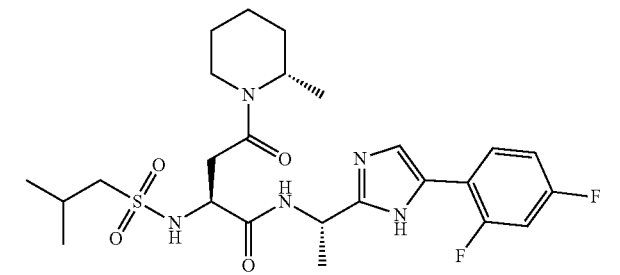 [SMILES: CC(C)CS(=O)(=O)N[C@@H](CC(=O)N1CCCC[C@@H]1C)C(=O)N[C@@H](C)c1ncc(-c2ccc(F)cc2F)[nH]1] | 4.9 |
| CEN-105 | 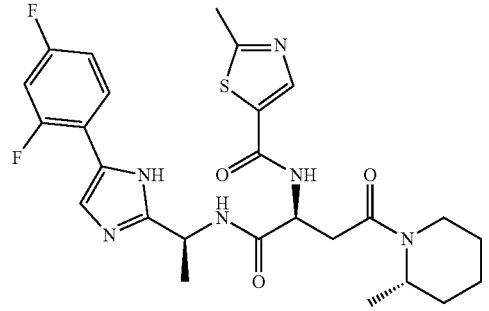 [SMILES: Cc1ncc(C(=O)N[C@@H](CC(=O)N2CCCC[C@@H]2C)C(=O)N[C@@H](C)c2ncc(-c3ccc(F)cc3F)[nH]2)s1] | 3.9 |
| CEN-106 | 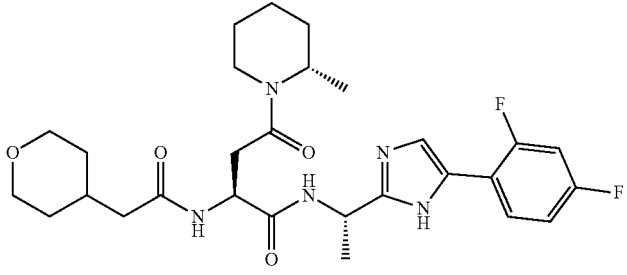 [SMILES: C[C@H](NC(=O)[C@H](CC(=O)N1CCCC[C@@H]1C)NC(=O)CC1CCOCC1)c1ncc(-c2ccc(F)cc2F)[nH]1] | 12.8 |
| CEN-107 | 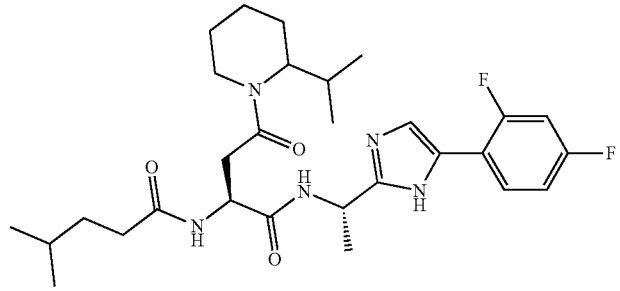 [SMILES: CC(C)CCC(=O)N[C@@H](CC(=O)N1CCCCC1C(C)C)C(=O)N[C@@H](C)c1ncc(-c2ccc(F)cc2F)[nH]1] | 2.8 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-108 | 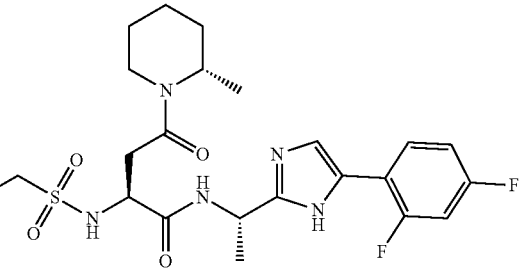 | 6.2 |
| CEN-109 | 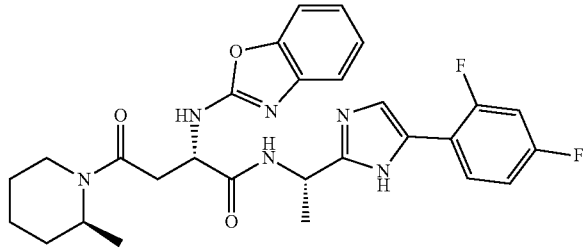 [SMILES: C[C@H](NC(=O)[C@H](CC(=O)N1CCCC[C@@H]1C)Nc1nc2ccccc2o1)c1ncc(-c2ccc(F)cc2F)[nH]1] | 7.3 |
| CEN-110 | 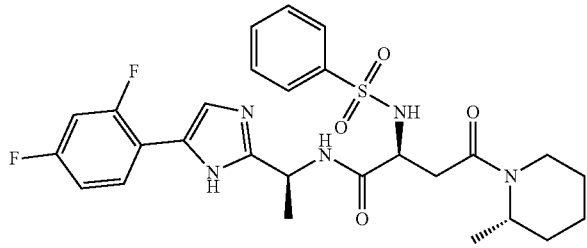 [SMILES: C[C@H](NC(=O)[C@H](CC(=O)N1CCCC[C@@H]1C)NS(=O)(=O)c1ccccc1)c1ncc(-c2ccc(F)cc2F)[nH]1] | 8.1 |
| CEN-111 | 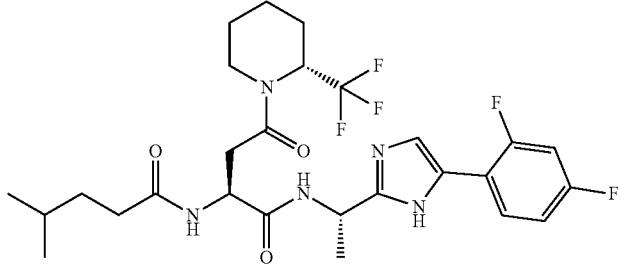 [SMILES: CC(C)CCC(=O)N[C@@H](CC(=O)N1CCCC[C@@H]1C(F)(F)F)C(=O)N[C@@H](C)c1ncc(-c2ccc(F)cc2F)[nH]1] | 4.9 |
| CEN-112 | 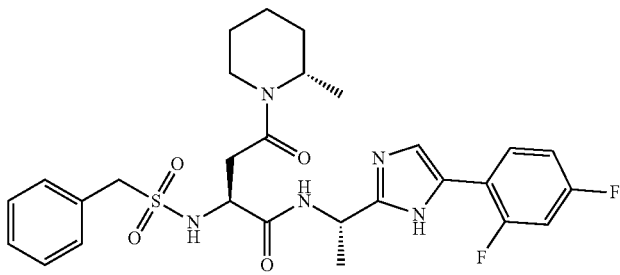 [SMILES: C[C@H](NC(=O)[C@H](CC(=O)N1CCCC[C@@H]1C)NS(=O)(=O)Cc1ccccc1)c1ncc(-c2ccc(F)cc2F)[nH]1] | 6.1 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-113 | | 6.5 |
| CEN-114 | | 9.7 |
| CEN-115 | | >100.0 |
| CEN-116 | | 9.5 |
| CEN-117 | | 11.0 |

TABLE 3-continued

IC$_{50}$ of Compounds Against Human Constitutive (Hu C-20S) β5 Active Subunit

| ID | Formula | Hu-C20S β5 (μM) |
|---|---|---|
| CEN-118 | | 15.8 |
| CEN-119 | | 18.0 |
| CEN-120 | | >100.0 |
| CEN-121 | | 10.6 |
| CEN-122 | | 13.5 |

TABLE 3-continued
IC$_{50}$ of Compounds Against Human Constitutive (Hu C-20S) β5 Active Subunit
| ID | Formula | Hu-C20S β5 (μM) |
|---|---|---|
| CEN-123 | 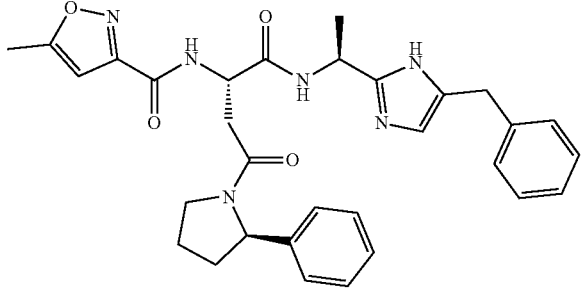 [SMILES: Cc1cc(C(=O)N[C@@H](CC(=O)N2CCC[C@@H]2c2ccccc2)C(=O)N[C@@H](C)c2ncc(Cc3ccccc3)[nH]2)no1] | 7.4 |
| CEN-124 | 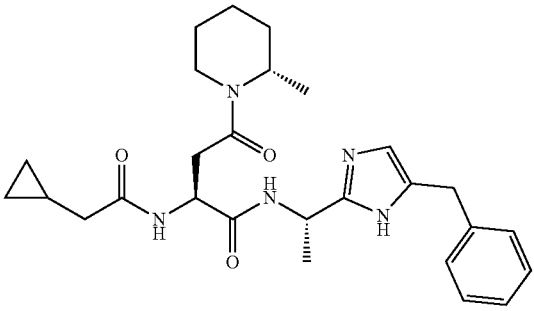 [SMILES: C[C@H](NC(=O)[C@H](CC(=O)N1CCCC[C@@H]1C)NC(=O)CC1CC1)c1ncc(Cc2ccccc2)[nH]1] | 10.4 |
| CEN-125 | 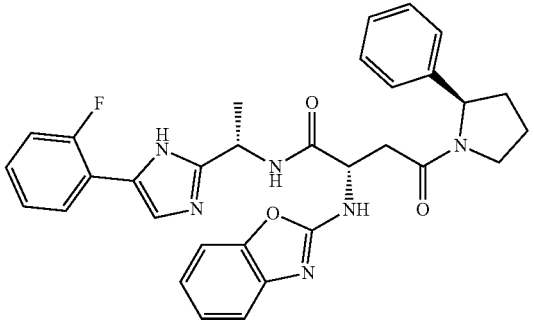 [SMILES: C[C@H](NC(=O)[C@H](CC(=O)N1CCC[C@@H]1c1ccccc1)Nc1nc2ccccc2o1)c1ncc(-c2ccccc2F)[nH]1] | 20.6 |

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed is:

1. A method of treating bacterial infections, parasite infections, fungal infections, cancer, autoimmune disorders, neurodegenerative diseases and disorders, inflammatory disorders, or muscular dystrophy, in a subject or for achieving immunosuppression in transplanted organs or tissues in a subject, said method comprising:

administering to the subject in need thereof a compound of Formula (I):

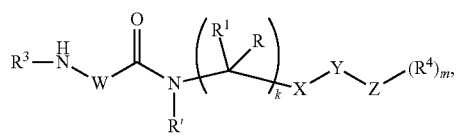

wherein
R is H or $C_{1-6}$ alkyl;
R' is H or $C_{1-6}$ alkyl;
$R^1$ is H or $C_{1-6}$ alkyl;
or R and $R^1$ are taken together with the carbon to which they are attached to form a $C_{3-8}$ cycloalkyl ring;
$R^2$ is independently selected at each occurrence thereof from

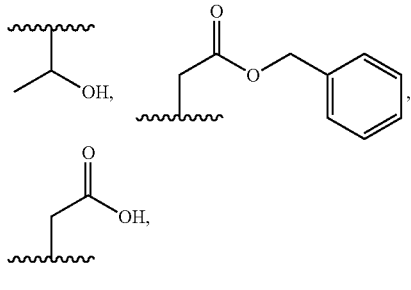

or $-(CH_2)_nC(O)NR^6R^7$;
$R^3$ is independently selected at each occurrence thereof from the group consisting of H, $C_{1-12}$ alkyl, -Boc, $-C(O)(CH_2)_nR^5$, $-(CH_2)_nC(O)R^5$, $-C(O)OR^5$, $-C(O)(CH_2)_nNR^6R^7$, $-S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $R^8$;
$R^4$ is H, halogen, $NH_2$, $NHCOOC_{1-12}$ alkyl, or $C_{1-12}$ alkyl;
$R^5$ is selected from the group consisting of $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;
$R^6$ and $R^7$ are each independently selected from the group consisting of H, $C_{1-6}$ alkyl, and arylalkyl;
or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;
$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;
$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;
W is $CHR^2$, $NR^2$, or

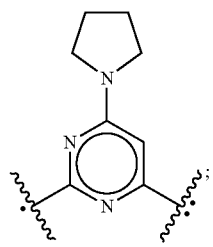

X is selected from the group consisting of $-C(O)-NH-$, monocyclic and bicyclic heteroaryl, monocyclic and bicyclic heterocyclyl, and monocyclic and bicyclic non-aromatic heterocycle;
Y is optional and, if present, is $-(CH_2)_m-$;
Z is optional and, if present, is aryl or bicyclic heteroaryl;

is the point of attachment to $NHR^3$ moiety;

is the point of attachment to C(O) moiety;
k is 1 or 2;
m is 0, 1, or 2; and
n is 0, 1, 2, 3, or 4,
with the proviso that $R^2$ is not $-CH_2C(O)NH_2$, $-CH_2C(O)NHCH_2C(CH_3)_3$, or $-(CH_2)_2C(O)NH_2$,
a pharmaceutically acceptable salt thereof or a solvate thereof,
wherein the autoimmune disorder is selected from the group consisting of arthritis, colitis, multiple sclerosis, lupus, Sjogren Syndrome, Systemic Lupus Erythematosus, lupus nephritis, glomerulonephritis, Rheumatoid Arthritis, Inflammatory bowel disease (IBD), ulcerative colitis, Crohn's diseases, Psoriasis, and asthma;

the inflammatory disorder is Crohn's disease;

the cancer is selected from the group consisting of neoplastic disorders, hematologic malignances, lymphocytic malignancies, mantel cell lymphoma, leukemia, Waldenstrom Macroglobulinemia, pancreatic cancer, bladder cancer, colorectal cancer, breast cancer, metastatic breast cancer, prostate cancer, androgen-dependent and androgen-independent prostate cancer, renal cancer, metastatic renal cell carcinoma, hepatocellular cancer, lung cancer, non-small cell lung cancer (NSCLC), bronchioloalveolar carcinoma (BAC), adenocarcinoma of the lung, ovarian cancer, progressive epithelial or primary peritoneal cancer, cervical cancer, gastric cancer, esophageal cancer, head and neck cancer, squamous cell carcinoma of the head and neck, melanoma, neuroendocrine cancer, metastatic neuroendocrine tumors, brain tumors, glioma, anaplastic oligodendroglioma, adult glioblastoma multiforme, and adult anaplastic astrocytoma, bone cancer, and soft tissue sarcoma; and the neurodegenerative disease or disorder is Amyotrophic Lateral Sclerosis (ALS) or Multiple Sclerosis (MS).

2. The method of claim 1, wherein the compound of Formula (I) has the Formula (IA), Formula (IB), or Formula (IC):

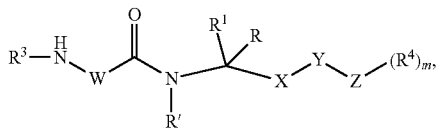

(IA)

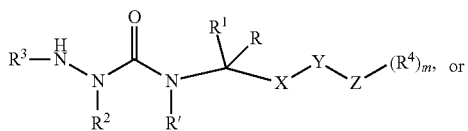

(IB)

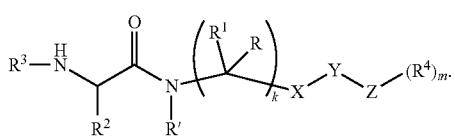

(IC)

3. The method of claim 1, wherein R and $R^1$ are taken together with the carbon to which they are attached to form

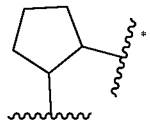

group, and wherein

is the point of attachment to NH; and

is the point of attachment to X.

4. The method of claim 1, wherein $R^3$ is

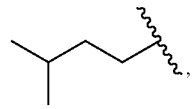

wherein

is the point of attachment to the corresponding carbon atom of the structure of Formula (I).

5. The method of claim 1, wherein X is

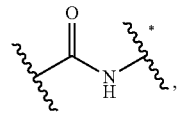 [SMILES: *NC(*)=O]

wherein

is the point of attachment to $C(R^1)(R^2)$ moiety;

is the point of attachment to Y, Z, or $R^4$.

6. The method of claim 1, wherein Z is

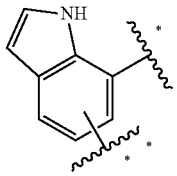

or
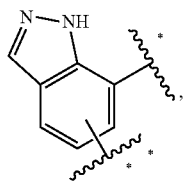
and
wherein
is the point of attachment to Y or X;
is the point of attachment to R$^4$.
7. The method of claim 1, wherein the compound of Formula (I) is selected from the group consisting of:
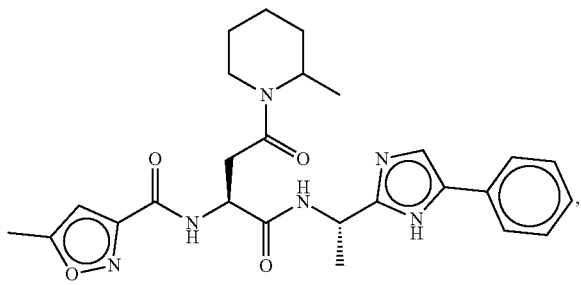
,
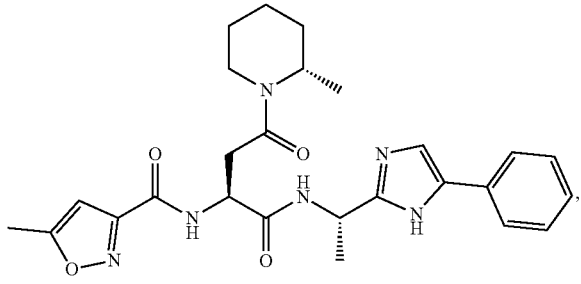
,
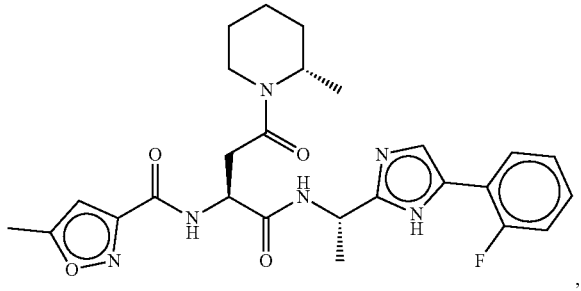
,
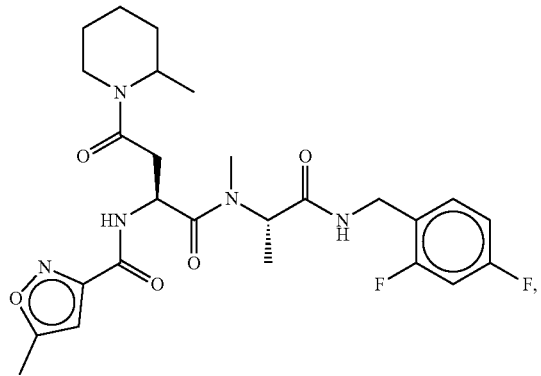
, -continued
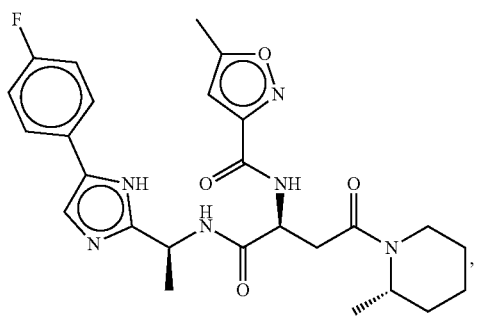
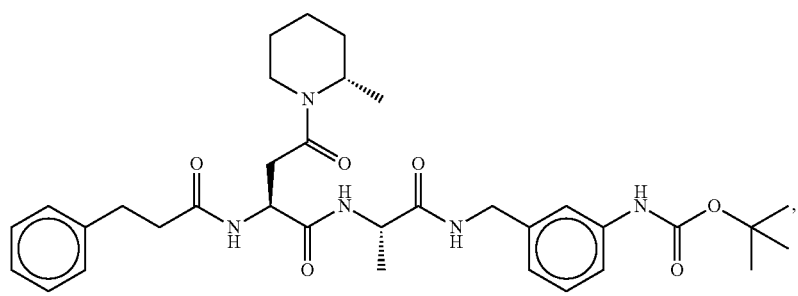
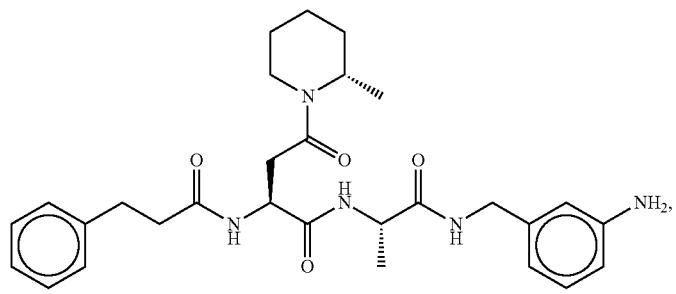
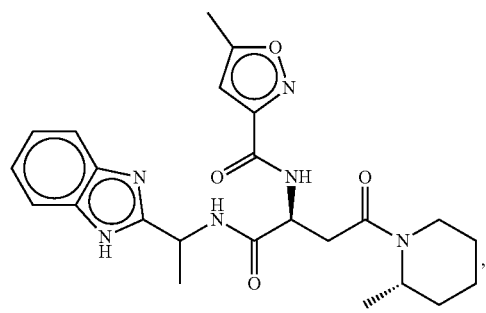
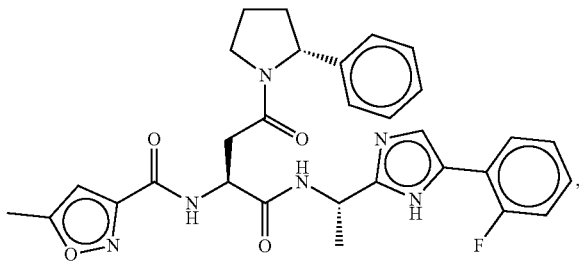
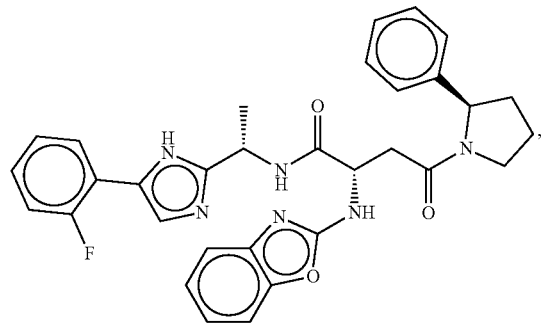
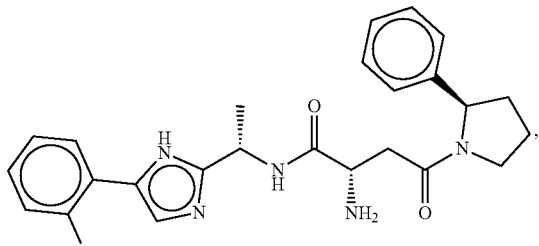

321
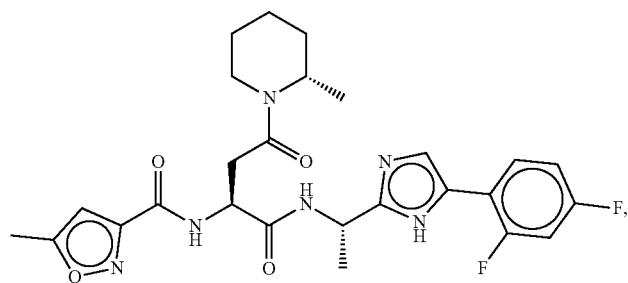
322
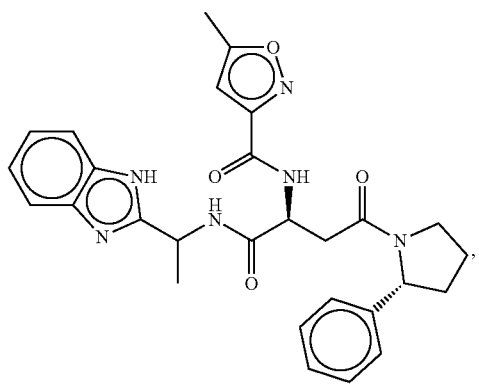
-continued
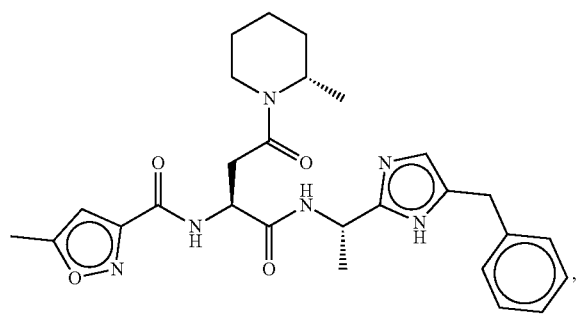
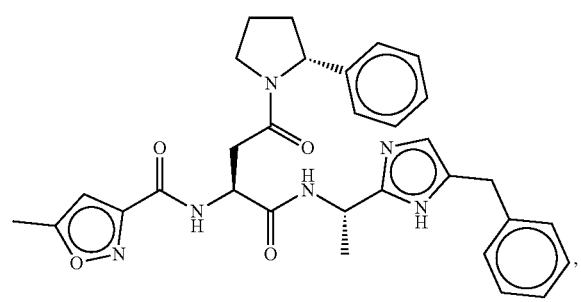
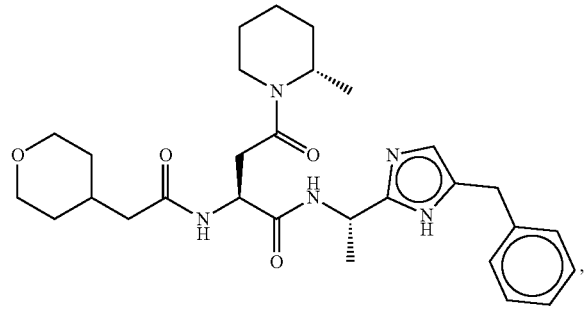
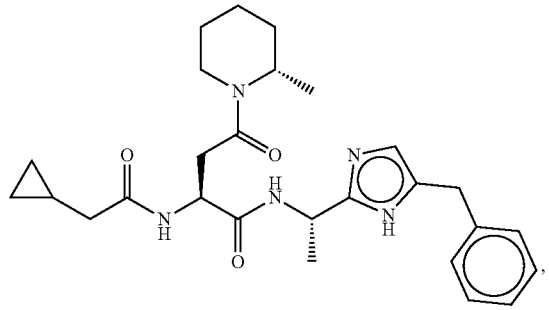
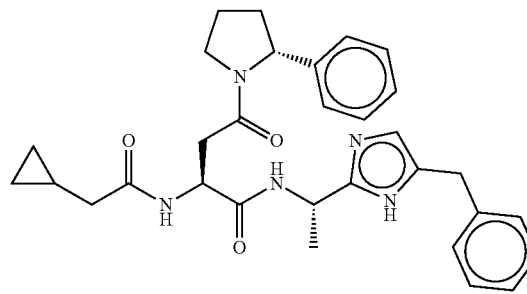
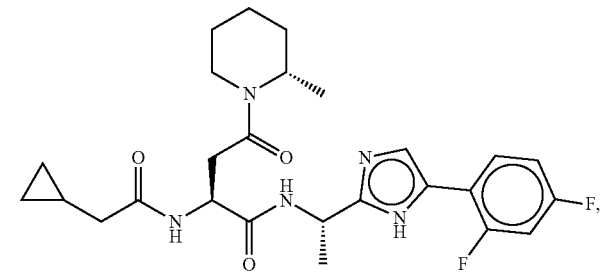
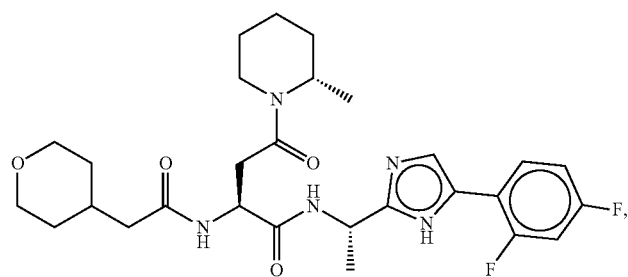

-continued
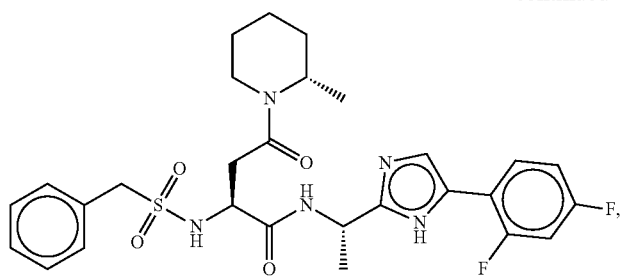
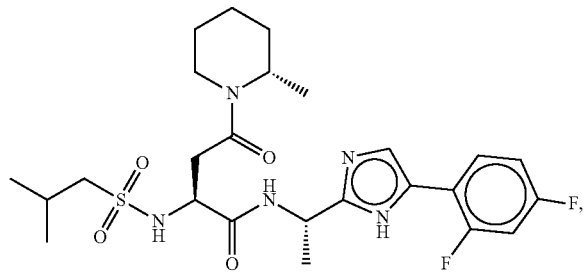
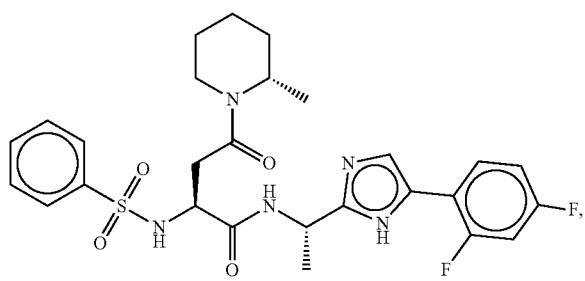
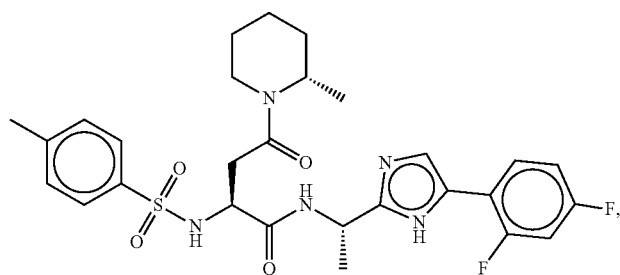
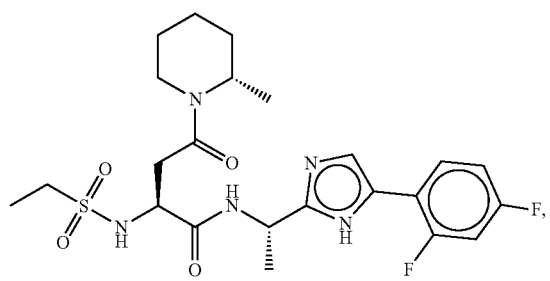
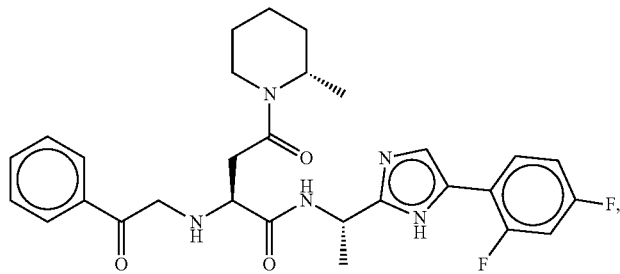

-continued
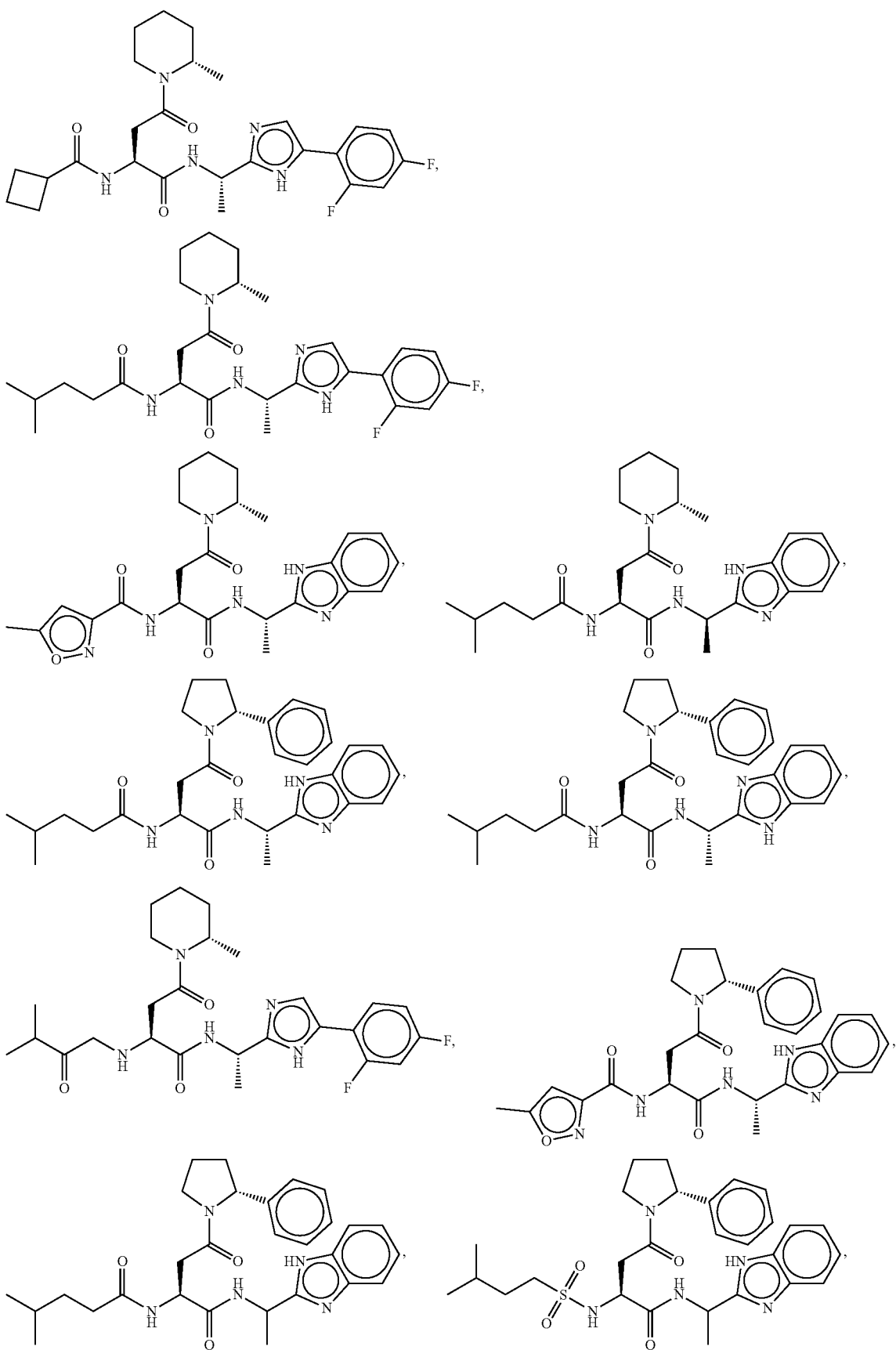

327
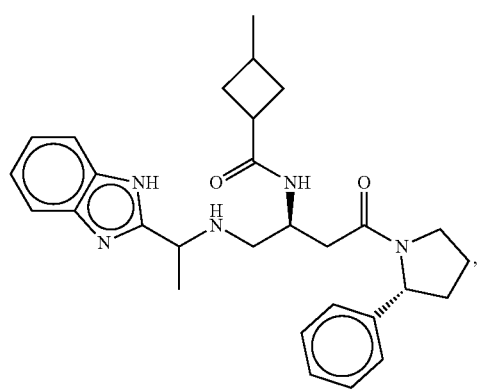
328
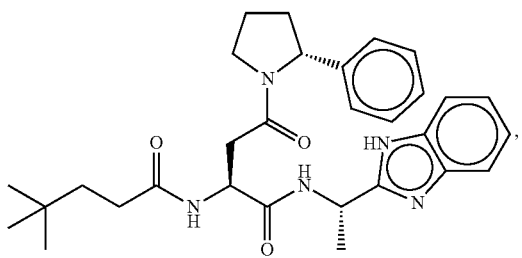
-continued
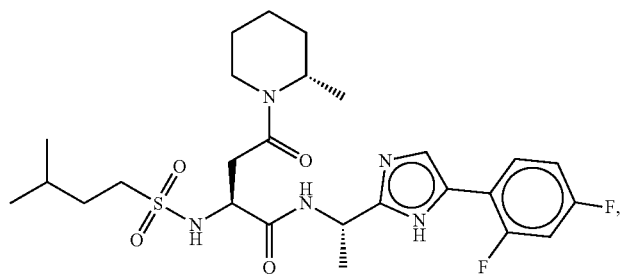
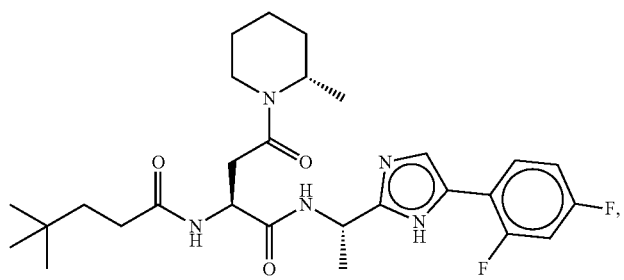
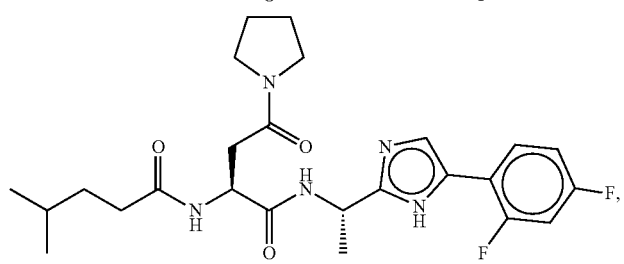
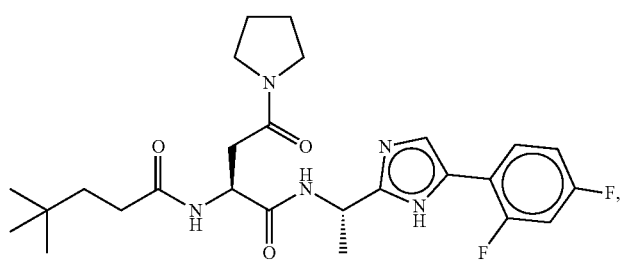
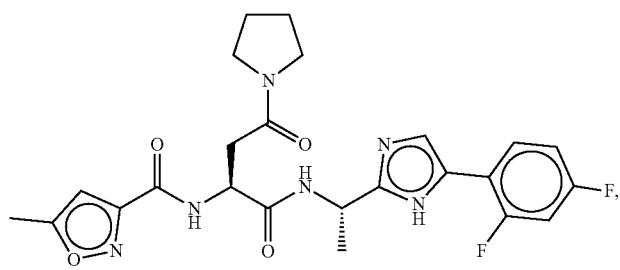

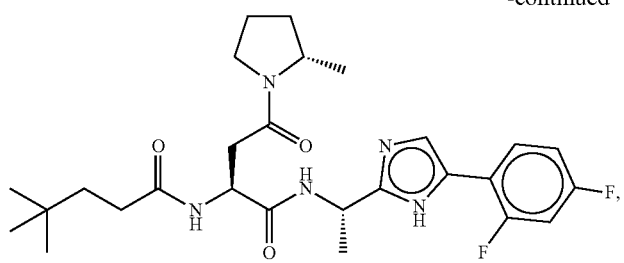
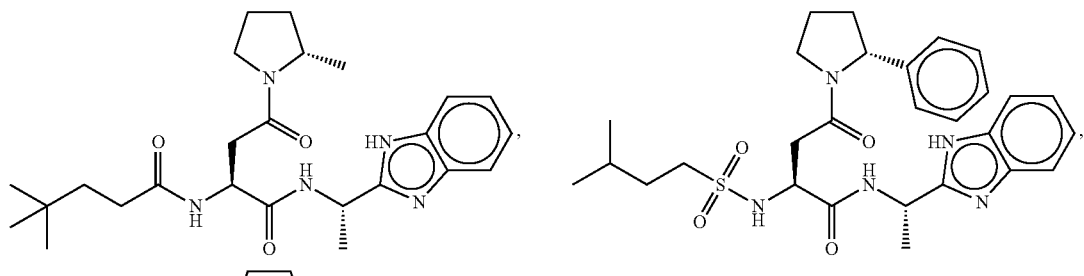
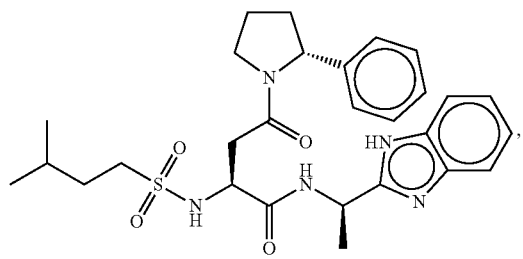
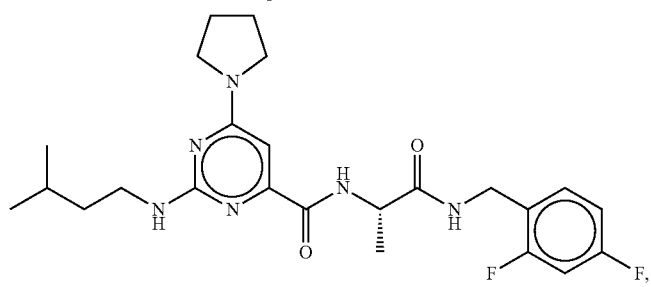
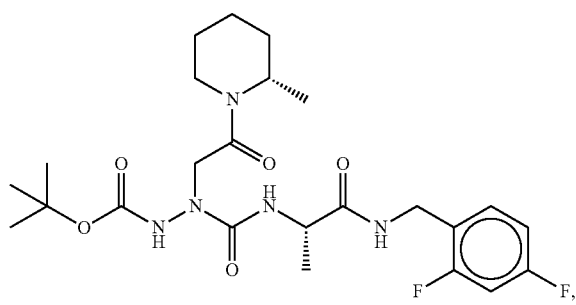
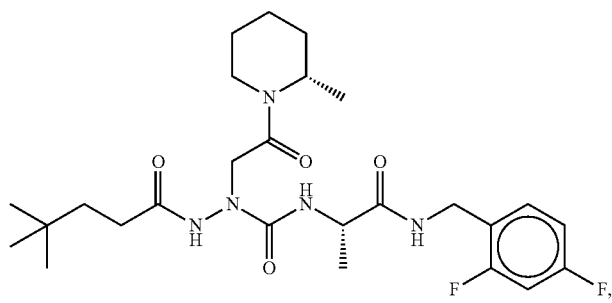

331
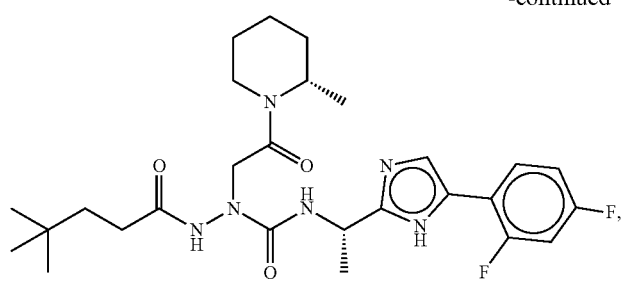
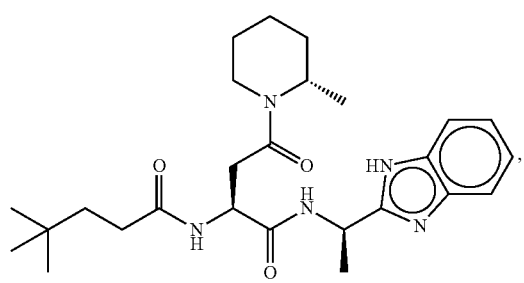
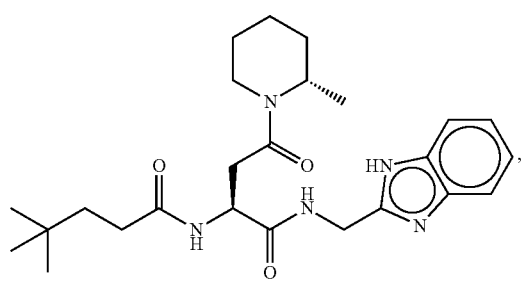
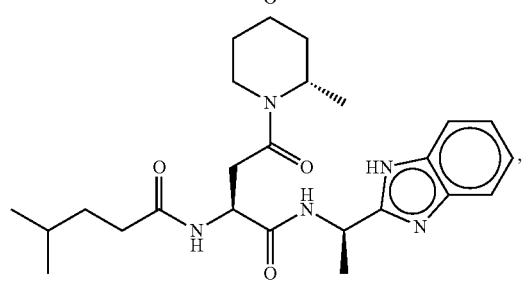
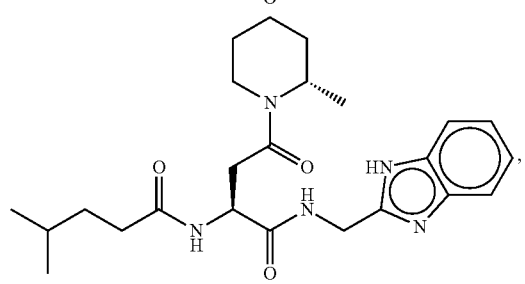
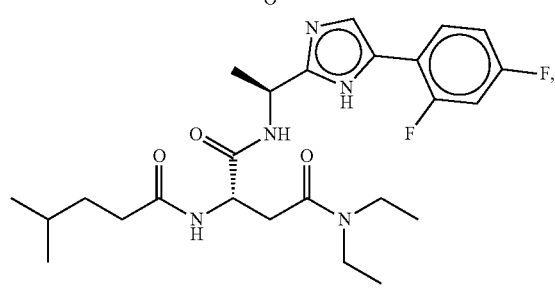
332
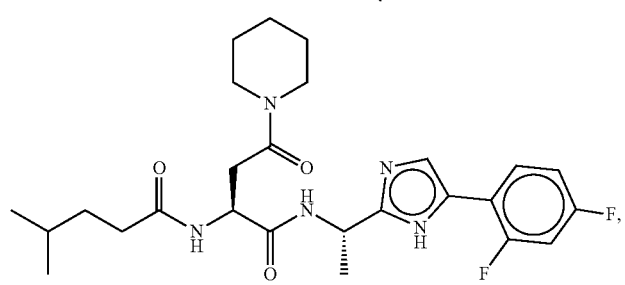
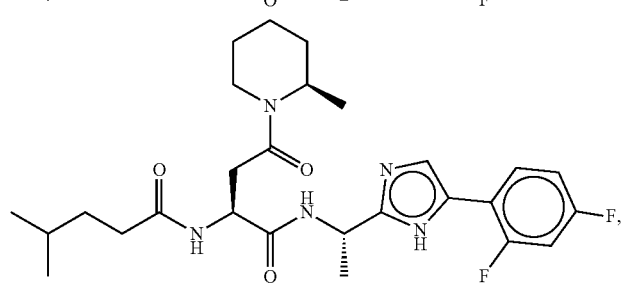

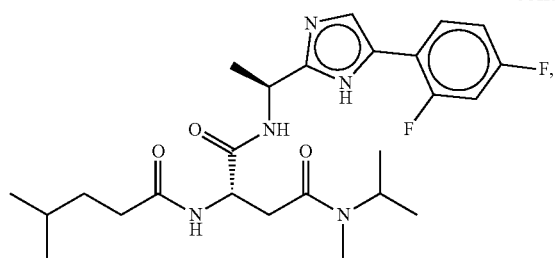
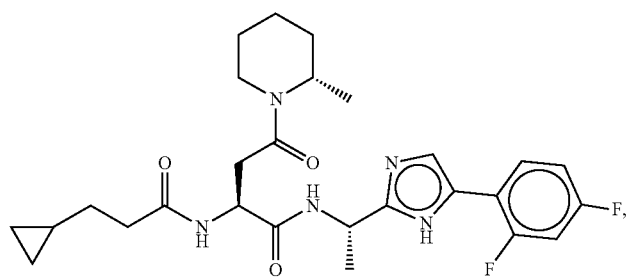
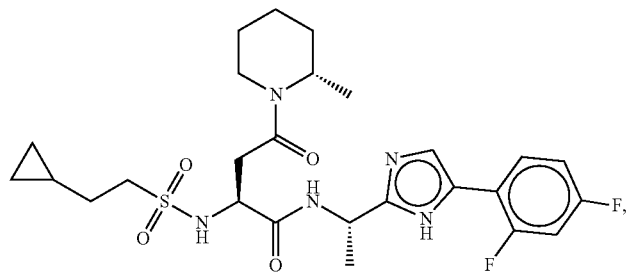
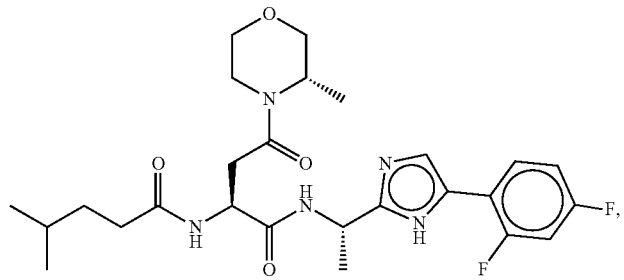
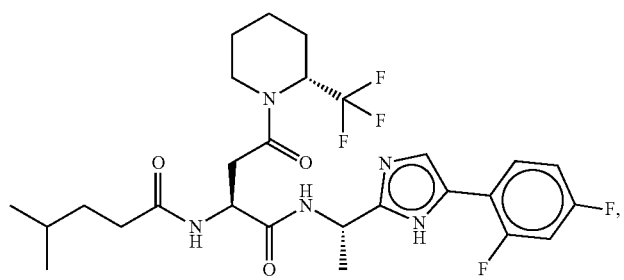
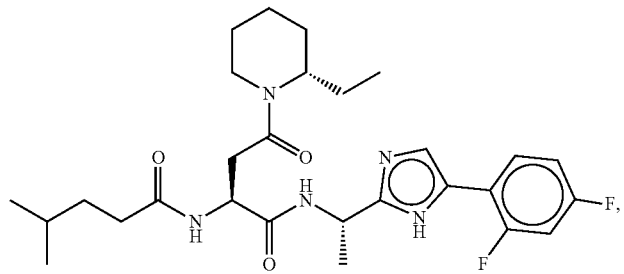

-continued
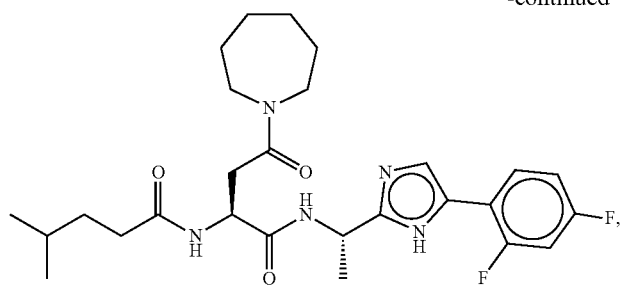
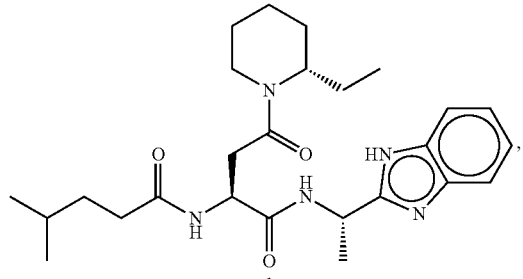
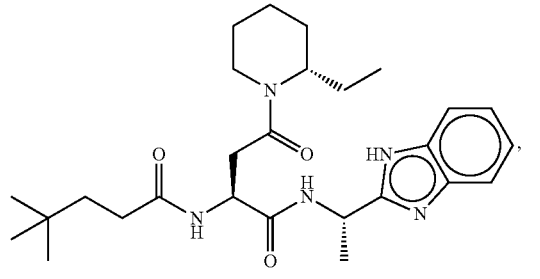
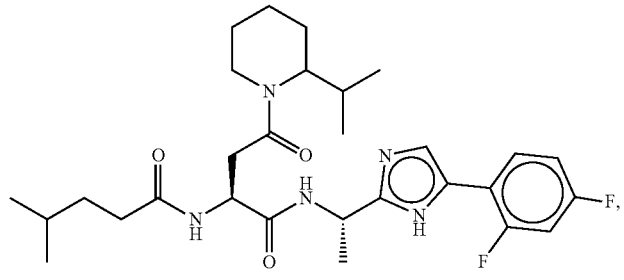
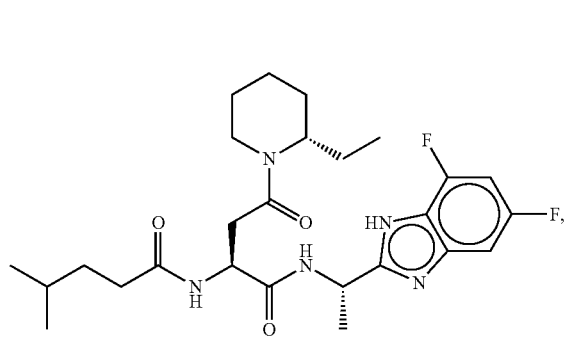
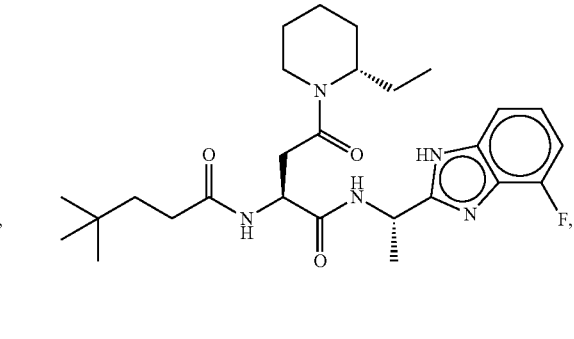
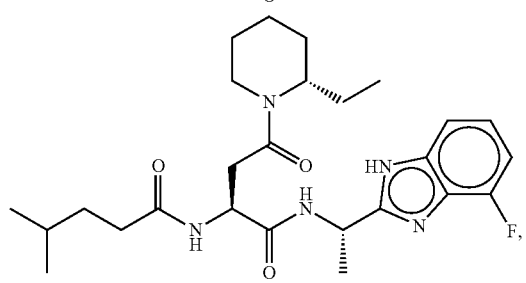
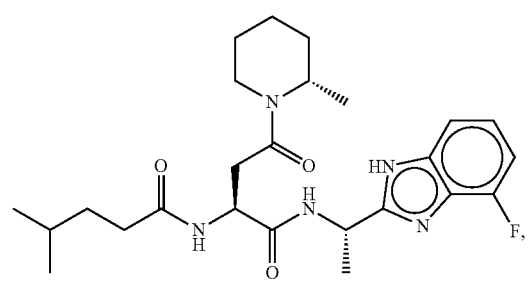
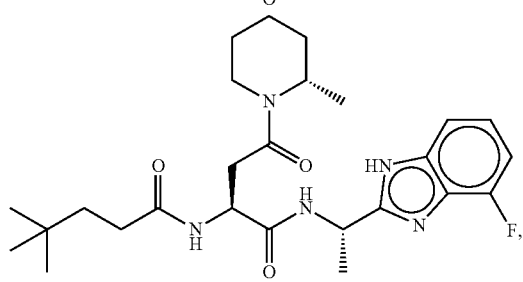
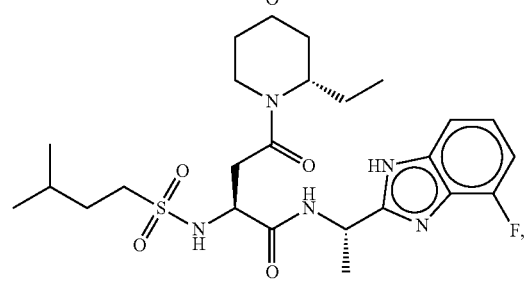

337 338
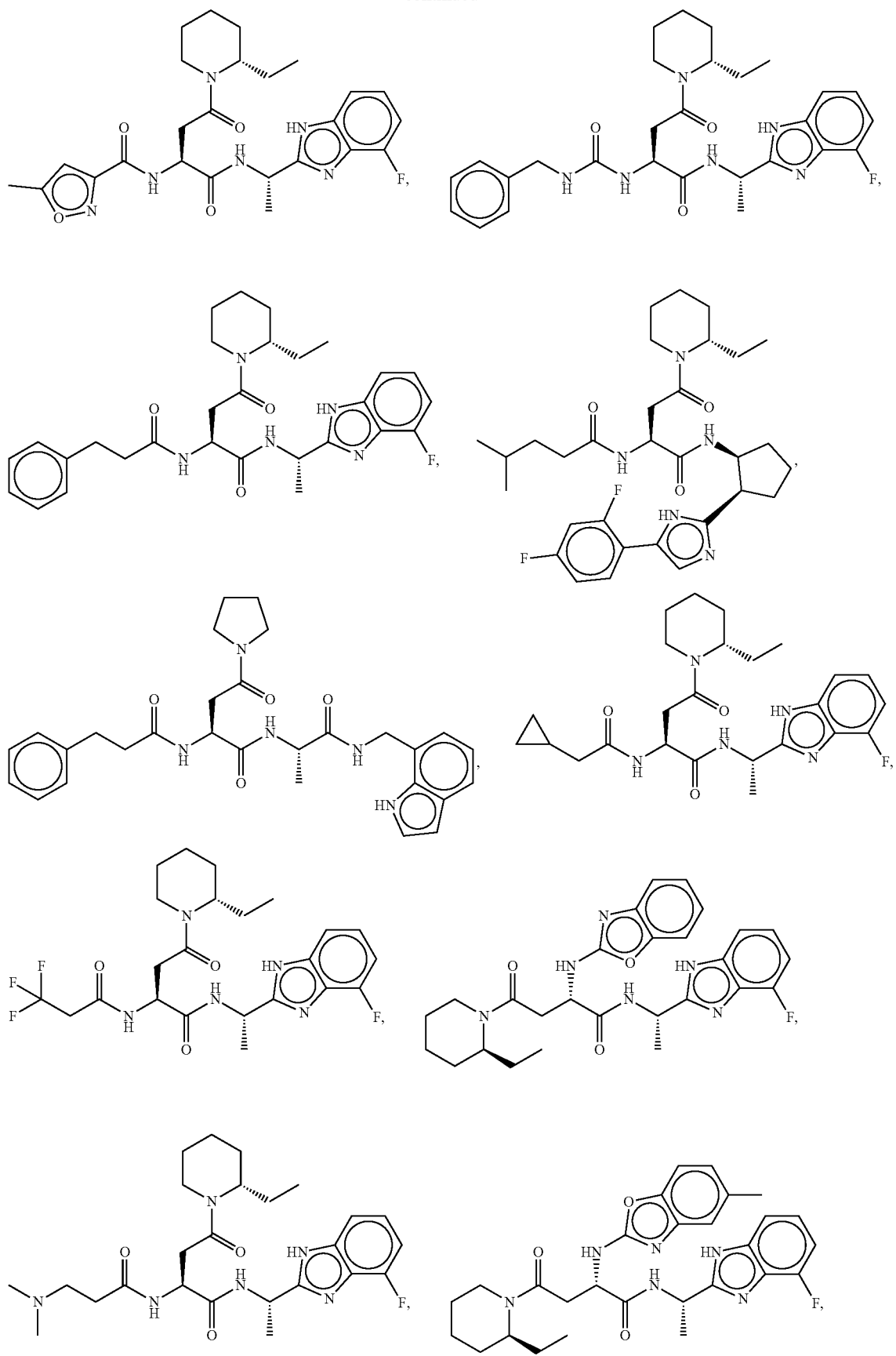

339
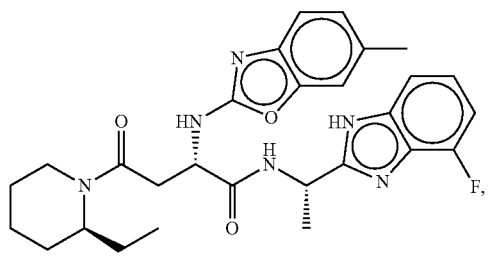
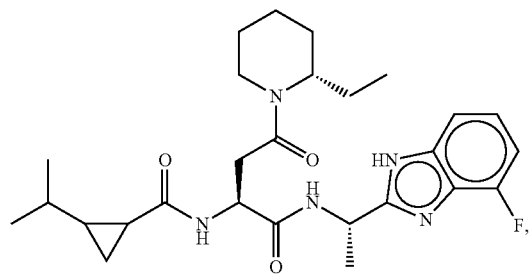
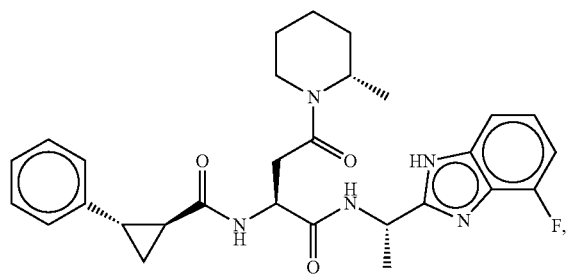
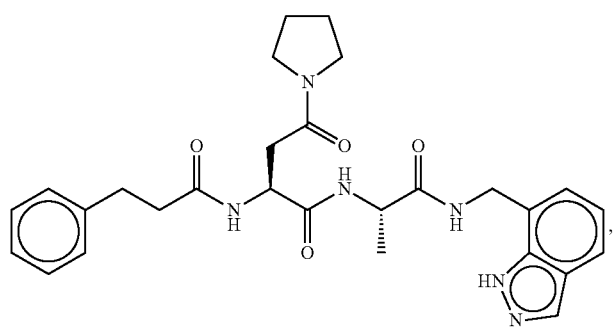
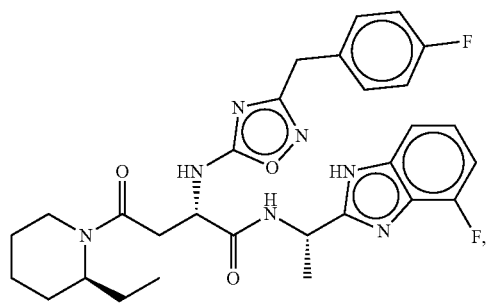
340
-continued
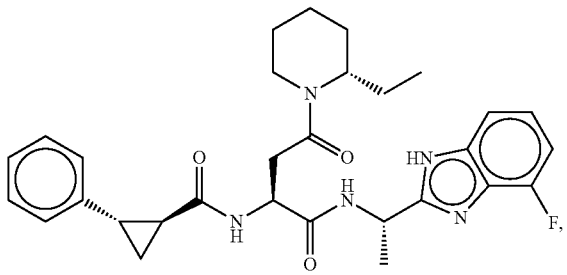
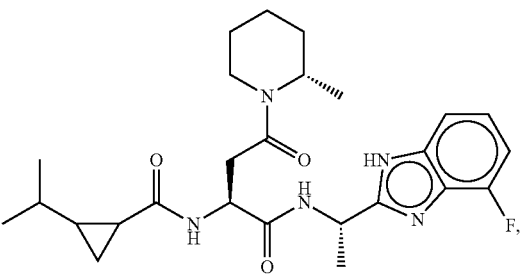
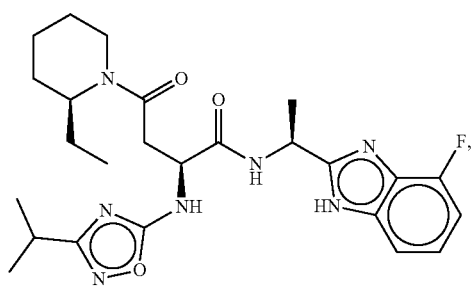
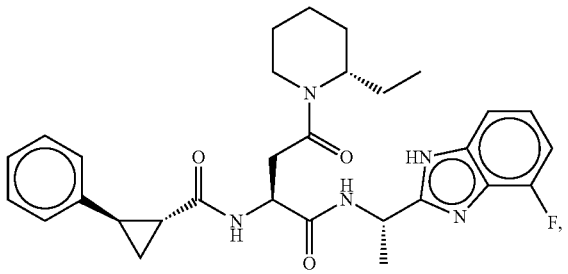

341 342
-continued
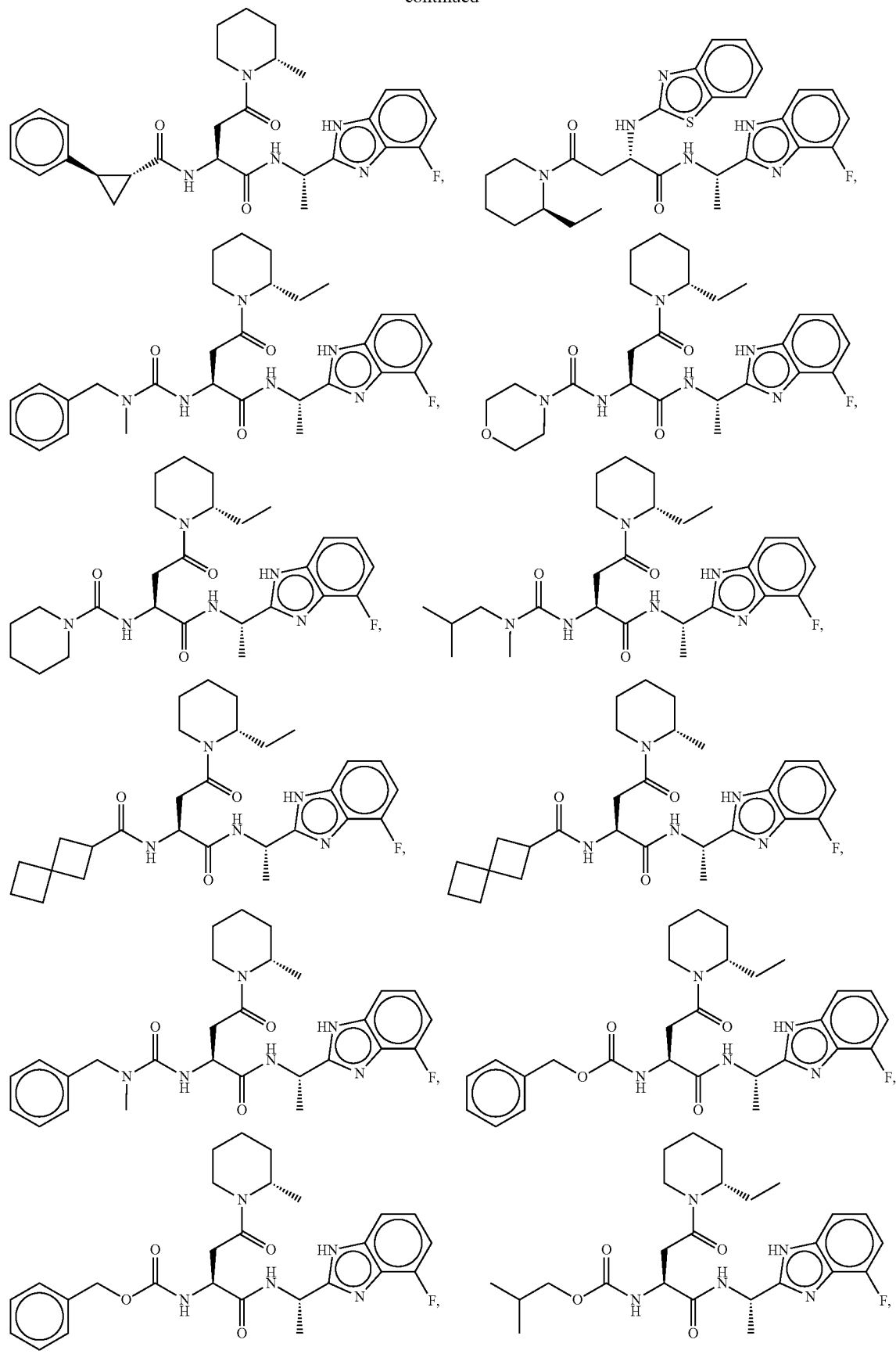

-continued
343
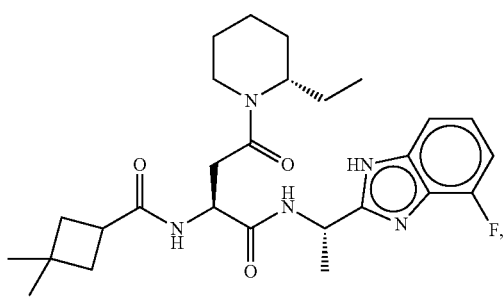
344
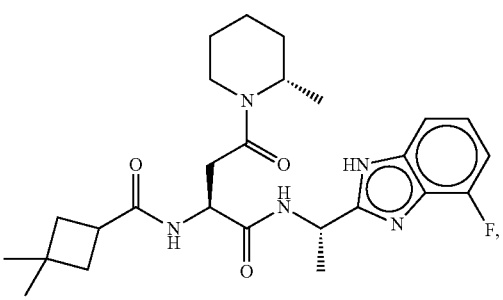
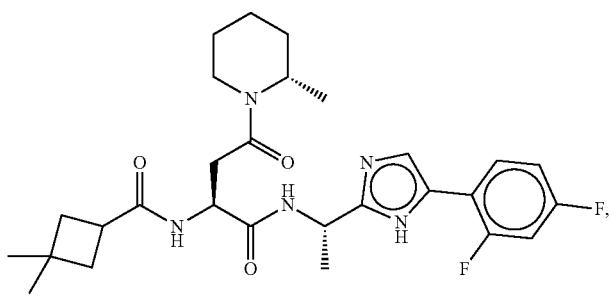
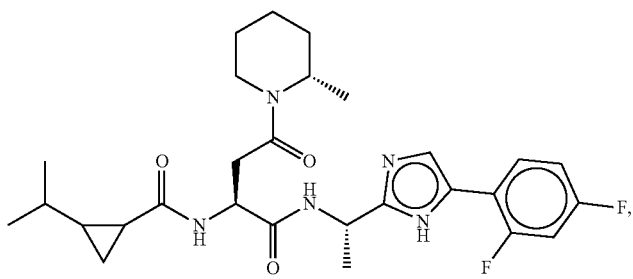
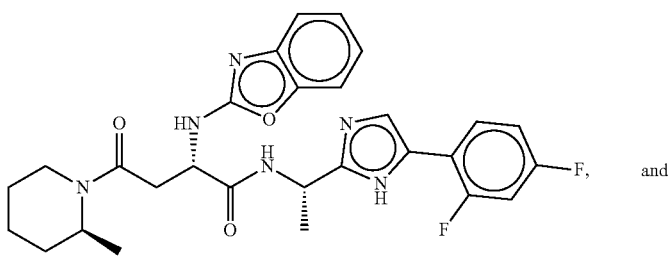
and
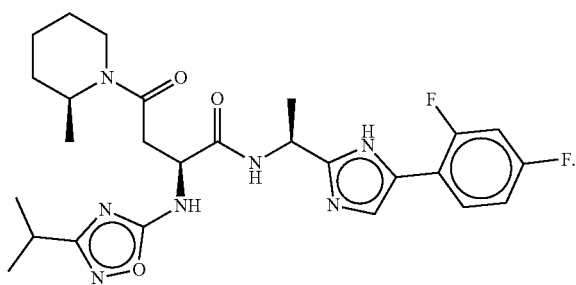

8. The method of claim 1, wherein a bacterial infection is treated, said bacterial infection being *Mycobacterium tuberculosis*.

9. The method of claim 1, wherein a parasite infection is treated, said parasite infection being malaria, leishmaniasis, river blindness, Chagas disease, or sleeping disease.

10. The method of claim 1, wherein a parasite infection is treated, said parasite infection being cryptosporidiosis, amebiasis, cyclosporiasis, giardiasis, or toxoplasmosis.

11. The method of claim 1, wherein a parasite infection is treated, said parasite infection being veterinary parasite infection.

12. The method of claim 11, wherein a veterinary parasite infection is caused by protozoan parasites, helminth parasites, arachnids, insects, or crustaceans.

13. The method of claim 1, wherein immunosuppression is provided for transplanted organs or tissues, said immunosuppression being used to prevent transplant rejection and graft-verse-host disease.

14. A method of inhibiting proteasome activity, said method comprising:
contacting a proteasome with a compound of Formula (I):

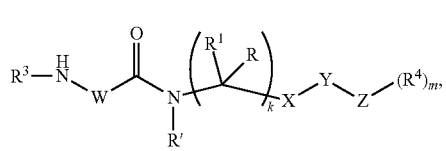

(I)

wherein
R is H or $C_{1-6}$ alkyl;
R' is H or $C_{1-6}$ alkyl;
$R^1$ is H or $C_{1-6}$ alkyl;
or R and $R^1$ are taken together with the carbon to which they are attached to form a $C_{3-8}$ cycloalkyl ring;
$R^2$ is independently selected at each occurrence thereof from

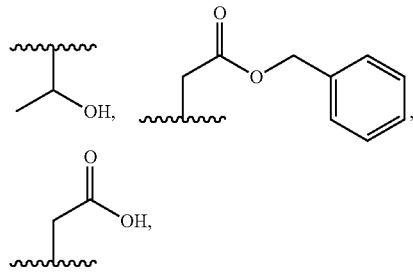

or $—(CH_2)_nC(O)NR^6R^7$;
$R^3$ is independently selected at each occurrence thereof from the group consisting of H, $C_{1-12}$ alkyl, -Boc, $—C(O)(CH_2)_nR^5$, $—(CH_2)_nC(O)R^5$, $—C(O)OR^5$, $—C(O)(CH_2)_nNR^6R^7$, $—S(O)_2R^5$, monocyclic and bicyclic heteroaryl, monocyclic and bicyclic heterocyclyl, and monocyclic and bicyclic non-aromatic heterocycle, wherein monocyclic and bicyclic heteroaryl, monocyclic and bicyclic heterocyclyl, and monocyclic and bicyclic non-aromatic heterocycle can be optionally substituted from 1 to 3 times with $R^8$;
$R^4$ is H, halogen, $NH_2$, $NHCOOC_{1-12}$ alkyl, or $C_{1-12}$ alkyl;
$R^5$ is selected from the group consisting of $C_{1-12}$ alkyl, monocyclic or bicyclic $C_3$-10 cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle, wherein $C_{1-12}$ alkyl, monocyclic or bicyclic $C_{3-10}$ cycloalkyl, $C_{3-12}$ cycloalkylalkyl, $C_{1-12}$ alkoxy, monocyclic and bicyclic aryl, monocyclic and bicyclic heteroaryl, monocyclic and bicyclic heterocyclyl, and monocyclic and bicyclic non-aromatic heterocycle can be optionally substituted from 1 to 3 times with $R^8$;

$R^6$ and $R^7$ are each independently selected from the group consisting of H, $C_{1-6}$ alkyl, and arylalkyl;
or $R^6$ and $R^7$ are taken together with the nitrogen to which they are attached to form a piperidine, pyrrolidine, azepane, or morpholine ring, wherein piperidine, pyrrolidine, azepane, or morpholine ring can be optionally substituted 1 to 3 times with $R^9$;
$R^8$ is selected independently at each occurrence thereof from the group consisting of halogen, $C_{1-6}$ alkyl, $C_{3-8}$ cycloalkyl, aryl, and arylalkyl, wherein $C_{1-6}$ alkyl, $C_{3-8}$ cycloalkyl, aryl, and arylalkyl can be optionally substituted 1 to 3 times with $R^9$;
$R^9$ is selected from the group consisting of H, halogen, $C_{1-6}$ alkyl, $C_{3-8}$ cycloalkyl, and aryl, wherein $C_{1-6}$ alkyl can be optionally substituted 1 to 3 times with halogen;
W is $CHR^2$, $NR^2$, or

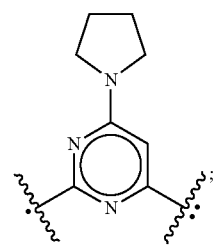

X is selected from the group consisting of —C(O)—NH—, monocyclic and bicyclic heteroaryl, monocyclic and bicyclic heterocyclyl, and monocyclic and bicyclic non-aromatic heterocycle;
Y is optional and, if present, is $—(CH_2)_m—$;
Z is optional and, if present, is aryl or bicyclic heteroaryl;

is the point of attachment to $NHR^3$ moiety;

is the point of attachment to C(O) moiety;
k is 1 or 2;
m is 0, 1, or 2; and
n is 0, 1, 2, 3, or 4,
with the proviso that $R^2$ is not $—CH_2C(O)NH_2$, $—CH_2C(O)NHCH_2C(CH_3)_3$, or $—(CH_2)_2C(O)NH_2$,
or a pharmaceutically acceptable salt thereof or a solvate thereof; under conditions effective to inhibit proteasome activity.

15. The method of claim 14, wherein the compound of Formula (I) is selected from the group consisting of:
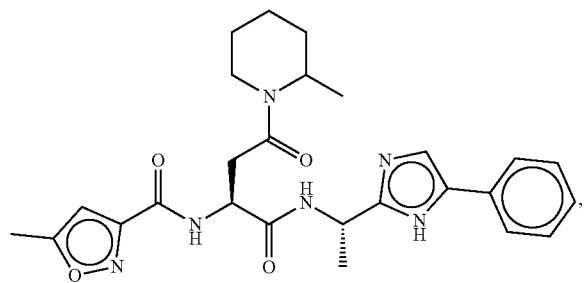
,
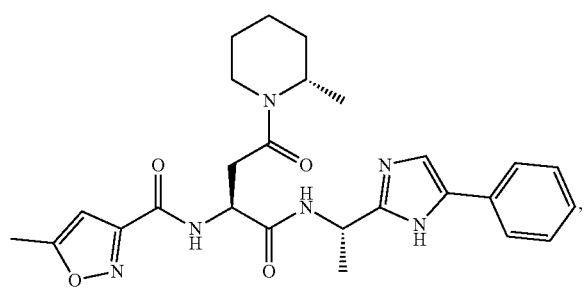
,
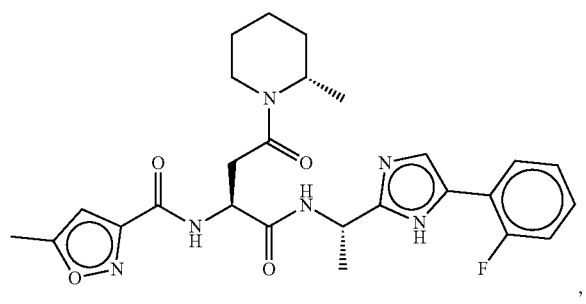
,
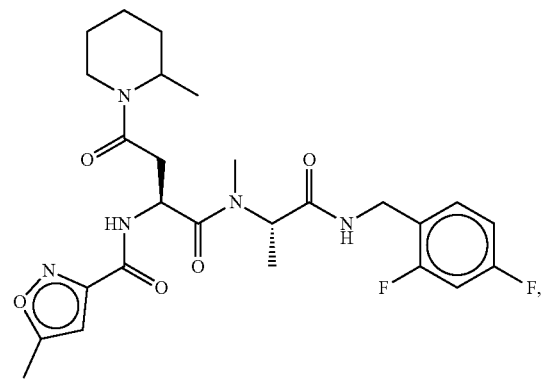
,
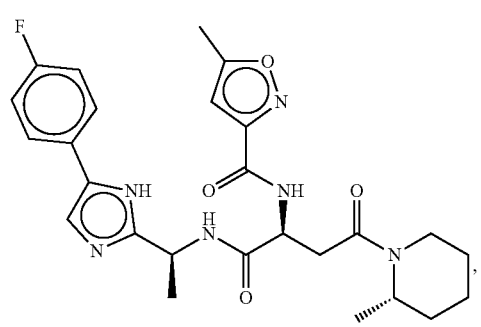
,
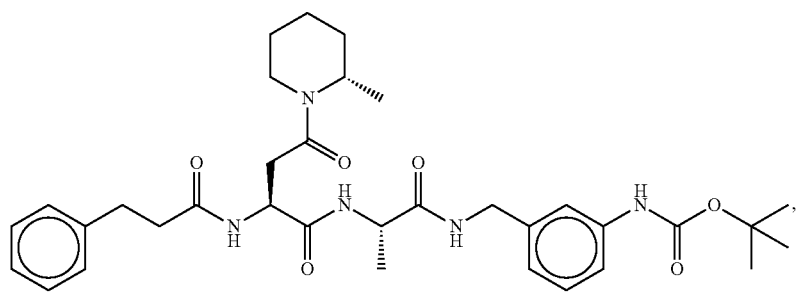
, 349 350
-continued
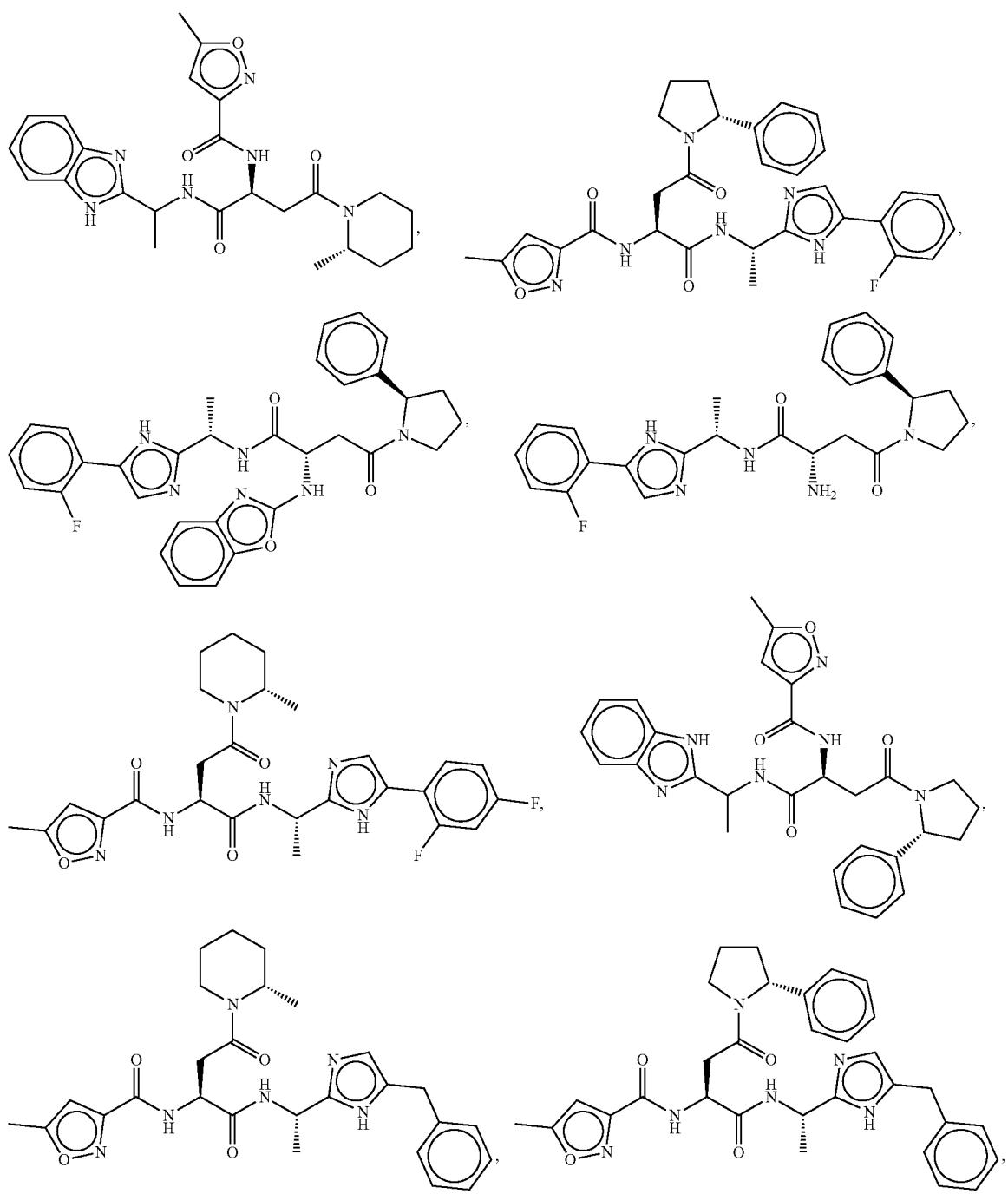

351 352
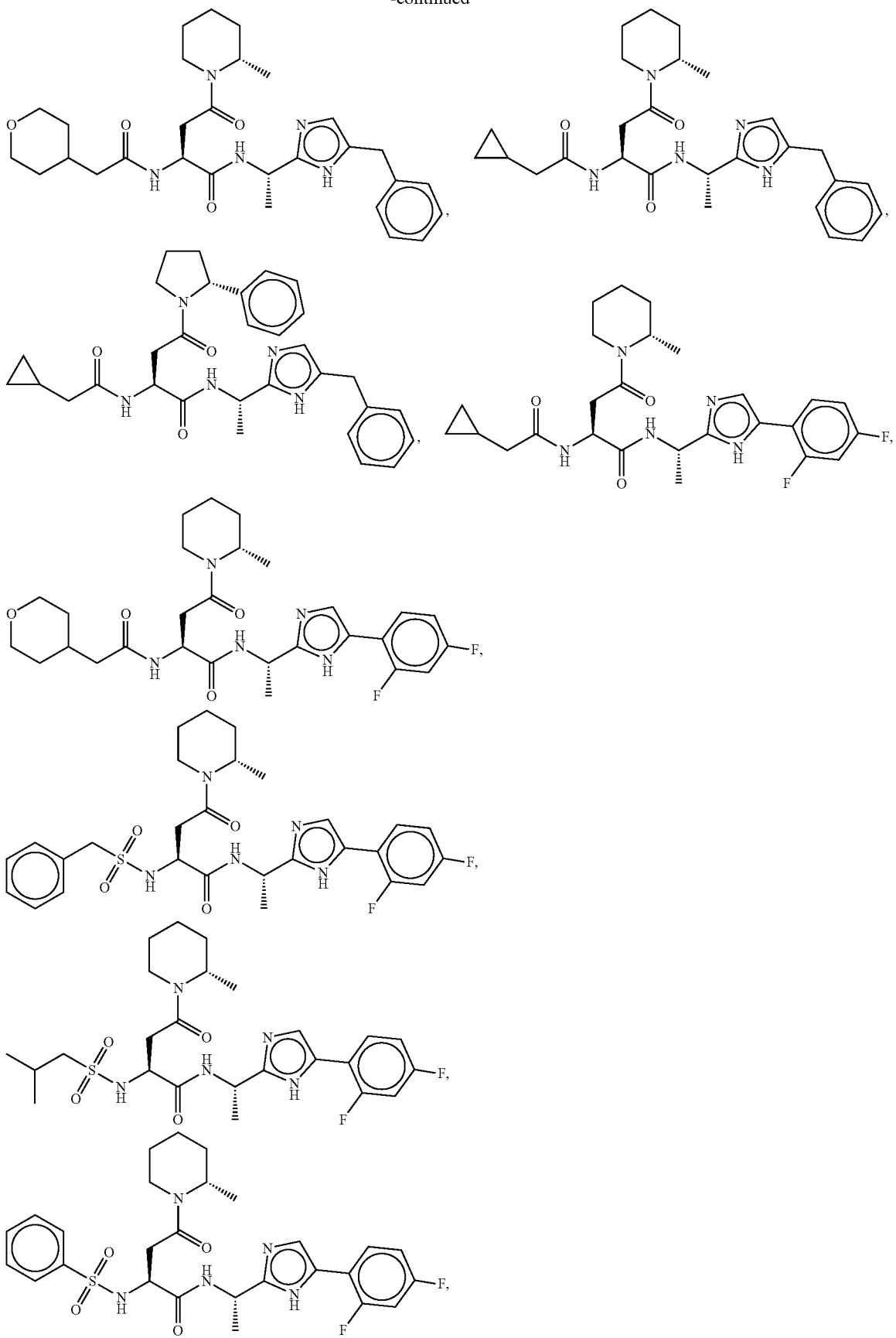

353
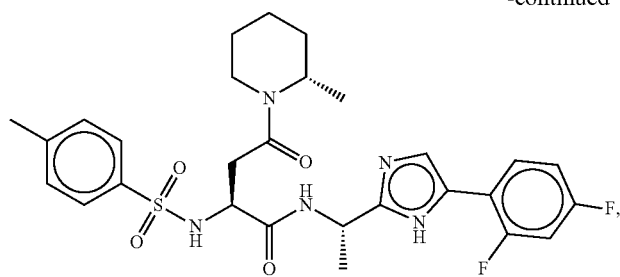
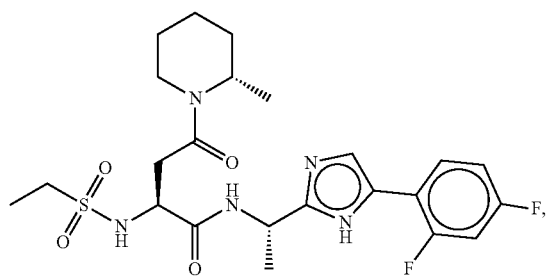
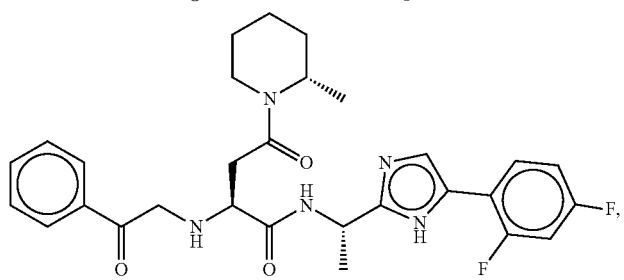
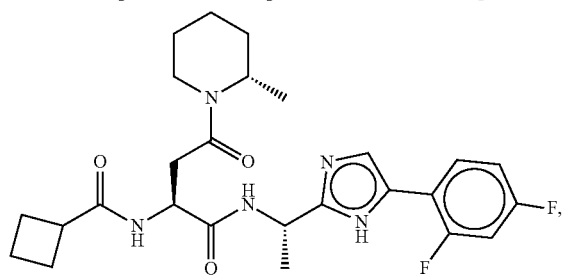
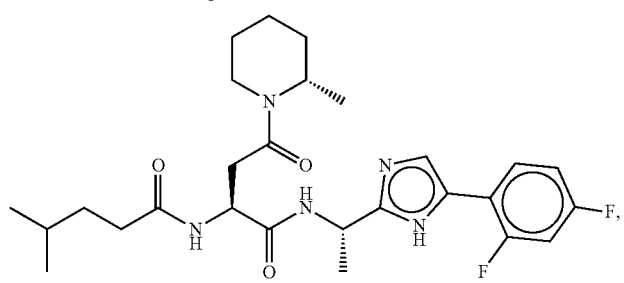
354
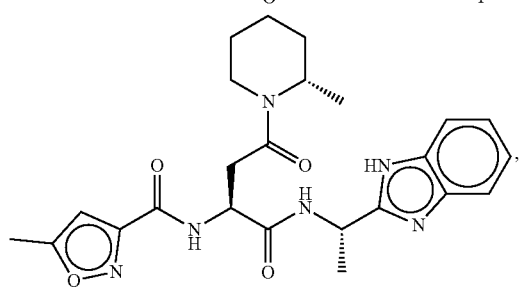
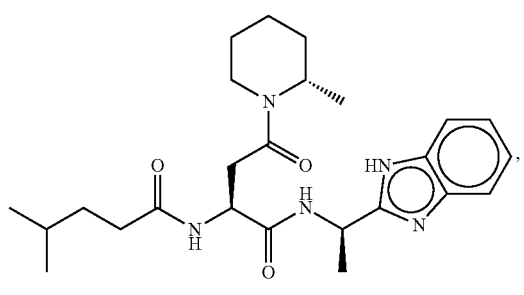

355
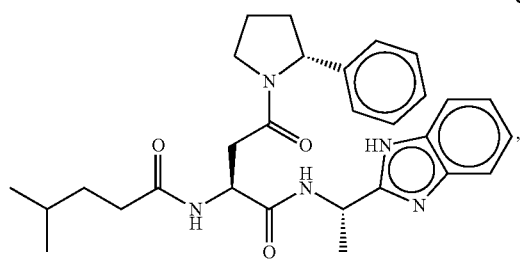
356
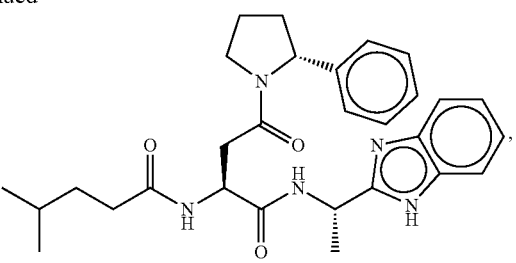
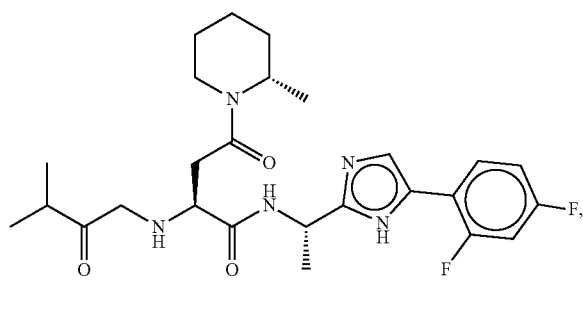
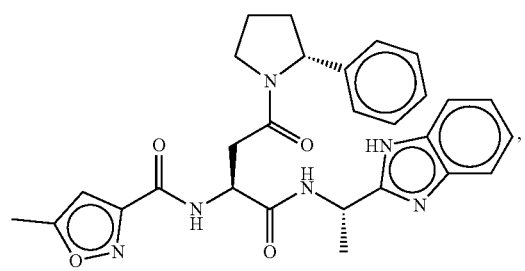
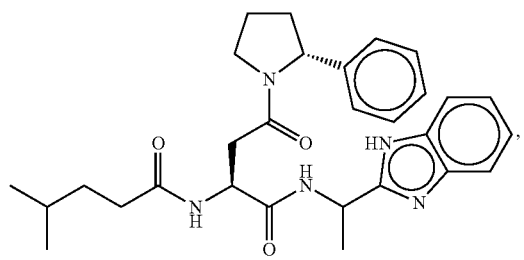
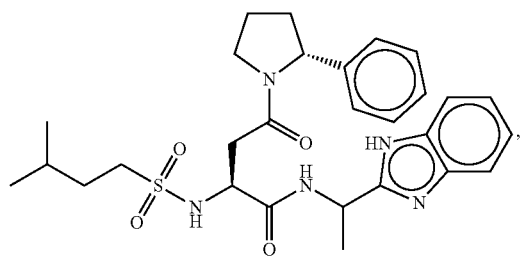
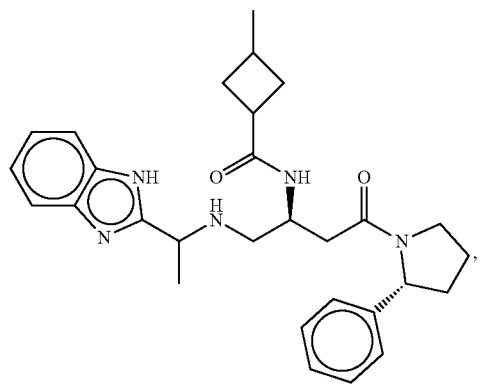
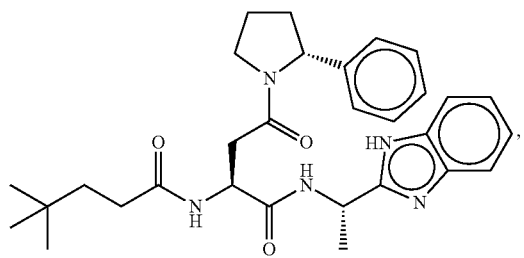
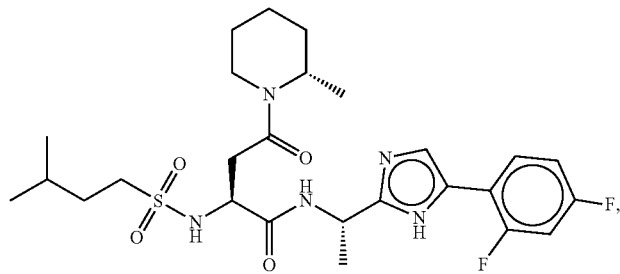

357
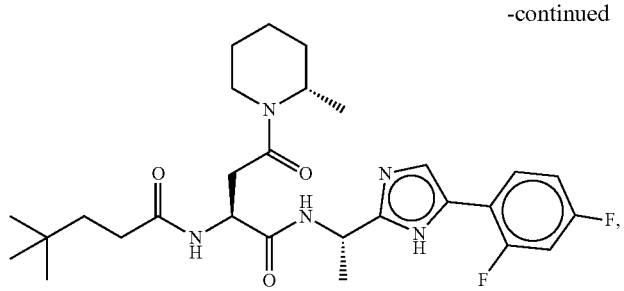
-continued
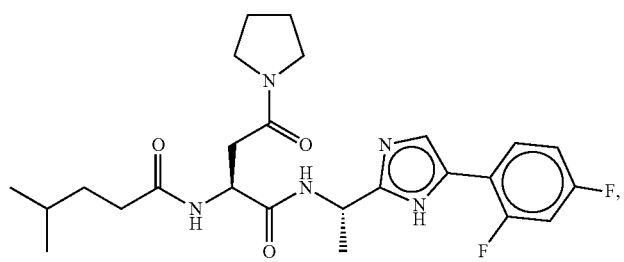
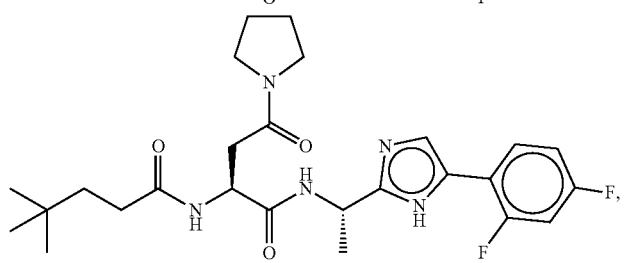
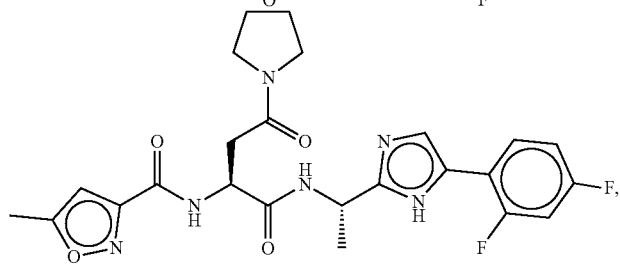
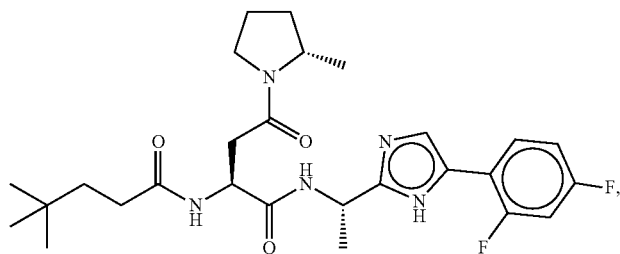
358
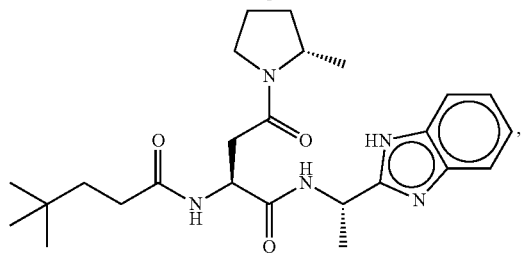
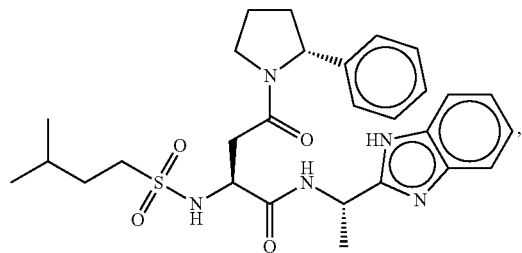

-continued
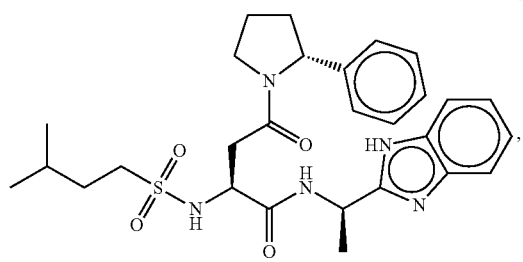
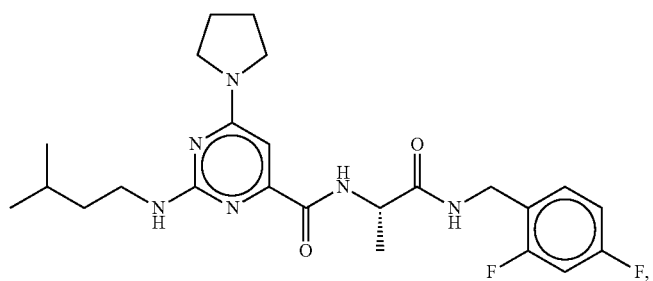
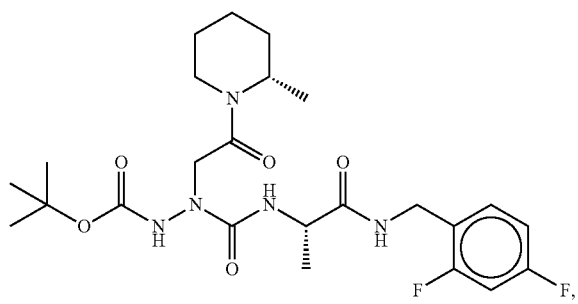
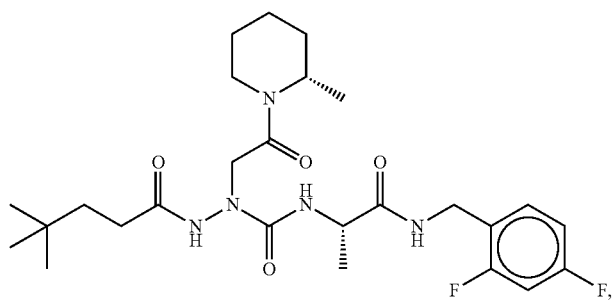
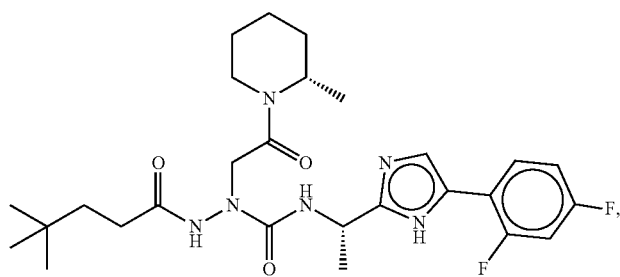
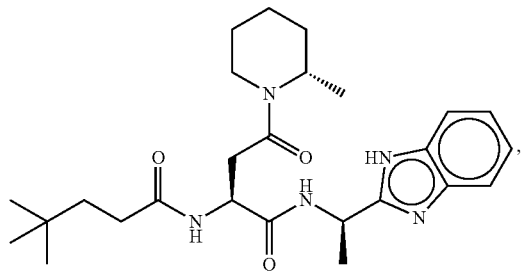
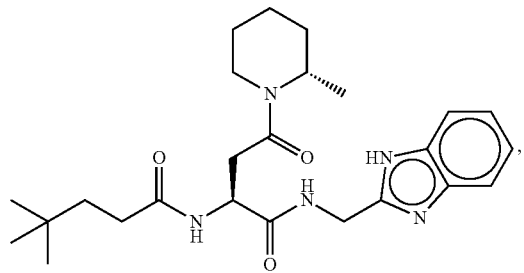

361     362
-continued
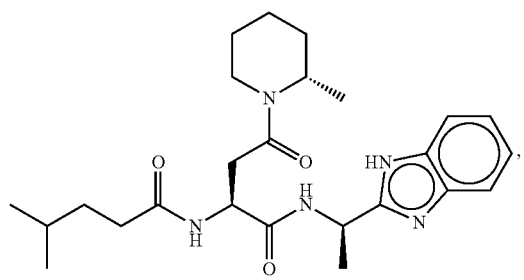 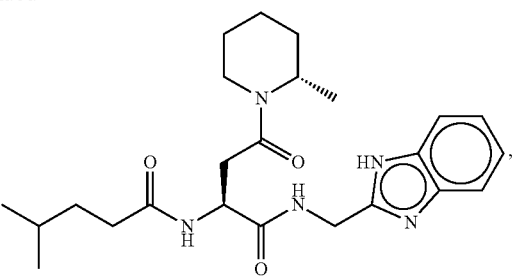
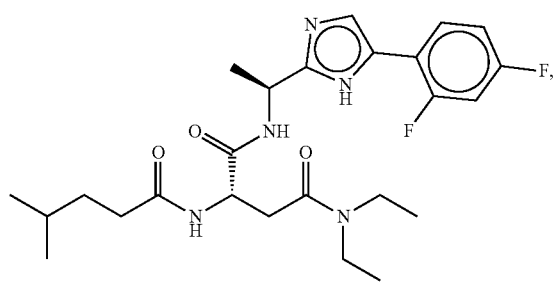
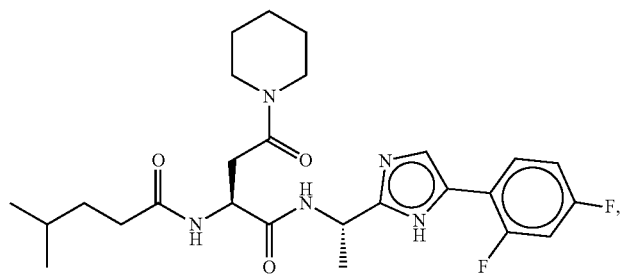
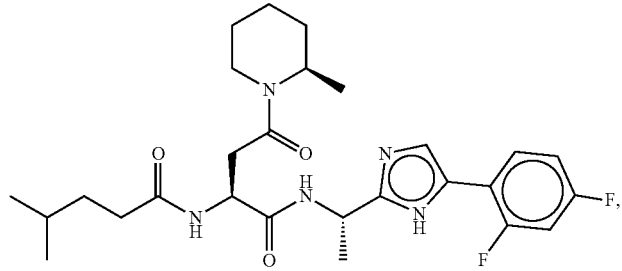
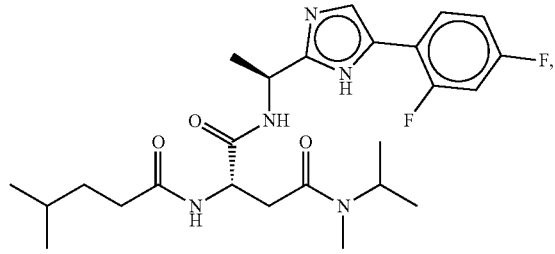
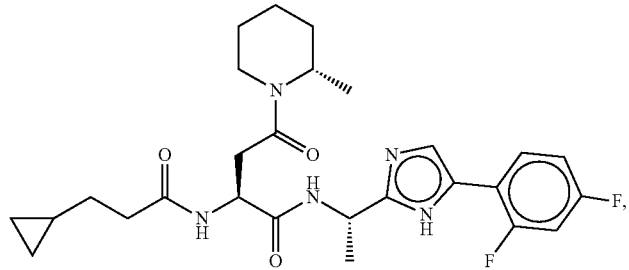

-continued
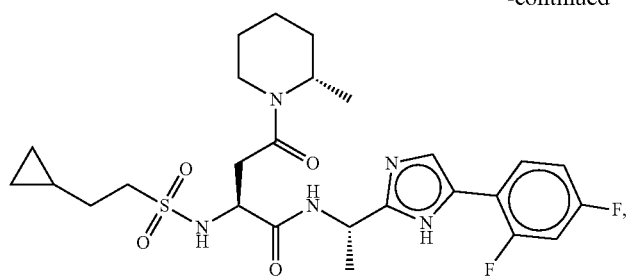
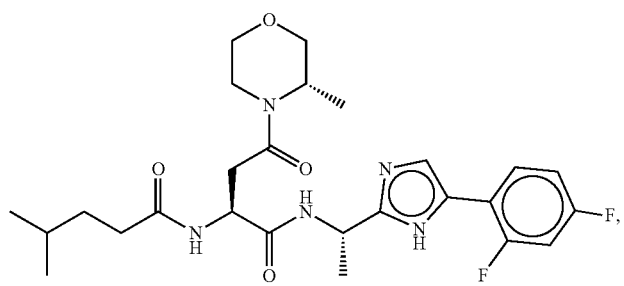
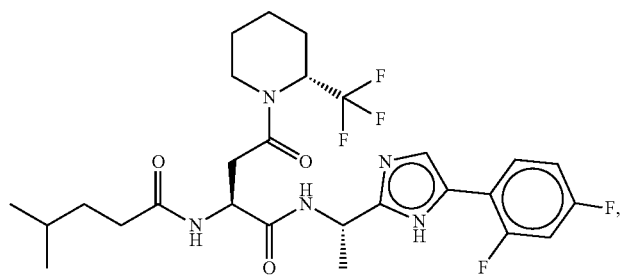
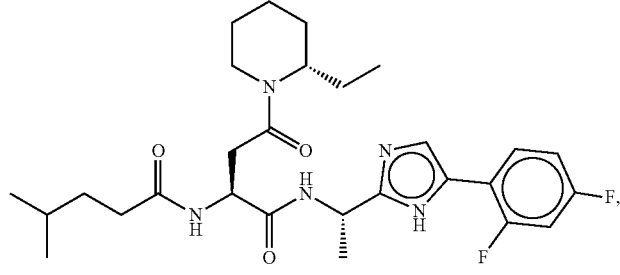
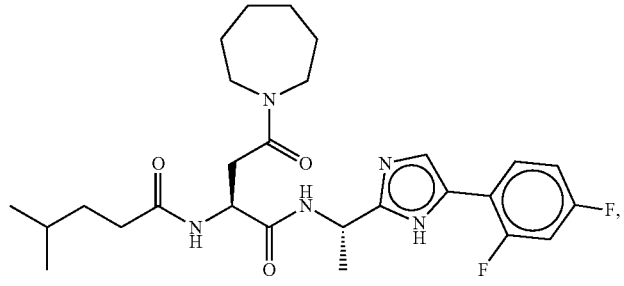
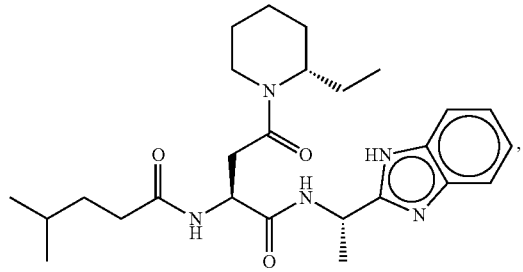
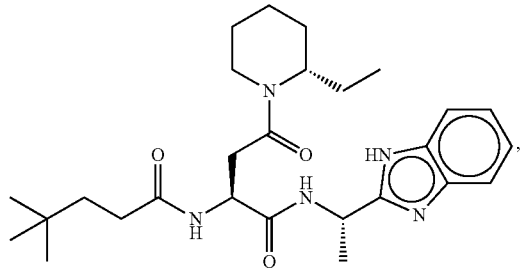

365
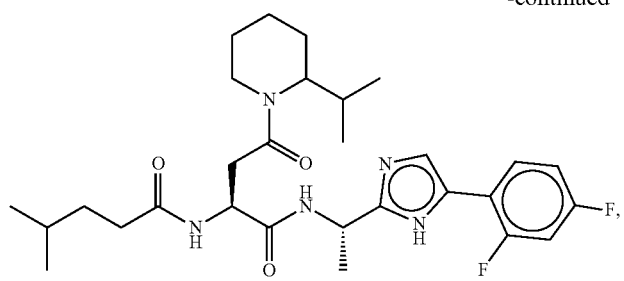
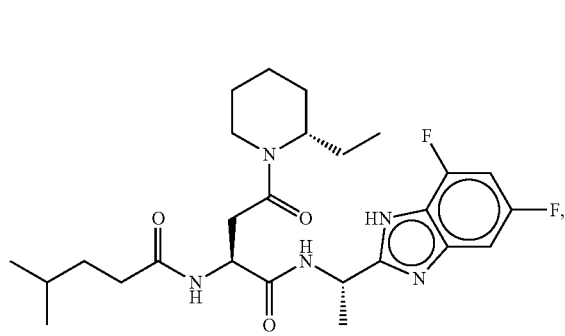
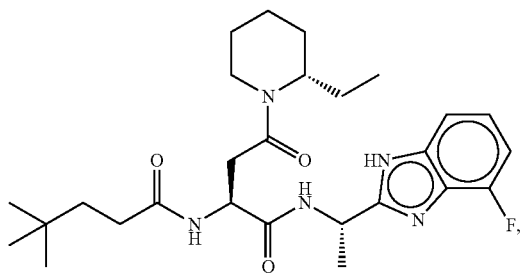
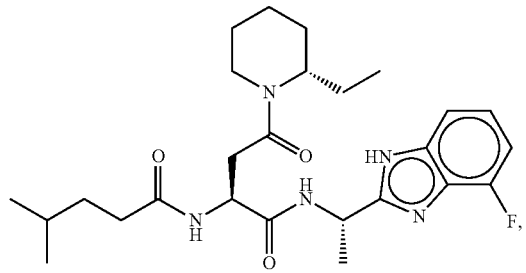
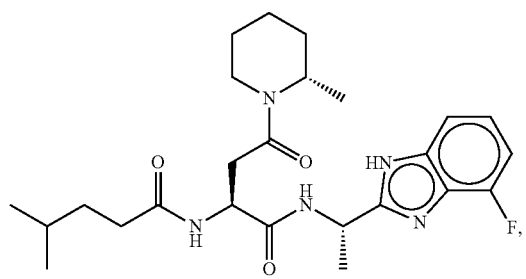
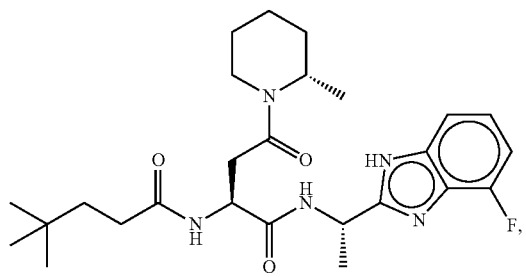
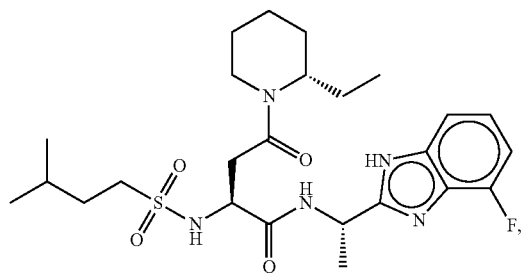
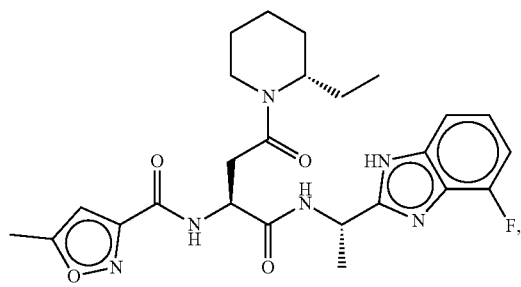
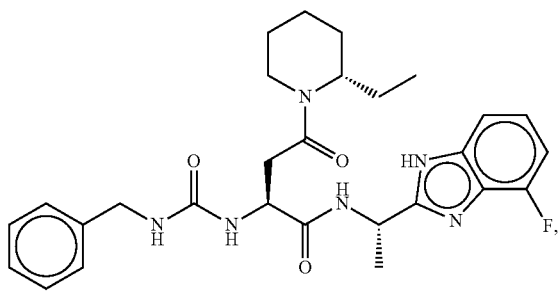
366
-continued 367 368
-continued
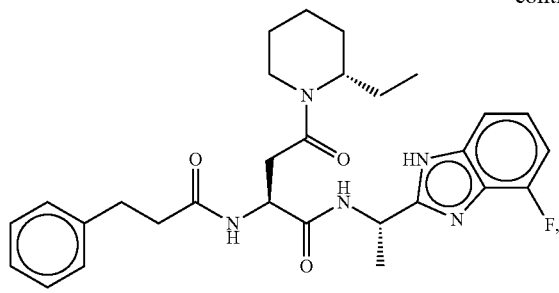 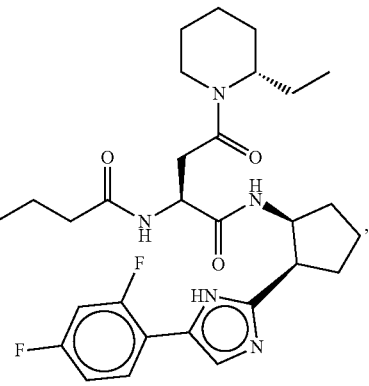
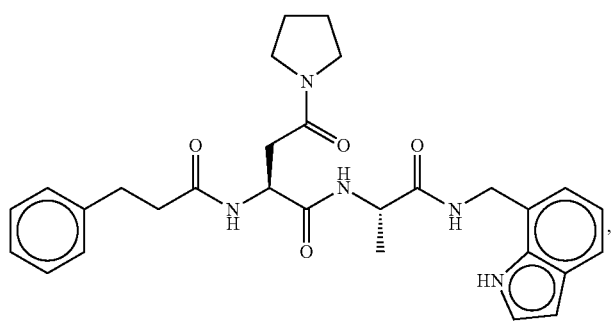 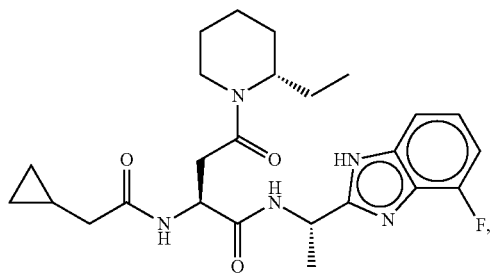
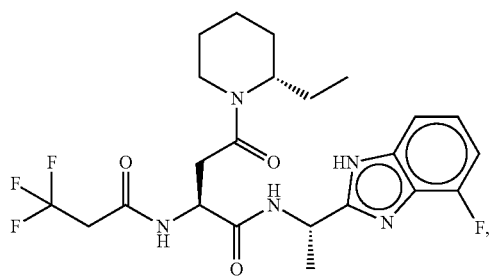 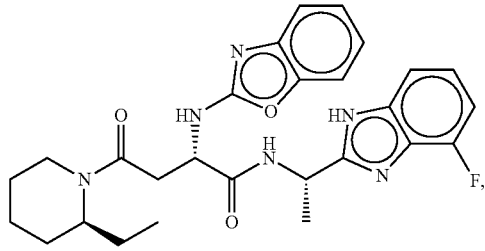
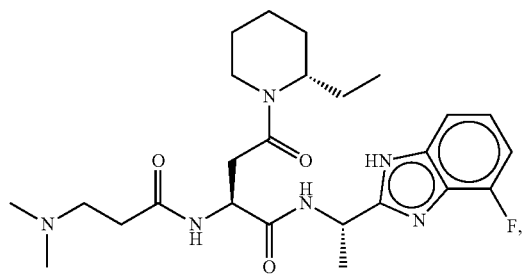 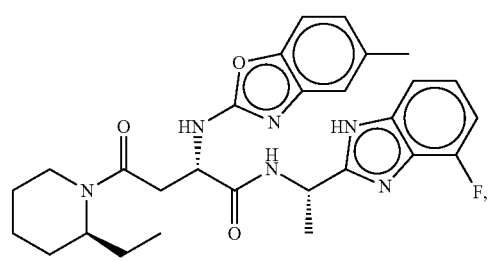
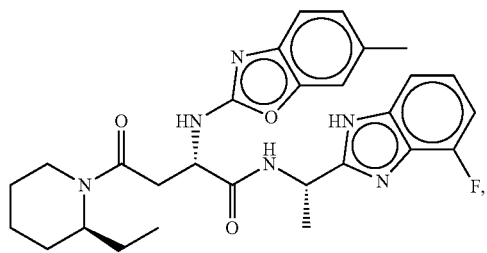 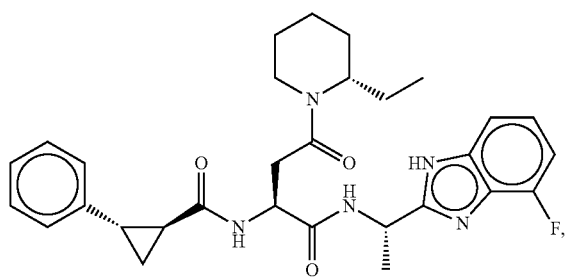

369 370
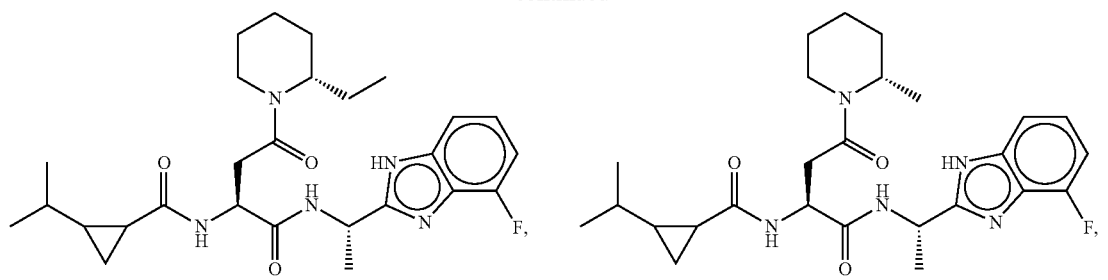
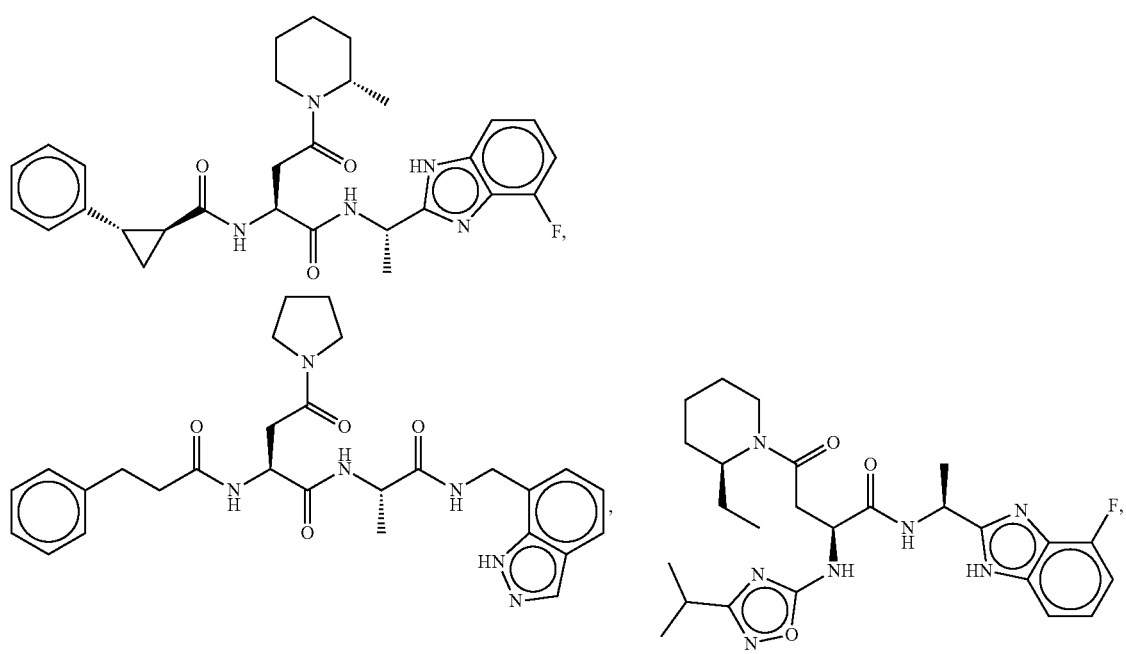
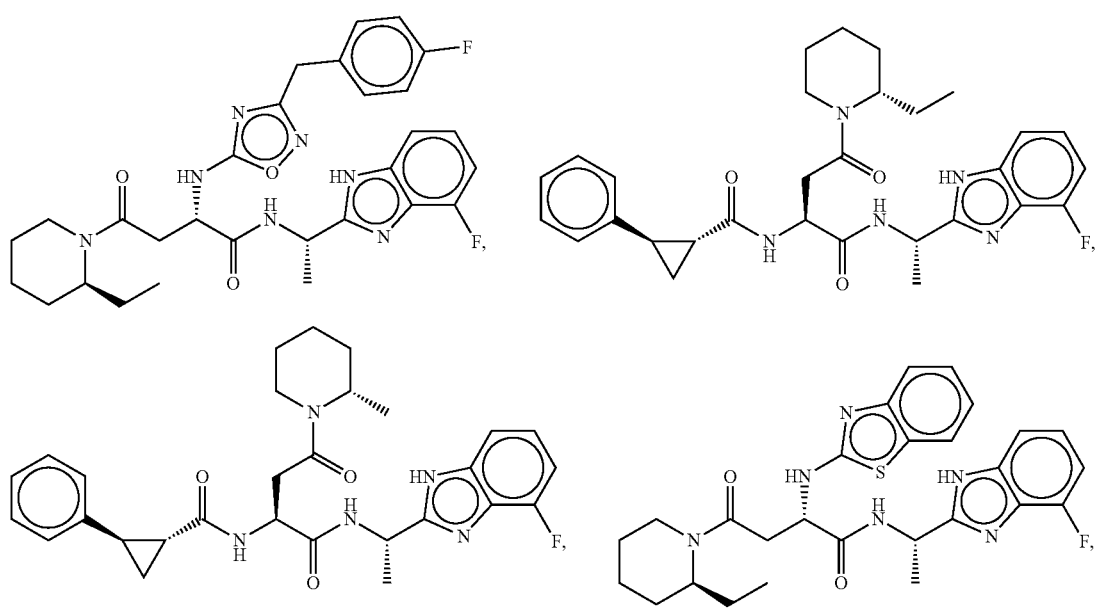

371 372
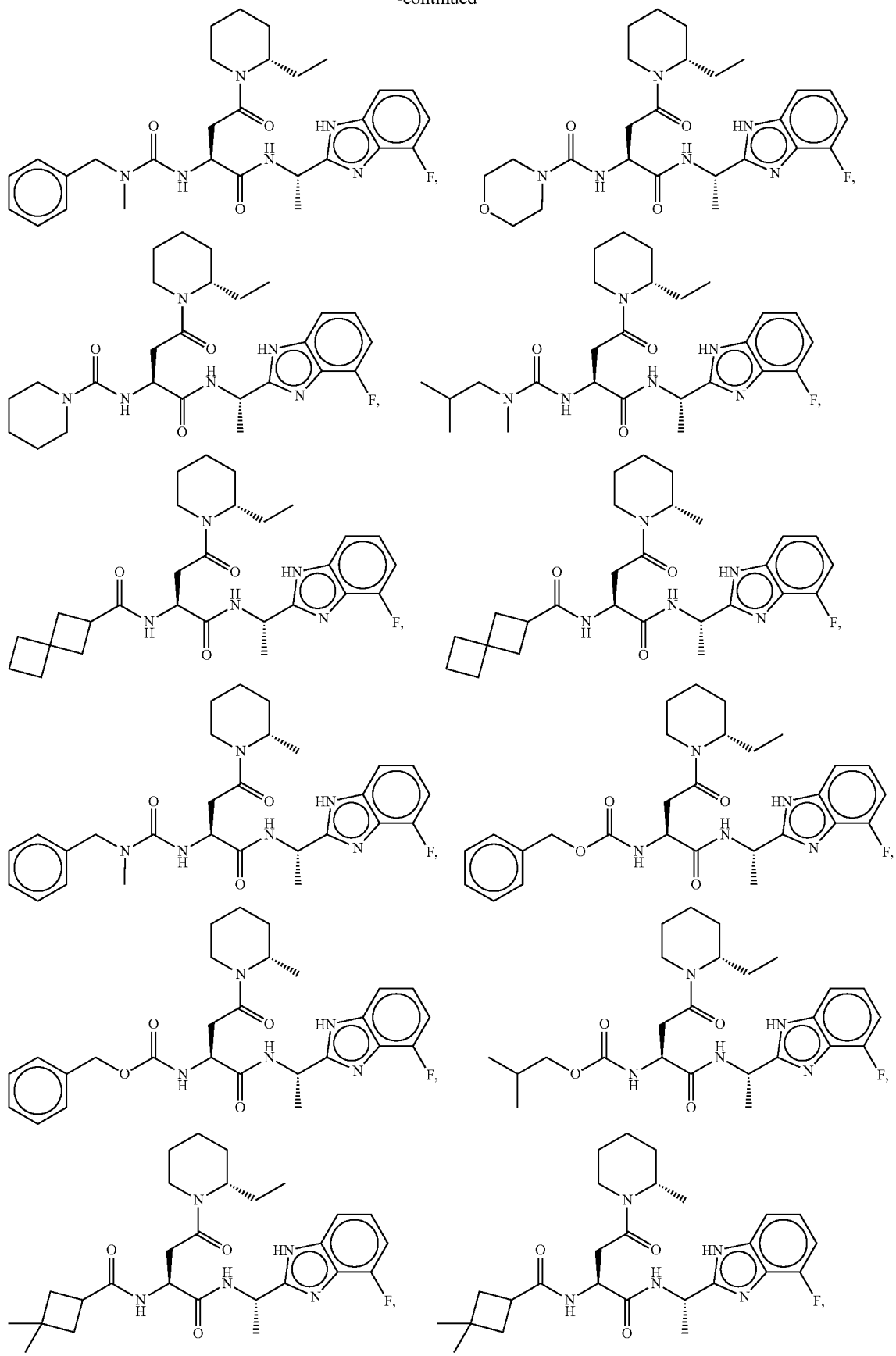
-continued

-continued
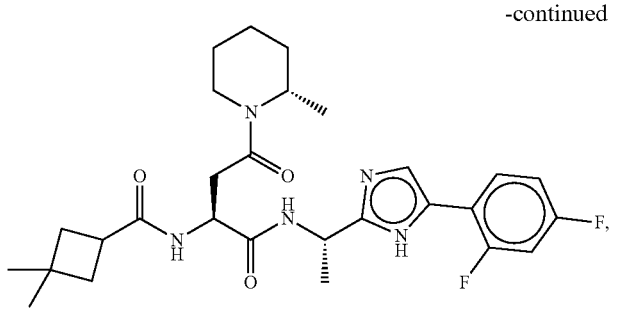
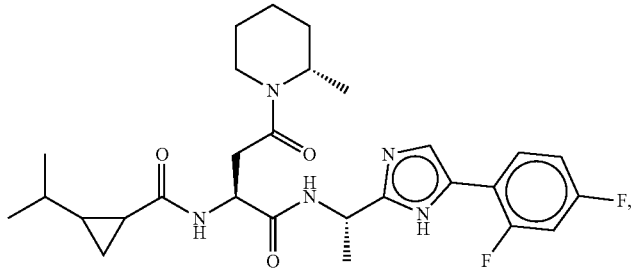
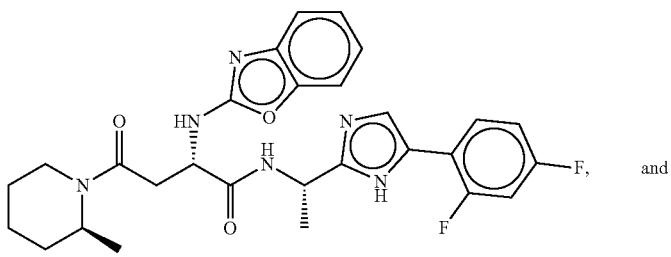 and
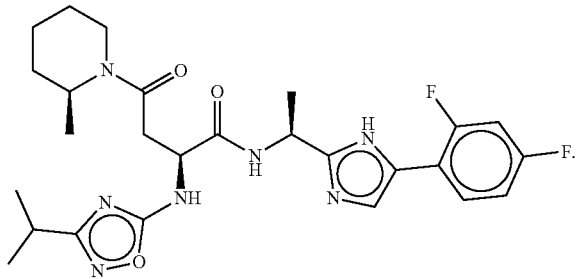
* * * * *

UNITED STATES PATENT AND TRADEMARK OFFICE
CERTIFICATE OF CORRECTION

PATENT NO. : 11,732,005 B2
APPLICATION NO. : 17/521328
DATED : August 22, 2023
INVENTOR(S) : Gang Lin et al.

Page 1 of 4

It is certified that error appears in the above-identified patent and that said Letters Patent is hereby corrected as shown below:

In the Claims

At Claim 1, Column 314, Lines 34-35, delete "—C(O)—" and "NH—" and insert -- —C(O)-NH— -- in its place.

At Claim 1, Column 314, Lines 60-61, delete "—CH$_2$C" and "(O)NHCH$_2$C(CH$_3$)$_3$" and insert -- —CH$_2$C(O)NHCH$_2$C(CH$_3$)$_3$-- in its place.

At Claim 7, Column 326, first structure, delete " 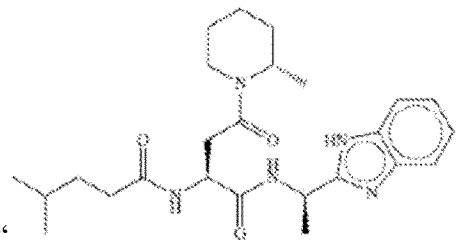 " and insert -- 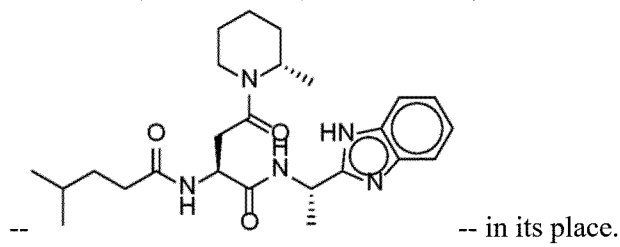 -- in its place.

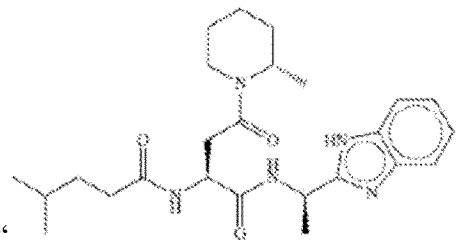

At Claim 7, Column 326, second structure, delete " 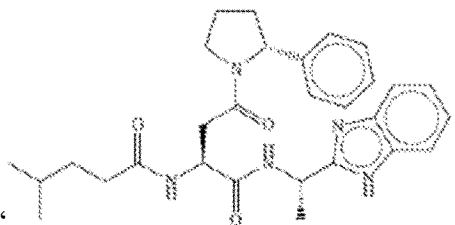 " and insert

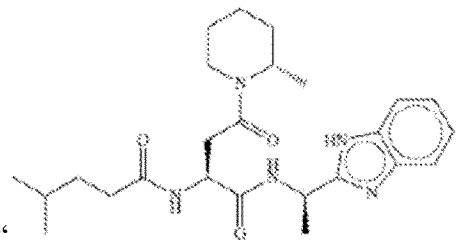

Signed and Sealed this
Twenty-fourth Day of October, 2023

Katherine Kelly Vidal
*Director of the United States Patent and Trademark Office*

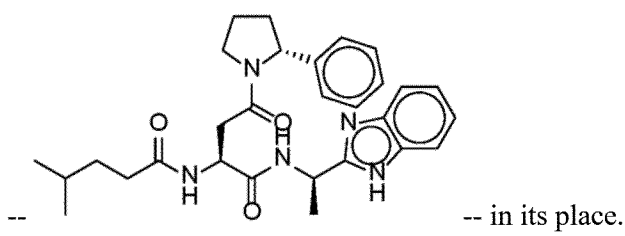 -- in its place.
At Claim 7, Column 327, first structure, delete " 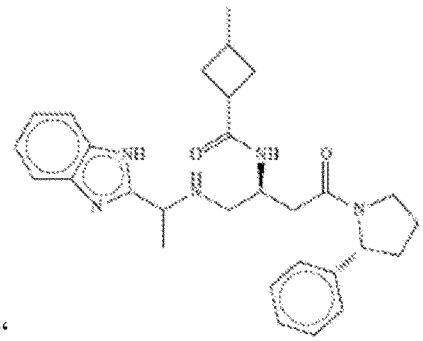 " and insert
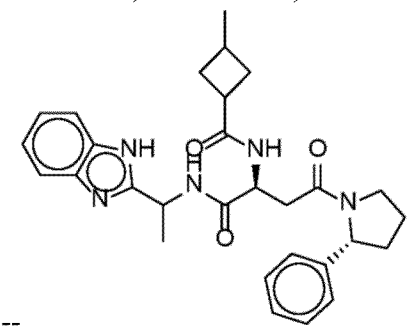 -- in its place.
At Claim 7, Column 335, fourth structure, delete " 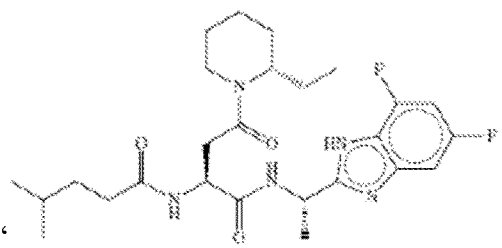 " and insert -- 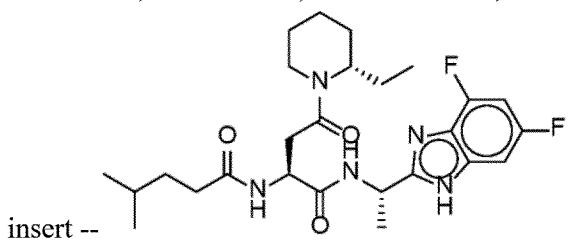 -- in its place.
At Claim 14, Column 346, Lines 36-37, delete "—C(O)—" and "NH—" and insert -- —C(O)-NH— -- in its place.
At Claim 14, Column 346, Lines 63-64, delete "—CH₂C" and "(O)NHCH₂C(CH₃)₃" and insert -- —CH₂C(O)NHCH₂C(CH₃)₃-- in its place.

At Claim 15, Column 354, first structure, delete " 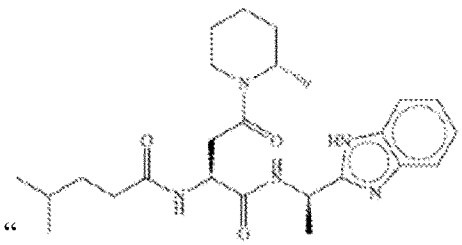 " and insert
 -- in its place.
At Claim 15, Column 355, fourth structure, delete " 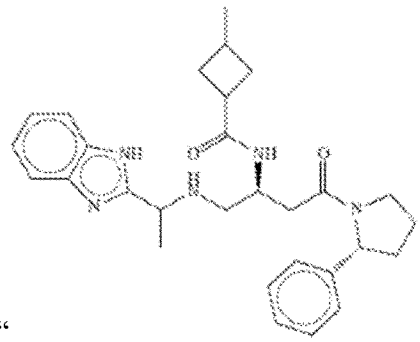 " and insert
 -- in its place.
At Claim 15, Column 356, first structure, delete " 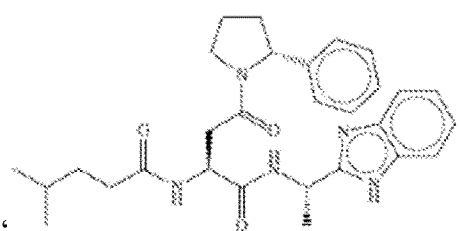 " and insert

CERTIFICATE OF CORRECTION (continued)
U.S. Pat. No. 11,732,005 B2

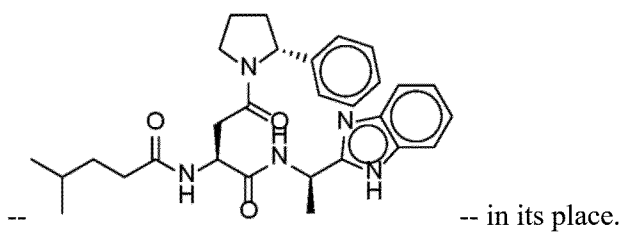 -- in its place.

At Claim 15, Column 365, second structure, delete " 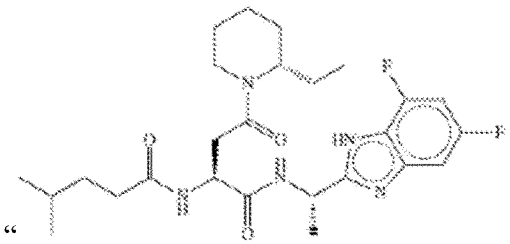 " and insert -- 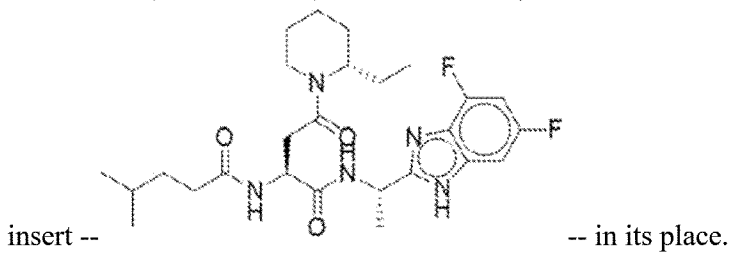 -- in its place.